(12) United States Patent
McGee et al.

(10) Patent No.: US 12,398,178 B2
(45) Date of Patent: Aug. 26, 2025

(54) COLLECTIONS OF PEPTIDES, PEPTIDE AGENTS, AND METHODS OF USE THEREOF

(71) Applicant: Parabilis Medicines, Inc., Cambridge, MA (US)

(72) Inventors: John Hanney McGee, Somerville, MA (US); Ty Matthew Thomson, Arlington, MA (US); Sebastian Christof Theodor Wahl, Zurich (CH); Gregory L. Verdine, Boston, MA (US); Raheleh Rezaei Araghi, Brookline, MA (US); Yue-Mei Zhang, Wellesley, MA (US); Mark Joseph Mulvihill, Sudbury, MA (US)

(73) Assignee: Parabilis Medicines, Inc., Cambridge, MA (US)

( * ) Notice: Subject to any disclaimer, the term of this patent is extended or adjusted under 35 U.S.C. 154(b) by 99 days.

(21) Appl. No.: 17/269,939

(22) PCT Filed: Aug. 20, 2019

(86) PCT No.: PCT/US2019/047206
§ 371 (c)(1),
(2) Date: Feb. 19, 2021

(87) PCT Pub. No.: WO2020/041270
PCT Pub. Date: Feb. 27, 2020

(65) Prior Publication Data
US 2021/0179665 A1  Jun. 17, 2021

Related U.S. Application Data

(60) Provisional application No. 62/719,996, filed on Aug. 20, 2018.

(51) Int. Cl.
*C07K 7/08* (2006.01)
*C07K 14/00* (2006.01)
*A61K 38/00* (2006.01)

(52) U.S. Cl.
CPC .............. *C07K 7/08* (2013.01); *C07K 14/001* (2013.01); *A61K 38/00* (2013.01)

(58) Field of Classification Search
CPC ......... C07K 7/08; C07K 14/001; A61K 38/00
See application file for complete search history.

(56) References Cited

U.S. PATENT DOCUMENTS

| | | | |
|---|---|---|---|
| 7,723,469 B2 | 5/2010 | Walensky et al. |
| 8,198,405 B2 | 6/2012 | Walensky et al. |
| 8,592,377 B2 | 11/2013 | Verdine et al. |
| 8,796,418 B2 | 8/2014 | Walensky et al. |
| 8,889,632 B2 | 11/2014 | Bernal et al. |
| 8,921,323 B2 | 12/2014 | Walensky et al. |
| 8,957,026 B2 | 2/2015 | Verdine et al. |
| 9,074,009 B2 | 7/2015 | Bradner et al. |
| 9,079,970 B2 | 7/2015 | Walensky et al. |
| 9,163,330 B2 | 10/2015 | Verdine et al. |
| 9,273,099 B2 | 3/2016 | Walensky et al. |
| 9,290,545 B2 | 3/2016 | Walensky et al. |
| 9,296,805 B2 | 3/2016 | Walensky et al. |
| 9,303,024 B2 | 4/2016 | Walensky et al. |
| 9,458,189 B2 | 10/2016 | Verdine et al. |
| 9,464,115 B2 | 10/2016 | Walensky et al. |
| 9,487,562 B2 | 11/2016 | Moellering et al. |
| 9,505,816 B2 | 11/2016 | Walensky et al. |
| 9,527,896 B2 | 12/2016 | Bernal et al. |
| 9,556,227 B2 | 1/2017 | Verdine et al. |
| 9,617,309 B2 | 4/2017 | Verdine et al. |
| 9,695,224 B2 | 7/2017 | Walensky et al. |
| 9,822,165 B2 | 11/2017 | Walensky et al. |
| 9,926,306 B2 | 3/2018 | Walensky |
| 10,000,478 B2 | 6/2018 | Walensky et al. |
| 10,000,511 B2 | 6/2018 | Walensky et al. |
| 10,077,290 B2 | 9/2018 | Walensky et al. |
| 10,081,654 B2 | 9/2018 | Verdine et al. |
| 10,087,215 B2 | 10/2018 | Leshchiner et al. |
| 10,106,590 B2 | 10/2018 | Walensky et al. |
| 10,202,431 B2 | 2/2019 | Bernal et al. |
| 10,227,390 B2 | 3/2019 | Verdine et al. |

(Continued)

FOREIGN PATENT DOCUMENTS

| WO | WO-2008/121767 A2 | 10/2008 |
| WO | WO-2011/008260 A2 | 1/2011 |

(Continued)

OTHER PUBLICATIONS

Acetamide, N,N'-1,3-phenylenebis[2-bromo-_C10H10Br2N2O2—PubChem_12499317; retrieved from https://pubchem.ncbi.nlm.nih.gov/compound/12499317; Jun. 2, 2022 (Year: 2007).*
Sidhu, S.S. et al., [21] Phage Display for Selection of Novel Binding Peptides, Phage Display for Selection of Novel Binding Peptides, Methods in Enzymology, 328: 333-363. (Year: 2000).*
Grossman, T. N. et al., Inhibition of oncogenic Wnt signaling through direct targeting of β-catenin, PNAS, 109(44):17942-17947, with Supplemental Information, 9 pages. (Year: 2012).*
Chen, S. and Heinis, C., Phage Selection of Bicyclic Peptides Based on Two Disulfide Bridges, Chapter 9, Ratmir Derda (ed.), Peptide Libraries: Methods and Protocols, Methods in Molecular Biology, 1248: 119-137, (Year: 2015).*
NCBI Conserved Domain Search_WP_115971347, generated by examiner on Oc. 14, 2022. (Year: 2018).*

(Continued)

*Primary Examiner* — Jeanette M Lieb
(74) *Attorney, Agent, or Firm* — Choate, Hall & Stewart LLP; Xiaodong Li; William C. Howland

(57) ABSTRACT

The present disclosure provides powerful technologies for the development, production, characterization, and/or use of stapled peptide compositions. Among other things, the present disclosure provides strategies for defining amino acid sequences particularly amenable or useful for stapling, as well as technologies, reagents, and systems for developing, producing, characterizing, and/or using stapled peptides having such amino acid sequences.

11 Claims, 31 Drawing Sheets

Specification includes a Sequence Listing.

(56) References Cited

U.S. PATENT DOCUMENTS

| | | |
|---|---|---|
| 10,259,848 B2 | 4/2019 | Walensky et al. |
| 10,273,290 B2 | 4/2019 | Walensky et al. |
| 10,301,351 B2 | 5/2019 | Verdine et al. |
| 10,308,926 B2 | 6/2019 | Walensky et al. |
| 10,351,554 B2 | 7/2019 | Walensky et al. |
| 10,464,975 B2 | 11/2019 | Walensky et al. |
| 10,487,129 B2 | 11/2019 | Walensky et al. |
| 10,533,039 B2 | 1/2020 | Verdine et al. |
| 10,703,785 B2 | 7/2020 | Walensky et al. |
| 10,716,828 B2 | 7/2020 | Danial et al. |
| 10,822,374 B2 | 11/2020 | Walensky et al. |
| 10,844,053 B2 | 11/2020 | Walensky et al. |
| 11,198,713 B2 | 12/2021 | Hilinski et al. |
| 11,332,496 B2 | 5/2022 | Verdine et al. |
| 11,377,476 B2 | 7/2022 | Verdine et al. |
| 2010/0184628 A1 | 7/2010 | Nash |
| 2011/0218155 A1 | 9/2011 | Walensky et al. |
| 2013/0035304 A1 | 2/2013 | Walensky et al. |
| 2014/0256912 A1 | 9/2014 | Moellering et al. |
| 2015/0225471 A1 | 8/2015 | Liang et al. |
| 2015/0284437 A1 | 10/2015 | Verdine et al. |
| 2016/0122405 A1 | 5/2016 | Palchaudhuri et al. |
| 2016/0152667 A1 | 6/2016 | Walensky et al. |
| 2016/0171150 A1 | 6/2016 | Walensky et al. |
| 2016/0244494 A1 | 8/2016 | Verdine et al. |
| 2016/0257725 A1 | 9/2016 | Verdine et al. |
| 2017/0008930 A1 | 1/2017 | Walensky et al. |
| 2018/0009847 A1 | 1/2018 | Verdine et al. |
| 2018/0010001 A1 | 1/2018 | Hersam et al. |
| 2018/0057565 A1 | 3/2018 | Liang et al. |
| 2018/0100001 A1 | 4/2018 | Verdine et al. |
| 2018/0201658 A1 | 7/2018 | Rezaei-Araghi et al. |
| 2018/0265524 A1 | 9/2018 | Walensky et al. |
| 2019/0002506 A1 | 1/2019 | Walensky et al. |
| 2019/0002514 A1 | 1/2019 | Walensky et al. |
| 2019/0092822 A1 | 3/2019 | Walensky et al. |
| 2019/0202862 A1 | 7/2019 | Verdine et al. |
| 2020/0231638 A1 | 7/2020 | Walensky et al. |
| 2020/0239533 A1 | 7/2020 | Verdine et al. |
| 2020/0247858 A1 | 8/2020 | Hilinski et al. |
| 2021/0002336 A1 | 1/2021 | Walensky et al. |
| 2021/0032234 A1 | 2/2021 | Walensky et al. |
| 2022/0177522 A1 | 6/2022 | Verdine et al. |
| 2022/0213154 A1 | 7/2022 | Hilinski et al. |
| 2022/0306708 A1 | 9/2022 | Verdine et al. |
| 2022/0372075 A1 | 11/2022 | Verdine et al. |
| 2023/0046728 A1 | 2/2023 | Chandhoke et al. |
| 2023/0137773 A1 | 5/2023 | Verdine et al. |
| 2023/0271917 A1 | 8/2023 | Jewett et al. |
| 2023/0357320 A1 | 11/2023 | Verdine et al. |
| 2024/0376151 A1 | 11/2024 | Tokareva et al. |

FOREIGN PATENT DOCUMENTS

| | | | |
|---|---|---|---|
| WO | WO-2012040459 A2 * | 3/2012 | ............ C07K 1/113 |
| WO | WO-2014/052647 A2 | 4/2014 | |
| WO | WO-2014/055564 A1 | 4/2014 | |
| WO | WO-2014/159969 A1 | 10/2014 | |
| WO | WO-2014/201370 A1 | 12/2014 | |
| WO | WO-2015/051030 A2 | 4/2015 | |
| WO | WO-2015/095406 A1 | 6/2015 | |
| WO | WO-2015/179635 A2 | 11/2015 | |
| WO | WO-2016/209978 A2 | 12/2016 | |
| WO | WO-2018017485 A1 * | 1/2018 | ............ C07K 1/006 |
| WO | WO-2019/051327 A2 | 3/2019 | |
| WO | WO-2020/041270 A1 | 2/2020 | |
| WO | WO-2020/041270 A9 | 4/2020 | |
| WO | WO-2021/119537 A1 | 6/2021 | |
| WO | WO-2021/188659 A1 | 9/2021 | |
| WO | WO-2022/020651 A1 | 1/2022 | |
| WO | WO-2022/020652 A2 | 1/2022 | |
| WO | WO-2022/261257 A1 | 12/2022 | |
| WO | WO-2024/130217 A1 | 6/2024 | |
| WO | WO-2024/130218 A1 | 6/2024 | |

OTHER PUBLICATIONS

NCBI Conserved Domain Search_XP_032335171, generated by examiner on Oc. 14, 2022. (Year: 2020).*

Fairlie, D.P. and Dantas De Araujo, A., Stapling Peptides Using Cysteine Crosslinking, Biopolymers (Peptide Science), 106(6): 843-852 (Year: 2016).*

Rebollo and Heinis, Phage selection of bicyclic peptides, Methods; 60: 46-54. (Year: 2013).*

Jafari, M.R. et al., Discovery of Light-Responsive Ligands through Screening of a Light-Responsive Genetically Encoded Library, ACS Chem. Biol., 9: 443-450. (Year: 2014).*

Chen, S. et al., Peptide Ligands Stabilized by Small Molecules, Angewandte Chemie, 126(6):1628-1632. (Year: 2014).*

Iyer, A. et al., Stapling monomeric GCN4 peptides allows for DNA binding and enhanced cellular uptake, Organic & Biomolecular Chemistry, 13(13)3856-3862. (Year: 2015).*

Diderich, P. et al., Phage Selection of Chemically Stabilized a-Helical Peptide Ligands, ACS Chem. Biol., 11(5):1422-1427. (Year: 2016).*

U.S. Appl. No. 16/298,093, filed Mar. 11, 2019, Verdine et al.
U.S. Appl. No. 16/822,722, filed Mar. 18, 2020, Walensky et al.
U.S. Appl. No. 16/950,540, filed Nov. 17, 2020, Verdine et al.
U.S. Appl. No. 17/091,541, filed Nov. 6, 2020, Walensky et al.

Assem, N. et al., Acetone-Linked Peptides: A Convergent Approach for Peptide Macrocyclization and Labeling, Angew. Chem. Int. Ed., 54: 8665-8668 (2015).

Chen, S. and Heinis, C., Phage Selection of Bicyclic Peptides Based on Two Disulfide Bridges, Chapter 9, Ratmir Derda (ed.), Peptide Libraries: Methods and Protocols, Methods in Molecular Biology, 1248: 119-137 (2015).

Fairlie, D.P. and Dantas De Araujo, A., Stapling Peptides Using Cysteine Crosslinking, Biopolymers (Peptide Science), 106(6): 843-852 (2016).

International Search Report for PCT/US2019/47206, 5 pages (Jan. 21, 2020).

Jafari, M.R. et al., Discovery of Light-Responsive Ligands through Screening of a Light-Responsive Genetically Encoded Library, ACS Chem. Biol., 9: 443-450 (2014).

Jo, H. et al,. Development of a-Helical Calpain Probes by Mimicking a Natural Protein-Protein Interaction, J. Am. Chem. Soc., 134: 17704-17713 (2012).

Kale, S. S. et al., Cyclization of peptides with two chemical bridges affords large scaffold diversities, Article and Reporting Summary, Nat. Chem., 12 pages (2018).

Kalhor-Monfared, S. et al., Rapid biocompatible macrocyclization of peptides with decafluoro-diphenylsulfone, Chem. Sci., 7: 3785-3790 (2016).

Ng, S. and Derda, R., Phage-displayed macrocyclic glycopeptide libraries, Org. Biomol. Chem., 14: 5539-5545 (2016).

Peraro, L. et al., Diversity-Oriented Stapling Yields Intrinsically Cell-Penetrant Inducers of Autophagy, J. Am. Chem. Soc., 139:7792-7802 (2017).

Pub Chem CID 23678, N,N'-Ethylenebis(iodoacetamide) (2005), <https://pubchem.ncbi.nlm.nih.gov/compound/23678>. Retrieved on Nov. 7, 2019.

Pub Chem CID 621238, 4,4'-Bis (bromomethyl)biphenyl (2005), <https://pubchem.ncbi.nlm.nih.gov/compound/621238>. Retrieved on Nov. 7, 2019.

PubChem CID 12499317, Create: Feb. 8, 2008. Modify: Nov. 2, 2019. URL: https://pubchem.ncbi.nlm.nih.gov/compound/12499317 [Retrieved Nov. 6, 2019).

Sidhu, S.S. et al., [21] Phage Display for Selection of Novel Binding Peptides, Phage Display for Selection of Novel Binding Peptides, Methods in Enzymology, 328: 333-363 (2000).

Wang, Y. and Chou, D. H-C., AThiol-Ene Coupling Approach to Native Peptide Stapling and Macrocyclization, Angew. Chem. Int. Ed., 54: 10931-10934 (2015).

Written Opinion for PCT/US2019/47206, 8 pages (Jan. 21, 2020).

Bellotto, S. et al., Phage Selection of Photoswitchable Peptide Ligands, J. Am. Chem. Soc., 136:5880-5883, (2014).

Chen, S. et al., Peptide Ligands Stabilized by Small Molecules, Angewandte Chemie, 126(6):1628-1632, (2014).

(56) References Cited

OTHER PUBLICATIONS

Grossman, T. N. et al., Inhibition of oncogenic Wnt signaling through direct targeting of β-catenin, PNAS, 109(44):17942-17947, (2012), with Supplemental Information, 9 pages.
Iyer, A. et al., Stapling monomeric GCN4 peptides allows for DNA binding and enhanced cellular uptake, Organic & Biomolecular Chemistry, 13(13)3856-3862, (2015).
Schafmeister et al., An All-Hydrocarbon Cross-Linking System for Enhancing the Helicity and Metabolic Stability of Peptides, J. Am. Chem. Soc., 122: 5891-5892 (2000).
Bernal, F. et al., A stapled p53 helix overcomes HDMX-mediated suppression of p53, Cancer Cell, 18(5):411-422 (2010).
Bernal, F. et al., A Stapled p53 Helix Targets HDMX to Overcome Nutlin-3 Resistance and Reactivate the p53 Tumor Suppressor Pathway in Cancer, Blood, 112(11):2645 (2008).
Chen, S. and Heinis, C., Phage selection of bicyclic peptides based on two disulfide bridges, Methods Mol. Biol., 1248:119-137 (2015).
De Paola, I. et al., Cullin3-BTB interface: a novel target for stapled peptides, PLoS One, 10(4):e012114 (2015).
Diderich, P. et al., Phage Selection of Chemically Stabilized a-Helical Peptide Ligands, ACS Chem. Biol., 11(5):1422-1427 (2016).
Dietrich, L. et al., Cell Permeable Stapled Peptide Inhibitor of Wnt Signaling that Targets β-Catenin Protein-Protein Interactions, Cell Chem. Bio., 24:958-968 (2017).
Distefano, M.D. and Miranda, L., APS 2022 27th American Peptide Symposium, 122 pages, (2022).
Grossmann, T. N. et al., Inhibition of oncogenic Wnt signaling through direct targeting of β-catenin, PNAS, 109(44):17942-17947 (2012).
Heinis, C. et al., Phage-encoded combinatorial chemical libraries based on bicyclic peptides, Nat. Chem. Biol., 5(7):502-507 (2009).
Misawa, T. et al., Structural development of stapled short helical peptides as vitamin D receptor (VDR)-coactivator interaction inhibitors, Bioorg. Med. Chem., 23(5):1055-1061 (2015).
Neri, D. and Brandli, A.W., Encoding chemistry, Nat. Chem. Biol., 5(7):452-453 (2009).
Nevola, L. et al., Light-regulated stapled peptides to inhibit protein-protein interactions involved in clathrin-mediated endocytosis, Angew. Chem. Int. Ed. Engl., 52(30):7704-7708 (2013).
Ortet, P. et al., Exploring the scope of i,i+4 thioether staples on a b-catenin peptide inhibitor, Fog Pharmaceuticals, Inc., 1 page, (2022).
Phillips, C. et al., Design and structure of stapled peptides binding to estrogen receptors, J. Am. Chem. Soc., 133(25):9696-9699 (2011).
Rebollo, I.R., et al., Identification of target-binding peptide motifs by high-throughput sequencing of phage-selected peptides, Nucleic Acids Research, 42(22):e169 (2014).
Spiegel, J. et al., Direct targeting of Rab-GTPase-effector interactions, Angew. Chem. Int. Ed. Engl., 53(9):2498-2503 (2014).
Takeda, K. et al., Targeted disruption of the BCL9/β-catenin complex inhibits oncogenic Wnt signaling, Sci. Transl. Med., 4(148):148ra117 (2012).
Walensky, L.D. et al., Activation of apoptosis in vivo by a hydrocarbon-stapled BH3 helix, Science, 305(5689):1466-70 (2004).
U.S. Appl. No. 17/751,451, filed May 23, 2023, Verdine et al.
U.S. Appl. No. 17/912,029, filed Sep. 15, 2022, Tremblay et al.
U.S. Appl. No. 18/017,024, filed Jan. 19, 2023, White et al.
U.S. Appl. No. 18/017,033, filed Jan. 19, 2023, Tremblay et al.
Chen, Q. et al., Optimization of PROTAC Ternary Complex Using DNA Encoded Library Approach, ACS Chem. Biol., 18:25-33 (2023).
Li, K. et al., De novo mapping of α-helix recognition sites on protein surfaces using unbiased libraries, Proc. National Acad. Sci., 119(e2210435119):1-11 (2022).
Mason, J. W. et al., DNA-encoded library (DEL)-enabled discovery of proximity-inducing small molecules, Biorxiv, 1-29 (2022).
Mcgee, J.H. et al., Exceptionally high-affinity Ras binders that remodel its effector domain, J. Biol. Chem., 293(9):3265-3280 (2018).
Mund, T. et al., Peptide and small molecule inhibitors of HECT-type ubiquitin ligases, Proc. National Acad. Sci., 111(47):16736-16741 (2014).
U.S. Appl. No. 18/345,550, filed Jun. 30, 2023, Verdine et al.
U.S. Appl. No. 18/453,118, filed Aug. 21, 2023, Verdine et al.
U.S. Appl. No. 18/497,597, filed Oct. 30, 2023, Tokareva et al.
U.S. Appl. No. 18/568,212, filed Dec. 7, 2023, White et al.
Armstrong, A., Introducing Fierce Biotech's 2023 Fierce 15, Fierce Biotech, 25 pages, posted Aug. 28, 2023, <https://www.fiercebiotech.com/special-reports/introducing-fierce-15-2023>.
U.S. Appl. No. 18/427,677, filed Jan. 30, 2024, Tokareva et al.

* cited by examiner

| Linker ID | ① | ② | ③ | ④ | ⑤ | ⑥ | ⑦ | ⑧ | ⑨ |
|---|---|---|---|---|---|---|---|---|---|
| i,i+7 binder | 2.9 | >50 | 25.4 | 8.7 | 14.6 | 5.3 | 0.6 | 16.3 | 10.5 |
| i,i+7 non-binder | >50 | >50 | >50 | >50 | >50 | >50 | >50 | >50 | >50 |
| i,i+4 binder | >50 | 3.1 | 7.1 | 10.1 | 8.6 | 5.6 | 7.8 | 28.7 | 2.4 |
| i,i+4 non-binder | >50 | >50 | >50 | >50 | >50 | >50 | >50 | >50 | >50 |

FIGURE 10

E

| full.seq | IC50 | . | X1 | X2 | X3 | X4 | X5 | X6 | X7 | X8 | X9 | X10 | X11 |
|---|---|---|---|---|---|---|---|---|---|---|---|---|---|
| DPAADDCILAAHLCYIWGGS | 15 | | A | D | D | C | I | L | A | A | H | L | C |
| DPADEDCMLAAHICFMEGGS | 26 | | D | E | D | C | M | L | A | A | H | I | C |
| DPAHDYCILAAHVCRWDGGS | 29 | | H | D | Y | C | I | L | A | A | H | V | C |
| DPAYEECILAAHICQTWGGS | 29 | | Y | E | E | C | I | L | A | A | H | I | C |
| DPATDECFLAAHLCWWEGGS | 36 | | T | D | E | C | F | L | A | A | H | L | C |
| DPADASCILAAHECDWDGGS | 42 | | D | A | S | C | I | L | A | A | H | E | C |
| DPAQADCILAAHMCRIIGGS | 43 | | Q | A | D | C | I | L | A | A | H | M | C |
| DPALADCILAAHMCQLWGGS | 49 | | L | A | D | C | I | L | A | A | H | M | C |
| DPASQDCILAAHWCRIDGGS | 50 | | S | Q | D | C | I | L | A | A | H | W | C |
| DPAESDCILAAYLCSWEGGS | 51 | | E | S | D | C | I | L | A | A | Y | L | C |
| DPAEAMCDLAAHICNWDGGS | 53 | | E | A | M | C | D | L | A | A | H | I | C |
| DPAMDECILAAHMCRHIGGS | 60 | | M | D | E | C | I | L | A | A | H | M | C |
| DPASDECILAAHMCSVRGGS | 69 | | S | D | E | C | I | L | A | A | H | M | C |
| DPAEAQCTLAAHVCRLEGGS | 77 | | E | A | Q | C | T | L | A | A | H | V | C |
| DPAEAECQMAAHICALWGGS | 90 | | E | A | E | C | Q | M | A | A | H | I | C |

FIGURE 13 (Continued)

| X12 | X13 | X14 | 0 | 0(2) | 0(3) | 0(4) | 0(5) | 0(6) | 10 | 30 | 100 | 300 | 1000 | 1000(2) |
|---|---|---|---|---|---|---|---|---|---|---|---|---|---|---|
| Y | I | W | 1 | 4 | 1 | 1 | 1 | 0 | 203 | 416 | 561 | 493 | 423 | 412 |
| F | M | E | 1 | 0 | 0 | 0 | 0 | 0 | 1 | 24 | 8 | 14 | 39 | 45 |
| R | W | D | 1 | 0 | 0 | 0 | 0 | 0 | 1 | 30 | 58 | 50 | 26 | 56 |
| Q | T | W | 0 | 1 | 1 | 0 | 0 | 0 | 11 | 76 | 122 | 148 | 96 | 97 |
| W | W | E | 0 | 0 | 0 | 0 | 0 | 0 | 2 | 24 | 59 | 59 | 31 | 59 |
| D | W | D | 2 | 0 | 0 | 0 | 0 | 1 | 7 | 41 | 94 | 110 | 74 | 93 |
| R | I | I | 4 | 0 | 0 | 0 | 0 | 0 | 9 | 53 | 185 | 184 | 148 | 145 |
| Q | L | W | 1 | 1 | 0 | 0 | 0 | 0 | 1 | 23 | 59 | 65 | 100 | 56 |
| R | W | D | 1 | 0 | 0 | 2 | 0 | 0 | 0 | 4 | 18 | 19 | 17 | 19 |
| S | W | E | 1 | 0 | 0 | 1 | 0 | 1 | 4 | 12 | 50 | 58 | 26 | 45 |
| N | H | D | 0 | 1 | 1 | 0 | 1 | 0 | 10 | 15 | 48 | 61 | 26 | 67 |
| R | H | I | 2 | 1 | 0 | 0 | 1 | 0 | 1 | 8 | 34 | 36 | 35 | 59 |
| S | V | R | 0 | 0 | 0 | 0 | 0 | 0 | 2 | 7 | 26 | 33 | 31 | 52 |
| R | L | E | 0 | 0 | 0 | 0 | 1 | 0 | 1 | 13 | 27 | 44 | 61 | 37 |
| A | L | W | 0 | 0 | 0 | 0 | 0 | 0 | 0 | 6 | 19 | 26 | 22 | 56 |

FIGURE 13 (Continued)

| full.seq | IC50 | X1 | X2 | X3 | X4 | X5 | X6 | X7 | X8 | X9 | X10 |
|---|---|---|---|---|---|---|---|---|---|---|---|
| DPAQDICDWAAIHCDLVGGS | 45 | Q | D | I | C | D | W | A | A | I | H |
| DPATYFCEWAALHCELNGGS | 48 | T | Y | F | C | E | W | A | A | L | H |
| DPATEECFWAAFHCEFLGGS | 49 | T | E | E | C | F | W | A | A | F | H |
| DPAWDHCEIAALHCQLNGGS | 49 | W | D | H | C | E | I | A | A | L | H |
| DPADADCQWAALHCELIGGS | 50 | D | A | D | C | Q | W | A | A | L | H |
| DPATHRCEWAALHCELVGGS | 50 | T | H | R | C | E | W | A | A | L | H |
| DPAQDFCFWAAEHCELLGGS | 54 | Q | D | F | C | F | W | A | A | L | H |
| DPAAEICEFAALHCSLIGGS | 54 | A | E | I | C | E | F | A | A | L | H |
| DPADQTCMWAAEHCALVGGS | 58 | D | Q | T | C | M | W | A | A | E | H |
| DPAMATCEVAALHCELIGGS | 58 | M | A | T | C | E | V | A | A | L | H |
| DPAYWECEWAAEHCSLTGGS | 59 | Y | W | E | C | E | W | A | A | E | H |
| DPAYITCEWAAEHCDLIGGS | 60 | Y | I | T | C | E | W | A | A | L | H |
| DPADEYCMWAAFHCDFVGGS | 63 | D | E | Y | C | M | W | A | A | F | H |
| DPATRRCEIAALHCELIGGS | 93 | T | R | R | C | E | I | A | A | L | H |
| DPADEHCEMAALHCALIGGS | 101 | D | E | H | C | E | M | A | A | L | H |

FIGURE 14 (Continued)

| X11 | X12 | X13 | X14 | 0 | 0(2) | 20 | 20(2) | 200 | 200(2) | 2000 | 2000(2) |
|---|---|---|---|---|---|---|---|---|---|---|---|
| C | D | L | V | 1 | 0 | 13 | 10 | 64 | 34 | 41 | 45 |
| C | E | L | N | 10 | 0 | 16 | 17 | 71 | 98 | 36 | 75 |
| C | E | F | L | 0 | 0 | 31 | 9 | 80 | 97 | 56 | 90 |
| C | Q | L | N | 0 | 0 | 24 | 25 | 131 | 137 | 118 | 98 |
| C | E | L | I | 0 | 0 | 6 | 6 | 37 | 31 | 41 | 23 |
| C | E | L | V | 0 | 0 | 30 | 13 | 145 | 91 | 36 | 83 |
| C | E | L | L | 1 | 2 | 17 | 27 | 188 | 140 | 62 | 128 |
| C | E | L | I | 2 | 0 | 39 | 18 | 218 | 201 | 159 | 173 |
| C | S | L | V | 0 | 1 | 5 | 8 | 71 | 83 | 56 | 45 |
| C | A | L | I | 0 | 1 | 7 | 4 | 58 | 69 | 21 | 68 |
| C | E | L | T | 0 | 0 | 13 | 13 | 263 | 175 | 97 | 75 |
| C | S | L | T | 1 | 0 | 9 | 2 | 80 | 92 | 46 | 98 |
| C | D | L | V | 0 | 0 | 0 | 1 | 10 | 22 | 5 | 45 |
| C | D | F | L | 1 | 0 | 5 | 9 | 66 | 78 | 103 | 98 |
| C | E | L | L | 2 | 0 | 11 | 4 | 179 | 152 | 231 | 241 |

FIGURE 14 (Continued)

| fullseq | IC50 | X1 | X2 | X3 | X4 | X5 | X6 | X7 | X8 | X9 | X10 |
|---|---|---|---|---|---|---|---|---|---|---|---|
| DPAYWQCDHAALICEIEGGS | 33 | Y | W | Q | C | D | H | A | A | L | I |
| DPAFWDCEHAALICQADGGS | 36 | F | W | D | C | E | H | A | A | L | I |
| DPALWACEHAALICETQGGS | 41 | L | W | A | C | E | H | A | A | L | I |
| DPAAWDCEHAALICDLQGGS | 42 | A | W | D | C | E | H | A | A | L | L |
| DPADWDCVHAALICDLVGGS | 50 | D | W | D | C | V | H | A | A | L | I |
| DPADWDCFHAALICDSMGGS | 50 | D | W | D | C | F | H | A | A | L | L |
| DPAQWNCEHAALICETNGGS | 50 | Q | W | N | C | E | H | A | A | L | L |
| DPASWSCEHAALICDQWGGS | 51 | S | W | S | C | E | H | A | A | L | L |
| DPADWFCEHAALICSEIGGS | 51 | D | W | F | C | E | H | A | A | L | L |
| DPAVWDCVHAALICETEGGS | 53 | V | W | D | C | V | H | A | A | L | L |
| DPARWACEHAALICDMHGGS | 53 | R | W | A | C | E | H | A | A | L | L |
| DPATWECEHAALLCAQDGGS | 55 | T | W | E | C | E | H | A | A | L | L |
| DPAYWDCYHAAFICEEIGGS | 58 | Y | W | D | C | Y | H | A | A | F | I |
| DPASWRCLHAALICDSQGGS | 61 | S | W | R | C | L | H | A | A | L | I |
| DPANWMCEHAALMCEEYGGS | 62 | N | W | M | C | E | H | A | A | L | M |

FIGURE 15

Compound 2 >

| X11 | X12 | X13 | X14 | 0 | 0(2) | 20 | 20(2) | 200 | 200 (2) | 2000 | 2000 (2) |
|---|---|---|---|---|---|---|---|---|---|---|---|
| C | E | I | E | 0 | 0 | 112 | 98 | 322 | 266 | 156 | 188 |
| C | Q | A | D | 0 | 1 | 37 | 22 | 92 | 80 | 41 | 15 |
| C | E | T | Q | 1 | 0 | 69 | 43 | 223 | 169 | 113 | 98 |
| C | D | L | Q | 0 | 0 | 51 | 20 | 132 | 108 | 46 | 98 |
| C | D | L | V | 0 | 0 | 25 | 17 | 113 | 115 | 46 | 60 |
| C | D | S | M | 0 | 1 | 28 | 27 | 157 | 151 | 72 | 211 |
| C | E | T | N | 0 | 0 | 134 | 149 | 918 | 804 | 631 | 625 |
| C | D | Q | W | 1 | 1 | 15 | 8 | 77 | 54 | 26 | 98 |
| C | S | E | I | 0 | 1 | 28 | 16 | 98 | 166 | 67 | 105 |
| C | E | T | E | 0 | 0 | 11 | 6 | 61 | 63 | 36 | 38 |
| C | D | M | H | 0 | 0 | 3 | 6 | 37 | 31 | 26 | 38 |
| C | A | Q | D | 0 | 0 | 21 | 15 | 183 | 145 | 97 | 166 |
| C | E | E | I | 1 | 0 | 26 | 20 | 167 | 103 | 133 | 158 |
| C | D | S | Q | 0 | 0 | 9 | 0 | 61 | 62 | 41 | 38 |
| C | E | E | Y | 0 | 2 | 7 | 1 | 84 | 72 | 51 | 83 |

FIGURE 15 (Continued)

SEQUENCE LISTING

<160> NUMBER OF SEQ ID NOS: 164

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Cys Ile Leu Asp Cys His Ile Gln Arg
1               5                   10

<210> SEQ ID NO 2
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 2

Ala Cys Ile Leu Asp Ala His Ile Cys Arg
1               5                   10

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (16)..(18)
<223> OTHER INFORMATION: Any amino acid

<400> SEQUENCE: 3

Ala Asp Pro Ala Xaa Xaa Xaa Cys Xaa Xaa Ala Ala Xaa Xaa Cys Xaa
1               5                   10                  15

Xaa Xaa

<210> SEQ ID NO 4
<211> LENGTH: 31
<212> TYPE: PRT
<213> ORGANISM: Homo sapiens

<400> SEQUENCE: 4

Pro Ser Lys Pro Asp Asn Pro Gly Glu Asp Ala Pro Ala Glu Asp Met
1               5                   10                  15

Ala Arg Tyr Tyr Ser Ala Leu Gly His Tyr Ile Asn Leu Ile Thr
                20                  25                  30

<210> SEQ ID NO 5
<211> LENGTH: 31
<212> TYPE: PRT
<213> ORGANISM: Ictalurus punctatus

<400> SEQUENCE: 5

Pro Ser Lys Pro Glu Asn Pro Gly Glu Asp Ala Ala Pro Glu Glu Leu
1               5                   10                  15

Ala Lys Tyr Tyr Thr Ala Leu Arg His Tyr Ile Asn Leu Ile Thr
                20                  25                  30

<210> SEQ ID NO 6
<211> LENGTH: 31
<212> TYPE: PRT
<213> ORGANISM: Marmota marmota

<400> SEQUENCE: 6

Pro Leu Glu Pro Val Tyr Pro Gly Asp Asn Ala Thr Pro Glu Gln Met
1               5                   10                  15
```

Ala Gln Tyr Ala Ala Glu Leu Arg Arg Tyr Ile Asn Met Leu Thr
            20                  25                  30

<210> SEQ ID NO 7
<211> LENGTH: 31
<212> TYPE: PRT
<213> ORGANISM: Myotis lucifugus

<400> SEQUENCE: 7

Pro Ser Lys Pro Glu Lys Pro Gly Glu Asn Ala Ser Ala Glu Leu
1               5                   10                  15

Ala Arg Tyr Tyr Ser Ala Leu Arg His Tyr Ile Asn Leu Ile Thr
            20                  25                  30

<210> SEQ ID NO 8
<211> LENGTH: 31
<212> TYPE: PRT
<213> ORGANISM: Betta splendens

<400> SEQUENCE: 8

Pro Pro Lys Pro Glu Asn Pro Gly Glu Asp Ala Pro Pro Glu Leu
1               5                   10                  15

Ala Lys Tyr Tyr Thr Ala Leu Arg His Tyr Ile Asn Leu Ile Thr
            20                  25                  30

<210> SEQ ID NO 9
<211> LENGTH: 31
<212> TYPE: PRT
<213> ORGANISM: Notechis scutatus

<400> SEQUENCE: 9

Pro Pro Lys Pro Glu Ser Pro Gly Glu Asn Ala Ser Pro Glu Met
1               5                   10                  15

Ala Lys Tyr Leu Ala Asp Leu Arg His Tyr Ile Asn Leu Val Thr
            20                  25                  30

<210> SEQ ID NO 10
<211> LENGTH: 31
<212> TYPE: PRT
<213> ORGANISM: Orcinus orca

<400> SEQUENCE: 10

Pro Ala Lys Pro Glu Ala Pro Gly Ser His Ala Ser Pro Glu Leu
1               5                   10                  15

Lys Arg Tyr Tyr Leu Ser Leu Arg His Phe Leu Asn Leu Val Thr
            20                  25                  30

<210> SEQ ID NO 11
<211> LENGTH: 31
<212> TYPE: PRT
<213> ORGANISM: Calypte anna

<400> SEQUENCE: 11

Pro Pro Lys Pro Glu Thr Pro Gly Asp Glu Ala Ser Pro Glu Val
1               5                   10                  15

Ala Lys Tyr Phe Ser Ala Leu Arg His Tyr Ile Asn Leu Val Thr
            20                  25                  30

<210> SEQ ID NO 12
<211> LENGTH: 31
<212> TYPE: PRT
<213> ORGANISM: Podarcis muralis -continued

```
<400> SEQUENCE: 12

Pro Gln Gln Pro Glu His Pro Gly Glu Asp Ala Ser Ala Glu Glu Met
1               5                   10                  15

Ala Arg Tyr Leu Ser Ala Leu Arg His Tyr Leu Asn Leu Val Thr
            20                  25                  30

<210> SEQ ID NO 13
<211> LENGTH: 31
<212> TYPE: PRT
<213> ORGANISM: Vombatus ursinus

<400> SEQUENCE: 13

Pro Ser Lys Pro Lys Pro Pro Ser Glu Asn Ala Ser Arg Glu Glu Leu
1               5                   10                  15

Ser Arg Tyr Tyr Ala Ala Leu Arg Gln Tyr Leu Asn Leu Val Thr
            20                  25                  30

<210> SEQ ID NO 14
<211> LENGTH: 31
<212> TYPE: PRT
<213> ORGANISM: Ornithorhynchus anatinus

<400> SEQUENCE: 14

Pro Val Lys Pro Gln Pro Pro Asp Asn Ala Thr Pro Glu Glu Leu
1               5                   10                  15

Ala Gln Tyr Phe Ala Ser Leu Arg His Tyr Leu Asn Leu Val Thr
            20                  25                  30

<210> SEQ ID NO 15
<211> LENGTH: 31
<212> TYPE: PRT
<213> ORGANISM: Otolemur garnettii

<400> SEQUENCE: 15

Pro Leu Glu Pro Val Tyr Pro Gly Glu Asn Ala Thr Pro Glu Gln Met
1               5                   10                  15

Ala Gln Tyr Ala Ala Glu Leu Arg Arg Tyr Ile Asn Met Leu Thr
            20                  25                  30

<210> SEQ ID NO 16
<211> LENGTH: 31
<212> TYPE: PRT
<213> ORGANISM: Gulo gulo

<400> SEQUENCE: 16

Pro Ser Lys Pro Asp Asn Pro Gly Glu Asp Ala Pro Ala Glu Asp Met
1               5                   10                  15

Ala Arg Tyr Tyr Ser Ala Leu Arg His Tyr Ile Asn Leu Ile Thr
            20                  25                  30

<210> SEQ ID NO 17
<211> LENGTH: 31
<212> TYPE: PRT
<213> ORGANISM: Crocodylus porosus

<400> SEQUENCE: 17

Pro Ser Lys Pro Asp Asn Pro Gly Glu Asp Ala Pro Ala Glu Asp Met
1               5                   10                  15

Ala Arg Tyr Tyr Ser Ala Leu Arg His Tyr Ile Asn Leu Ile Thr
            20                  25                  30
```

```
<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Gly Pro Ala Lys Pro Glu Ala Gly Glu Asp Ala Ser Pro
1               5                   10

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid

<400> SEQUENCE: 19

Xaa Xaa Xaa Xaa Xaa Cys Xaa Xaa Ala Ala Xaa Xaa Cys Xaa Xaa Xaa
1               5                   10                  15

Xaa Xaa

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(14)
<223> OTHER INFORMATION: Any amino acid
<220> FEATURE:
<221> NAME/KEY: MOD_RES
<222> LOCATION: (16)..(18)
<223> OTHER INFORMATION: Any amino acid

<400> SEQUENCE: 20

Ala Asp Pro Ala Xaa Xaa Xaa Cys Xaa Xaa Xaa Xaa Xaa Xaa Cys Xaa
1               5                   10                  15

Xaa Xaa

<210> SEQ ID NO 21
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid

<400> SEQUENCE: 21

Ala Asp Pro Ala Xaa Xaa Xaa Cys Xaa Xaa Xaa Cys Xaa Xaa Xaa
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (10)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid

<400> SEQUENCE: 22

Pro Xaa Xaa Xaa Cys Xaa Xaa Ala Ala Xaa Xaa Cys Xaa Xaa Xaa
1               5                   10                  15

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccctcatagt tagcgtaacg                                            20

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Asp Pro Ala Ser Val Tyr Cys Glu Met Val Cys Trp Thr Phe
1               5                   10                  15

<210> SEQ ID NO 25
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Asp Pro Ala Leu His Ser Cys His Trp Met Cys Ala Trp Gln
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Asp Pro Ala Phe Met Gln Cys His Asn Thr Cys Tyr Thr Thr
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Asp Pro Ala Trp Glu Ile Cys Glu Val Asn Cys Phe Gln Ser
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Asp Pro Ala Arg Met Ala Cys Gln Phe Val Cys Glu Val Phe
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Asp Pro Ala Thr Trp Ser Cys Glu Ser Met Cys Trp Tyr Glu
1               5                   10                  15

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30
```

Ala Asp Pro Ala Gln Ile Phe Cys Asp Met Ala Ala Arg Cys Met
1               5                   10                  15

Glu Ile

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Asp Pro Ala Met Gln Thr Cys Thr Asn Ala Ala Leu Leu Cys Gln
1               5                   10                  15

Gln Gln

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Asp Pro Ala Glu Phe Val Cys Met Asp Ala Ala Asp Thr Cys Asp
1               5                   10                  15

Met Glu

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Asp Pro Ala Asn Leu Ile Cys Trp Asp Ala Ala Val Ala Cys Tyr
1               5                   10                  15

Trp Ile

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Asp Pro Ala Arg His Phe Cys Gln Leu Ala Ala His Leu Cys Gln
1               5                   10                  15

Trp Tyr

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Ala Asp Pro Ala Ser Tyr Ala Cys Val Arg Ala Ala Phe Ser Cys Asp
1               5                   10                  15

Tyr Ile
```

<210> SEQ ID NO 36
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (26)..(27)
<223> OTHER INFORMATION: Any amino acid
<220> FEATURE:
<221> NAME/KEY: MOD_RES
<222> LOCATION: (30)..(31)
<223> OTHER INFORMATION: Any amino acid

<400> SEQUENCE: 36

```
Ala Gly Pro Ala Lys Pro Glu Ala Pro Gly Glu Asp Ala Ser Pro Xaa
1               5                   10                  15

Glu Leu Xaa Xaa Tyr Tyr Xaa Xaa Leu Xaa Xaa Tyr Leu Xaa Xaa Val
            20                  25                  30

Ala
```

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (19)..(20)
<223> OTHER INFORMATION: Any amino acid
<220> FEATURE:
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (26)..(27)
<223> OTHER INFORMATION: Any amino acid
<220> FEATURE:
<221> NAME/KEY: MOD_RES
<222> LOCATION: (30)..(31)
<223> OTHER INFORMATION: Any amino acid

<400> SEQUENCE: 37

```
Ala Gly Pro Ala Lys Pro Glu Ala Pro Gly Glu Asp Ala Ser Pro Xaa
1               5                   10                  15
```

```
Glu Leu Xaa Xaa Tyr Tyr Xaa Xaa Leu Xaa Xaa Tyr Leu Xaa Xaa Val
        20                  25                  30

Ala Gly Gly Ser
        35

<210> SEQ ID NO 38
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Gly Pro Ala Lys Pro Glu Ala Pro Gly Glu Asp Ala Ser Pro Thr
1               5                   10                  15

Glu Leu Arg Asn Tyr Tyr His Asn Leu Thr Met Tyr Leu His Met Val
            20                  25                  30

Ala Gly Gly Ser
        35

<210> SEQ ID NO 39
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala Gly Pro Ala Lys Pro Glu Ala Pro Gly Glu Asp Ala Ser Pro Trp
1               5                   10                  15

Glu Leu Gln Asn Tyr Tyr Leu Ser Leu Gln Asn Tyr Leu Tyr Ile Val
            20                  25                  30

Ala Gly Gly Ser
        35

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ala Gly Pro Ala Lys Pro Glu Ala Pro Gly Glu Asp Ala Ser Pro Met
1               5                   10                  15

Glu Leu Thr Arg Tyr Tyr Ser Gln Leu Met Glu Tyr Leu Ala Thr Val
            20                  25                  30

Ala Gly Gly Ser
        35

<210> SEQ ID NO 41
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ala Gly Pro Ala Lys Pro Glu Ala Pro Gly Glu Asp Ala Ser Pro Phe
1               5                   10                  15
```

```
Glu Leu His Met Tyr Tyr Gln Asn Leu Tyr Phe Tyr Leu Pro Ala Val
            20                  25                  30

Ala Gly Gly Ser
        35

<210> SEQ ID NO 42
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ala Gly Pro Ala Lys Pro Glu Ala Pro Gly Glu Asp Ala Ser Pro Phe
1               5                   10                  15

Glu Leu Gln Phe Tyr Tyr Asn Tyr Leu Ile Asp Tyr Leu Ala Asp Val
            20                  25                  30

Ala Gly Gly Ser
        35

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 43

His His His His His His
1               5

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 44

Arg Arg Trp Pro Arg Xaa Ile Leu Asp Xaa His Val Arg Arg Val Trp
1               5                   10                  15

Arg

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Asp Pro Ala Thr His Arg Cys Glu Trp Ala Ala Leu His Cys Glu
1               5                   10                  15
```

Leu Val

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Asp Pro Ala Leu Trp Ala Cys Glu His Ala Ala Leu Ile Cys Glu
1               5                   10                  15

Thr Gln

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Asp Pro Ala Tyr Glu Glu Cys Ile Leu Ala Ala His Ile Cys Gln
1               5                   10                  15

Thr Trp

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Asp Pro Ala Leu Ala Asp Cys Ile Leu Ala Ala His Met Cys Gln
1               5                   10                  15

Leu Trp

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Asp Pro Ala His Ala Glu Cys Val Leu Asp Tyr His Ile Cys Gln
1               5                   10                  15

Ile Trp

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Asp Pro Ala Gln Asp His Cys Ile Leu Asp Thr His Ile Cys Arg
1               5                   10                  15

Ile Trp

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Asp Pro Ala Glu Asp Glu Cys Ile Leu Asn Asn His Ile Cys Arg
1               5                   10                  15

Ile Trp

<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Asp Pro Ala Glu Asp Glu Cys Ile Leu Ala Ala His Met Cys Arg
1               5                   10                  15

Trp Trp

<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Asp Pro Ala Asp Glu Asp Cys Ile Leu Ala Ala His Ile Cys Gln
1               5                   10                  15

Trp Asp

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Asp Pro Ala Gln Trp His Cys Glu His Ala Ala Leu Ile Cys Glu
1               5                   10                  15

Leu Asp

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Asp Pro Ala Pro Trp Gln Cys Glu His Ala Ala Leu Leu Cys Glu

```
                1               5                  10                  15

Leu Glu

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Asp Pro Ala Asp Trp Glu Cys Glu His Ala Ala Leu Ile Cys Asp
1               5                  10                  15

Ala Met

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Asp Pro Ala Tyr Trp Leu Cys Glu His Ala Ala Leu Ile Cys Glu
1               5                  10                  15

Val Glu

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Asp Pro Ala Gln Trp Pro Cys Glu His Ala Ala Leu Leu Cys Glu
1               5                  10                  15

Ile Glu

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Pro Ala Lys Pro Glu Ala Pro Gly Glu Asp Ala Ser Pro Asp Glu
1               5                  10                  15

Leu His His Tyr Tyr Gln Asn Leu Glu Thr Tyr Leu Tyr Arg Val Ala
                20                  25                  30

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60
```

Gly Pro Ala Lys Pro Glu Ala Pro Gly Glu Asp Ala Ser Pro Asp Glu
1               5                   10                  15

Leu Ile His Tyr Tyr Asn Ser Leu Asp Glu Tyr Leu Tyr Glu Val Ala
            20                  25                  30

<210> SEQ ID NO 61
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gly Pro Ala Lys Pro Glu Ala Pro Gly Glu Asp Ala Ser Pro Asp Glu
1               5                   10                  15

Leu Tyr His Tyr Tyr Thr His Leu Glu Glu Tyr Leu Tyr Asp Val Ala
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gly Pro Ala Lys Pro Glu Ala Pro Gly Glu Asp Ala Ser Pro Asp Glu
1               5                   10                  15

Leu Met His Tyr Tyr Thr Ser Leu Glu Asp Tyr Leu Asp His Val Pro
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Pro Ala Lys Pro Glu Ala Pro Gly Glu Asp Ala Ser Pro Asp Glu
1               5                   10                  15

Leu Thr Tyr Tyr Tyr Asp Glu Leu Arg Asp Tyr Leu Tyr Ser Val Ala
            20                  25                  30

<210> SEQ ID NO 64
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gly Pro Ala Lys Pro Glu Ala Pro Gly Glu Asp Ala Ser Pro Asp Glu
1               5                   10                  15

Leu Ile Phe Tyr Tyr Asp His Leu Ser Arg Tyr Leu Thr Asp Val Ala
            20                  25                  30

<210> SEQ ID NO 65
<211> LENGTH: 32
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 65

Gly Pro Ala Lys Pro Glu Ala Pro Gly Glu Asp Ala Ser Pro Asp Glu
1               5                   10                  15

Leu Arg Met Tyr Tyr His Glu Leu Asp Asn Tyr Leu Asp Gln Val Ala
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gly Pro Ala Lys Pro Glu Ala Pro Gly Glu Asp Ala Ser Pro Asp Glu
1               5                   10                  15

Leu His Thr Tyr Tyr Asp Thr Leu Tyr His Tyr Leu Thr Ser Val Ala
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gly Pro Ala Lys Pro Glu Ala Pro Gly Glu Asp Ala Ser Pro Asp Glu
1               5                   10                  15

Leu Tyr Tyr Tyr Tyr Asp Asp Leu Arg Gln Tyr Leu Ser Thr Val Ala
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gly Pro Ala Lys Pro Glu Ala Pro Gly Glu Asp Ala Ser Pro Thr Glu
1               5                   10                  15

Leu Tyr Tyr Tyr Tyr Asp His Leu Thr Asp Tyr Leu Asp Val Val Pro
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Pro Ala Lys Pro Glu Ala Pro Gly Glu Asp Ala Ser Pro Asn Glu
1               5                   10                  15

Leu Tyr Tyr Tyr Tyr Asp Glu Leu His Tyr Tyr Leu His Asp Val Ala
```

<210> SEQ ID NO 70
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gly Pro Ala Lys Pro Glu Ala Pro Gly Glu Asp Ala Ser Pro Gln Glu
1               5                   10                  15

Leu His Asp Tyr Tyr Glu Ile Leu Asp Asn Tyr Leu Asp Trp Val Ala
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Pro Ala Lys Pro Glu Ala Pro Gly Glu Asp Ala Ser Pro Asn Glu
1               5                   10                  15

Leu His Tyr Tyr Tyr Trp Glu Leu Asp Ser Tyr Leu Glu Asn Val Ala
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gly Pro Ala Lys Pro Glu Ala Pro Gly Glu Asp Ala Ser Pro Glu Glu
1               5                   10                  15

Leu Tyr His Tyr Tyr Trp Asp Leu Asp Asp Tyr Leu Asp Arg Val Ala
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gly Pro Ala Lys Pro Glu Ala Pro Gly Glu Asp Ala Ser Pro Ile Glu
1               5                   10                  15

Leu Trp Glu Tyr Tyr Glu Ser Leu Glu Thr Tyr Leu Asp Asn Val Ala
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 74

Gly Pro Ala Lys Pro Glu Ala Pro Gly Glu Asp Ala Ser Pro Leu Glu
1               5                   10                  15

Leu Asn Leu Tyr Tyr Leu Asp Leu His Asp Tyr Leu Gln Gln Val Ala
                20                  25                  30

<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Pro Ala Ala Asp Asp Cys Ile Leu Ala Ala His Leu Cys Tyr Ile
1               5                   10                  15

Trp Gly Gly Ser
            20

<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Pro Ala Asp Glu Asp Cys Met Leu Ala Ala His Ile Cys Phe Met
1               5                   10                  15

Glu Gly Gly Ser
            20

<210> SEQ ID NO 77
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asp Pro Ala His Asp Tyr Cys Ile Leu Ala Ala His Val Cys Arg Trp
1               5                   10                  15

Asp Gly Gly Ser
            20

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Pro Ala Tyr Glu Glu Cys Ile Leu Ala Ala His Ile Cys Gln Thr
1               5                   10                  15

Trp Gly Gly Ser
            20

<210> SEQ ID NO 79
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Pro Ala Thr Asp Glu Cys Phe Leu Ala Ala His Leu Cys Trp Trp
1               5                   10                  15

Glu Gly Gly Ser
            20

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Pro Ala Asp Ala Ser Cys Ile Leu Ala Ala His Glu Cys Asp Trp
1               5                   10                  15

Asp Gly Gly Ser
            20

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Pro Ala Gln Ala Asp Cys Ile Leu Ala Ala His Met Cys Arg Ile
1               5                   10                  15

Ile Gly Gly Ser
            20

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Pro Ala Leu Ala Asp Cys Ile Leu Ala Ala His Met Cys Gln Leu
1               5                   10                  15

Trp Gly Gly Ser
            20

<210> SEQ ID NO 83
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Pro Ala Ser Gln Asp Cys Ile Leu Ala Ala His Trp Cys Arg Ile
1               5                   10                  15
```

-continued

Asp Gly Gly Ser
            20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Pro Ala Glu Ser Asp Cys Ile Leu Ala Ala Tyr Leu Cys Ser Trp
1               5                   10                  15

Glu Gly Gly Ser
            20

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Pro Ala Glu Ala Met Cys Asp Leu Ala Ala His Ile Cys Asn Trp
1               5                   10                  15

Asp Gly Gly Ser
            20

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Pro Ala Met Asp Glu Cys Ile Leu Ala Ala His Met Cys Arg His
1               5                   10                  15

Ile Gly Gly Ser
            20

<210> SEQ ID NO 87
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Pro Ala Ser Asp Glu Cys Ile Leu Ala Ala His Met Cys Ser Val
1               5                   10                  15

Arg Gly Gly Ser
            20

<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 88

Asp Pro Ala Glu Ala Gln Cys Thr Leu Ala Ala His Val Cys Arg Leu
1               5                   10                  15

Glu Gly Gly Ser
            20

<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Pro Ala Glu Ala Glu Cys Gln Met Ala Ala His Ile Cys Ala Leu
1               5                   10                  15

Trp Gly Gly Ser
            20

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Asp Asp Cys Ile Leu Ala Ala His Leu Cys Tyr Ile Trp
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Glu Asp Cys Met Leu Ala Ala His Ile Cys Phe Met Glu
1               5                   10

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

His Asp Tyr Cys Ile Leu Ala Ala His Val Cys Arg Trp Asp
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93
```

Tyr Glu Glu Cys Ile Leu Ala Ala His Ile Cys Gln Thr Trp
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Asp Glu Cys Phe Leu Ala Ala His Leu Cys Trp Trp Glu
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Ala Ser Cys Ile Leu Ala Ala His Glu Cys Asp Trp Asp
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Ala Asp Cys Ile Leu Ala Ala His Met Cys Arg Ile Ile
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Ala Asp Cys Ile Leu Ala Ala His Met Cys Gln Leu Trp
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Gln Asp Cys Ile Leu Ala Ala His Trp Cys Arg Ile Asp
1               5                   10

<210> SEQ ID NO 99
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 99

Glu Ser Asp Cys Ile Leu Ala Ala Tyr Leu Cys Ser Trp Glu
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Glu Ala Met Cys Asp Leu Ala Ala His Ile Cys Asn Trp Asp
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Met Asp Glu Cys Ile Leu Ala Ala His Met Cys Arg His Ile
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Asp Glu Cys Ile Leu Ala Ala His Met Cys Ser Val Arg
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Glu Ala Gln Cys Thr Leu Ala Ala His Val Cys Arg Leu Glu
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Glu Ala Glu Cys Gln Met Ala Ala His Ile Cys Ala Leu Trp
1               5                   10

```
<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asp Pro Ala Gln Asp Ile Cys Asp Trp Ala Ala Ile His Cys Asp Leu
1               5                   10                  15

Val Gly Gly Ser
            20

<210> SEQ ID NO 106
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Pro Ala Thr Tyr Phe Cys Glu Trp Ala Ala Leu His Cys Glu Leu
1               5                   10                  15

Asn Gly Gly Ser
            20

<210> SEQ ID NO 107
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asp Pro Ala Thr Glu Glu Cys Phe Trp Ala Ala Phe His Cys Glu Phe
1               5                   10                  15

Leu Gly Gly Ser
            20

<210> SEQ ID NO 108
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Pro Ala Trp Asp His Cys Glu Ile Ala Ala Leu His Cys Gln Leu
1               5                   10                  15

Asn Gly Gly Ser
            20

<210> SEQ ID NO 109
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp Pro Ala Asp Ala Asp Cys Gln Trp Ala Ala Leu His Cys Glu Leu
```

Ile Gly Gly Ser
            20

<210> SEQ ID NO 110
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asp Pro Ala Thr His Arg Cys Glu Trp Ala Ala Leu His Cys Glu Leu
1               5                   10                  15

Val Gly Gly Ser
            20

<210> SEQ ID NO 111
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Pro Ala Gln Asp Phe Cys Phe Trp Ala Ala Glu His Cys Glu Leu
1               5                   10                  15

Leu Gly Gly Ser
            20

<210> SEQ ID NO 112
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp Pro Ala Ala Glu Ile Cys Glu Phe Ala Ala Leu His Cys Ser Leu
1               5                   10                  15

Ile Gly Gly Ser
            20

<210> SEQ ID NO 113
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Pro Ala Asp Gln Thr Cys Met Trp Ala Ala Glu His Cys Ala Leu
1               5                   10                  15

Val Gly Gly Ser
            20

<210> SEQ ID NO 114
<211> LENGTH: 20
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 114

Asp Pro Ala Met Ala Thr Cys Glu Val Ala Ala Leu His Cys Glu Leu
1               5                   10                  15

Ile Gly Gly Ser
            20

<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Pro Ala Tyr Trp Glu Cys Glu Trp Ala Ala Glu His Cys Ser Leu
1               5                   10                  15

Thr Gly Gly Ser
            20

<210> SEQ ID NO 116
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asp Pro Ala Tyr Ile Thr Cys Glu Trp Ala Ala Glu His Cys Asp Leu
1               5                   10                  15

Thr Gly Gly Ser
            20

<210> SEQ ID NO 117
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Pro Ala Asp Glu Tyr Cys Met Trp Ala Ala Phe His Cys Asp Phe
1               5                   10                  15

Val Gly Gly Ser
            20

<210> SEQ ID NO 118
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Pro Ala Thr Arg Arg Cys Glu Ile Ala Ala Leu His Cys Glu Leu
1               5                   10                  15

Leu Gly Gly Ser
            20
```

```
<210> SEQ ID NO 119
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asp Pro Ala Asp Glu His Cys Glu Met Ala Ala Leu His Cys Ala Leu
1               5                   10                  15

Ile Gly Gly Ser
            20

<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Asp Ile Cys Asp Trp Ala Ala Ile His Cys Asp Leu Val
1               5                   10

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Thr Tyr Phe Cys Glu Trp Ala Ala Leu His Cys Glu Leu Asn
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Thr Glu Glu Cys Phe Trp Ala Ala Phe His Cys Glu Phe Leu
1               5                   10

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Trp Asp His Cys Glu Ile Ala Ala Leu His Cys Gln Leu Asn
1               5                   10

<210> SEQ ID NO 124
<211> LENGTH: 14
<212> TYPE: PRT
<213> ORGANISM: Artificial Sequence
<220> FEATURE:
```

<223> OTHER INFORMATION: Description of Artificial Sequence: Synthetic
       peptide

<400> SEQUENCE: 124

Asp Ala Asp Cys Gln Trp Ala Ala Leu His Cys Glu Leu Ile
1               5                   10

<210> SEQ ID NO 125
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 125

Thr His Arg Cys Glu Trp Ala Ala Leu His Cys Glu Leu Val
1               5                   10

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 126

Gln Asp Phe Cys Phe Trp Ala Ala Glu His Cys Glu Leu Leu
1               5                   10

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 127

Ala Glu Ile Cys Glu Phe Ala Ala Leu His Cys Ser Leu Ile
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 128

Asp Gln Thr Cys Met Trp Ala Ala Glu His Cys Ala Leu Val
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 129

Met Ala Thr Cys Glu Val Ala Ala Leu His Cys Glu Leu Ile
1               5                   10

```
<210> SEQ ID NO 130
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Tyr Trp Glu Cys Glu Trp Ala Ala Glu His Cys Ser Leu Thr
1               5                   10

<210> SEQ ID NO 131
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Tyr Ile Thr Cys Glu Trp Ala Ala Glu His Cys Asp Leu Thr
1               5                   10

<210> SEQ ID NO 132
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Glu Tyr Cys Met Trp Ala Ala Phe His Cys Asp Phe Val
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Arg Arg Cys Glu Ile Ala Ala Leu His Cys Glu Leu Leu
1               5                   10

<210> SEQ ID NO 134
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Glu His Cys Glu Met Ala Ala Leu His Cys Ala Leu Ile
1               5                   10

<210> SEQ ID NO 135
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135
```

```
Asp Pro Ala Tyr Trp Gln Cys Asp His Ala Ala Leu Ile Cys Glu Ile
1               5                   10                  15

Glu Gly Gly Ser
            20

<210> SEQ ID NO 136
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Pro Ala Phe Trp Asp Cys Glu His Ala Ala Leu Ile Cys Gln Ala
1               5                   10                  15

Asp Gly Gly Ser
            20

<210> SEQ ID NO 137
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asp Pro Ala Leu Trp Ala Cys Glu His Ala Ala Leu Ile Cys Glu Thr
1               5                   10                  15

Gln Gly Gly Ser
            20

<210> SEQ ID NO 138
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asp Pro Ala Ala Trp Asp Cys Glu His Ala Ala Leu Leu Cys Asp Leu
1               5                   10                  15

Gln Gly Gly Ser
            20

<210> SEQ ID NO 139
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Pro Ala Asp Trp Asp Cys Val His Ala Ala Leu Ile Cys Asp Leu
1               5                   10                  15

Val Gly Gly Ser
            20

<210> SEQ ID NO 140
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 140

Asp Pro Ala Asp Trp Asp Cys Phe His Ala Ala Leu Ile Cys Asp Ser
1               5                   10                  15

Met Gly Gly Ser
            20

<210> SEQ ID NO 141
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Asp Pro Ala Gln Trp Asn Cys Glu His Ala Ala Leu Leu Cys Glu Thr
1               5                   10                  15

Asn Gly Gly Ser
            20

<210> SEQ ID NO 142
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Pro Ala Ser Trp Ser Cys Glu His Ala Ala Leu Ile Cys Asp Gln
1               5                   10                  15

Trp Gly Gly Ser
            20

<210> SEQ ID NO 143
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Pro Ala Asp Trp Phe Cys Glu His Ala Ala Leu Leu Cys Ser Glu
1               5                   10                  15

Ile Gly Gly Ser
            20

<210> SEQ ID NO 144
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Asp Pro Ala Val Trp Asp Cys Val His Ala Ala Leu Ile Cys Glu Thr
1               5                   10                  15

Glu Gly Gly Ser
```

<210> SEQ ID NO 145
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asp Pro Ala Arg Trp Ala Cys Glu His Ala Ala Leu Leu Cys Asp Met
1               5                   10                  15

His Gly Gly Ser
            20

<210> SEQ ID NO 146
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asp Pro Ala Thr Trp Glu Cys Glu His Ala Ala Leu Leu Cys Ala Gln
1               5                   10                  15

Asp Gly Gly Ser
            20

<210> SEQ ID NO 147
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asp Pro Ala Tyr Trp Asp Cys Tyr His Ala Ala Phe Ile Cys Glu Glu
1               5                   10                  15

Ile Gly Gly Ser
            20

<210> SEQ ID NO 148
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Asp Pro Ala Ser Trp Arg Cys Leu His Ala Ala Leu Ile Cys Asp Ser
1               5                   10                  15

Gln Gly Gly Ser
            20

<210> SEQ ID NO 149
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 149

Asp Pro Ala Asn Trp Met Cys Glu His Ala Ala Leu Met Cys Glu Glu
1               5                   10                  15

Tyr Gly Gly Ser
            20

<210> SEQ ID NO 150
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Tyr Trp Gln Cys Asp His Ala Ala Leu Ile Cys Glu Ile Glu
1               5                   10

<210> SEQ ID NO 151
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Phe Trp Asp Cys Glu His Ala Ala Leu Ile Cys Gln Ala Asp
1               5                   10

<210> SEQ ID NO 152
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Leu Trp Ala Cys Glu His Ala Ala Leu Ile Cys Glu Thr Gln
1               5                   10

<210> SEQ ID NO 153
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Trp Asp Cys Glu His Ala Ala Leu Leu Cys Asp Leu Gln
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Asp Trp Asp Cys Val His Ala Ala Leu Ile Cys Asp Leu Val
1               5                   10
```

```
<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Trp Asp Cys Phe His Ala Ala Leu Ile Cys Asp Ser Met
1               5                   10

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gln Trp Asn Cys Glu His Ala Ala Leu Leu Cys Glu Thr Asn
1               5                   10

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Trp Ser Cys Glu His Ala Ala Leu Ile Cys Asp Gln Trp
1               5                   10

<210> SEQ ID NO 158
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Asp Trp Phe Cys Glu His Ala Ala Leu Leu Cys Ser Glu Ile
1               5                   10

<210> SEQ ID NO 159
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Val Trp Asp Cys Val His Ala Ala Leu Ile Cys Glu Thr Glu
1               5                   10

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160
```

Arg Trp Ala Cys Glu His Ala Ala Leu Leu Cys Asp Met His
1               5                   10

<210> SEQ ID NO 161
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Thr Trp Glu Cys Glu His Ala Ala Leu Leu Cys Ala Gln Asp
1               5                   10

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Tyr Trp Asp Cys Tyr His Ala Ala Phe Ile Cys Glu Glu Ile
1               5                   10

<210> SEQ ID NO 163
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ser Trp Arg Cys Leu His Ala Ala Leu Ile Cys Asp Ser Gln
1               5                   10

<210> SEQ ID NO 164
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asn Trp Met Cys Glu His Ala Ala Leu Met Cys Glu Glu Tyr
1               5                   10

COLLECTIONS OF PEPTIDES, PEPTIDE AGENTS, AND METHODS OF USE THEREOF

CROSS-REFERENCE TO RELATED APPLICATIONS

This application is a National Stage Entry of International Application No. PCT/US19/47206, filed Aug. 20, 2019, which claims priority to U.S. Provisional Application No. 62/719,996, filed Aug. 20, 2018, the entirety of which is incorporated herein by reference.

SEQUENCE LISTING

The instant application contains a Sequence Listing which has been submitted electronically in ASCII format and is hereby incorporated by reference in its entirety. Said ASCII copy, created on Sep. 19, 2019, is named SL.txt and is 54,303 bytes in size.

BACKGROUND

Stapled peptides have been reported to have improved properties relative to peptides that lack staples, and can be useful for various biological purposes.

SUMMARY OF THE INVENTION

The present disclosure provides powerful technologies for the development, production, characterization, and/or use of stapled peptide compositions. Among other things, the present disclosure provides strategies for defining amino acid sequences particularly amenable or useful for stapling, as well as technologies, reagents, and systems for developing, producing, characterizing, and/or using stapled peptides having such amino acid sequences.

Existing stapling technologies have developed useful and potent stapled peptides, typically utilizing a known (and often naturally occurring) amino acid sequence. The present disclosure identifies the source of a problem with such technologies that are necessarily constrained to pre-selected amino acid sequences. Among other things, the present disclosure encompasses the recognition that certain cysteine stapling technologies can be implemented in biological systems (e.g., phage display systems) so that multiple peptide sequences can be queried, permitting high-throughput generation and analysis of stapled peptides, including in the absence of predetermined sequence selection or bias. Thus, for example, in some embodiments, the present disclosure permits development of stapled peptides (and collections thereof) that bind to a particular target but that have amino acid sequence(s) that differ from (and, in some embodiments, lack significant identity to) that of a naturally occurring protein interaction partner(s) for the target, and in some embodiments, to a target that have no known protein interaction partners at all. Provided technologies therefore permit identification of amino acid sequences that show desirable binding characteristic(s) with respect to a particular target, and in particular show desirable binding characteristic(s) when provided in a stapled form. The present disclosure thus provides peptide agents that bind to a target of interest, having an amino acid sequence identified, characterized, and/or produced as described herein; in some embodiments such peptide agents comprise stapled peptides.

As described herein, cysteine stapling strategies may be employed to facilitate production and/or characterization of stapled peptides in or by a biological system. In some embodiments, such production and/or characterization may comprise identification and/or selection of a useful amino acid sequence. Those skilled in the art, reading the present disclosure, will appreciate that, once such an amino acid sequence is identified and/or selected, a stapled peptide agent having such amino acid sequence may be prepared using any desired stapling technology.

In some embodiments, the present disclosure provides a collection of peptides (or nucleic acids that encode them) whose amino acid sequences show significant diversity relative to one another and/or to a reference naturally-occurring protein. In some embodiments, such stapled peptides are implemented in (e.g., expressed by and/or in) a biological system (e.g., a phage display library). In some embodiments, peptides of the collection share a common length. In some embodiments, peptides of the collection share one or more particular sequence elements (e.g., residues of identity, number and/or relative spacing of cysteine residues, etc.).

In some embodiments, the present disclosure provides a collection of peptides. In some embodiments, a collection of peptides is a collection of stapled peptides. In some embodiments, peptides within a collection as described herein may share one or more structural features (e.g. length within a particular range; presence of particular sequence elements such as, for example, a sequence element found in a known interaction partner for a target or interest, or a set of amino acids that together support formation of a staple [e.g., two or more cysteine residues, positioned relative to one another so that a cysteine staple as described herein is or may be produced between a pair of them], presence of one or more staples which may, in some embodiments, be of the same type, etc., or any combination thereof, and in some embodiments, a particular collection may be characterized and/or defined by such shared structural feature(s)). In some embodiments, a common structural feature of peptides in a collection of peptides as described herein is or at least two cysteine residues, positioned relative to one another so that a cysteine staple as described herein is or may be formed between a pair of them; in some embodiments, such peptides can be reacted with a compound of formula R-I, to produce a collection of cysteine stapled peptides.

In some embodiments, a provided peptide collection is a collection of stapled peptides, each of which independently has an amino acid sequence that:
  has a length within a range of a* and b*, where a* and b* are each integers independently selected from 2 through 100 and b* is greater than a*; and
  includes at least one pair of residues covalently linked with one another via a linker.

In some embodiments, a provided collection of peptides (or nucleic acids that encode them) is characterized in that peptides of the collection all include cysteine residues (e.g. a pair of cysteine residues), spaced relative to one another to permit cysteine stapling as described herein, but otherwise have independent amino acid sequences and, optionally, in that peptides of the collection all have the same length. In some such embodiments, the cysteine residues are located at corresponding positions in each of the peptides. In some embodiments, all positions other than the cysteine residues are degenerate within the collection (i.e., different peptides in the collection may have different residues at any given position); in some such embodiments, one or more positions is fully degenerate within the collection in that every utilized amino acid (e.g., every natural amino acid) is included at the position in at least one peptide in the collection. In some embodiments, each position other than the cysteines is fully degenerate across the collection. In some embodiments, one or more positions is biased across the collection in that a plurality of different amino acids, each of which is selected from a restricted set (i.e., fewer than all possible amino acid residues and, in some embodiments, fewer than all natural amino acids). In some embodiments, degeneracy and/or bias is introduced in one or more positions through genetic engineering and/or expression of selected nucleic acid sequences in a biological system. In some embodiments, degree of degeneracy or bias at one or more positions in peptides of a peptide collection or library as described here is informed and/or selected by prior assessment one or more binding characteristics of a related library or collection (e.g., with comparable cysteine residues), In some embodiments, such prior assessment is by high-throughput analysis (e.g., screening) of a collection or collections of cysteine stapled peptides against a target of interest and the use of high-throughput sequencing to decode the genotypes of a subset of the collection of peptides can inform the production of a biased library.

In some embodiments, the present disclosure provides technologies for identification, characterization, and/or production of stapled peptide agents that bind a target of interest. In some embodiments, provided technologies involve contacting a target of interest with a collection of peptides (e.g., a collection of stapled peptides; in some embodiments, peptides of the collection share one or more structural features), and determining one or more characteristics (e.g., on-rate, off-rate, affinity [e.g., at one or more concentrations], specificity, binding curve, etc.) of an interaction between individual peptide(s) and the target. In some embodiments, such determining involves comparison with an appropriate reference (e.g., a positive or negative control, such as a previously known or characterized interaction between the target and a known interactor, or between different interacting partners).

In some embodiments, a target of interest may be or comprise a naturally-occurring epitope (e.g., that is or comprises a polypeptide, a glycan, etc.). In some embodiments, a target of interest is one for which a naturally-occurring interaction partner is not known. In some embodiments, a target of interest is one for which a naturally-occurring interaction partner is known (and, e.g., there is a desire to identify an alternative interaction partner—for example that may compete with a known interaction partner—and/or there is a desire to identify an alternative format of a known interaction partner).

In some embodiments, provided technologies may provide and/or utilize a phage expression system in which candidate peptides (e.g., whose amino acid sequences include at least two cysteine residues positioned relative to one another so as to support cysteine stapling as described herein). are produced as fusion proteins with a phage coat (e.g., protein pIII).

In some embodiments, the present disclosure provides technologies for developing (e.g., identifying and/or characterizing), producing, and/or using stapled peptide agents that bind to a target of interest, optionally with one or more predetermined characteristics of binding. In some such embodiments, one or more cysteine stapled peptides designed, produced, and/or characterized (e.g., via analysis utilizing phage display as described herein) is modified to substitute a cysteine staple with a non-cysteine staple. That is, in some embodiments, cysteine stapling technologies are utilized to identify and/or characterize peptides (i.e., peptide amino acid sequences and/or other structures) amenable to stapling to produce a stable structure with one or more desired binding attributes. Such peptides can be re-formatted in accordance with the present invention into corresponding peptides in which the cysteine staple has been replaced by a non-cysteine staple (e.g., through, optionally among other things, substitution of the cysteine residues involved in the staple(s) with other residues amendable to alternative stapling technologies (e.g., hydrocarbon stapling, heteroatom stapling, etc.).

In some embodiments, technologies provided by the present disclosure relate to peptides (e.g., individual peptides and/or peptide collections) having the structure of formula I.

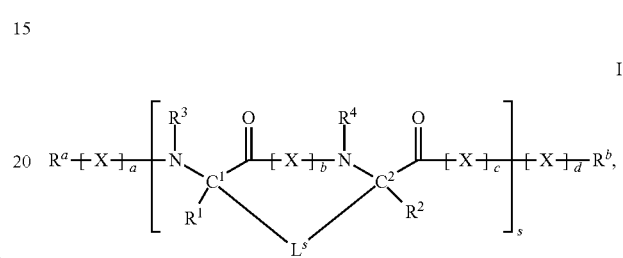

or a salt thereof, wherein:
each of $R^a$, $R^1$, $R^2$, $R^3$, and $R^4$ is independently R';
$R^b$ is R', —OR' or —N(R')$_2$;
each X is independently an amino acid residue;
each of a, b, c, s, and d is independently an integer 1-20 inclusive;
each of $C^1$ and $C^2$ is independently a carbon atom; $L^s$ is -$L^{s1}$-S-$L^{s2}$-S-$L^{s3}$-;
$L^{s1}$ and $L^{s3}$ are each independently L;
$L^{s2}$ is L and comprises at least one —C(O)—; and
each L is independently a covalent bond, or an optionally substituted, bivalent $C_1$-$C_{25}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
each R' is independently —R, —C(O)R, —CO$_2$R, or —SO$_2$R;
each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond; or two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, $R^a$ is R', wherein R' is as described in the present disclosure. In some embodiments, $R^a$ is —H. In some embodiments, $R^a$ is R—C(O)—.

In some embodiments, the present disclosure provides a collection of stapled peptides, wherein each of the stapled peptides independently has the structure of formula I or a salt thereof.

In some embodiments, a is 1. In some embodiments, a is 2. In some embodiments, a is 3. In some embodiments, a is 4. In some embodiments, a is 5. In some embodiments, a is 6. In some embodiments, a is 7. In some embodiments, a is 8. In some embodiments, a is 9. In some embodiments, a is 10. In some embodiments, a is 11. In some embodiments, a is 12. In some embodiments, a is 13. In some embodiments, a is 14. In some embodiments, a is 15. In some embodiments, a is 16. In some embodiments, a is 17. In some embodiments, a is 18. In some embodiments, a is 19. In some embodiments, a is 20.

In some embodiments, $R^1$ is R' as described in the present disclosure. In some embodiments, $R^1$ is R as described in the present disclosure. In some embodiments, $R^1$ is —H. In some embodiments, $R^1$ is not H.

In some embodiments, $R^2$ is R' as described in the present disclosure. In some embodiments, $R^2$ is R as described in the present disclosure. In some embodiments, $R^2$ is —H. In some embodiments, $R^2$ is not H.

In some embodiments, $R^3$ is R' as described in the present disclosure. In some embodiments, $R^3$ is R as described in the present disclosure. In some embodiments, $R^3$ is —H. In some embodiments, $R^3$ is not H.

In some embodiments, $R^4$ is R' as described in the present disclosure. In some embodiments, $R^4$ is R as described in the present disclosure. In some embodiments, $R^4$ is —H. In some embodiments, $R^4$ is not H.

In some embodiments, $C^1$ is achiral. In some embodiments, $C^1$ is chiral. In some embodiments, $C^1$ is (R). In some embodiments, $C^1$ is (S).

In some embodiments, $C^2$ is achiral. In some embodiments, $C^2$ is chiral. In some embodiments, $C^2$ is (R). In some embodiments, $C^2$ is (S).

In some embodiments, b is 2-11. In some embodiments, b is 2. In some embodiments, b is 3. In some embodiments, b is 4. In some embodiments, b is 5. In some embodiments, b is 6. In some embodiments, b is 7. In some embodiments, b is 8. In some embodiments, b is 9. In some embodiments, b is 10. In some embodiments, b is 11.

In some embodiments, c is 1. In some embodiments, c is 2. In some embodiments, c is 3. In some embodiments, c is 4. In some embodiments, c is 5. In some embodiments, c is 6. In some embodiments, c is 7. In some embodiments, c is 8. In some embodiments, c is 9. In some embodiments, c is 10. In some embodiments, c is 11. In some embodiments, c is 12. In some embodiments, c is 13. In some embodiments, c is 14. In some embodiments, c is 15. In some embodiments, c is 16. In some embodiments, c is 17. In some embodiments, c is 18. In some embodiments, c is 19. In some embodiments, c is 20.

In some embodiments, s is 1-5. In some embodiments, s is 1. In some embodiments, s is 2. In some embodiments, s is 3. In some embodiments, s is 4. In some embodiments, s is 5.

In some embodiments, d is 1. In some embodiments, d is 2. In some embodiments, d is 3. In some embodiments, d is 4. In some embodiments, d is 5. In some embodiments, d is 6. In some embodiments, d is 7. In some embodiments, d is 8. In some embodiments, d is 9. In some embodiments, d is 10. In some embodiments, d is 11. In some embodiments, d is 12. In some embodiments, d is 13. In some embodiments, d is 14. In some embodiments, d is 15. In some embodiments, d is 16. In some embodiments, d is 17. In some embodiments, d is 18. In some embodiments, d is 19. In some embodiments, d is 20.

In some embodiments, $R^b$ is R' as described in the present disclosure. In some embodiments, $R^b$ is R as described in the present disclosure. In some embodiments, $R^b$ is —H. In some embodiments, $R^b$ is —OR' wherein R' is as described in the present disclosure. In some embodiments, $R^b$ is —OH. In some embodiments, $R^b$ is —N(R')$_2$, wherein each R' is independently as described in the present disclosure. In some embodiments, $R^b$ is —NH(R'), wherein R' is independently as described in the present disclosure. In some embodiments, $R^b$ is —NH$_2$, wherein R' is independently as described in the present disclosure.

BRIEF DESCRIPTION OF THE DRAWING

FIG. 10. Summary of binding affinities of binding and non-binding derivatives of xStAx41 stapled at positions (i, i+4) or (i, i+7) with Linkers 1-9. Values are micromolar.

DETAILED DESCRIPTION OF CERTAIN EMBODIMENTS

Definitions

Figure 1:
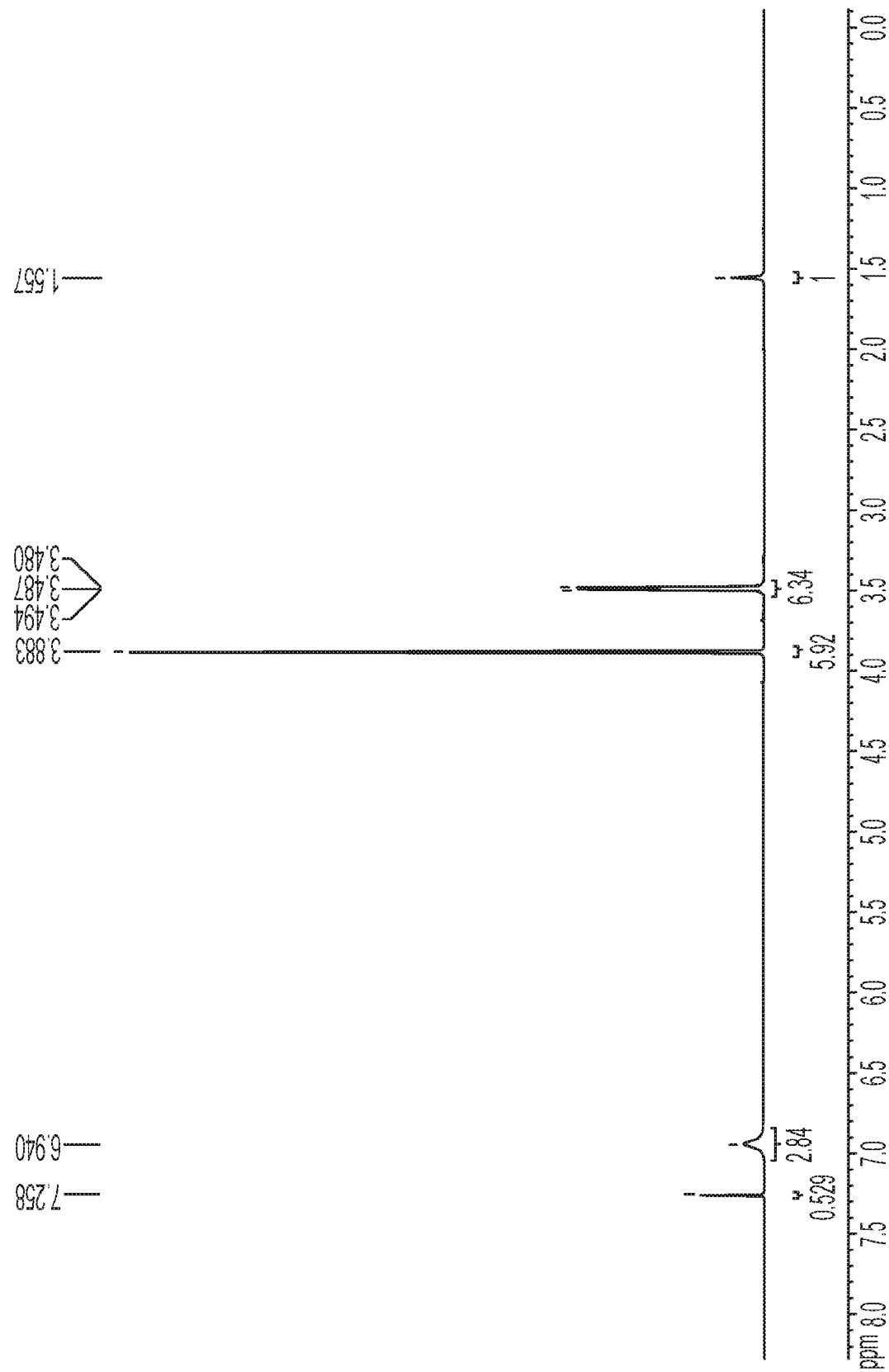
FIG. 1. $^1$H NMR spectrum for purified Linker 3 (see Example 1).
Figure 2:
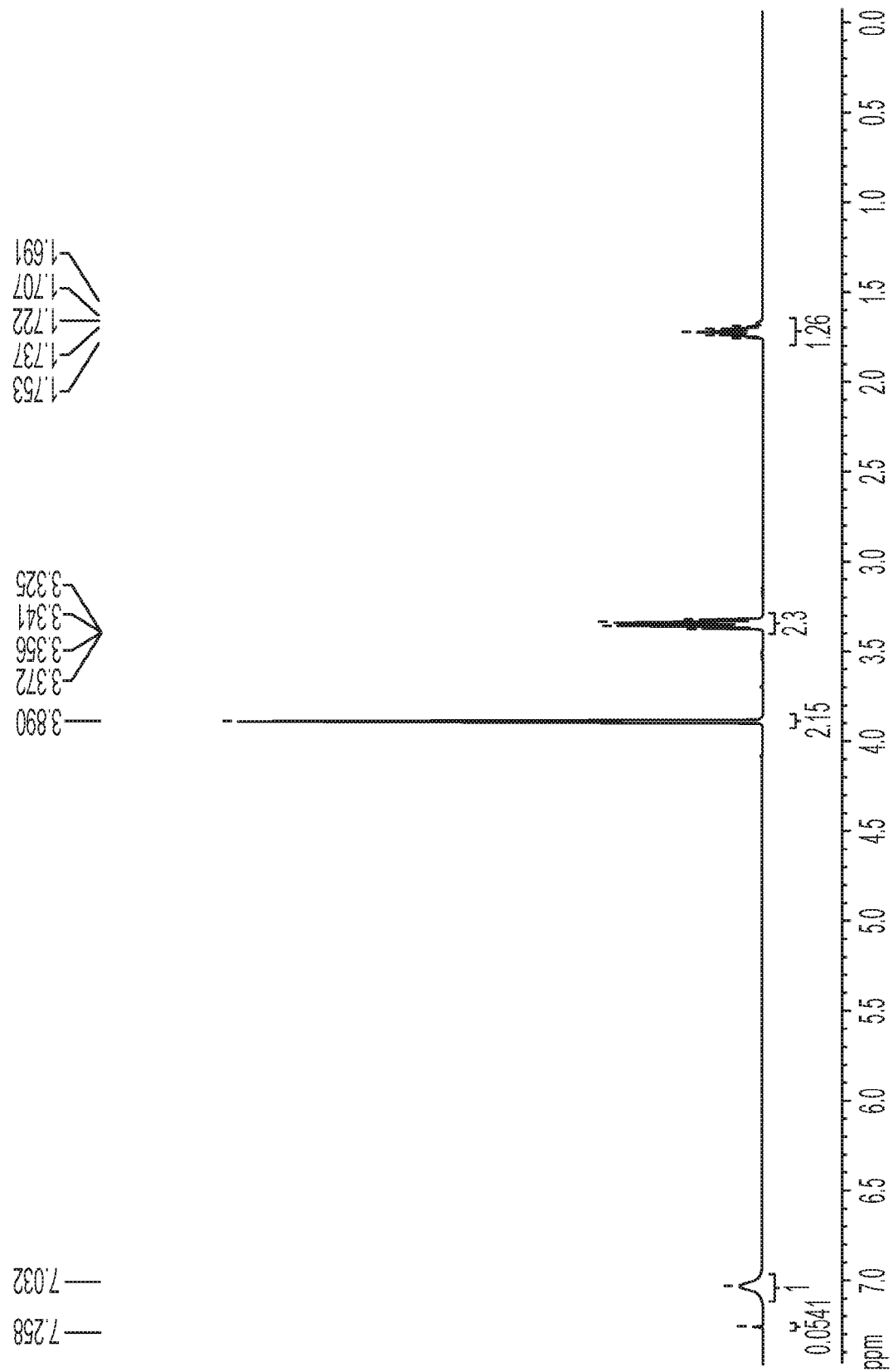
FIG. 2. $^1$H NMR spectrum for purified Linker 4 (see Example 1).
Figure 3:
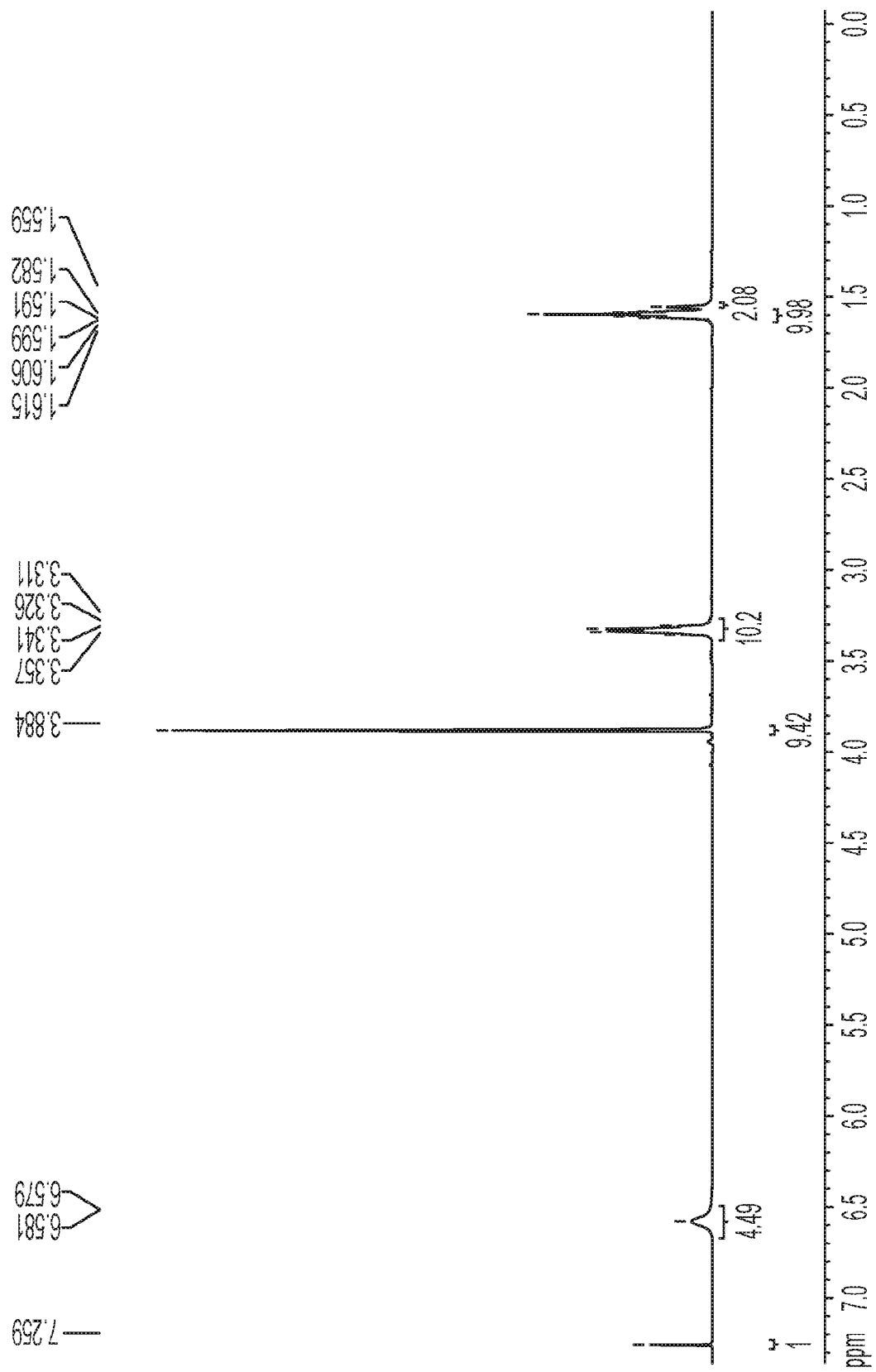
FIG. 3. $^1$H NMR spectrum for purified Linker 5 (see Example 1).
Figure 4:
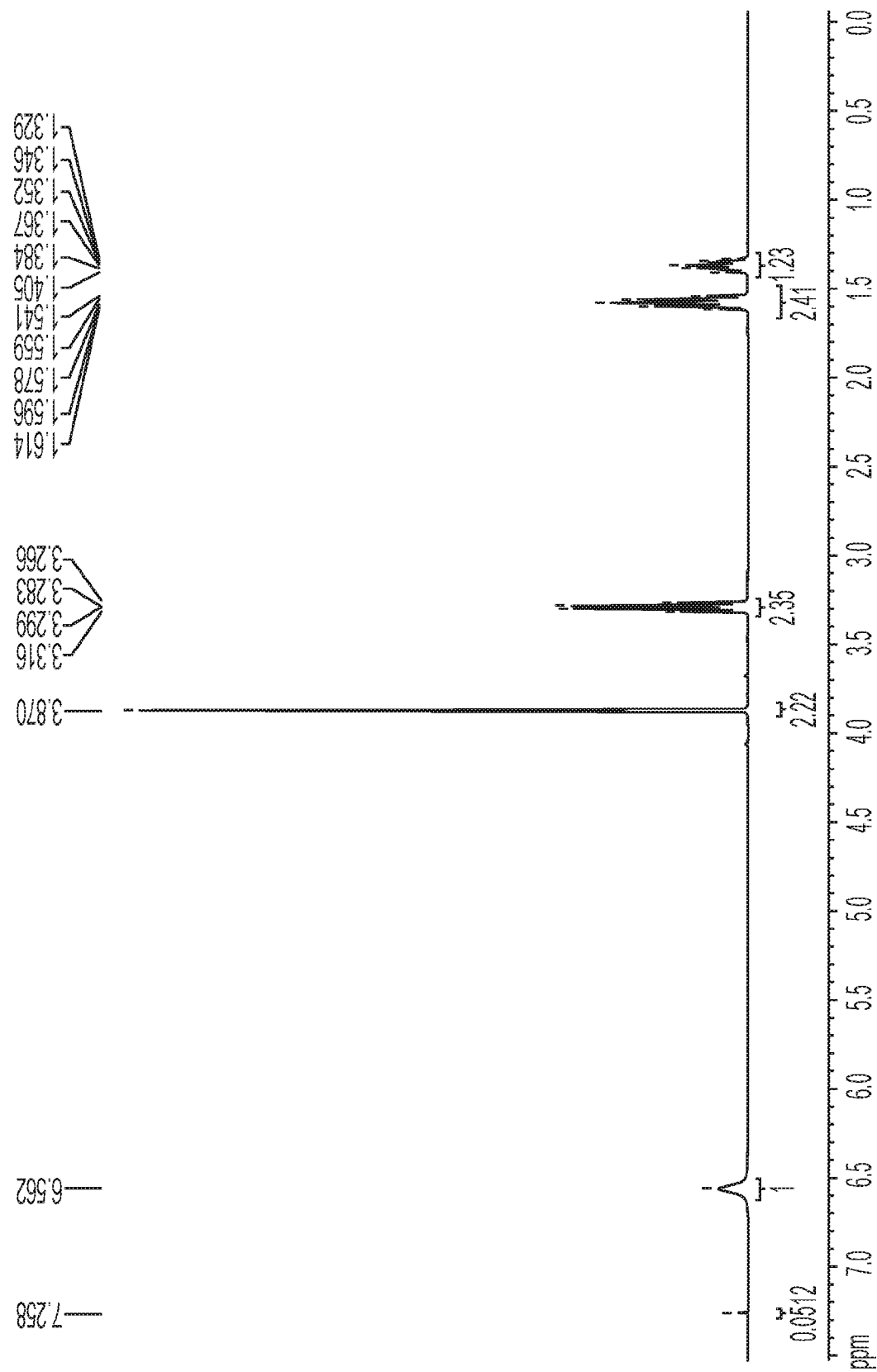
FIG. 4. $^1$H NMR spectrum for purified Linker 6 (see Example 1).
Figure 5:
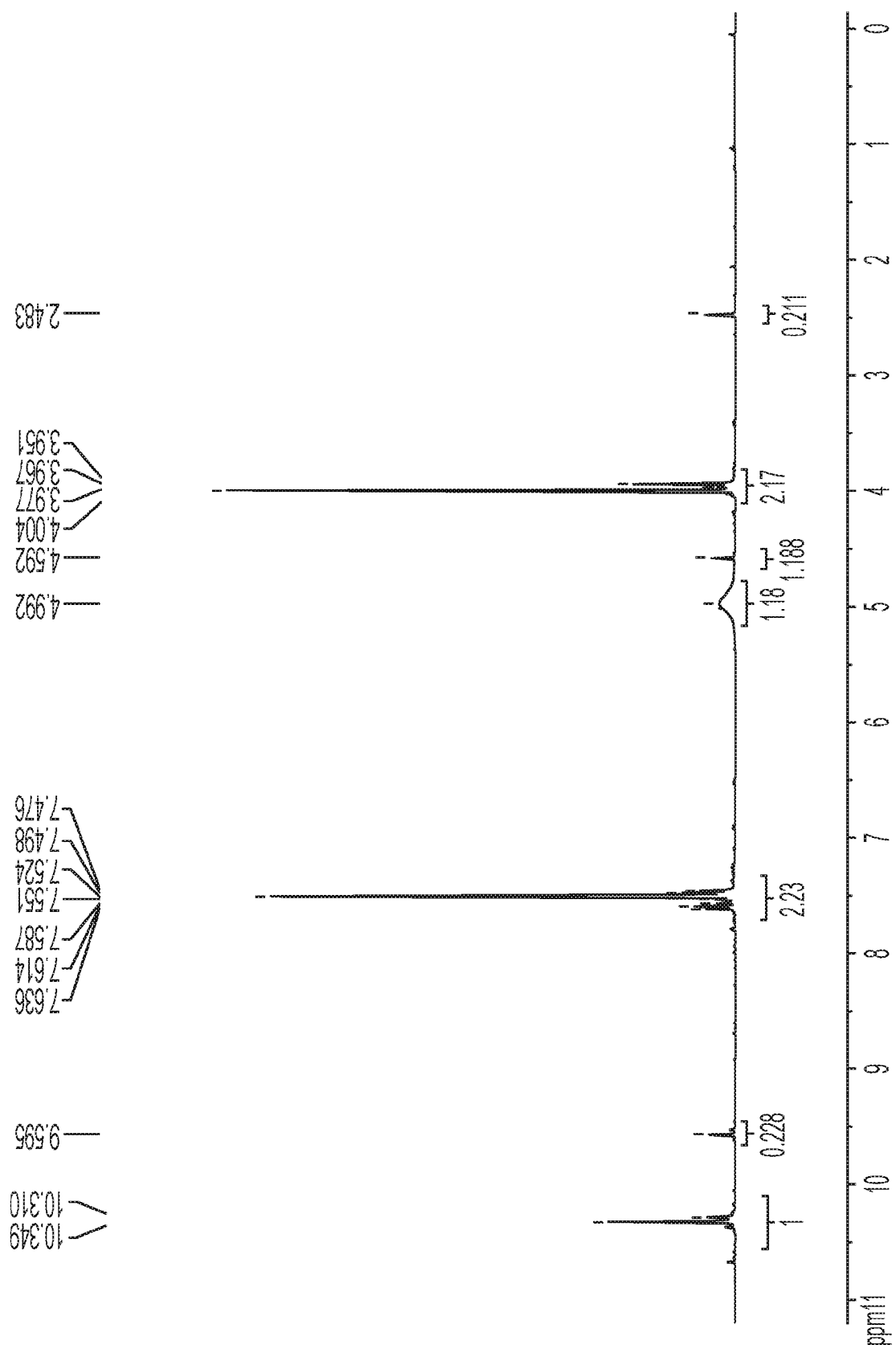
FIG. 5. $^1$H NMR spectrum for purified Linker 7 (see Example 1).
Figure 6:
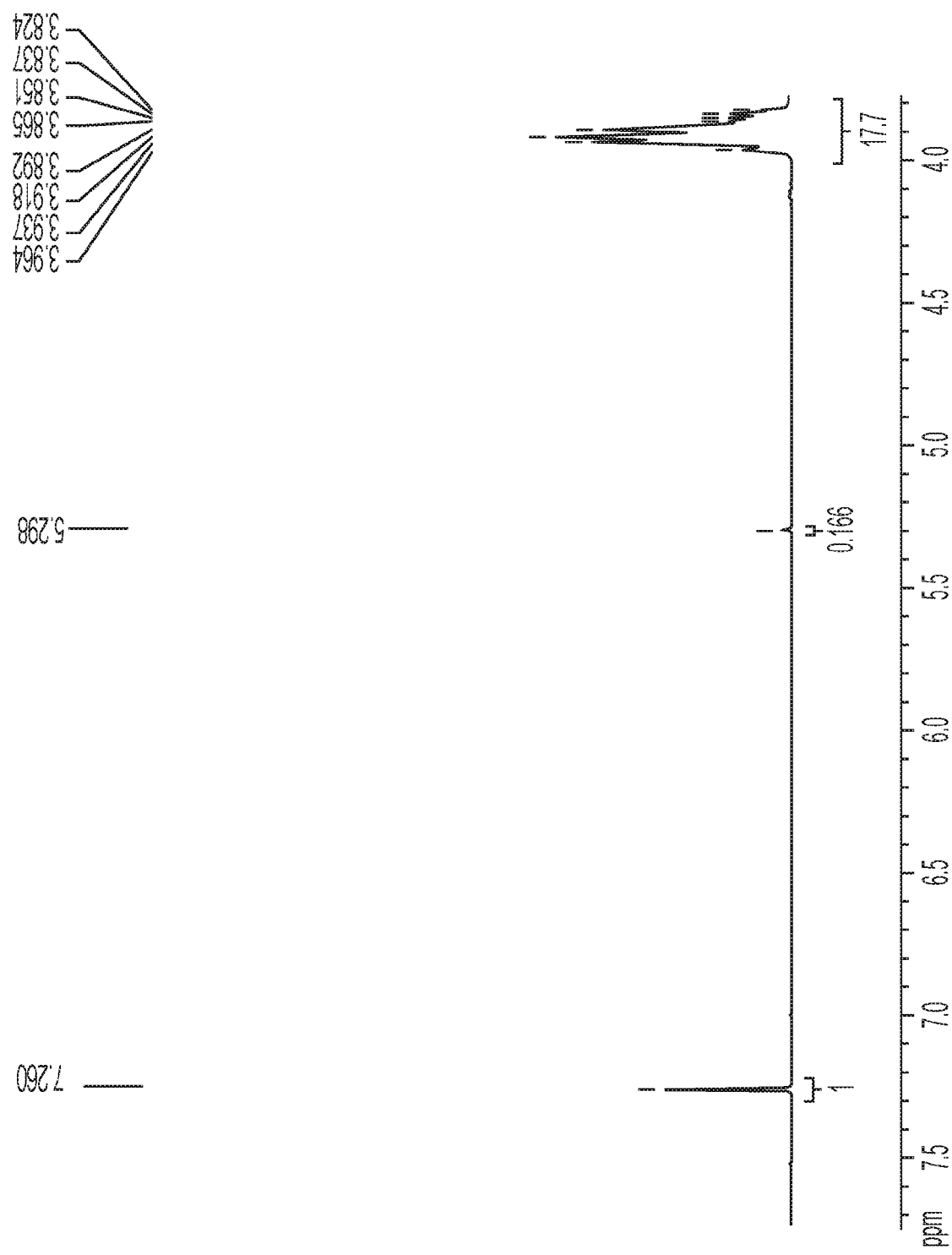
FIG. 6. $^1$H NMR spectrum for purified Linker 8 (see Example 1).
Figure 6:
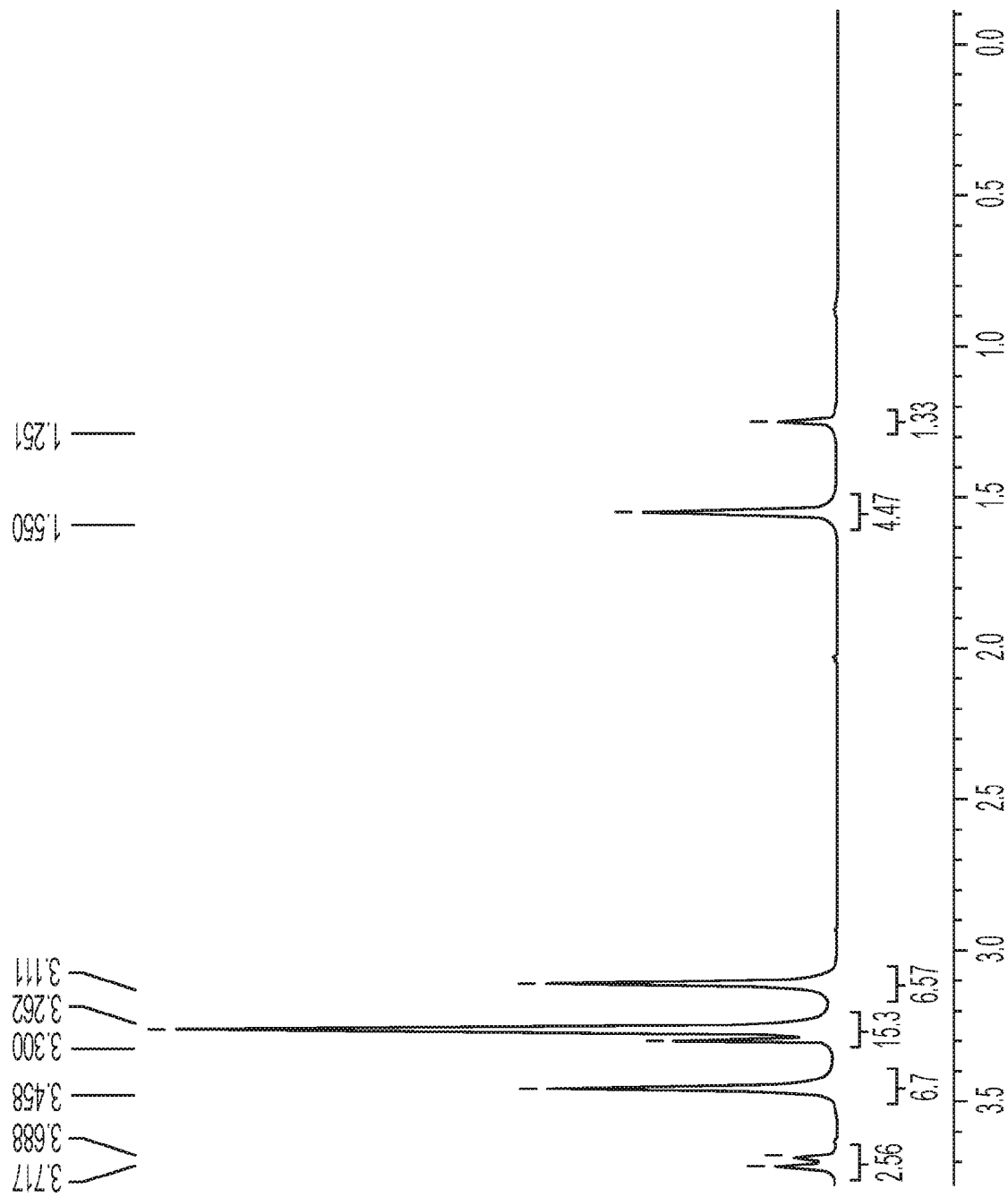
Figure 7:
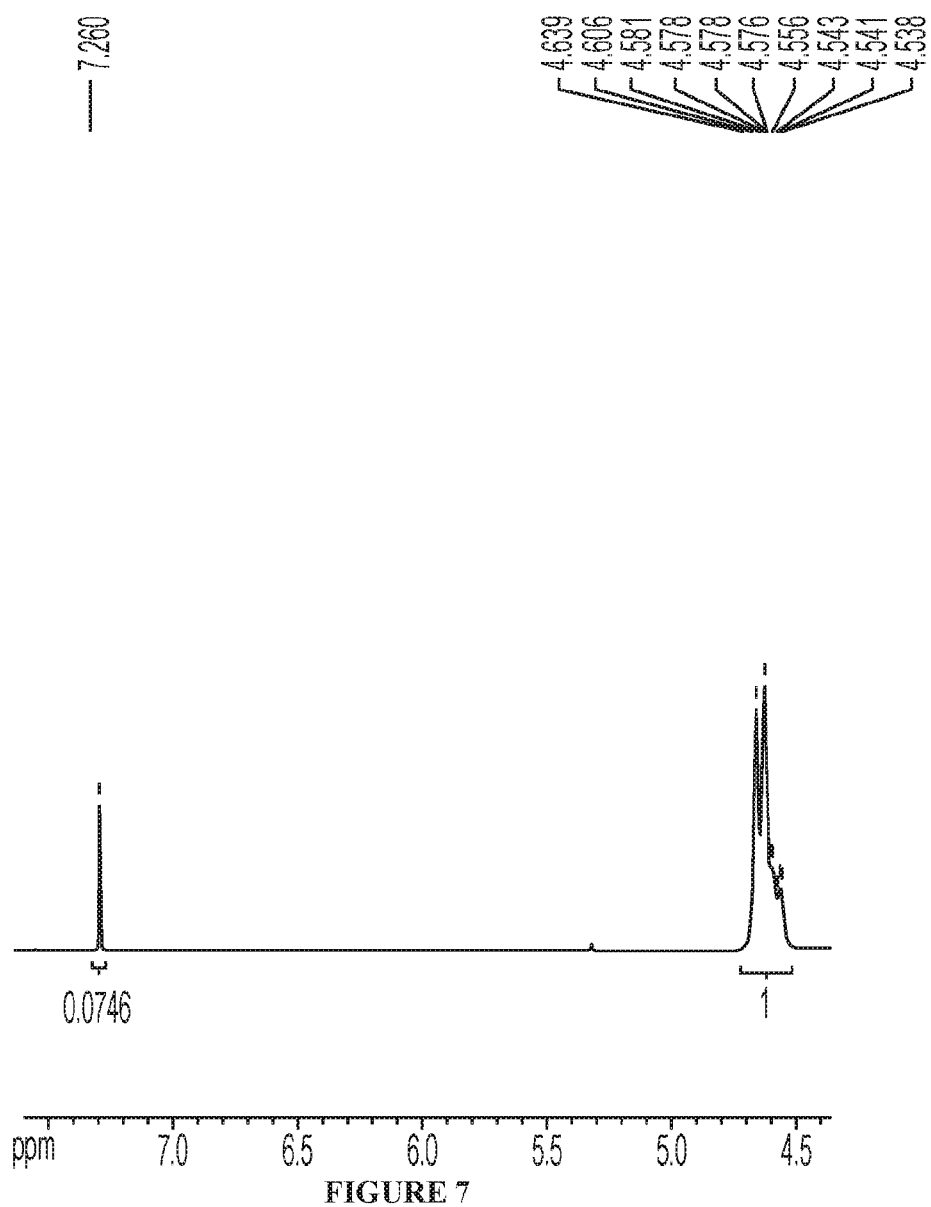
FIG. 7. $^1$H NMR spectrum for purified Linker 9 (see Example 1).
Figure 7:
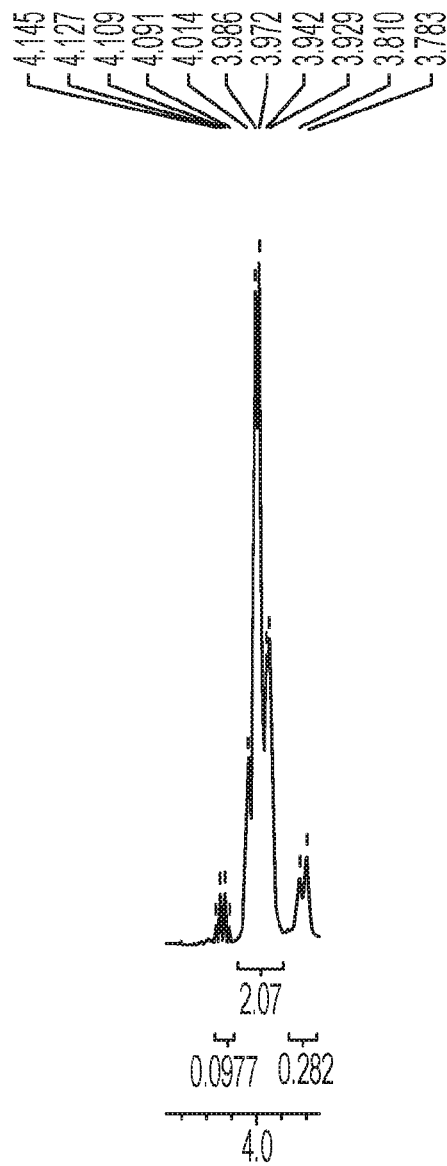
Figure 7:
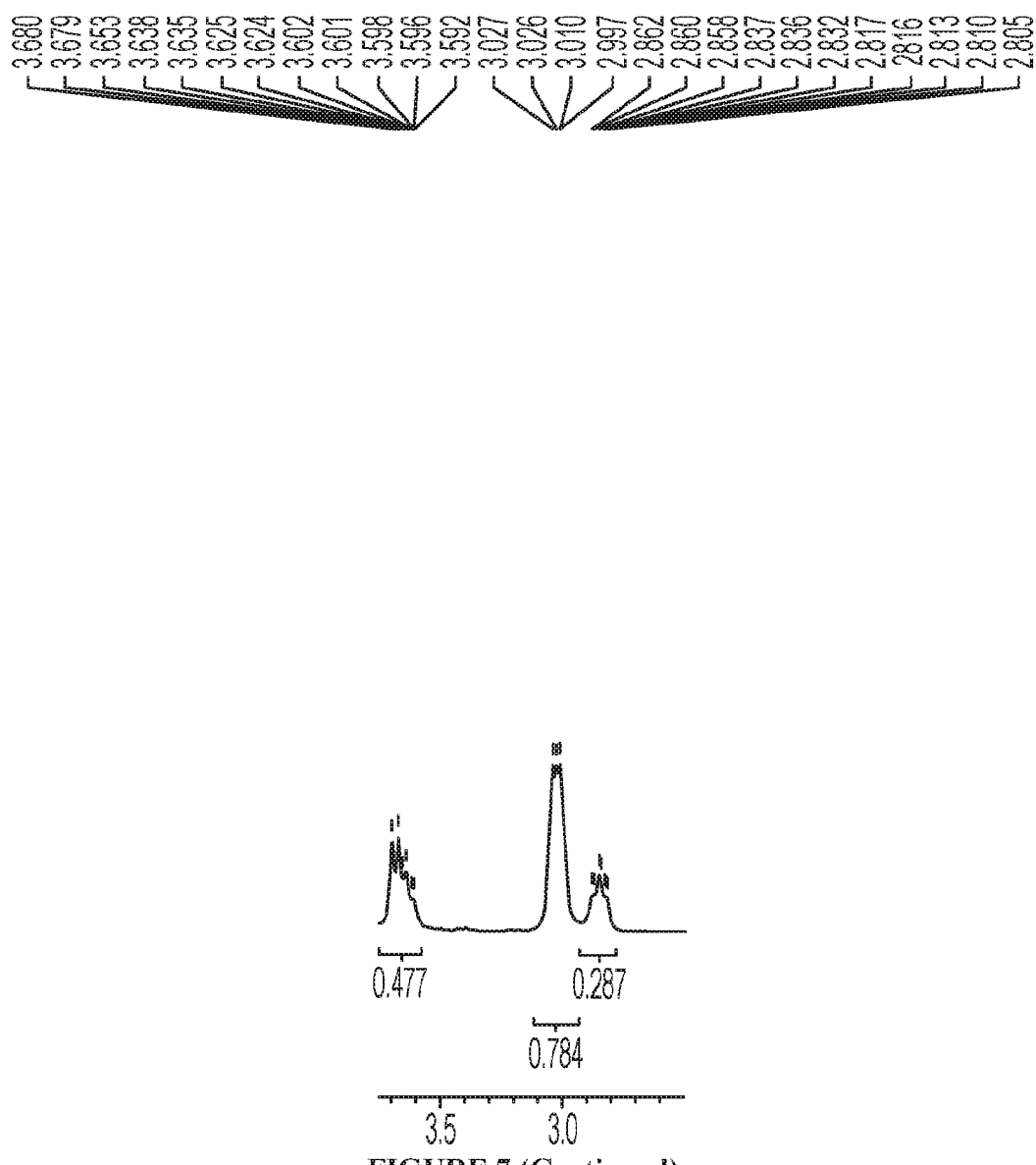
Figure 7:
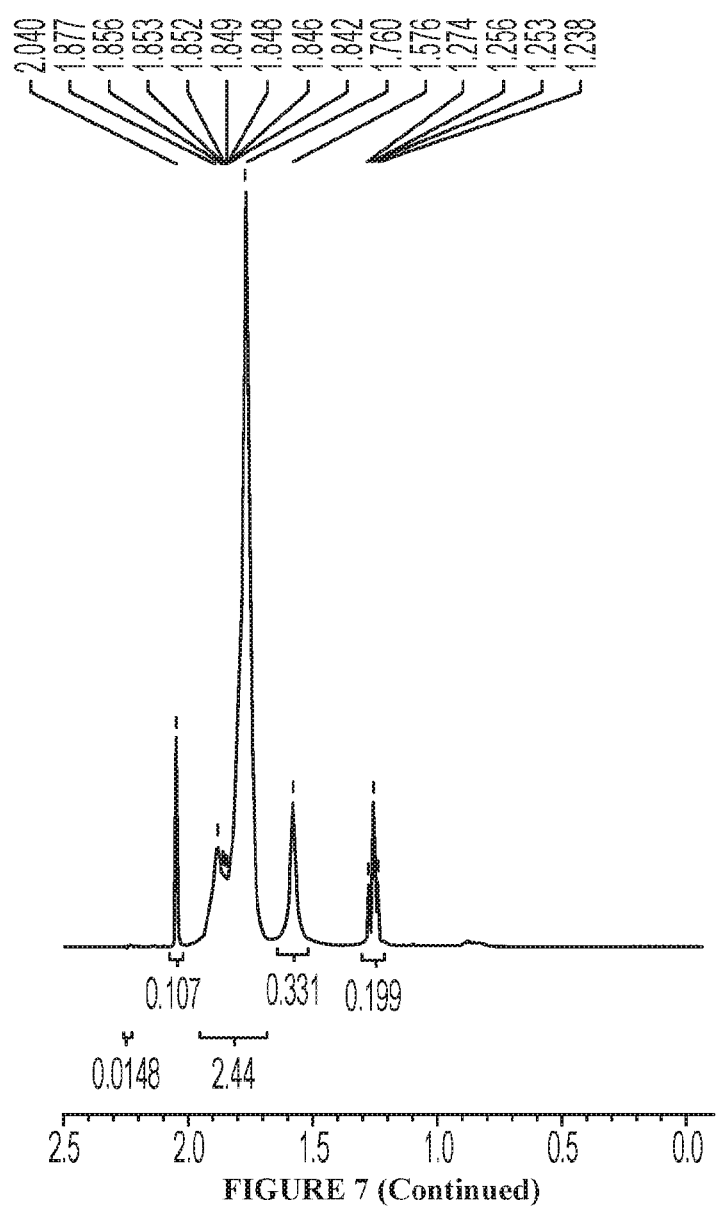

As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety. In some embodiments, an agent is a compound. In some embodiments, an agent is a stapled peptide.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation, or combinations thereof. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Alkenyl: As used herein, the term "alkenyl" refers to an aliphatic group, as defined herein, having one or more double bonds.

Alkenylene: The term "alkenylene" refers to a bivalent alkenyl group.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkylene: The term "alkylene" refers to a bivalent alkyl group.

Amino acid: In its broadest sense, as used herein, refers to any compound and/or substance that can be incorporated into a polypeptide chain, e.g., through formation of one or more peptide bonds. In some embodiments, an amino acid comprising an amino group and an a carboxylic acid group. In some embodiments, an amino acid has the structure of $NH(R^{a1})$-$L^{a}i$-$C(R^{a2})(R^{a3})$-$L^{a2}$-$COOH$, wherein each variable is independently as described in the present disclosure. In some embodiments, an amino acid has the general structure $NH(R')$—$C(R')_2$—$COOH$, wherein each R' is independently as described in the present disclosure. In some embodiments, an amino acid has the general structure $H_2N$—$C(R')_2$—$COOH$, wherein R' is as described in the present disclosure. In some embodiments, an amino acid has the general structure $H_2N$—$C(H)(R')$—$COOH$, wherein R' is as described in the present disclosure. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, one or more hydrogens, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Animal: As used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Aryl: The term "aryl" used alone or as part of a larger moiety as in "aralkyl," "aralkoxy," "aryloxyalkyl," etc. refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but is not limited to, phenyl, biphenyl, naphthyl, binaphthyl, anthracyl and the like, which may bear one or more substituents. In some embodiments, also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like, where a radical or point of attachment is on an aryl ring.

Associated with: Two events or entities are "associated" with one another, as that term is used herein, if the presence, level and/or form of one is correlated with that of the other. For example, a particular entity (e.g., nucleic acid (e.g., genomic DNA, transcripts, mRNA, etc.), polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population).

Carrier: as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Cycloaliphatic: The term "cycloaliphatic," as used herein, refers to saturated or partially unsaturated aliphatic monocyclic, bicyclic, or polycyclic ring systems having, e.g., from 3 to 30, members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic" may also include aliphatic rings that are fused to one or more aromatic or nonaromatic rings, such as decahydronaphthyl or tetrahydronaphthyl, where a radical or point of attachment is on an aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_5$-$C_{10}$ bicyclic hydrocarbon that is completely saturated or that contains one or more units of unsaturation, but which is not aromatic, or a $C_9$-$C_{16}$ tricyclic hydrocarbon that is completely saturated or that contains one or more units of unsaturation, but which is not aromatic.

Derivative: As used herein, the term "derivative" refers to a structural analogue of a reference substance. That is, a "derivative" is a substance that shows significant structural similarity with the reference substance, for example sharing a core or consensus structure, but also differs in certain discrete ways. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Dosageform or unit dosageform: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Halogen: The term "halogen" means F, Cl, Br, or I.

Heteroaliphatic: The term "heteroaliphatic" is given its ordinary meaning in the art and refers to aliphatic groups as described herein in which one or more carbon atoms are replaced with one or more heteroatoms (e.g., oxygen, nitrogen, sulfur, silicon, phosphorus, and the like).

Heteroalkyl: The term "heteroalkyl" is given its ordinary meaning in the art and refers to alkyl groups as described herein in which one or more carbon atoms is replaced with a heteroatom (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-," used alone or as part of a larger moiety, e.g., "heteroaralkyl," or "heteroaralkoxy," refer to monocyclic, bicyclic or polycyclic ring systems having, for example, a total of five to thirty, e.g., 5, 6, 9, 10, 14, etc., ring members, wherein at least one ring in the system is aromatic and at least one aromatic ring atom is a heteroatom. In some embodiments, a heteroatom is nitrogen, oxygen or sulfur. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where a radical or point of attachment is on a heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom" means an atom that is not carbon and is not hydrogen. In some embodiments, a heteroatom is oxygen, sulfur, nitrogen, phosphorus, boron or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or NR$^+$ (as in N-substituted pyrrolidinyl); etc.). In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur.

Heterocyclyl: As used herein, the terms "heterocycle," "heterocyclyl," "heterocyclic radical," and "heterocyclic ring" are used interchangeably and refer to a monocyclic, bicyclic or polycyclic ring moiety (e.g., 3-30 membered) that is saturated or partially unsaturated and has one or more heteroatom ring atoms. In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or ⁺NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where a radical or point of attachment is on a heteroaliphatic ring. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those ofordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

"Improved," "increased" or "reduced": As used herein, these terms, or grammatically comparable comparative terms, indicate values that are relative to a comparable reference measurement. For example, in some embodiments, an assessed value achieved with an agent of interest may be "improved" relative to that obtained with a comparable reference agent. Alternatively or additionally, in some embodiments, an assessed value achieved in a subject or system of interest may be "improved" relative to that obtained in the same subject or system under different conditions (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

Partially unsaturated: As used herein, the term "partially unsaturated" refers to a moiety that includes at least one double or triple bond. The term "partially unsaturated" is intended to encompass groups having multiple sites of unsaturation, but is not intended to include aryl or heteroaryl moieties.

Peptide: The term "peptide" as used herein refers to a polypeptide that is typically relatively short, for example having a length of less than about 100 amino acids, less than about 50 amino acids, less than about 40 amino acids less than about 30 amino acids, less than about 25 amino acids, less than about 20 amino acids, less than about 15 amino acids, or less than 10 amino acids.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; RingeR's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other known methods such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, pharmaceutically acceptable salts include, but are not limited to, nontoxic base addition salts, such as those formed by acidic groups of provided compounds (e.g., phosphate linkage groups of oligonucleotides, phosphorothioate linkage groups of oligonucleotides, etc.) with bases. Representative alkali or alkaline earth metal salts include salts of sodium, lithium, potassium, calcium, magnesium, and the like. In some embodiments, pharmaceutically acceptable salts are ammonium salts (e.g., —N(R)$_3$). In some embodiments, pharmaceutically acceptable salts are sodium salts. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Polypeptide: As used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Prevent or prevention: as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Protecting Group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, propionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Substitution: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. In some embodiments, example substituents are described below.

Suitable monovalent substituents are halogen; $-(CH_2)_{0-4}R°$; $-(CH_2)_{0-4}OR°$; $-O(CH_2)_{0-4}R°$, $-O-(CH_2)_{0-4}C(O)OR°$; $-(CH_2)_{0-4}CH(OR°)_2$; $-(CH_2)_{0-4}Ph$, which may be substituted with $R°$; $-(CH_2)_{0-4}O(CH_2)_{0-1}Ph$ which may be substituted with $R°$; $-CH=CHPh$, which may be substituted with $R°$; $-(CH_2)_{0-4}O(CH_2)_{0-1}$-pyridyl which may be substituted with $R°$; $-NO_2$; $-CN$; $-N_3$; $-(CH_2)_{0-4}N(R°)_2$; $-(CH_2)_{0-4}N(R°)C(O)R°$; $-N(R°)C(S)R°$; $-(CH_2)_{0-4}N(R°)C(O)N(R°)_2$; $-N(R°)C(S)N(R°)_2$; $-(CH_2)_{0-4}N(R°)C(O)OR°$; $-N(R°)N(R°)C(O)R°$; $-N(R°)N(R°)C(O)N(R°)_2$; $-N(R°)N(R°)C(O)OR°$; $-(CH_2)_{0-4}C(O)R°$; $-C(S)R°$; $-(CH_2)_{0-4}C(O)OR°$; $-(CH_2)_{0-4}C(O)SR°$; $-(CH_2)_{0-4}C(O)OSi(R°)_3$; $-(CH_2)_{0-4}OC(O)R°$; $-OC(O)(CH_2)_{0-4}SR°$, $-SC(S)SR°$; $-(CH_2)_{0-4}SC(O)R°$; $-(CH_2)_{0-4}C(O)N(R°)_2$; $-C(S)N(R°)_2$; $-C(S)SR°$; $-SC(S)SR°$, $-(CH_2)_{0-4}OC(O)N(R°)_2$; $-C(O)N(OR°)R°$; $-C(O)C(O)R°$; $-C(O)CH_2C(O)R°$; $-C(NOR°)R°$; $-(CH_2)_{0-4}SSR°$; $-(CH_2)_{0-4}S(O)_2R°$; $-(CH_2)_{0-4}S(O)_2OR°$; $-(CH_2)_{0-4}OS(O)_2R°$; $-S(O)_2N(R°)_2$; $-(CH_2)_{0-4}S(O)R°$; $-N(R°)S(O)_2N(R°)_2$; $-N(R°)S(O)_2R°$; $-N(OR°)R°$; $-C(NH)N(R°)_2$; $-Si(R°)_3$; $-OSi(R°)_3$; $-P(R°)_2$; $-P(OR°)_2$; $-OP(R°)_2$; $-OP(OR°)_2$; $-N(R°)P(R°)_2$; $-B(R°)_2$; $-OB(R°)_2$; $-P(O)(R°)_2$; $-OP(O)(R°)_2$; $-N(R°)P(O)(R°)_2$; $-(C_{1-4}$ straight or branched alkylene)$O-N(R°)_2$; or $-(C_{1-4}$ straight or branched alkylene)$C(O)O-N(R°)_2$; wherein each $R°$ may be substituted as defined below and is independently hydrogen, $C_{1-20}$ aliphatic, $C_{1-20}$ heteroaliphatic having 1-5 heteroatoms independently selected from nitrogen, oxygen, sulfur, silicon and phosphorus, $-CH_2-(C_{6-14}$ aryl), $-O(CH_2)_{0-1}(C_{6-14}$ aryl), $-CH_2-(5-14$ membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R°$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on $R°$ (or the ring formed by taking two independent occurrences of $R°$ together with their intervening atoms), are independently halogen, $-(CH_2)_{0-2}R^•$, -(haloR$^•$), $-(CH_2)_{0-2}OH$, $-(CH_2)_{0-2}OR^•$, $-(CH_2)_{0-2}CH(OR^•)_2$; $-O(haloR^•)$, $-CN$, $-N_3$, $-(CH_2)_{0-2}C(O)R^•$, $-(CH_2)_{0-2}C(O)OH$, $-(CH_2)_{0-2}C(O)OR^•$, $-(CH_2)_{0-2}SR^•$, $-(CH_2)_{0-2}SH$, $-(CH_2)_{0-2}NH_2$, $-(CH_2)_{0-2}NHR^•$, $-(CH_2)_{0-2}NR^•_2$, $-NO_2$, $-SiR^•_3$, $-OSiR^•_3$, $-C(O)SR^•$, $-(C_{1-4}$ straight or branched alkylene)$C(O)OR^•$, or $-SSR^•$ wherein each $R^•$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R°$ include $=O$ and $=S$.

Suitable divalent substituents are the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* are halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

In some embodiments, suitable substituents on a substitutable nitrogen are —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(RT)S(O)$_2$R$^†$; wherein each R is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^†$ are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Subject: As used herein, the term "subject" or "test subject" refers to any organism to which a provided compound or composition is administered in accordance with the present disclosure e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition. In some embodiments, a subject is a human.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutic agent: As used herein, the phrase "therapeutic agent" refers to an agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutic regimen: A "therapeutic regimen", as that term is used herein, refers to a dosing regimen whose administration across a relevant population may be correlated with a desired or beneficial therapeutic outcome.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Unsaturated: The term "unsaturated" as used herein, means that a moiety has one or more units of unsaturation.

Wild-type: As used herein, the term "wild-type" has its art-understood meaning that refers to an entity having a structure and/or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

Unless otherwise specified, salts, such as pharmaceutically acceptable acid or base addition salts, stereoisomeric forms, and tautomeric forms, of provided compound are included.

Unless otherwise clear from context, in the present disclosure, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Peptide Agents

Technologies provided by and/or described in the present disclosure particularly relate to peptide agents, e.g., to agents that are or comprise stapled peptides.

Among other things, the present disclosure provides technologies for developing, identifying, characterizing, and/or making stapled peptides that can modulate one or more functions of a target of interest. In some embodiments, stapled peptides are useful for treating various conditions, disorders, and/or diseases that are associated with the target of interest. Exemplary structural elements of provided stapled peptides are described herein.

Among other things, as discussed herein, the present disclosure encompasses the insight that biological systems can be utilized to generate peptide agents that include cysteine residues appropriate for and/or amenable to cysteine stapling. The present disclosure further appreciates that use of such biological systems can permit high-throughput production and/or assessment of cysteine stapled peptides (e.g., with respect to one or more (e.g., specificity, affinity, on-rate, off-rate, stability to competition, binding curve over a range of conditions such as concentration, temperature, pH, osmolality, presence or amount of competitor, etc.) characteristics of their binding interaction(s) with one or more targets of interest.

Thus, in some embodiments, the present disclosure provides peptide agents that include two or more cysteine residues, spaced apart from one another appropriately so as to support cysteine stapling. In some embodiments, provided are collections of such peptide agents. In some embodiments, provided are cysteine stapled peptides and/or collections thereof.

The present disclosure further appreciates that insights gleaned from producing, screening and/or otherwise analyzing or characterizing one or more cysteine stapled peptides can inform design, production, and/or use of analogous or comparable (e.g., containing the same or substantially the same [e.g., but for one or more conservative substitutions and/or one or a small number of other changes]amino acid sequence except for substitution of those cysteine residue(s) that participate in a staple with non-cysteine residue(s) that can or do participate in an analogous or comparable staple) peptide agents that share with their "parent" cysteine stapled peptide one or more binding characteristics with a particular target of interest. The present disclosure therefore provides peptide agents (e.g., that are or comprise stapled peptides) that correspond to cysteine stapled peptides (but include non-cysteine residue(s) rather than cysteines that participate in the staple).

Amino Acid Sequence

One particular advantage of technologies provided by the present disclosure is that they permit discovery of and/or define amino acid sequences that are particularly useful for stapled peptides (e.g., that bind to a particular target of interest).

Thus, in some embodiments, the present disclosure provides amino acid sequences for stapled peptides. In some embodiments, stapled peptides comprising provided amino acid sequences interact with (e.g., directly bind to) a target of interest, and, in some embodiments, such binding displays one or more characteristics as discussed herein.

As will be appreciated by those skilled in the art reading the present disclosure, in some embodiments, the present disclosure defines useful amino acid sequences from a collection that may be highly diverse—e.g., that may include two or more amino acid alternatives at any one or collection (including all) of positions along the amino acid chain, except for those that participate in a staple which, in many embodiments, are cysteines.

In some embodiments, amino acid sequences utilized in peptide agents as described herein may be or comprises, or be derived from, a sequence that is found in nature or in an otherwise appropriate reference polypeptide (e.g., one that may be known to bind to a relevant target of interest, for example via an interaction characterized by one or more features as described herein.

In some embodiments, an amino acid sequence that is utilized in a peptide agent, or in a collection of peptide agents, as described herein, is a variant of a reference sequence in that (1) it includes a pair of cysteine residues, at least one or which is not found at a corresponding position in the reference sequence, that are amenable to or participate in a cysteine staple; and/or (2) it includes an amino acid substitution at one or more positions of the reference sequence. In some embodiments, a substitution may be a conservative substitution, as understood in the art. In some embodiments, a substitution may involve substitution of a homolog. In some embodiments, a homolog of an amino acid is a naturally occurring or non-naturally occurring amino acid that has one or more similar properties to the amino acid and or amino acid side-chains being replaced, for example, that is typically classified as similar to one another as "non-polar", "polar", "hydrophobic", "hydrophilic", "basic", "acidic", "aliphatic", "aromatic", and/or "similar size".

For example, in some embodiments, depending on context, a homolog of leucine can be an optionally substituted amino acid selected from isoleucine, alanine, homoleucine, 3-cyclobutylalanine, alpha-neopentylglycine, 3-cyclopropy-lalanine, alpha-methylleucine, and 3-cyclohexylalanine; a homolog of isoleucine can be an optionally substituted amino acid selected from alanine, leucine, homoleucine, 3-cyclobutylalanine, alpha-neopentylglycine, 3-cyclopropy-lalanine, L-alloisoleucine, and alpha-methylleucine; a homolog of phenylalanine can be an optionally substituted amino acid residue selected from tryptophan, tyrosine, 3-(1-naphthylalanine), 3-(2-naphthylalanine), 2-chlorophenyla-nine, 3-chlorophenylalanine, 4-chlorophenylalanine, 4-tert-butylphenylalanine, O-methyl tyrosine, homophenylalanine, 4-fluorophenylalanine, 4-methylphenylalanine, 4-brom-ophenylalanine, 4-phenyl-L-phenylalanine, 5-chlorotrypto-phan, 5-hydroxytryptophan, 4-trifluoromethylphenylala-nine, 4-guanidino-L-phenylalanine, 2-quinoyl-L-alanine, 3-cyclobutylalanine, alpha-neopentylglycine, and L-2-ami-noadipic acid; etc.

In some embodiments, a homolog of a non-polar amino acid is another non-polar amino acid. In some embodiments, a homolog of an amino acid comprising a non-polar side chain is another non-polar amino acid comprising a non-polar side chain.

In some embodiments, a homolog of a polar amino acid is another polar amino acid. In some embodiments, a homolog of an amino acid comprising a polar side chain is another polar amino acid comprising a polar side chain.

In some embodiments, a homolog of a hydrophobic amino acid is another hydrophobic amino acid. In some embodiments, a homolog of an amino acid comprising a hydrophobic side chain is another hydrophobic amino acid comprising a hydrophobic side chain.

In some embodiments, a homolog of a hydrophilic amino acid is another hydrophilic amino acid. In some embodiments, a homolog of an amino acid comprising a hydrophilic side chain is another hydrophilic amino acid comprising a hydrophilic side chain.

In some embodiments, a homolog of a basic amino acid is another basic amino acid. In some embodiments, a homolog of an amino acid comprising a basic side chain is another basic amino acid comprising a basic side chain.

In some embodiments, a homolog of an acidic amino acid is another acidic amino acid. In some embodiments, a homolog of an amino acid comprising an acidic side chain is another acidic amino acid comprising an acidic side chain.

In some embodiments, a homolog of an aliphatic amino acid is another aliphatic amino acid. In some embodiments, a homolog of an amino acid comprising an aliphatic side chain is another aliphatic amino acid comprising an aliphatic side chain.

In some embodiments, a homolog of an aromatic amino acid is another aromatic amino acid. In some embodiments, a homolog of an amino acid comprising an aromatic side chain is another aromatic amino acid comprising an aromatic side chain.

In some embodiments, a homolog of an amino acid is sterically similar to the amino acid. In some embodiments, a homolog of an amino acid comprises a side chain that has a similar size to the side chain of the amino acid.

Provided amino acid sequences and stapled peptides can be various lengths, e.g. 2-100, 5-50, 5-40, 5-35, a range from and including 2, 3, 4, 5, 6, or 7 to and including 8, 9, 10, 11, 12, 13, 14, 15, 16, 17, 18, 19, 20, 21, 22, 23, 24, 25, 26, 27, 28, 29, 30, 31, 32, 33, 34, or 35 amino acid residues.

In some embodiments, a length is at least 5 amino acid residues. In some embodiments, a length is at least 6 amino acid residues. In some embodiments, a length is at least 7 amino acid residues. In some embodiments, a length is at least 8 amino acid residues. In some embodiments, a length is at least 9 amino acid residues. In some embodiments, a length is at least 10 amino acid residues. In some embodiments, a length is at least 11 amino acid residues. In some embodiments, a length is at least 12 amino acid residues. In some embodiments, a length is at least 13 amino acid residues. In some embodiments, a length is at least 14 amino acid residues. In some embodiments, a length is at least 15 amino acid residues. In some embodiments, a length is at least 16 amino acid residues. In some embodiments, a length is at least 17 amino acid residues. In some embodiments, a length is at least 18 amino acid residues. In some embodiments, a length is at least 19 amino acid residues. In some embodiments, a length is at least 20 amino acid residues. In some embodiments, a length is at least 21 amino acid residues. In some embodiments, a length is at least 22 amino acid residues. In some embodiments, a length is at least 23 amino acid residues. In some embodiments, a length is at least 24 amino acid residues. In some embodiments, a length is at least 25 amino acid residues. In some embodiments, a length is at least 26 amino acid residues. In some embodiments, a length is at least 27 amino acid residues. In some embodiments, a length is at least 28 amino acid residues. In some embodiments, a length is at least 29 amino acid residues. In some embodiments, a length is at least 30 amino acid residues. In some embodiments, a length is at least 31 amino acid residues. In some embodiments, a length is at least 32 amino acid residues. In some embodiments, a length is at least 33 amino acid residues. In some embodiments, a length is at least 34 amino acid residues. In some embodiments, a length is at least 35 amino acid residues.

In some embodiments, a length is 5 amino acid residues. In some embodiments, a length is 6 amino acid residues. In some embodiments, a length is 7 amino acid residues. In some embodiments, a length is 8 amino acid residues. In some embodiments, a length is 9 amino acid residues. In some embodiments, a length is 10 amino acid residues. In some embodiments, a length is 11 amino acid residues. In some embodiments, a length is 12 amino acid residues. In some embodiments, a length is 13 amino acid residues. In some embodiments, a length is 14 amino acid residues. In some embodiments, a length is 15 amino acid residues. In some embodiments, a length is 16 amino acid residues. In some embodiments, a length is 17 amino acid residues. In some embodiments, a length is 18 amino acid residues. In some embodiments, a length is 19 amino acid residues. In some embodiments, a length is 20 amino acid residues. In some embodiments, a length is 21 amino acid residues. In some embodiments, a length is 22 amino acid residues. In some embodiments, a length is 23 amino acid residues. In some embodiments, a length is 24 amino acid residues. In some embodiments, a length is 25 amino acid residues. In some embodiments, a length is 26 amino acid residues. In some embodiments, a length is 27 amino acid residues. In some embodiments, a length is 28 amino acid residues. In some embodiments, a length is 29 amino acid residues. In some embodiments, a length is 30 amino acid residues. In some embodiments, a length is 31 amino acid residues. In some embodiments, a length is 32 amino acid residues. In some embodiments, a length is 33 amino acid residues. In some embodiments, a length is 34 amino acid residues. In some embodiments, a length is 35 amino acid residues.

In some embodiments, a length is no more than 17 amino acid residues. In some embodiments, a length is no more than 18 amino acid residues. In some embodiments, a length is no more than 19 amino acid residues. In some embodiments, a length is no more than 20 amino acid residues. In some embodiments, a length is no more than 21 amino acid residues. In some embodiments, a length is no more than 22 amino acid residues. In some embodiments, a length is no more than 23 amino acid residues. In some embodiments, a length is no more than 24 amino acid residues. In some embodiments, a length is no more than 25 amino acid residues. In some embodiments, a length is no more than 26 amino acid residues. In some embodiments, a length is no more than 27 amino acid residues. In some embodiments, a length is no more than 28 amino acid residues. In some embodiments, a length is no more than 29 amino acid residues. In some embodiments, a length is no more than 30 amino acid residues. In some embodiments, a length is no more than 35 amino acid residues. In some embodiments, a length is no more than 40 amino acid residues. In some embodiments, a length is no more than 50 amino acid residues.

Both naturally occurring and non-naturally occurring amino acids can be utilized in accordance with the present disclosure. In some embodiments, an amino acid is a compound comprising an amino group that can form an amide group with a carboxyl group and a carboxyl group.

In some embodiments, an amino acid is a compound having the structure of formula A-I.

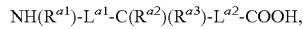

$$NH(R^{a1})\text{-}L^{a1}\text{-}C(R^{a2})(R^{a3})\text{-}L^{a2}\text{-}COOH, \quad \text{A-I}$$

or a salt thereof, wherein:

each of $R^{a1}$, $R^{a2}$, $R^{a3}$ is independently -$L^a$-R';

each of $L^a$, $L^{a1}$ and $L^{a2}$ is independently L;

each L is independently a covalent bond, or an optionally substituted, bivalent $C_1$-$C_{25}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —CO$_2$R, or —SO$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, $L^{a1}$ is a covalent bond. In some embodiments, a compound of formula A-1 is of the structure NH($R^{a1}$)—C($R^{a2}$)($R^{a3}$)-$L^{a2}$-COOH.

In some embodiments, $L^{a2}$ is a covalent bond. In some embodiments, a compound of formula A-1 is of the structure NH($R^{a1}$)—C($R^{a2}$)($R^{a3}$)-$L^{a2}$-COOH.

In some embodiments, $L^{a1}$ is a covalent bond and $L^{a2}$ is a covalent bond. In some embodiments, a compound of formula A-1 is of the structure NH($R^{a1}$)—C($R^{a2}$)($R^{a3}$)—COOH.

In some embodiments, $L^a$ is a covalent bond. In some embodiments, R' is R. In some embodiments, $R^{a1}$ is R, wherein R is as described in the present disclosure. In some embodiments, $R^{a2}$ is R, wherein R is as described in the present disclosure. In some embodiments, $R^{a3}$ is R, wherein R is as described in the present disclosure. In some embodiments, each of $R^{a1}$, $R^{a2}$, and $R^{a3}$ is independently R, wherein R is as described in the present disclosure.

In some embodiments, $R^{a1}$ is hydrogen. In some embodiments, $R^{a2}$ is hydrogen. In some embodiments, $R^{a3}$ is hydrogen. In some embodiments, $R^{a1}$ is hydrogen, and at least one of $R^{a2}$ and $R^{a3}$ is hydrogen. In some embodiments, $R^{a1}$ is hydrogen, one of $R^{a2}$ and $R^{a3}$ is hydrogen, and the other is not hydrogen.

In some embodiments, $R^{a2}$ is -$L^a$-R, wherein R is as described in the present disclosure. In some embodiments, $R^{a2}$ is -$L^a$-R, wherein R is an optionally substituted group selected from $C_{3-30}$ cycloaliphatic, $C_{5-30}$ aryl, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon. In some embodiments, $R^{a2}$ is -$L^a$-R, wherein R is an optionally substituted group selected from $C_{6-30}$ aryl and 5-30 membered heteroaryl having 1-10 heteroatoms independently selected from oxygen, nitrogen, sulfur, phosphorus and silicon. In some embodiments, $R^2$ is a side chain of an amino acid. In some embodiments, $R^{a2}$ is a side chain of a standard amino acid.

In some embodiments, $R^{a3}$ is -$L^a$-R, wherein R is as described in the present disclosure. In some embodiments, $R^{a3}$ is -$L^a$-R, wherein R is an optionally substituted group selected from $C_{3-30}$ cycloaliphatic, $C_{5-30}$ aryl, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon. In some embodiments, $R^{a3}$ is -$L^a$-R, wherein R is an optionally substituted group selected from $C_{6-30}$ aryl and 5-30 membered heteroaryl having 1-10 heteroatoms independently selected from oxygen, nitrogen, sulfur, phosphorus and silicon. In some embodiments, $R^{a3}$ is a side chain of an amino acid. In some embodiments, $R^{a3}$ is a side chain of a standard amino acid.

An amino acid sequence can have various degrees of homology to naturally occurring amino acid sequences. As appreciated by those skilled in the art, the present disclosure can be utilized to design and identify sequences with either high or low homology, or no homology (e.g., sequences completely unrelated to any sequences encoded in a genome). In some embodiments, the present disclosure provides technologies for identifying useful amino acid sequences that share low degree of homology to naturally occurring amino acid sequences, e.g., from libraries designed with many random positions compared to natural amino acid sequences, or from totally random libraries. In some embodiments, an amino acid sequence is at least 5%, 10%, 20%, 30%, 40%, 50%, 60%, 70%, 80%, 90%, or 95% homologous to naturally occurring amino acid sequence. In some embodiments, an amino acid sequence is no more than 5%, 10%, 20%, 30%, 40%, 50%, 60%, 70%, 80%, 90%, or 95% homologous to naturally occurring amino acid sequence. In some embodiments, the homology is at least 5%. In some embodiments, the homology is at least 10%. In some embodiments, the homology is at least 20%. In some embodiments, the homology is at least 30%. In some embodiments, the homology is at least 40%. In some embodiments, the homology is at least 50%. In some embodiments, the homology is at least 60%. In some embodiments, the homology is at least 70%. In some embodiments, the homology is at least 80%. In some embodiments, the homology is at least 90%. In some embodiments, the homology is at least 95%. In some embodiments, the homology is no more than 5%. In some embodiments, the homology is no more than 10%. In some embodiments, the homology is no more than 20%. In some embodiments, the homology is no more than 30%. In some embodiments, the homology is no more than 40%. In some embodiments, the homology is no more than 50%. In some embodiments, the homology is no more than 60%. In some embodiments, the homology is no more than 70%. In some embodiments, the homology is no more than 80%. In some embodiments, the homology is no more than 90%. In some embodiments, the homology is no more than 95%.

An amino acid sequence can be various lengths. In some embodiments, a length is or comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, or 50 amino acid residues. In some embodiments, a length is or comprises at least 5 amino acid residues. In some embodiments, a length is or comprises at least 6 amino acid residues. In some embodiments, a length is or comprises at least 7 amino acid residues. In some embodiments, a length is or comprises at least 8 amino acid residues. In some embodiments, a length is or comprises at least 9 amino acid residues. In some embodiments, a length is or comprises at least 10 amino acid residues. In some embodiments, a length is or comprises at least 11 amino acid residues. In some embodiments, a length is or comprises at least 12 amino acid residues. In some embodiments, a length is or comprises at least 13 amino acid residues. In some embodiments, a length is or comprises at least 14 amino acid residues. In some embodiments, a length is or comprises at least 15 amino acid residues. In some embodiments, a length is or comprises at least 16 amino acid residues. In some embodiments, a length is or comprises at least 17 amino acid residues. In some embodiments, a length is or comprises at least 18 amino acid residues. In some embodiments, a length is or comprises at least 18 amino acid residues. In some embodiments, a length is or comprises at least 20 amino acid residues. In some embodiments, a length is or comprises at least 25 amino acid residues. In some embodiments, a length is or comprises at least 30 amino acid residues.

As demonstrated herein, provided technologies can be utilized with or without a starting amino acid sequence (e.g., either totally random libraries or libraries comprising certain pre-determined amino acid residues at certain positions) to identify useful amino acid sequences with desired properties and/or activities. In some embodiments, the present disclosure provide useful amino acid sequences for modulating targets, e.g., proteins associated with various conditions, disorders or diseases. In some embodiments, a provided amino acid sequence comprises $X_{s1}X_1X_2X_3X_4X_5X_6X_{s2}$, wherein $X_{s1}$ and $X_{s2}$ are amino acid residues connected via a staple, and each of $X_1$, $X_2$, $X_3$, $X_4$, $X_5$, and $X_6$ is independently an amino acid residue. In some embodiments, $X_3$ and $X_4$ are A, and $X_5$ is H. In some embodiments, $X_2$ is L, $X_3$ and $X_4$ are A, and $X_5$ is H. In some embodiments, $X_2$ is L. In some embodiments, $X_1$ is I. In some embodiments, a provided amino acid sequence comprises $X_{s1}X_1X_2X_3X_4X_5X_6X_{s2}X_7X_8$, wherein $X_{s1}$ and $X_{s2}$ are amino acid residues connected via a staple, and each of $X_1$, $X_2$, $X_3$, $X_4$, $X_5$, $X_6$, $X_7$, and $X_8$ is independently an amino acid residue. In some embodiments, $X_3$ and $X_4$ are A, and $X_6$ is H. In some embodiments, $X_2$ is an aromatic amino acid residue, $X_3$ and $X_4$ are A, and $X_6$ is H. In some embodiments, $X_2$ is W. In some embodiments, $X_1$ is E. In some embodiments, $X_7$ is an acidic amino acid residue. In some embodiments, $X_7$ is E. In some embodiments, $X_8$ is L. In some embodiments, a provided amino acid sequence comprises $X_{-2}X_{-1}X_{s1}X_1X_2X_3X_4X_5X_6X_{s2}X_7$, wherein $X_{s1}$ and $X_{s2}$ are amino acid residues connected via a staple, and each of $X_{-2}$, $X_{-1}$, $X_1$, $X_2$, $X_3$, $X_4$, $X_5$, $X_6$, and $X_7$ is independently an amino acid residue. In some embodiments, $X_2$ is H, $X_3$ is A, and $X_4$ is A. In some embodiments, $X_{-2}$ is W. In some embodiments, $X_{-1}$ is an acidic amino acid residue. In some embodiments, $X_{-1}$ is E. In some embodiments, $X_{-1}$ is D. In some embodiments, $X_1$ is an acidic amino acid residue. In some embodiments, $X_1$ is E. In some embodiments, $X_1$ is D. In some embodiments, $X_5$ is L or I. In some embodiments, $X_5$ is L. In some embodiments, $X_5$ is I. In some embodiments, $X_6$ is L or I. In some embodiments, $X_6$ is L. In some embodiments, $X_6$ is I. In some embodiments, $X_7$ is an acidic amino acid residue. In some embodiments, $X_7$ is E. In some embodiments, $X_7$ is D.

Peptide Libraries

In some embodiments, the present disclosure provides a collection of peptides. In some embodiments, a collection of peptides is a collection of stapled peptides. In some embodiments, peptides within a collection as described herein may share one or more structural features (e.g. length within a particular range; presence of particular sequence elements such as, for example, a sequence element found in a known interaction partner for a target or interest, or a set of amino acids that together support formation of a staple [e.g., two or more cysteine residues, positioned relative to one another so that a cysteine staple as described herein is or may be produced between a pair of them], presence of one or more staples which may, in some embodiments, be of the same type, etc., or any combination thereof, and in some embodiments, a particular collection may be characterized and/or defined by such shared structural feature(s)). In some embodiments, a common structural feature of peptides in a collection of peptides as described herein is or at least two cysteine residues, positioned relative to one another so that a cysteine staple as described herein is or may be formed between a pair of them; in some embodiments, such peptides can be reacted with a compound of formula R-I, to produce a collection of stapled peptides.

In some embodiments, a collection of peptides is a collection of stapled peptides, each of which independently has an amino acid sequence that:
has a length within a range of a* and b*, where a* and b* are each integers independently selected from 2 through 100 and b* is greater than a*; and
includes at least one pair of residues covalently linked with one another via a linker.

In some embodiments, a* and b* are each integers independently selected from 2 through 50 and b* is greater than a*. In some embodiments, a* and b* are each integers independently selected from 6 through 36 and b* is greater than a*.

In some embodiments, a* is 1. In some embodiments, a* is 2. In some embodiments, a* is 3. In some embodiments, a* is 4. In some embodiments, a* is 5. In some embodiments, a* is 6. In some embodiments, a* is 7. In some embodiments, a* is 8. In some embodiments, a* is 9. In some embodiments, a* is 10. In some embodiments, a* is 11. In some embodiments, a* is 12. In some embodiments, a* is 13. In some embodiments, a* is 14. In some embodiments, a* is 15. In some embodiments, a* is 16. In some embodiments, a* is 17. In some embodiments, a* is 18. In some embodiments, a* is 19. In some embodiments, a* is 20. In some embodiments, a* is 21. In some embodiments, a* is 22. In some embodiments, a* is 23. In some embodiments, a* is 24. In some embodiments, a* is 25. In some embodiments, a* is 26. In some embodiments, a* is 27. In some embodiments, a* is 28. In some embodiments, a* is 29. In some embodiments, a* is 30. In some embodiments, a* is 31. In some embodiments, a* is 32. In some embodiments, a* is 33. In some embodiments, a* is 34. In some embodiments, a* is 35. In some embodiments, a* is 36. In some embodiments, a* is 37. In some embodiments, a* is 38. In some embodiments, a* is 39. In some embodiments, a* is 40. In some embodiments, a* is 41. In some embodiments, a* is 42. In some embodiments, a* is 43. In some embodiments, a* is 44. In some embodiments, a* is 45. In some embodiments, a* is 46. In some embodiments, a* is 47. In some embodiments, a* is 48. In some embodiments, a* is 49.

In some embodiments, b* is 2. In some embodiments, b* is 3. In some embodiments, b* is 4. In some embodiments, b* is 5. In some embodiments, b* is 6. In some embodiments, b* is 7. In some embodiments, b* is 8. In some embodiments, b* is 9. In some embodiments, b* is 10. In some embodiments, b* is 11. In some embodiments, b* is 12. In some embodiments, b* is 13. In some embodiments, b* is 14. In some embodiments, b* is 15. In some embodiments, b* is 16. In some embodiments, b* is 17. In some embodiments, b* is 18. In some embodiments, b* is 19. In some embodiments, b* is 20. In some embodiments, b* is 21. In some embodiments, b* is 22. In some embodiments, b* is 23. In some embodiments, b* is 24. In some embodiments, b* is 25. In some embodiments, b* is 26. In some embodiments, b* is 27. In some embodiments, b* is 28. In some embodiments, b* is 29. In some embodiments, b* is 30. In some embodiments, b* is 31. In some embodiments, b* is 32. In some embodiments, b* is 33. In some embodiments, b* is 34. In some embodiments, b* is 35. In some embodiments, b* is 36. In some embodiments, b* is 37. In some embodiments, b* is 38. In some embodiments, b* is 39. In some embodiments, b* is 40. In some embodiments, b* is 41. In some embodiments, b* is 42. In some embodiments, b* is 43. In some embodiments, b* is 44. In some embodiments, b* is 45. In some embodiments, b* is 46. In some embodiments, b* is 47. In some embodiments, b* is 48. In some embodiments, b* is 49.

In some embodiments, a pair of residues covalently linked with one another via a linker is covalently linked via a staple. In some embodiments, a pair of residues covalently linked with one another via a linker covalently linked via a non-hydrocarbon staple. In some embodiments, a pair of residues covalently linked with one another via a linker is covalently linked with via a cysteine staple. In some embodiments, a cysteine staple has the structure as described in the present disclosure.

In some embodiments, the present disclosure provides a collection of stapled peptides, each of which independently has an amino acid sequence that:
has a length within a range of a* and b*, where a* and b* are integers selected from 2 through 100 inclusive and b* is greater than a*;
includes at least one pair of cysteine residues covalently linked with one another via a linker comprising a moiety —S-$L^{s2}$-S—, where each S is independently a sulfur atom of a cysteine residue;
$L^{s2}$ is described in the present disclosure; and
cysteine residues of a pair are independently separated by c* residues, where c* is an integer selected from 0 through 12.

In some embodiments, a pair of cysteine residues covalently linked with one another via linker are separated by c* residues, wherein c* is an integer 1 to 12 inclusive. In some embodiments, c* is 1. In some embodiments, c* is 2. In some embodiments, c* is 3. In some embodiments, c* is 4. In some embodiments, c* is 5. In some embodiments, c* is 6. In some embodiments, c* is 7. In some embodiments, c* is 8. In some embodiments, c* is 9. In some embodiments, c* is 10. In some embodiments, c* is 11. In some embodiments, c* is 12.

In some embodiments, the present disclosure provides a collection of stapled peptides of the structure:

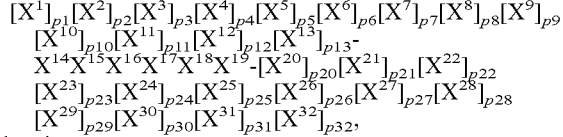

wherein:
each of p1, p2, p3, p4, p5, p6, p7, p8, p9, p10, p11, p12, p13, p20, p21, p22, p23, p24, p25, p26, p27, p28, p29, p30, p31, p32 is independently 0 or 1;
each of $X^1$ to $X^{32}$ is independently an amino acid residue;
at least two of $X^1$ to $X^{32}$ comprise cysteine chains that are optionally linked together to form a cysteine staple.

In some embodiments, each $X^j$ is independently selected from the group of standard amino acids, wherein j is an integer from 1 to 32 inclusive. In some embodiments, $X^j$ is selected from a subset of standard amino acids. In some embodiments, $X^j$ is selected from a group of all natural amino acids except cysteine. In some embodiments, $X^j$ is selected from fewer than 20 of the standard amino acids. In some embodiments, $X^j$ is selected from fewer than 19 of the standard amino acids. In some embodiments, $X^j$ is selected from fewer than 18 of the standard amino acids. In some embodiments, $X^j$ is selected from fewer than 17 of the standard amino acids. In some embodiments, $X^j$ is selected from fewer than 16 of the standard amino acids. In some embodiments, $X^j$ is selected from fewer than 15 of the standard amino acids. In some embodiments, $X^j$ is selected from fewer than 14 of the standard amino acids. In some embodiments, $X^j$ is selected from fewer than 13 of the standard amino acids. In some embodiments, $X^j$ is selected from fewer than 12 of the standard amino acids. In some embodiments, $X^j$ is selected from fewer than 11 of the standard amino acids. In some embodiments, $X^j$ is selected from fewer than 10 of the standard amino acids. In some embodiments, $X^j$ is selected from fewer than 9 of the standard amino acids. In some embodiments, $X^j$ is selected from fewer than 8 of the standard amino acids. In some embodiments, $X^j$ is selected from fewer than 7 of the standard amino acids. In some embodiments, $X^j$ is selected from fewer than 6 of the standard amino acids. In some embodiments, $X^j$ is selected from fewer than 5 of the standard amino acids. In some embodiments, $X^j$ is selected from fewer than 4 of the standard amino acids. In some embodiments, $X^j$ is selected from fewer than 3 of the standard amino acids. In some embodiments.

In some embodiments, each $X^j$ is independently selected from 20 of the standard amino acids. In some embodiments, $X^j$ is selected from 19 of the standard amino acids. In some embodiments, $X^j$ is selected from 18 of the standard amino acids. In some embodiments, $X^j$ is selected from 17 of the standard amino acids. In some embodiments, $X^j$ is selected from 16 of the standard amino acids. In some embodiments, $X^j$ is selected from 15 of the standard amino acids. In some embodiments, $X^j$ is selected from 14 of the standard amino acids. In some embodiments, $X^j$ is selected from 13 of the standard amino acids. In some embodiments, $X^j$ is selected from 12 of the standard amino acids. In some embodiments, $X^j$ is selected from 11 of the standard amino acids. In some embodiments, $X^j$ is selected from 10 of the standard amino acids. In some embodiments, $X^j$ is selected from 9 of the standard amino acids. In some embodiments, $X^j$ is selected from 8 of the standard amino acids. In some embodiments, $X^j$ is selected from 7 of the standard amino acids. In some embodiments, $X^j$ is selected from 6 of the standard amino acids. In some embodiments, $X^j$ is selected from 5 of the standard amino acids. In some embodiments, $X^j$ is selected from 4 of the standard amino acids. In some embodiments, $X^j$ is selected from 3 of the standard amino acids. In some embodiments, $X^j$ is selected from 2 of the standard amino acids. In some embodiments, $X^j$ is selected from 1 of the standard amino acids.

In some embodiments, j is 1. In some embodiments, j is 2. In some embodiments, j is 3. In some embodiments, j is 4. In some embodiments, j is 5. In some embodiments, j is 6. In some embodiments, j is 7. In some embodiments, j is 8. In some embodiments, j is 9. In some embodiments, j is 10. In some embodiments, j is 11. In some embodiments, j is 12. In some embodiments, j is 13. In some embodiments, j is 14. In some embodiments, j is 15. In some embodiments, j is 16. In some embodiments, j is 17. In some embodiments, j is 18. In some embodiments, j is 19. In some embodiments, j is 20. In some embodiments, j is 21. In some embodiments, j is 22. In some embodiments, j is 23. In some embodiments, j is 24. In some embodiments, j is 25. In some embodiments, j is 26. In some embodiments, j is 27. In some embodiments, j is 28. In some embodiments, j is 29. In some embodiments, j is 30. In some embodiments, j is 31. In some embodiments, j is 32.

Those skilled in the art, reading the present disclosure, will appreciate that peptide collections as described herein can be prepared, provided and/or utilized in a variety of formats. In some embodiments, a peptide collection is prepared, provided, and or utilized in a format such as, for example, phage display, yeast display, bacteria display, ribosome display, mRNA display, on a solid support, on a solid phase, on a resin, in liquid solution, as a dried sample or set thereof, etc.

In some embodiments, a collection of peptides can be provided and or utilized in phage display. In some embodiments, a collection of peptides are fused to a phage protein. In some embodiments, a collection of peptides are fused to a phage coat protein. In some embodiments, a collection of peptides are fused to a phage coat protein pIII.

Peptide collections may be displayed using a number of technologies. In some embodiments, peptides of libraries are displayed on p4 of M13 phage. In some embodiments, peptides of libraries are displayed on p7 of M13 phage. In some embodiments, peptides of libraries are displayed on p8 of M13 phage. In some embodiments, peptides of libraries are displayed on p9 of M13 phage.

In some embodiments, libraries, e.g., phage libraries, may be prepared with one or more barcodes within the DNA sequence of the library members, for example, comprising "silent" mutations (e.g., distinct codons that all encode the same amino acid), amino acid mutations, etc. In some embodiments, barcodes are used to identify certain features of library members and/or certain features of uses, e.g., experiments they are screened in, so that those features may be associated with the library member screening results, e.g., during analyses of DNA sequencing outputs of the screens. For example, in some embodiments, barcodes are incorporated into multiple libraries so that those libraries can be screened together, and their results are identified (and separated) by use of the barcodes. In some embodiments, barcodes are used to identify features of processes, e.g., experiments that a library member were screened in. Exemplary features include targets (e.g., proteins, nucleic acids, cells, etc.), buffer conditions, binding partners, competitors included in screens, temperatures of experiments, duration of experiments, washing procedures, and/or other features of experimental procedures. In some embodiments, barcodes are utilized to identify crosslinkers, e.g., those used to prepare chemically modified phage libraries comprising stapled peptides.

Various technologies can be utilized to incorporate unnatural amino acids into peptides, collections (e.g., various libraries described herein), etc., in accordance with the present disclosure. In some embodiments, incorporation comprises the use of codon suppression and/or aminoacyl-tRNA synthetase/tRNA pairs that result in the incorporation of unnatural amino acids. In some embodiments, useful methods comprise the addition of glyphosate (or other agents that selectively suppress the biosynthesis of one or more amino acids) and unnatural amino acid(s) in growth media. In some embodiments, useful methods comprise the use of cell lines lacking the ability to synthesize certain amino acids and the addition of unnatural amino acid(s) in growth media. In some embodiments, useful methods comprise the addition of unnatural amino acid(s) in growth media. In some embodiments, barcodes are used to identify the incorporation of unnatural amino acids into library designs.

In some embodiments, known phage or DNA sequence(s) are added during a step of a phage screen, for the purpose of scaling or normalizing DNA sequencing data using the known sequence(s) ("spike-in" samples).

In some embodiments, in the context of a collection of peptides (or proteins, etc.; e.g., of a provided library), diversity may refer to either a) the actual number of unique amino acid sequences present in said collection of peptides or b) the theoretical number of unique amino acid sequences that could exist, e.g., based on design and/or preparation of the collection. In some embodiments, diversity is actual diversity, e.g., as measured and described in the Examples.

In some embodiments, a peptide collection as described herein is characterized by an actual diversity of at least $1\times10^4$ unique peptide sequences. In some embodiments, a peptide collection is characterized by an actual diversity of at least $1\times10^5$ unique peptide sequences. In some embodiments, a peptide collection is characterized by an actual diversity of at least $1\times10^6$ unique peptide sequences. In some embodiments, a peptide collection is characterized by an actual diversity of at least $1\times10^7$ unique peptide sequences. In some embodiments, a peptide collection is characterized by an actual diversity of at least $1\times10^8$ unique peptide sequences. In some embodiments, a peptide collection is characterized by an actual diversity of at least $1\times10^9$ unique peptide sequences. In some embodiments, a peptide collection is characterized by an actual diversity of at least $1\times10^{10}$ unique peptide sequences. In some embodiments, a peptide collection is characterized by an actual diversity of at least $1\times10^{11}$ unique peptide sequences. In some embodiments, a peptide collection is characterized by an actual diversity of at least $1\times10^{12}$ unique peptide sequences. In some embodiments, a peptide collection is characterized by an actual diversity of at least $1\times10^{13}$ unique peptide sequences. In some embodiments, a peptide collection is characterized by an actual diversity of at least $1\times10^{14}$ unique peptide sequences. In some embodiments, a peptide collection is characterized by an actual diversity of at least $1\times10^{15}$ unique peptide sequences. In some embodiments, a preferred actual diversity for a peptide collection e.g., of a library, is $10^8$-$10^9$ unique peptide sequences. In some embodiments, such a collection may have a theoretical diversity that is often 1,000-10,000-fold greater than the actual diversity, for example, 10 positions with 16 amino acid possibilities at each position can have a theoretical diversity of $10^{12}$; depending on procedures, purposes, etc., a collection of peptides, e.g., of a library may be prepared with a subset of the theoretical diversity, e.g., of $10^8$ unique sequences.

In some embodiments, one or more, or each of the amino acid residue positions are randomized. In some embodiments, at a randomized position a variety of amino acid residues are independently presented in a collection of peptides (e.g., a library described in an example). In some embodiments, each position is randomized. In some embodiments, a collection is provided without amino acid residue preferences at any positions (e.g., in some embodiments, a "naïve" or "unbiased" collection/library). As appreciated by those skilled in the art, incorporation of randomized positions in some embodiments can be done by encoding a degenerate codon in an oligonucleotide primer used to generate a library, for example, NNN or NNK where N=A, T, C, G and K=T, G. Alternatively, randomized positions can be incorporated by the use of trimer phosphoroamidite mixtures, e.g., those available from Glen research, wherein a defined mixture of trimer codons that encode a corresponding defined mixture of amino acids are incorporated in the oligonucleotide primer used to generate the library. For example, a library could be constructed using a mixture of all 20 naturally occurring amino acids, or alternatively by using a subset of all 20 naturally occurring amino acids (e.g., A, D, E, F, H, I, L, M, N, Q, R, S, T, V, W, Y, etc.). In some embodiments, non-natural amino acids may also be incorporated using various technologies.

In some embodiments, peptides of a collection, e.g., a library, comprise fixed or a subset of preferred amino acids within at one or more positions for one or more desired property and/or activity, e.g., in some embodiments, to favor an alpha-helical conformation. For example, incorporation of alanine residues at defined positions in the middle of the peptide (e.g. library designs b), e), and h) above), a proline at the N-terminus (e.g. library designs g), h), i) above), or an aspartic acid followed by a proline at the N-terminus (e.g. library designs d), e), f) in the list above). In some embodiments, a desired property or activity is binding to a particular target (e.g., protein, nucleic acid, etc.). In some embodiments, a desired property or activity is cell penetration. In some embodiments, a desired property or activity is stability (e.g., to proteases or other types of degradation). In some embodiments, a desired property or activity is low immunogenicity. In some embodiments, a desired property or activity is improved physicochemical property. In some embodiments, a desired property or activity is improved pharmacokinetic properties. In some embodiments, a desired property or activity is selectivity for a target or tissue. As those skilled in the art will appreciate, fixed and/or a subset of preferred amino acids may be independently presented at each of one or more positions to provide one or more desired properties and/or activities.

In some embodiments, collections, e.g., peptide libraries, can be designed on the basis of one or more preferred or parent sequences. In some embodiments, a parent sequence is systematically diversified to give rise to many collection members. In some embodiments, a parent sequence is subjected to an "alanine scan" where each residue within the sequence is changed to alanine, either individually or in combination with other changes, mutations and/or modifications, to provide a number of peptides in a collection. In some embodiments, alanine scan is useful for assessing importance of one or more residues for certain properties and/or activities, e.g., binding, interactions, stability, physicochemical properties, cell penetration, immunogenicity, selectivity (e.g., for a target (e.g., protein, nucleic acid, etc.), tissue, etc.), pharmacokinetic properties, etc. A parent sequence could similarly be systematically changed/mutated to proline or glycine e.g., for assessing the effect of structural and/or conformational changes. A parent sequence could also be systematically changed/mutated to charged residues, e.g., for interrogating roles of charge in binding, stability, physicochemical properties, cell penetration, immunogenicity, selectivity, pharmacokinetic properties, etc. A parent sequence could also be systematically changed/mutated at each position to a variety of amino acids, e.g., for identifying point-mutations with improved properties and/or activities, e.g., binding, stability, physicochemical properties, cell penetration, immunogenicity, selectivity, pharmacokinetic properties, etc. As those skilled in the art will appreciate, collections can be designed using various established methods of library mutagenesis and directed evolution in accordance with the present disclosure.

In some embodiments, a parent sequence is pancreatic polypeptide, neuropeptide Y, or peptide YY, or a fragment thereof. In some embodiments, a fragment has a length of 5, 6, 7, 8, 9, 10, 11, 12, 13, 14, 15, 16, 17, 18, 19, 20, or more, amino acid residues. For example, in some embodiments, a sequence is selected from:

TABLE S-1

| Species | Sequence |
|---|---|
| Homo sapiens | PSKPDNPGEDAPAEDMARYYSALGHYINLIT (SEQ ID NO: 4) |

TABLE S-1-continued

| Species | Sequence |
| --- | --- |
| Ictalurus punctatus | PSKPENPGEDAAPEELAKYYTALRHYINLIT (SEQ ID NO: 5) |
| Marmota marmota | PLEPVYPGDNATPEQMAQYAAELRRYINMLT (SEQ ID NO: 6) |
| Myotis lucifugus | PSKPEKPGENASAEELARYYSALRHYINLIT (SEQ ID NO: 7) |
| Betta splendens | PPKPENPGEDAPPEELAKYYTALRHYINLIT (SEQ ID NO: 8) |
| Notechis scutatus | PPKPESPGENASPEEMAKYLADLRHYINLVT (SEQ ID NO: 9) |
| Orcinus orca | PAKPEAPGSHASPEELKRYYLSLRHFLNLVT (SEQ ID NO: 10) |
| Calypte anna | PPKPETPGDEASPEEVAKYFSALRHYINLVT (SEQ ID NO: 11) |
| Podarcis muralis | PQQPEHPGEDASAEEMARYLSALRHYLNLVT (SEQ ID NO: 12) |
| Vombatus ursinus | PSKPKPPSENASREELSRYYAALRQYLNLVT (SEQ ID NO: 13) |
| Ornithorhynchus anatinus | PVKPQPPPDNATPEELAQYFASLRHYLNLVT (SEQ ID NO: 14) |
| Otolemur garnettii | PLEPVYPGENATPEQMAQYAAELRRYINMLT (SEQ ID NO: 15) |
| Gulo gulo | PSKPDNPGEDAPAEDMARYYSALRHYINLIT (SEQ ID NO: 16) |
| Crocodylus porosus | PSKPDNPGEDAPAEDMARYYSALRHYINLIT (SEQ ID NO: 17) |

In some embodiments, a parent sequence is a sequence that shares certain level of homology with another sequence, e.g., pancreatic polypeptide sequences above. In some embodiments, a level is 85%, 90%, 95% or more. In some embodiments, a level is 90%. In some embodiments, a level is 95%. In some embodiments, amino acid sequences of stapled peptides are the same as parent sequences except one or more residues of the parent sequences are replaced with residues for stapling (e.g., cysteine residues for cysteine stapling as described herein). In some embodiments, amino acid sequences of stapled peptides are the same as parent sequences except two or more residues of the parent sequences are replaced with residues for stapling. In some embodiments, amino acid sequences of stapled peptides are the same as parent sequences except two residues of the parent sequences are replaced with residues for stapling.

In some embodiments, collections of peptides, e.g., various libraries, are based on pancreatic polypeptides. In some embodiments, libraries of pancreatic polypeptides comprise randomization of one or more residues in an alpha-helical region. In some embodiments, libraries of pancreatic polypeptide, neuropeptide Y, or peptide YY comprise randomization of one or more residues in the PPII region. In some embodiments, libraries of pancreatic polypeptide, neuropeptide Y, or peptide YY comprise randomization of one or more residues in a loop region. In some embodiments, libraries of pancreatic polypeptide, neuropeptide Y, or peptide YY comprise randomization of one or more residues in two or more regions of the peptide. In some embodiments, such libraries are prepared by randomizing residues one or more regions.

In some embodiments, pancreatic polypeptide, neuropeptide Y, or peptide YY is from *Homo sapiens*. In some embodiments, pancreatic polypeptide, neuropeptide Y, or peptide YY is from *Ictalurus punctatus*. In some embodiments, pancreatic polypeptide, neuropeptide Y, or peptide YY is from *Marmota marmota*. In some embodiments, pancreatic polypeptide, neuropeptide Y, or peptide YY is from *Myotis lucifugus*. In some embodiments, pancreatic polypeptide, neuropeptide Y, or peptide YY is from Betta *splendens*. In some embodiments, pancreatic polypeptide, neuropeptide Y, or peptide YY is from *Notechis scutatus*. In some embodiments, pancreatic polypeptide, neuropeptide Y, or peptide YY is from *Orcinus orca*. In some embodiments, pancreatic polypeptide, neuropeptide Y, or peptide YY is from *Calypte anna*. In some embodiments, protein folds with higher thermal stability are preferred scaffolds for randomization/generation of libraries. In some embodiments, libraries, e.g., of pancreatic polypeptides, are prepared by randomizing residues of a naturally occurring pancreatic polypeptide fold with high thermal stability. In some embodiments, libraries of pancreatic polypeptides are prepared by randomizing residues of a pancreatic polypeptide fold that has been modified to improve thermal stability.

In some embodiments, the present disclosure provides methods for optimizing a peptide of a parent sequence. In some embodiments, the present disclosure provides methods comprising:

modifying a peptide by replacing each of one or more amino acid residues independently with a different amino acid residue to provide a modified peptide, wherein the modified peptide comprises at least two residues suitable for stapling; and stapling the two residues suitable for stapling.

In some embodiments, a peptide is of or comprises a parent sequence as described herein (e.g., a peptide YY sequence or a fragment thereof). In some embodiments, the two residues suitable for stapling are cysteine residues. In some embodiments, two cysteine residues are stapled as described herein, e.g., using reagents described herein. In some embodiments, a modified peptide provides an improved properties and/or activity, e.g., improved affinity and/or selectivity for target binding, improved stability, improved helix formation, improved cell penetration, etc. In some embodiments, a collection of modified peptides are prepared, e.g., by randomizing one or more residues as described herein. In some embodiments, collections of modified peptides are provided as phase display libraries. In some embodiments, members of such collections/libraries have staples, e.g., cysteine staples, as described herein. In some embodiments, the present disclosure provides, comprising contacting provided collections, libraries or modified peptides with a target of interest so that one or more stapled peptides of the collection binds to the target, and determining amino acid sequences of stapled peptides that bind to the target as described herein.

As will be appreciated by those skilled in the art, provided technologies are applicable to various parent sequences and/or helical scaffolds. In some embodiments, a parent sequence is, or is a fragment (comprising, e.g., 5, 6, 7, 8, 9, 10, 11, 12, 13, 14, 15, 16, 17, 18, 19, 20, or more amino acid residues), or is a helical scaffold of, exendin-4, trp-cage peptides, retro trp-cage peptides, conotoxins, scyllatoxins, scorpion toxins, charybdotoxin, villin headpiece, beta-alpha-beta motif peptides, beta-beta-alpha motif peptides, mastoparan, zinc fingers, helix-linker-helix scaffolds, leucine zipper scaffolds, pancreatic polypeptide scaffolds, neuropeptide Y scaffolds, peptide YY scaffolds, mutants of the aforementioned scaffolds that have been modified for the purpose of increased helix stabilization, and other helical display scaffolds in the art. In some embodiments, peptides of provided collections comprise helix-initiating or helix-termination sequences. In some embodiments, peptides of provided collections comprise an N-terminal leader sequence such as AAA, DPA, NPA, APA, PA, P, or AP, and/or a C-terminal leader sequence such as R, RR, RP, RG, GR, PR, G, GG, P, PP, GP, or PG.

In some embodiments, cysteines are incorporated into sequences of peptides, e.g. displayed peptides using various display technologies. In some embodiments, peptides which bind a target peptide or protein at a site within close distance of one or more cysteines on the target protein may be identified via the formation a covalent bond between the cysteine on a peptide and a cysteine of the target protein (e.g., on its surface), either directly or through a linker (e.g., through using various reagents suitable for cross-linking cysteine residues), which in some embodiments can lead to an observed high-affinity and/or slow off-rate interactions in an assay (e.g., a screen assay assessing binding). Among other things, identification of such cysteines are useful for various purposes, e.g., development of agents that can interact the targets (e.g., covalent target inhibitors), use of disulfide tethering for library synthesis, compound optimization, etc. Those skilled in the art will appreciates that various uses of target cysteines, e.g., surface cysteines on targets, are available in the art.

Peptides of the present disclosure can have various sequences. Useful sequences can have various percentage and/or numbers of one or more amino acid residues. For example, in some embodiments, a sequence comprises 2 and no more than 2 cysteine residues (either stapled or not). In some embodiments, a sequence comprises more than 2 cysteine residues (either stapled or not). In some embodiments, a sequence comprises 2 and no more than 2 stapled cysteine residues. In some embodiments, a sequence comprises more than 2 stapled cysteine residues. In some embodiments, a percentage of stapled cysteine residues in a sequence is 5%-50%. In some embodiments, a percentage is no more than 5%, 6%, 7%, 8%, 9%, 10%, 11%, 12%, 13%, 14%, 15%, 20%, 25%, 30%, 35%, 40%, or 50%. In some embodiments, a percentage is about 5%, 6%, 7%, 8%, 9%, 10%, 11%, 12%, 13%, 14%, 15%, 20%, 25%, 30%, 35%, 40%, or 50%. In some embodiments, a percentage is about or no more than about 5%. In some embodiments, a percentage is about or no more than about 6%. In some embodiments, a percentage is about or no more than about 7%. In some embodiments, a percentage is about or no more than about 8%. In some embodiments, a percentage is about or no more than about 9%. In some embodiments, a percentage is about or no more than about 10%. In some embodiments, a percentage is about or no more than about 11%. In some embodiments, a percentage is about or no more than about 12%. In some embodiments, a percentage is about or no more than about 13%. In some embodiments, a percentage is about or no more than about 14%. In some embodiments, a percentage is about or no more than about 15%. In some embodiments, a percentage is about or no more than about 20%.

In some embodiments, collections of peptides, e.g., provided peptide libraries, are utilized to screen for peptides of certain properties and/or activities. Various screening technologies are described in the art and can be utilized in accordance with the present disclosure. In some embodiments, a library is screened against a target, e.g., a protein, a nucleic acid, etc. In some embodiments, all amino acid residues in a target are D configured amino acids (e.g., a mirror-image display). In some embodiments, libraries are screened against cells, e.g., cell samples, cells grown in culture, etc., or in vivo, using various technologies described in the art. In some embodiments, libraries are screened against human cells. In some embodiments, libraries are screened in a living mammal. In some embodiments, libraries are screened in a living primate.

In some embodiments, libraries are screened for binding affinity to targets, e.g., proteins, nucleic acids, etc. In some embodiments, libraries are screened for selectivity for one target (e.g., a protein) over another target (e.g., a protein). In some embodiments, libraries are screened for one or more desired characteristics such as stability, physicochemical properties, cell penetration, immunogenicity (e.g., low immunogenicity), pharmacokinetic properties, etc. In some embodiments, libraries are screened for affinity to lipids, for optimizing physicochemical properties, and/or cell penetration. In some embodiments, libraries are screened against immobilized lipids, for optimizing physicochemical properties and/or cell penetration. In some embodiments, libraries are screened for crossing blood-brain-barrier or neural barriers, either in vivo or with in vitro models of a blood-brain-barrier or neural barriers. In some embodiments, libraries are screened for crossing intestine or other relevant epithelial cells, either in vivo or with in vitro models of intestine or other relevant epithelial cells. In some embodiments, libraries are screened using organoid models.

In some embodiments, screens are performed in buffers that have been optimized, e.g., for targets (e.g., proteins, cells. etc.) that are subjects of the screens. In some embodiments, screens are performed in buffers that reduce nonspecific binding, for example, buffers comprising bovine serum albumin, bovine gamma-globulin, collagen and sheared collagen, milk proteins, randomized mixtures of synthetic peptides, lysates of bacteria or mammalian cells, lysates or protein preparations subjected to limited proteolysis, poly (deoxyinosinic-deoxycytidylic) acid, salmon sperm DNA, sheared DNA, polylysine, glycerol, trehalose, detergents such as Triton X-100, NP-40, Tween-20, Tween-80, Pleuronic F-127, octyl beta-D-glucopyranoside, etc. Additional additives are known to those skilled in the art and can be utilized in accordance with the present disclosure.

Using technologies described herein, e.g., peptide collections (libraries), screens, etc., peptide binders for diverse protein targets (e.g., beta-catenin (CTNNB1), CBL, CBLB, TEAD4, ERG) were identified.

In some embodiments, stapled peptides or collections thereof may be assessed relative to reference peptides and/or collections thereof. In some embodiments, a reference peptide is an unstapled peptide. In some embodiments, a reference peptide is an unstapled peptide of the same or a comparable sequence. In some embodiments, a peptide is a peptide comprising cysteine stapling, and a reference peptide does not have such cysteine stapling. In some embodiments, a reference peptide do not contain cysteines utilized in cysteine stapling. In some embodiments, a reference peptide does not contain a PPII region of pancreatic polypeptide, neuropeptide Y, or peptide YY which can be utilized to stabilize helical structures.

In some embodiments, a peptide collection as described herein is characterized by a certain redundancy. In some embodiments, redundancy in the context of a collection of peptides (or proteins, etc.; e.g., of a provided library) refers to the number of copies of a unique amino acid sequence within said collection of peptides. In some embodiments, a peptide collection as described herein is characterized by a redundancy of at least 10000. In some embodiments, a peptide collection as described herein is characterized by a redundancy of at least 5000. In some embodiments, a peptide collection as described herein is characterized by a redundancy of at least 1000. In some embodiments, a peptide collection as described herein is characterized by a redundancy of at least 500. In some embodiments, a peptide collection as described herein is characterized by a redundancy of at least 100. In some embodiments, a peptide collection as described herein is characterized by a redundancy of at least 50. In some embodiments, a peptide collection as described herein is characterized by a redundancy of at least 10. In some embodiments, a peptide collection as described herein is characterized by a redundancy of at least 1. In some embodiments, a preferred redundancy with respect to an actual diversity is 100-1000 phages for each unique sequence in a given screening sample, providing a good oversampling of each sequence. For example, a library of $10^8$ sequences and 1000 phages per sequence will contain $10^{11}$ phage particles; in a typical screen of 48 samples, there would therefore be $4.8*10^{12}$ total phages.

In some embodiments, a collection of peptides comprises a "spiked-in" standard. In some embodiments, a spiked-in standard is added to a collection of peptides after screening and prior to sequencing of identifying nucleic acid sequences (e.g., those encoding the peptides) of said collection of peptides. In some embodiments, a spiked-in standard is a spiked-in phage. In some embodiments, a spiked-in standard is a spiked-in nucleotide sequence. In some embodiments, a spiked-in standard serves an internal standard. In some embodiments, a spiked-in standard allows for measurement of enrichment of certain amino acid sequences.

In some embodiments, a collection of peptides can be provided and/or utilized in a phage display format. In some embodiments, the present disclosure provides a method comprising the steps of:
  i) expressing in a cell a nucleic acid encoding a peptide having an amino acid sequence that: has a length within a range of a* to b* amino acid residues, includes at least one pair of cysteine residues separated by 2 to 15 amino acid residues, and wherein the nucleic acid encodes a fusion protein that is incorporated into a phage particle;
  ii) isolating phage particles from the cell; and
  iii) contacting phage particles with a cross-linking agent, e.g., having the structure of $R^x$-$L^{s2}$-$R^x$ or a salt thereof or formula R-I:

$$R^x\text{-}L^{x1}\text{-}C(O)Q\text{-}L'\text{-}QC(O)\text{-}L^{x2}\text{-}R^x \qquad \text{R-I},$$

or a salt thereof, wherein:
  a*, b*, and $R^x$, Q, and L' are described in the present disclosure.

In some embodiments, a cross-linking agent is a reagent as described herein. In some embodiments, a cross-linking agent is a compound having the structure of $R^E$-$L^{s2}$-$R^E$ or a salt thereof. In some embodiments, a cross-linking agent is a compound having the structure of $R^E$-$L^{x1}$-$C(O)Q$-$L'$-$QC(O)$-$L^{x2}$-$R^E$ or a salt thereof. In some embodiments, a cross-linking agent is a compound having the structure of $R^E$—C(O)Q-L'-QC(O)—$R^E$ or a salt thereof. In some embodiments, a cross-linking agent is a compound having the structure of $R^x$-$L^{s2}$-$R^x$ or a salt thereof. In some embodiments, a cross-linking agent is a compound having the structure of RX-$L^{x1}$-C(O)Q-L'-QC(O)-$L^{x2}$-$R^x$ or a salt thereof.

In some embodiments, the present disclosure provides a method further comprising the steps of:
  iv) contacting the collection of peptides with a target of interest so that one or more stapled peptides of the collection binds to a target of interest; and
  v) determining amino acid sequences of stapled peptides that bind to a target of interest.

In some embodiments, each amino acid sequence is discretely associated with an identifier so that each amino acid sequence can be independently identified. In some embodiments, each amino acid sequence is independently associated with an identifier that comprises a nucleic acid sequence that encodes an amino acid sequence or a portion (e.g., 5, 6, 7, 8, 9, 10, 11, 12, 13, 14, 15, 16, 17, 18, 19, 20, 21, 22, 23, 24, 25 or more optionally consecutive amino acid residues, or 10%, 20%, 30%, 40%, 50%, 60%, 70%, 80%, 90%, 95% or more, of the amino acid sequence) thereof. In some embodiments, association is covalent. In some embodiments, association is through a discrete system comprising an amino acid sequence and its identifier. In some embodiments, a system is a cell, phage, etc. that comprises and/or expresses an amino acid sequence and its identifier. In some embodiments, determination of an amino acid sequence comprises determining nucleotide sequences that encode peptides of a fusion protein incorporated into a phage particle. In some embodiments, determining amino acid sequences comprises the use of high-throughput sequencing of nucleic acids encoding the amino acid sequences. In some embodiments, high-throughput sequencing comprises single-molecule real-time sequencing, ion semiconductor sequencing (e.g. Ion Torrent Sequencing), pyrosequencing, sequencing by synthesis, sequencing by ligation (e.g. SOLiD sequencing), nanopore sequencing, etc. As appreciated by those skilled in the art, various high-throughput sequencing technologies can be utilized in accordance with the present disclosure. In some embodiments, the present disclosure recognizes that technologies prior to the present disclosure can be severely and inherently limited and in many instances cannot be successfully performed when libraries containing large numbers of diverse amino acid sequences are utilized as e.g., amino acid sequences with desired properties and/or activities cannot be readily identified from background noise, e.g., due to the limited numbers of sequences that can be individually assessed. Among other things, the present disclosure demonstrates that the combination of peptide libraries and high-throughput sequencing of the corresponding encoding nucleic acid sequences are particularly powerful for screening peptide libraries comprising large numbers of diverse sequences and identifying from such libraries useful amino acid sequences, in some instances, amino acid sequences very different or totally different from natural amino acid sequences. In some embodiments, provided technologies greatly improve throughput and/or enable analysis/assessment of many candidate sequences at unprecedented level.

In some embodiments, the present disclosure provides a method further comprising the steps of:
  vi) synthesizing a new collection of peptides guided by patterns observed during the determination of amino acid sequences of stapled peptides that bind to a target of interest.

In some embodiments, the present disclosure provides a method comprising identifying or characterizing a binding agent specific for a target of interest, the method comprising steps of contacting the target of interest with members of a collection of stapled peptides; and detecting specific binding by one or more of the members to the target.

In some embodiments, a collection of peptides is a collection of polypeptides. In some embodiments, a collection of peptides is a collection of polypeptides with secondary structure. In some embodiments, a collection of peptides is a collection of polypeptides with a tertiary structure. In some embodiments, a collection of polypeptides is a collection of proteins. In some embodiments a collection of proteins is a collection of stapled proteins.

As described in the present disclosure, in some embodiments, peptides in a library comprise an amino acid sequences, e.g., for screening. In some embodiments, such amino acid sequences comprise stapled amino acid residues. In some embodiments, such amino acid sequences have the same length, and/or have the staples at the same positions. In some embodiments, the amino acid sequences in a collection of peptides of a library comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 random positions, the amino acid residue at each of such positions can independently be any amino acid residue (e.g., natural amino acid residue). In some embodiments, there are at least 5 random positions. In some embodiments, there are at least 6 random positions. In some embodiments, there are at least 7 random positions. In some embodiments, there are at least 8 random positions. In some embodiments, there are at least 9 random positions. In some embodiments, there are at least 10 random positions. In some embodiments, there are at least 11 random positions. In some embodiments, there are at least 12 random positions. In some embodiments, there are at least 13 random positions. In some embodiments, there are at least 14 random positions. In some embodiments, there are at least 15 random positions. In some embodiments, there are at least 16 random positions. In some embodiments, there are at least 17 random positions. In some embodiments, each amino acid residue except the stapled residues is independently random. In some embodiments, at a random position there are at least 2, 3, 4, 5, 6, 7, 8, 9, 10, 11, 12, 13, 14, 15, 16, 17, 18, 19 or 20 different amino acid residues with in a collection of peptides of a library. In some embodiments, there are at least 2 different amino acid residues. In some embodiments, there are at least 3 different amino acid residues. In some embodiments, there are at least 4 different amino acid residues. In some embodiments, there are at least 5 different amino acid residues. In some embodiments, there are at least 6 different amino acid residues. In some embodiments, there are at least 7 different amino acid residues. In some embodiments, there are at least 8 different amino acid residues. In some embodiments, there are at least 9 different amino acid residues. In some embodiments, there are at least 10 different amino acid residues. In some embodiments, there are at least 15 different amino acid residues. In some embodiments, there are at least 20 different amino acid residues.

Library Scaffold

In some embodiments, the present disclosure provides a collection of peptides of the structure:

$[X^0]_{p0}[X^1]_{p1}[X^2]_{p2}[X^3]_{p3}[X^4]_{p4}[X^5]_{p8}[X^6]_{p6}[X^7]_{p7}[X^8]_{p8}$
$[X^9]_{p9}[X^{10}]_{p10}[X^{11}]_{p11}[X^{12}]_{p12}[X^{13}]_{p13}$-
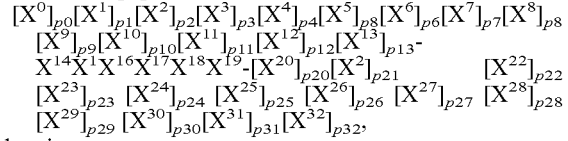
$[X^{23}]_{p23}[X^{24}]_{p24}[X^{25}]_{p25}[X^{26}]_{p26}[X^{27}]_{p27}[X^{28}]_{p28}$
$[X^{29}]_{p29}[X^{30}]_{p30}[X^{31}]_{p31}[X^{32}]_{p32}$, wherein:
$X^0$ is a scaffold constant region;
each of p0, p1, p2, p3, p4, p5, p6, p7, p8, p9, p10, p11, p12, p13, p20, p21, p22, p23, p24, p25, p26, p27, p28, p29, p30, p31, p32 is independently 0 or 1;
each of $X^1$ to $X^{32}$ is independently an amino acid residue;
at least two of $X^1$ to $X^{32}$ comprise side chains that are optionally linked together to form a staple.

In some embodiments, p0 is 0. In some embodiments, p0 is 1.

In some embodiments, a scaffold constant region provides a peptide sequence that is at least 50%, 60%, 70%, 80%, 90%, or 95% homologous to naturally occurring amino acid sequence. In some embodiments, the homology is at least 50%. In some embodiments, the homology is at least 60%. In some embodiments, the homology is at least 70%. In some embodiments, the homology is at least 80%. In some embodiments, the homology is at least 90%. In some embodiments, the homology is at least 95%. In some embodiments, a scaffold constant region comprises the amino acid sequence AGPAKPEAGEDASP (SEQ ID NO: 18).

Targets of Interest

In some embodiments, the present disclosure provides reagents, peptide agents, and combinations of peptides that interact with a target of interest. In some embodiments, a target of interest is a biomolecule (e.g. protein, RNA, DNA, etc.), a tissue, or a cell. In some embodiments, a target of interest has an activity or characteristic that is associated with a disease, disorder or condition. In some embodiments, a target of interest is a protein. In some embodiments, a target of interest is a protein associated with a condition, disorder or disease, e.g., a protein associated with cancer. Many targets associated with various conditions, disorders or diseases are known in the art and can be targeted using technologies of the present disclosure.

In some embodiments, a target of interest may be an entity that occurs in a biological system or organism (e.g., a human). In some embodiments, a target of interest may have a known interaction partner. In some embodiments, a target of interest may not have any known interaction partner, or may not have any known interaction partner whose binding interaction with the target is characterized by one or more features as described herein.

In some embodiments, a target of interest may be or comprise one or more of beta-catenin and Casitas B-lineage lymphoma proto-oncogene-b (Cbl-b). In some embodiments, a target of interest is beta-catenin. In some embodiments, a target of interest is Casitas B-lineage lymphoma proto-oncogene-b (Cbl-b).

Reagents

In some embodiments, the present disclosure provides reagents useful in the production, identification, characterization and/or use of stapled peptides (e.g., cysteine stapled peptides). In some embodiments, provided reagents are particularly useful, for example, they provide high yields and/or purities when used in combination of a biological system (e.g., a system that expresses amino acid sequences).

In some embodiments, the present disclosure provides compounds (e.g., that may be useful as reagents) having the structure of $R^E$-$L^{s2}$-$R^E$ or a salt thereof, wherein each variable is as described in the present disclosure. In some embodiments, $R^E$ is or comprises an electrophilic group. As appreciated by those skilled in the art, various electrophilic groups are known and utilized in the art and can be utilized in accordance with the present disclosure. In some embodiments, an electrophilic group reacts with —SH, e.g., —SH of an amino acid side chain, under suitable conditions (e.g., certain pH conditions utilized in the art) so that a reaction occurs between the —SH group and the electrophilic group forming a covalent bond between the —S— and the electrophilic group. In some embodiments, an electrophilic group comprises a leaving group bonded to a carbon atom, e.g., —CH$_2$R$^x$, wherein R$^x$ is a leaving group. In some embodiments, —SH reacts with —CH$_2$R$^x$ to form —CH$_2$—S—. In some embodiments, an electrophilic group is or comprises a double or triple bond. In some embodiments, a double or triple bond is bonded to one or more electron-withdrawing groups (e.g., one or more —C(O)— groups). In some embodiments, an electrophilic group is a Michael accepter. In some embodiments, an electrophilic group is or comprises

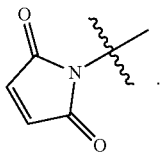 [SMILES: *N1C(=O)C=CC1=O]

In some embodiments, R$^E$ is

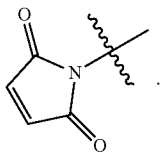 [SMILES: *N1C(=O)C=CC1=O]

In some embodiments, R$^E$ is R$^x$-L$^{x1}$-. In some embodiments, two R$^E$ in the same molecule is the same. In some embodiments, they are different. In some embodiments, useful compounds as reagents have the formula of R$^E$-L$^{x1}$-EWG-Q-L'-Q-EWG-L$^{x2}$-R$^E$ or a salt thereof, wherein each EWG is independently an electron-withdrawing group moiety (e.g., being or comprising —C(O)—, —S(O)—, —S(O)$_2$—, etc.) and each other variable is independently as described herein. In some embodiments, useful compounds as reagents have the formula of R$^E$-L$^{x1}$-C(O)Q-L'-QC(O)-L$^{x2}$-R$^E$ or a salt thereof, wherein each variable is independently as described herein. In some embodiments, useful compounds as reagents have the formula of R$^E$-L$^{x1}$-SO$_2$-Q-L'-Q-SO$_2$-L$^{x2}$-R$^E$ or a salt thereof, wherein each variable is independently as described herein. In some embodiments, useful compounds as reagents have the formula of R$^E$-EWG-Q-L'-Q-EWG-R$^E$ or a salt thereof, wherein each EWG is independently an electron-withdrawing group moiety (e.g., being or comprising —C(O)—, —S(O)—, —S(O)$_2$—, etc.) and each other variable is independently as described herein. In some embodiments, useful compounds as reagents have the formula of R$^E$-f-L'-QC(O)-R$^E$ or a salt thereof, wherein each variable is independently as described herein. In some embodiments, useful compounds as reagents have the formula of R$^E$—SO$_2$-Q-L'-Q-SO$_2$-R$^E$ or a salt thereof, wherein each variable is independently as described herein. In some embodiments, useful compounds as reagents have the formula of R$^E$-Q-L'-Q-R$^E$ or a salt thereof, wherein each variable is independently as described herein. In some embodiments, the present disclosure provides compounds (e.g., that may be useful as reagents) having the structure of R$^x$-L$^{s2}$-R$^x$ or a salt thereof, wherein each variable is as described in the present disclosure. In some embodiments, the present disclosure provides compounds (e.g., that may be useful as reagents) having the formula R-I:

R$^x$-L$^{x1}$-C(O)Q-L'-QC(O)-L$^{x2}$-R$^x$      R-I or a salt thereof, wherein:

each R$^x$ is independently a leaving group;

each Q is independently selected from a covalent bond, —N(R')—, —O—, and —S—;

each of L$^{x1}$, L$^{x2}$, and L' is independently a covalent bond, or an optionally substituted, bivalent C$_1$-C$_{20}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;

each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is —R, —C(O)R, —CO$_2$R, or —SO$_2$R;

each R is independently —H, or an optionally substituted group selected from C$_{1-30}$ aliphatic, C$_{1-30}$ heteroaliphatic having 1-10 heteroatoms independently selected from oxygen, nitrogen, sulfur, phosphorus and silicon, C$_{6-30}$ aryl, C$_{6-30}$ arylaliphatic, C$_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond; or two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon; and Various leaving groups are known in the art and may be utilized in accordance with the present disclosure, e.g., as embodiments for R$^x$. In some embodiments, a leaving group, e.g., R$^x$, is a halogen. In some embodiments R$^x$ is —Cl. In some embodiments RX is —Br. In some embodiments R$^x$ is —I. In some embodiments, a leaving group is —OSO$_2$R (e.g., wherein R is optionally substituted alkyl (e.g., perfluoroalkyl such as —CF$_3$)), optionally substituted phenyl, etc.). In some embodiments, a leaving group is —OTs or —OMs.

In some embodiments, R$^x$ groups within the same compound are the same. In some embodiments, R$^x$ groups within the same compound are different.

In some embodiments, L$^{x1}$ is an optionally substituted methylene group. In some embodiments, L$^{x1}$ is —CH$_2$—. In some embodiments, L$^2$ is an optionally substituted methylene group. In some embodiments, L$^{x2}$ is —CH$_2$—. In some embodiments, L$^{x1}$ and L$^{x2}$ are the same; in other embodiments, they are different. In some embodiments, both L$^{x1}$ and L$^{x2}$ are —CH$_2$—.

In some embodiments, Q is a covalent bond. In some embodiments, Q is selected from a covalent bond, —N(R')—, —O—, and —S—. In some embodiments, Q is —N(R')—, wherein R' is described in the present disclosure. In some embodiments, Q is —O—. In some embodiments, Q is —S—. In some embodiments, each Q is a covalent bond. In some embodiments, each Q is independently selected from —N(R')—, —O—, and —S—. In some embodiments, each Q is independently —N(R')—, wherein R' is described in the present disclosure. In some embodiments, each Q is independently —NH—. In some embodiments, each Q is independently —O—. In some embodiments, each Q is independently —S—.

In some embodiments, -Cy- is an optionally substituted bivalent $C_{3-20}$ cycloaliphatic ring. In some embodiments, -Cy- is an optionally substituted bivalent $C_{6-20}$ aryl ring. In some embodiments, -Cy- is an optionally substituted bivalent phenyl ring. In some embodiments, —Cy- is an optionally substituted 5-20 membered heteroaryl ring having 1-10 heteroatoms independently selected from oxygen, nitrogen, sulfur, phosphorus and silicon. In some embodiments, -Cy- is an optionally substituted 3-20 membered heterocyclyl ring having 1-10 heteroatoms independently selected from oxygen, nitrogen, sulfur, phosphorus and silicon. In some embodiments, -Cy- is monocyclic. In some embodiments, -Cy- is bicyclic. In some embodiments, -Cy- is polycyclic. In some embodiments, -Cy- comprises one or more optionally substituted heterocyclic rings, wherein each of the heterocyclic rings independently comprises one or more nitrogen atoms each of which is independently bonded to Q, or —C(O)— when Q is a covalent bond. In some embodiments, -Cy- is monocyclic. In some embodiments, —Cy- is bicyclic. In some embodiments, -Cy- is polycyclic.

In some embodiments, for a bicyclic or polycyclic ring, each of the monocyclic rings is independently a 3-10 (e.g., 3, 4, 5, 6, 7, 8, 9, or 10) membered saturated or partially unsaturated ring having 0-10 (e.g., 0, 1, 2, 3, 4, 5, 6, 7, 8, 9, or 10) heteroatoms (e.g., in some embodiments, selected from nitrogen, oxygen and sulfur) or a 5-10 (e.g., 3, 4, 5, 6, 7, 8, 9, or 10) membered aromatic ring having 0-10 (e.g., 0, 1, 2, 3, 4, 5, 6, 7, 8, 9, or 10) heteroatoms (e.g., in some embodiments, selected from nitrogen, oxygen and sulfur).

In some embodiments, L' is or comprises -Cy-. In some embodiments, L' is -Cy-.

In some embodiments, L' is optionally substituted bivalent $C_1$-$C_{19}$ aliphatic. In some embodiments, L' is optionally substituted bivalent $C_1$-$C_{15}$ aliphatic. In some embodiments, L' is optionally substituted bivalent $C_1$-$C_{10}$ aliphatic. In some embodiments, L' is optionally substituted bivalent $C_1$-$C_9$ aliphatic. In some embodiments, L' is optionally substituted bivalent $C_1$-$C_8$ aliphatic. In some embodiments, L' is optionally substituted bivalent $C_1$-$C_7$ aliphatic. In some embodiments, L' is optionally substituted bivalent $C_1$-$C_6$ aliphatic. In some embodiments, L' is optionally substituted bivalent $C_1$-$C_5$ aliphatic. In some embodiments, L' is optionally substituted bivalent $C_1$-$C_3$ aliphatic. In some embodiments, L' is optionally substituted bivalent $C_1$-$C_2$ aliphatic. In some embodiments, L' is optionally substituted bivalent $C_1$ aliphatic. In some embodiments, L' is —$CH_2$—. In some embodiments, L' is —$(CH_2)_2$—. In some embodiments, L' is —$(CH_2)_3$—. In some embodiments, L' is —$(CH_2)_4$—. In some embodiments, L' is —$(CH_2)_5$—. In some embodiments, L' is —$(CH_2)_6$—. In some embodiments, L' is —$(CH_2)_7$—. In some embodiments, L' is —$(CH_2)_5$—.

In some embodiments, L' is optionally substituted bivalent $C_{6-20}$ aryl ring. In some embodiments, L' is optionally substituted bivalent $C_{6-14}$ aryl ring. In some embodiments, L' is optionally substituted bivalent $C_{6-10}$ aryl ring. In some embodiments, L' is optionally substituted bivalent $C_6$ aryl ring. In some embodiments, L' is bivalent $C_6$ aryl ring substituted with at least one electron-withdrawing group as appreciated by those skilled in the art. In some embodiments, L' is bivalent $C_6$ aryl substituted with at least one halogen. In some embodiments, L' is bivalent $C_6$ aryl substituted with at least two halogen. In some embodiments, L' is bivalent $C_6$ aryl substituted with at least three halogen. In some embodiments, L' is bivalent $C_6$ aryl substituted with four halogen. In some embodiments, L' is bivalent $C_6$ aryl substituted with at least one fluorine. In some embodiments, L' is bivalent $C_6$ aryl substituted with at least two fluorine. In some embodiments, L' is bivalent $C_6$ aryl substituted with at least three fluorine. In some embodiments, L' is bivalent $C_6$ aryl substituted with four fluorine. In some embodiments, L' is bivalent $C_6$ aryl substituted with at least one chlorine. In some embodiments, L' is bivalent $C_6$ aryl substituted with at least two chlorine. In some embodiments, L' is bivalent $C_6$ aryl substituted with at least three chlorine. In some embodiments, L' is bivalent $C_6$ aryl substituted with four chlorine. In some embodiments, L' is bivalent $C_6$ aryl substituted at with least one —$O(CH_2)_{0-4}CH_3$. In some embodiments, L' is bivalent $C_6$ aryl substituted with at least two —$O(CH_2)_{0-4}CH_3$. In some embodiments, L' is bivalent $C_6$ aryl substituted with at least three —$O(CH_2)_{0-4}CH_3$. In some embodiments, L' is bivalent $C_6$ aryl substituted with four —$O(CH_2)_{0-4}CH_3$. In some embodiments, L' is optionally substituted

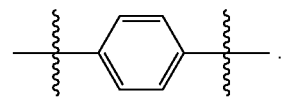 [SMILES: *c1ccc(*)cc1]

In some embodiments, L' is

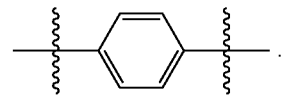 [SMILES: *c1ccc(*)cc1]

In some embodiments, L' is substituted

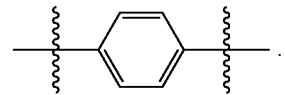

In some embodiments, L' is di-substituted

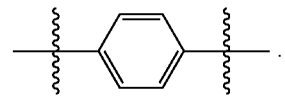

In some embodiments, L' is 2,5-di-substituted

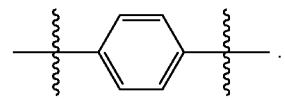

In some embodiments, L' comprises or is bivalent 5-20 membered heteroaryl ring having 1-10 heteroatoms independently selected from oxygen, nitrogen, sulfur, phosphorus and silicon. In some embodiments, L' is bivalent 5-6 membered heteroaryl ring having 1-4 heteroatoms independently selected from oxygen, nitrogen, sulfur, phosphorus and silicon. In some embodiments, L' is bivalent 5-6 membered heteroaryl ring having 1-4 heteroatoms independently selected from oxygen, nitrogen, and sulfur. In some embodiments, L' is bivalent 6 membered heteroaryl ring having 1-2 heteroatoms independently selected from oxygen, nitrogen, and sulfur. In some embodiments, L' is bivalent 6 membered heteroaryl ring having 2 nitrogen.

In some embodiments, L' is optionally substituted bivalent $C_{3-20}$ cycloaliphatic ring. In some embodiments, L' is optionally substituted bivalent $C_{3-15}$ cycloaliphatic ring. In some embodiments, L' is optionally substituted bivalent $C_{3-10}$ cycloaliphatic ring. In some embodiments, L' is optionally substituted bivalent $C_{3-9}$ cycloaliphatic ring. In some embodiments, L' is optionally substituted bivalent $C_{3-8}$ cycloaliphatic ring. In some embodiments, L' is optionally substituted bivalent $C_{3-7}$ cycloaliphatic ring. In some embodiments, L' is optionally substituted bivalent $C_{3-6}$ cycloaliphatic ring. In some embodiments, L' is optionally substituted bivalent $C_{3-5}$ cycloaliphatic ring. In some embodiments, L' is optionally substituted bivalent $C_{3-4}$ cycloaliphatic ring. In some embodiments, L' is optionally substituted bivalent $C_3$ cycloaliphatic ring. In some embodiments, L' is optionally substituted bivalent $C_4$ cycloaliphatic ring. In some embodiments, L' is optionally substituted bivalent $C_5$ cycloaliphatic ring. In some embodiments, L' is optionally substituted bivalent $C_5$ cycloalkyl ring. In some embodiments, L' is optionally substituted bivalent $C_5$ cycloalkenyl ring. In some embodiments, L' is optionally substituted bivalent $C_6$ cycloaliphatic ring. In some embodiments, L' is optionally substituted bivalent $C_6$ cycloalkyl ring.

In some embodiments, $L^{s2}$ comprises —N(R')-L'-N(R')— and L' is a covalent bond. In some embodiments $L^{s2}$ comprises —N(R)—N(R)—, wherein:
  each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or
  two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments $L^{s2}$ comprises —N(R)—N(R)—, wherein:
  each R is independently optionally substituted $C_{1-30}$ aliphatic; or
  two or more R groups on two or more atoms are optionally and independently taken together with their intervening atoms to form an optionally substituted, 3-30 membered monocyclic ring.

In some embodiments, $L^{s2}$ is -$L^{x1}$-C(O)Q-L'-QC(O)-$L^{x1}$-, wherein each variable is independently as described in the present disclosure. In some embodiments, $L^{s2}$ is —$CH_2$C(O)Q-L'-QC(O)$CH_2$—, wherein each —$CH_2$— is independently and optionally substituted. In some embodiments, $L^{s2}$ is —$CH_2$C(O)Q-L'-QC(O)$CH_2$—. In some embodiments, a provided compound, e.g., a compound of $R^x$-$L^{s2}$-$R^x$, is selected from the group consisting of: Table 1.

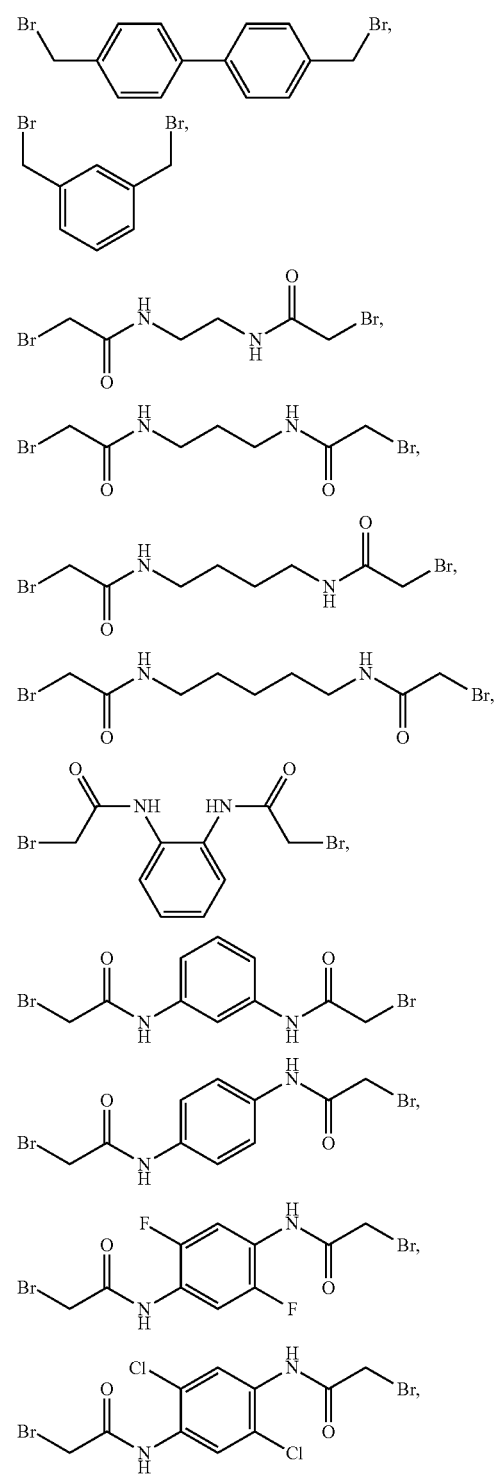

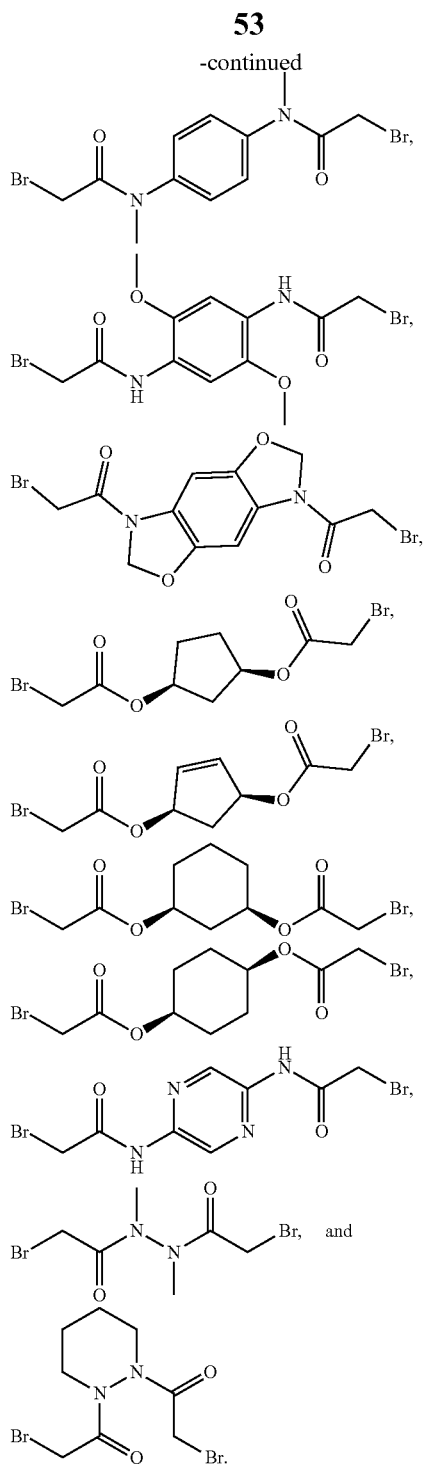
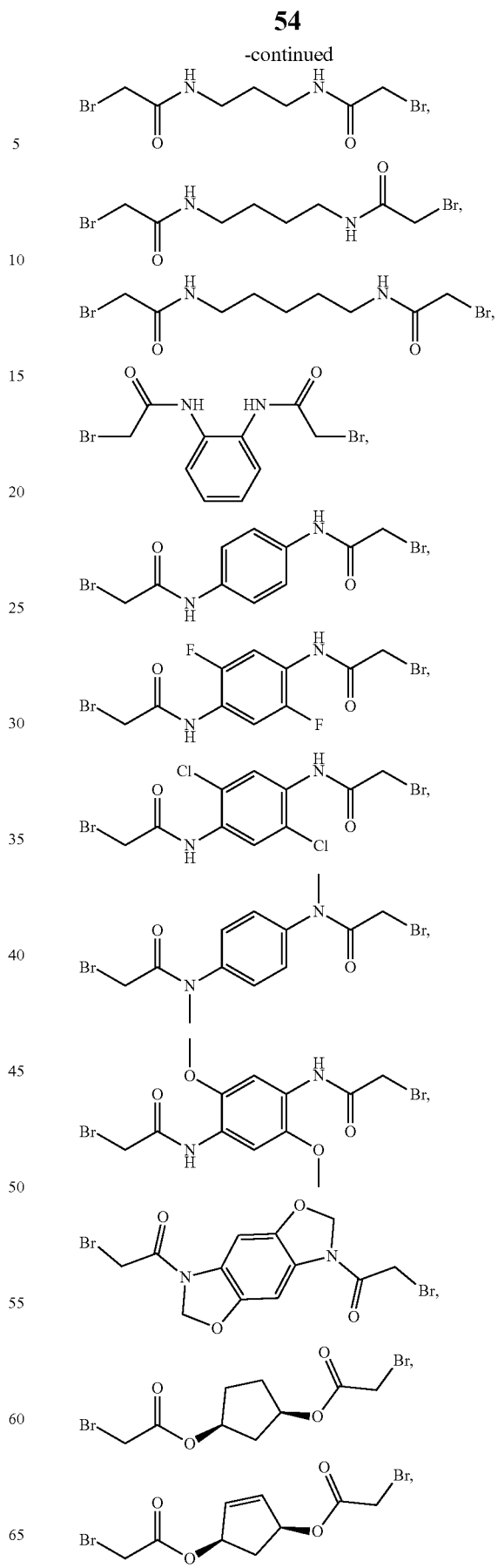
In some embodiments, a provided compound, e.g., a compound of $R^x$-$L^{s2}$-$R^x$, has the structure of $R^x$-$L^{x1}$-C(O)Q-L'-QC(O)-$L^{x2}$-$R^x$ or $R^x$—$CH_2$C(O)Q-L'-QC(O)$CH_2$—$R^x$ and is selected from the group consisting of Table 2:
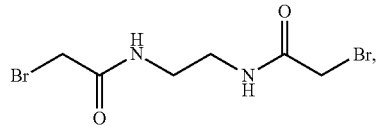

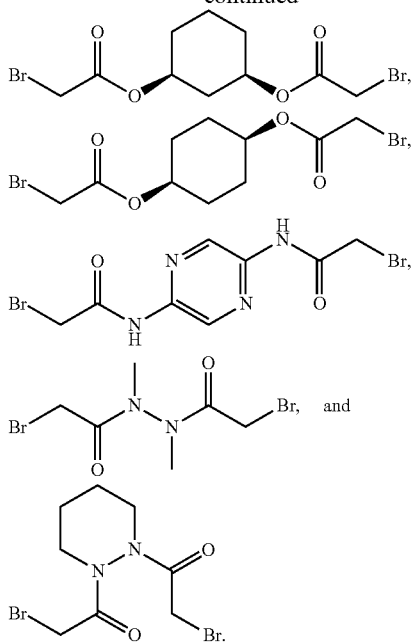

In some embodiments, a compound is not

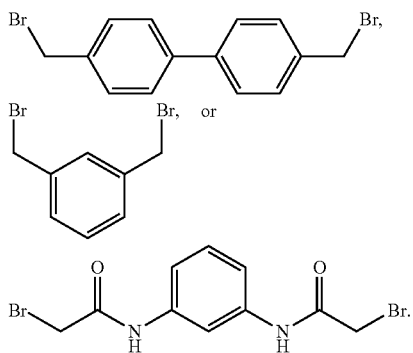

In some embodiments, a compound is not

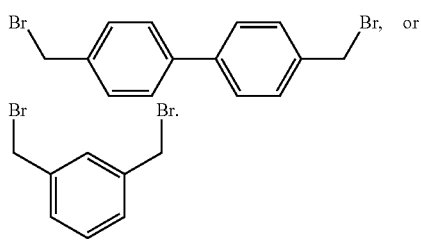

In some embodiments, a compound is not

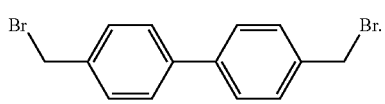 [SMILES: BrCc1ccc(-c2ccc(CBr)cc2)cc1]

In some embodiments, a compound is not

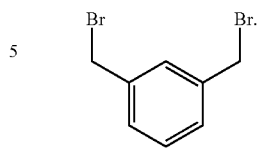

In some embodiments, a compound is not

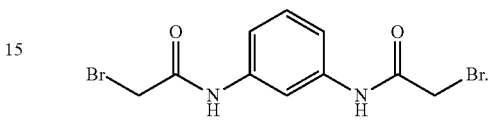

In some embodiments, $L^{s2}$ or —CH$_2$C(O)Q-L'-QC(O)CH$_2$— is as described in such compounds, wherein $R^x$ is —Br. In some embodiments $L^s$ or $L^{s2}$ is not

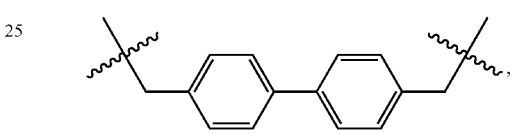

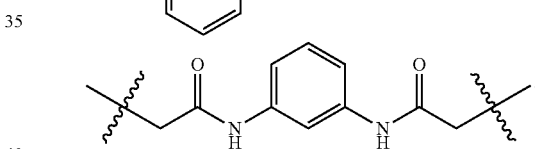

In some embodiments, $L^s$ or $L^{s2}$ is not

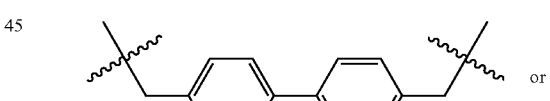

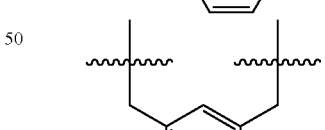

In some embodiments, $L^s$ or $L^{s2}$ is not

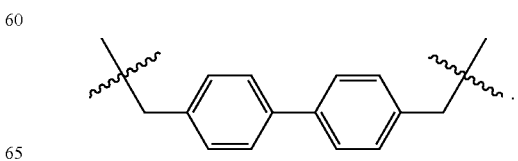

In some embodiments, $L^s$ or $L^{s2}$ is not

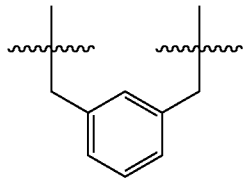

In some embodiments, $L^s$ or $L^{s2}$ is

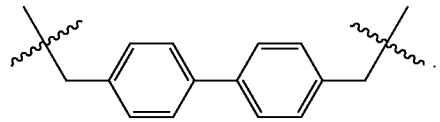 [SMILES: *Cc1ccc(-c2ccc(C*)cc2)cc1]

In some embodiments, $L^s$ or $L^{s2}$ is

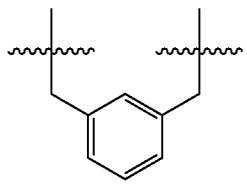

In some embodiments, $L^s$ or $L^{s2}$ is substituted

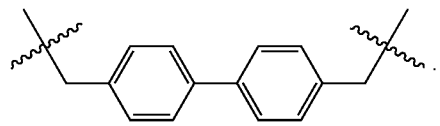 [SMILES: *Cc1ccc(-c2ccc(C*)cc2)cc1]

In some embodiments, $L^s$ or $L^{s2}$ is substituted

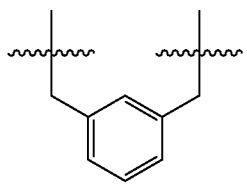

In some embodiments, $L^s$ or $L^{s2}$ or -$L^{x1}$-C(O)Q-L'-QC(O)-$L^{x1}$- or —CH$_2$C(O)Q-L'-QC(O)CH$_2$— is

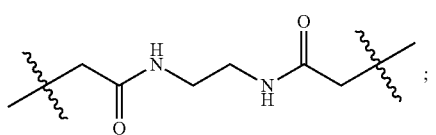 [SMILES: *CC(=O)NCCNC(=O)C*]

in some embodiments, it is substituted

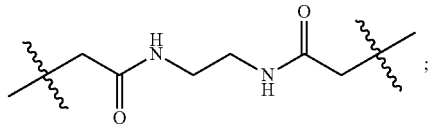 [SMILES: *CC(=O)NCCNC(=O)C*]

in some embodiments, it is

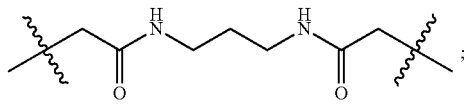 [SMILES: *CC(=O)NCCCNC(=O)C*]

in some embodiments, it is substituted

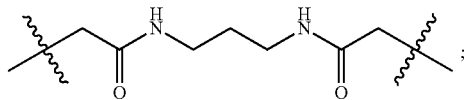 [SMILES: *CC(=O)NCCCNC(=O)C*]

in some embodiments, it is

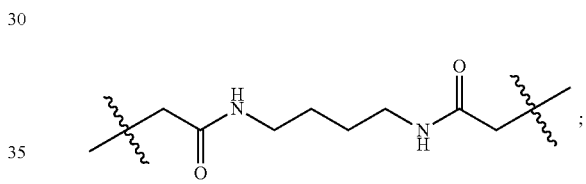

in some embodiments, it is substituted

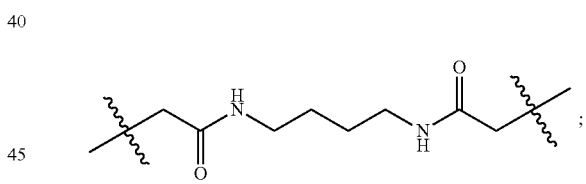

in some embodiments, it is

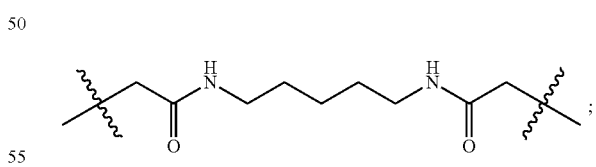

in some embodiments, it is substituted

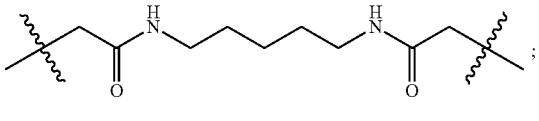 [SMILES: *CC(=O)NCCCCCNC(=O)C*]

in some embodiments, it is optionally substituted

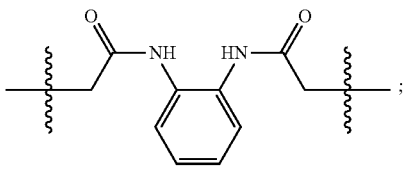 [SMILES: *CC(=O)Nc1ccccc1NC(=O)C*]

in some embodiments, it is substituted

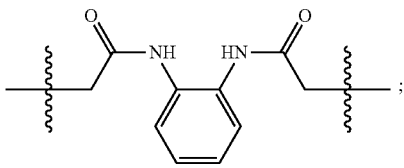 [SMILES: *CC(=O)Nc1ccccc1NC(=O)C*]

in some embodiments, it is

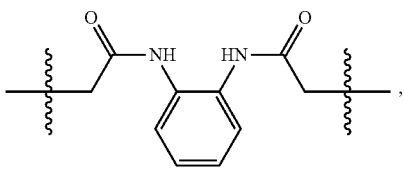 [SMILES: *CC(=O)Nc1ccccc1NC(=O)C*]

wherein the bivalent phenyl ring is optionally substituted; in some embodiments, it is

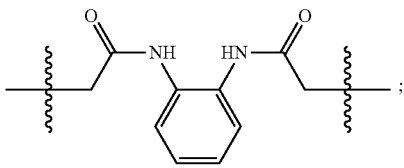

in some embodiments, it is optionally substituted

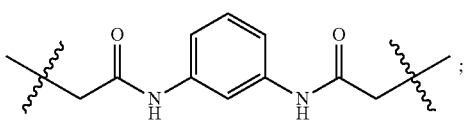 [SMILES: *CC(=O)Nc1cccc(NC(=O)C*)c1]

in some embodiments, it is

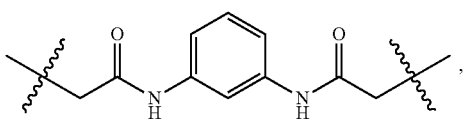 [SMILES: *CC(=O)Nc1cccc(NC(=O)C*)c1]

wherein the bivalent phenyl ring is optionally substituted; in some embodiments, it is not

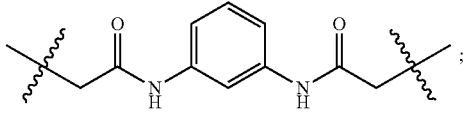 [SMILES: *CC(=O)Nc1cccc(NC(=O)C*)c1]

in some embodiments, it is

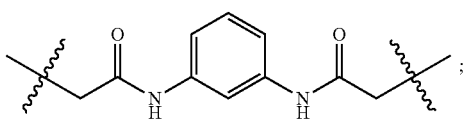 [SMILES: *CC(=O)Nc1cccc(NC(=O)C*)c1]

in some embodiments, it is substituted

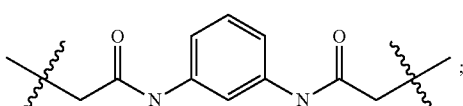

in some embodiments, it is optionally substituted

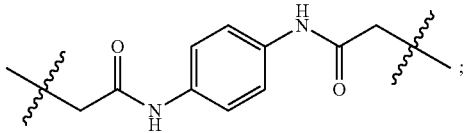 [SMILES: *CC(=O)Nc1ccc(NC(=O)C*)cc1]

in some embodiments, it is

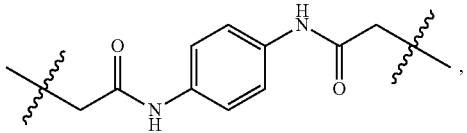 [SMILES: *CC(=O)Nc1ccc(NC(=O)C*)cc1]

wherein the bivalent phenyl ring is optionally substituted; in some embodiments it is

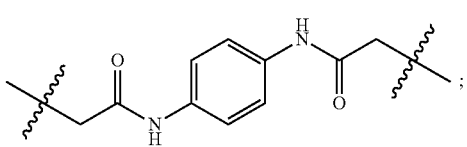 [SMILES: *CC(=O)Nc1ccc(NC(=O)C*)cc1]

in some embodiments, it is substituted

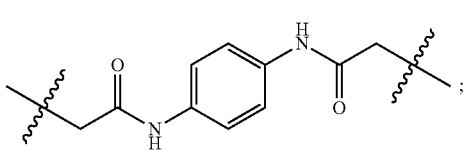 [SMILES: *CC(=O)Nc1ccc(NC(=O)C*)cc1]

in some embodiments, it is
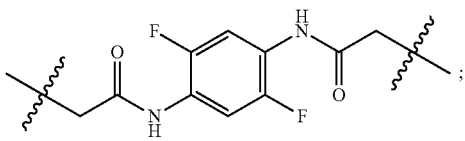 [SMILES: *CC(=O)Nc1cc(F)c(NC(=O)C*)cc1F]
in some embodiments, it is
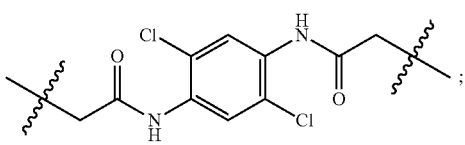 [SMILES: *CC(=O)Nc1cc(Cl)c(NC(=O)C*)cc1Cl]
in some embodiments, it is
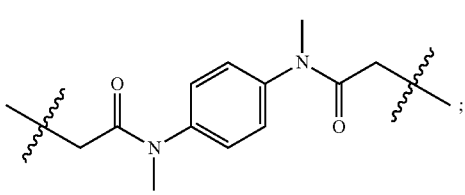 [SMILES: *CC(=O)N(C)c1ccc(N(C)C(=O)C*)cc1]
in some embodiments, it is
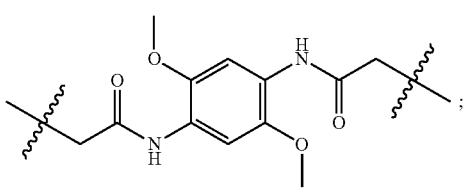 [SMILES: *CC(=O)Nc1cc(OC)c(NC(=O)C*)cc1OC]
in some embodiments, it is
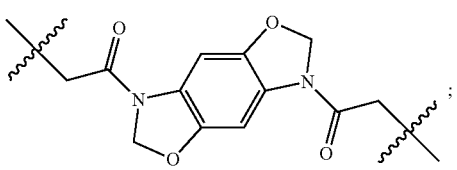 [SMILES: *CC(=O)N1COc2cc3c(cc21)OCN3C(=O)C*]
in some embodiments, it is substituted
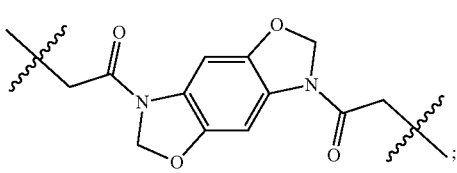 [SMILES: *CC(=O)N1COc2cc3c(cc21)OCN3C(=O)C*]
in some embodiments, it is
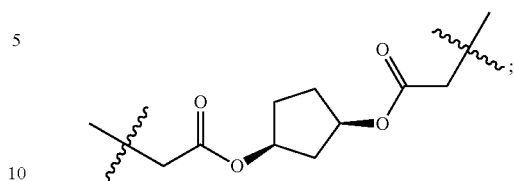
in some embodiments, it is substituted
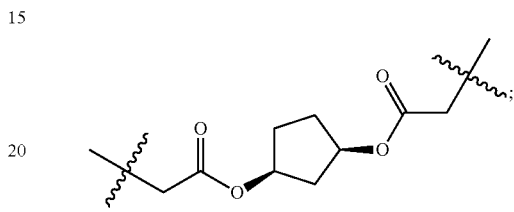
in some embodiments, it is
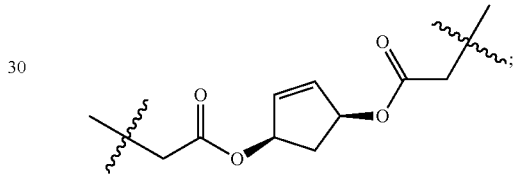
in some embodiments, it is substituted
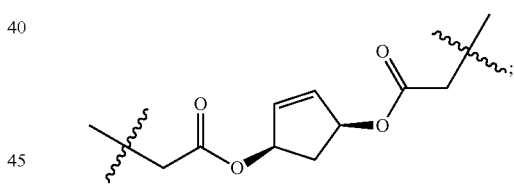
in some embodiments, it is
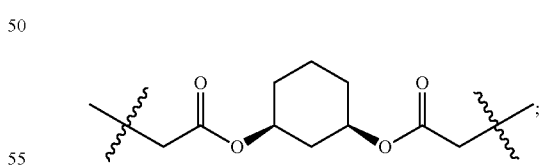
in some embodiments, it is substituted
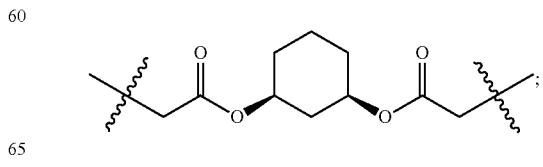

in some embodiments, it is
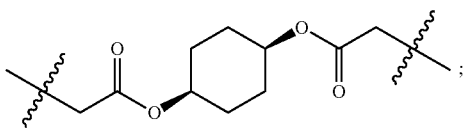 [SMILES: *CC(=O)O[C@H]1CC[C@@H](OC(=O)C*)CC1]
in some embodiments it is substituted
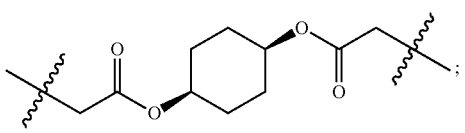 [SMILES: *CC(=O)O[C@H]1CC[C@@H](OC(=O)C*)CC1]
in some embodiments, it is
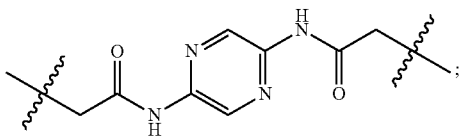 [SMILES: *CC(=O)Nc1cnc(NC(=O)C*)cn1]
in some embodiments, it is substituted
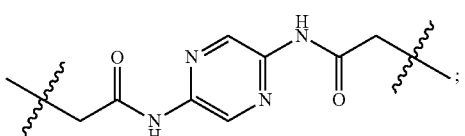
in some embodiments, it is
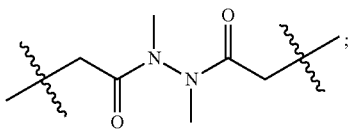 [SMILES: *CC(=O)N(C)N(C)C(=O)C*]
in some embodiments, it is substituted
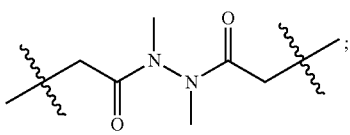 [SMILES: *CC(=O)N(C)N(C)C(=O)C*]
in some embodiments, it is
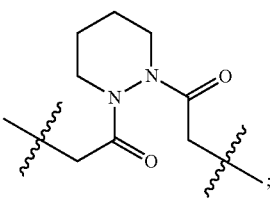 [SMILES: *CC(=O)N1CCCCN1C(=O)C*]
in some embodiments, it is substituted
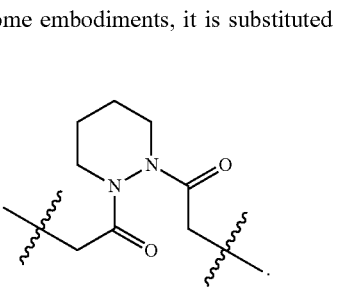
In some embodiments, a useful compound is selected from: Table 3.
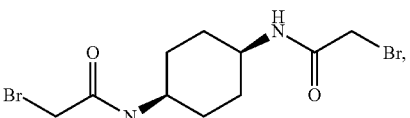
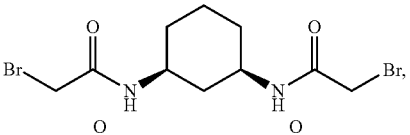
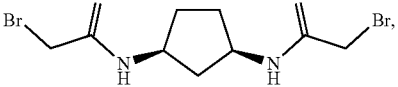
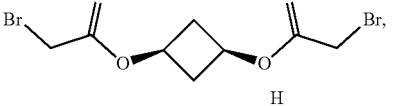
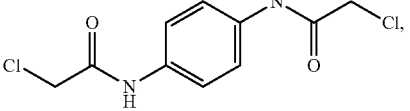
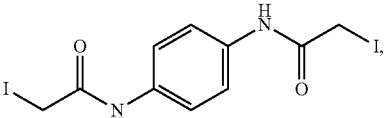
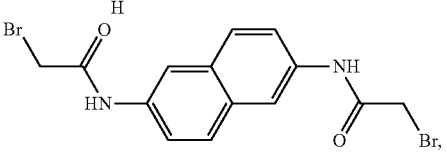

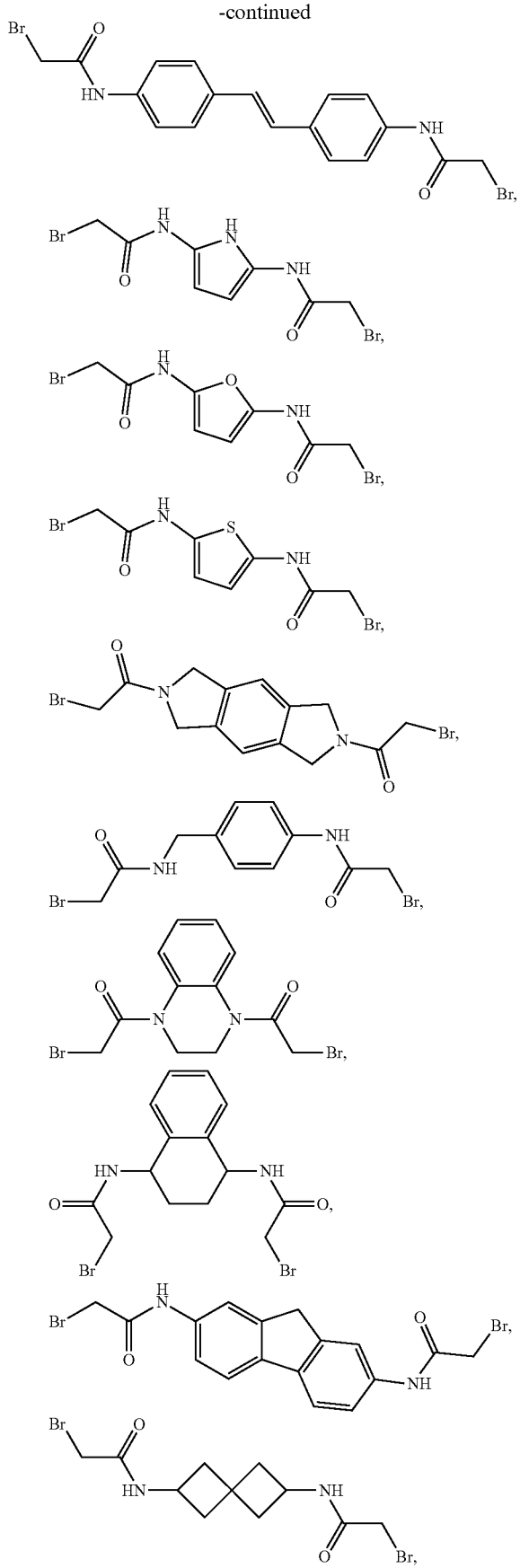
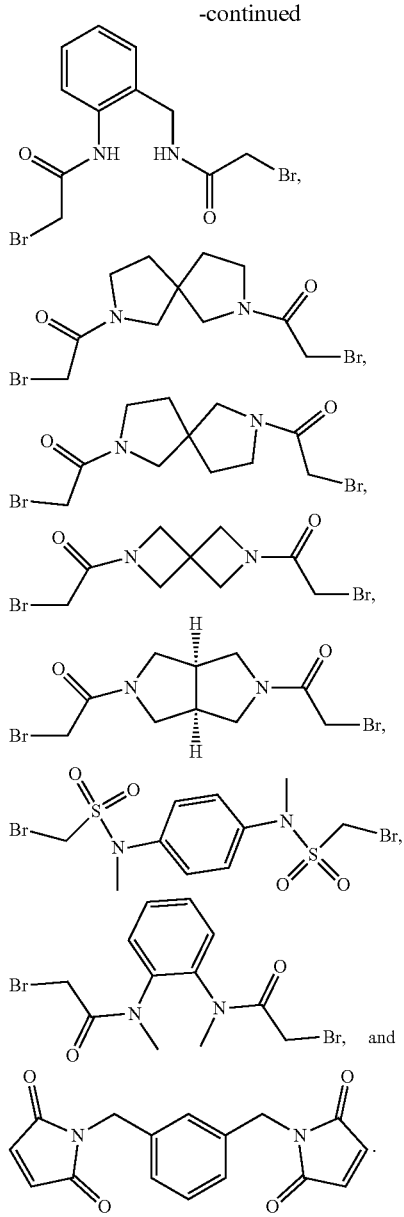

In some embodiments, $L^s$ or $L^{s2}$ or -$L^{x1}$-C(O)Q-L'-QC(O)-$L^{x1}$- or —CH$_2$C(O)Q-L'-QC(O)CH$_2$— comprise an optionally substituted saturated or partially unsaturated 3-20 (e.g., 3, 4, 5, 6, 7, 8, 9, 10, 11, 12, 13, 14, 15, 16, 17, 18, 19, or 20) membered monocyclic, bicyclic or polycyclic ring having 0-10 (0, 1, 2, 3, 4, 5, 6, 7, 8, 9, or 10) heteroatoms (e.g., in some embodiments, selected from nitrogen, oxygen and sulfur); in some embodiments, it comprises an optionally substituted 3-20 (e.g., 3, 4, 5, 6, 7, 8, 9, 10, 11, 12, 13, 14, 15, 16, 17, 18, 19, or 20) membered cycloaliphatic ring; in some embodiments, it is

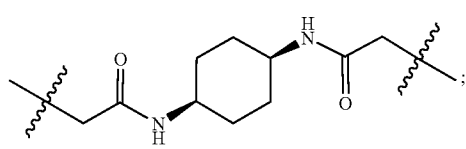 [SMILES: *CC(=O)N[C@H]1CC[C@@H](NC(=O)C*)CC1]

in some embodiments, it is substituted H

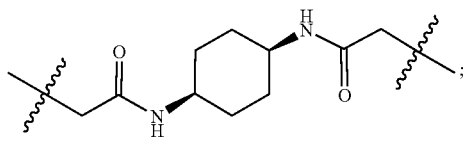 [SMILES: *CC(=O)N[C@H]1CC[C@@H](NC(=O)C*)CC1]

in some embodiments, it is

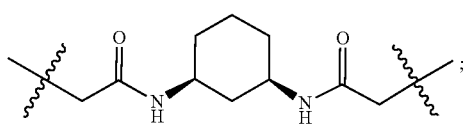 [SMILES: *CC(=O)N[C@@H]1CCC[C@H](NC(=O)C*)C1]

in some embodiments, it is substituted

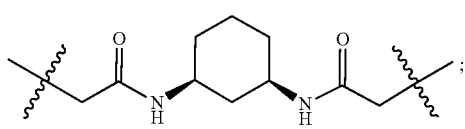 [SMILES: *CC(=O)N[C@@H]1CCC[C@H](NC(=O)C*)C1]

in some embodiments, it is

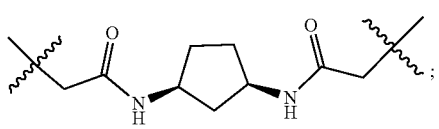 [SMILES: *CC(=O)N[C@@H]1CC[C@H](NC(=O)C*)C1]

in some embodiments, it is substituted

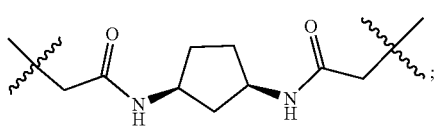 [SMILES: *CC(=O)N[C@@H]1CC[C@H](NC(=O)C*)C1]

in some embodiments, it is

in some embodiments it is substituted

in some embodiments, it is

in some embodiments, it is substituted

in some embodiments, it comprises an optionally substituted 6-20 (e.g., 6, 10, or 14) membered monocyclic, bicyclic or polycyclic aryl ring; in some embodiments, it is optionally substituted

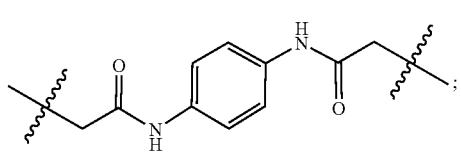 [SMILES: *CC(=O)Nc1ccc(NC(=O)C*)cc1]

in some embodiments, it is

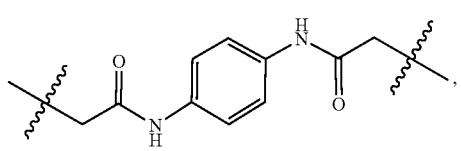 [SMILES: *CC(=O)Nc1ccc(NC(=O)C*)cc1]

wherein the phenyl ring is optionally substituted; in some embodiments, it is

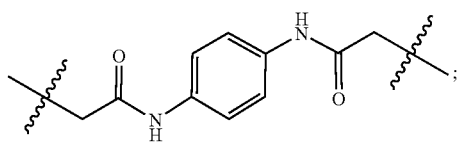 [SMILES: *CC(=O)Nc1ccc(NC(=O)C*)cc1]

in some embodiments, it is substituted

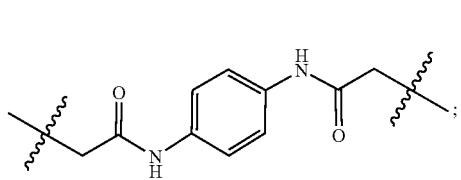 [SMILES: *CC(=O)Nc1ccc(NC(=O)C*)cc1]

in some embodiments, it is

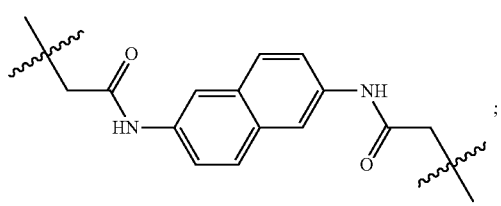 [SMILES: *CC(=O)Nc1ccc2cc(NC(=O)C*)ccc2c1]

in some embodiments, it is substituted

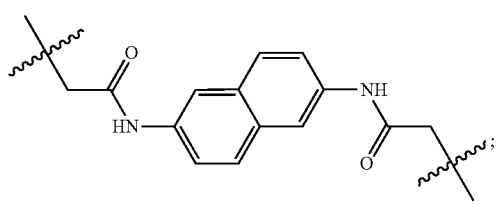 [SMILES: *CC(=O)Nc1ccc2cc(NC(=O)C*)ccc2c1]

in some embodiments, it is

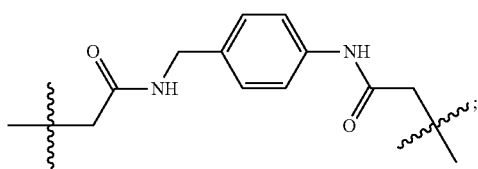

in some embodiments, it is substituted

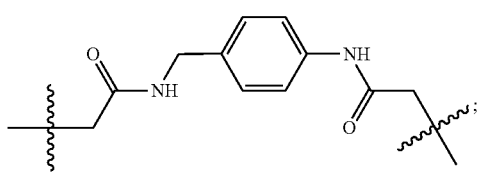 [SMILES: *CC(=O)NCc1ccc(NC(=O)C*)cc1]

in some embodiments, it is

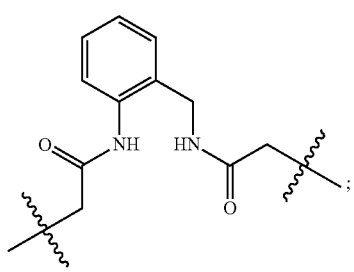 [SMILES: *CC(=O)NCc1ccccc1NC(=O)C*]

in some embodiments, it is substituted

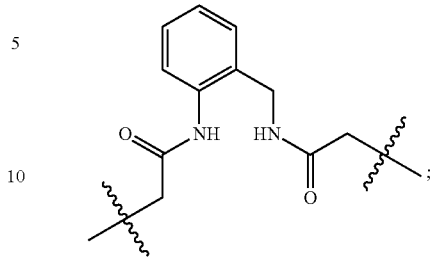

in some embodiments, it is

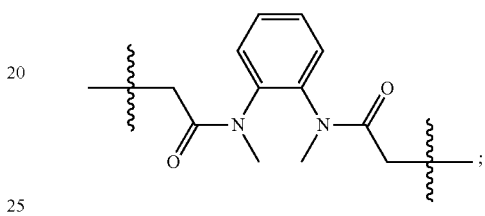

in some embodiments, it is substituted

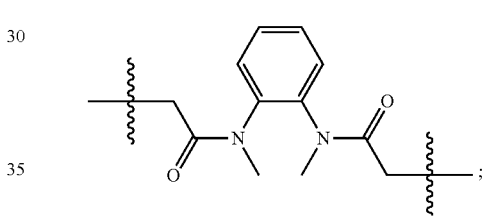

in some embodiments, it comprises an optionally substituted 5-20 (e.g., 5, 6, 7, 8, 9, 10, 11, 12, 13, 14, 15, 16, 17, 18, 19, or 20) membered monocyclic, bicyclic or polycyclic heteroaryl ring having 0-10 (e.g., 0, 1, 2, 3, 4, 5, 6, 7, 8, 9, or 10) heteroatoms (e.g., in some embodiments, selected from nitrogen, oxygen and sulfur); in some embodiments, it is

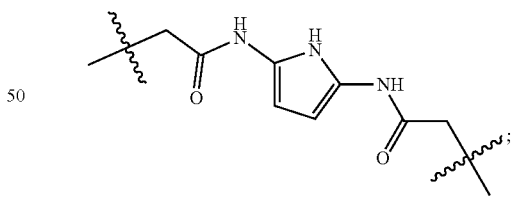

in some embodiments, it is substituted

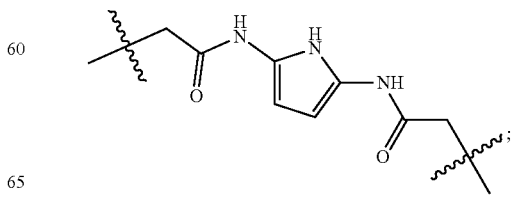

in some embodiments, it is

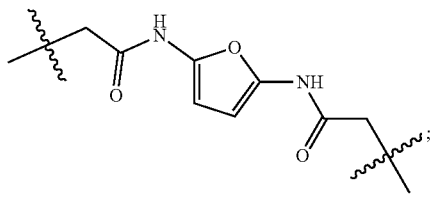 [SMILES: *CC(=O)Nc1ccc(NC(=O)C*)o1]

in some embodiments, it is substituted

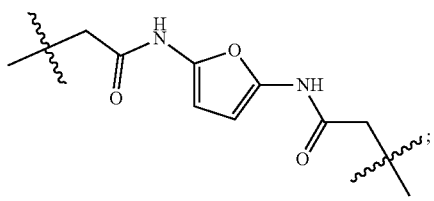 [SMILES: *CC(=O)Nc1ccc(NC(=O)C*)o1]

in some embodiments, it is

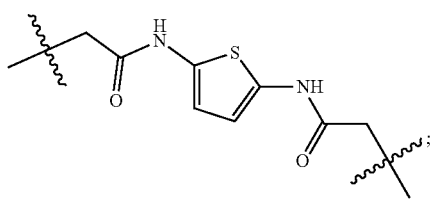 [SMILES: *CC(=O)Nc1ccc(NC(=O)C*)s1]

in some embodiments, it is substituted

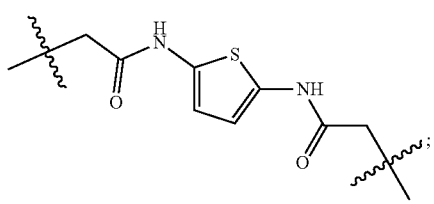 [SMILES: *CC(=O)Nc1ccc(NC(=O)C*)s1]

in some embodiments, it comprises two or more optionally substituted rings, each of which is independently a 3-10 (e.g., 3, 4, 5, 6, 7, 8, 9, or 10) membered saturated or partially unsaturated ring or 5-10 membered aromatic ring, and each of which independently has 0-10 (e.g., 0, 1, 2, 3, 4, 5, 6, 7, 8, 9, or 10) heteroatoms (e.g., in some embodiments, selected from nitrogen, oxygen and sulfur); in some embodiments, it is

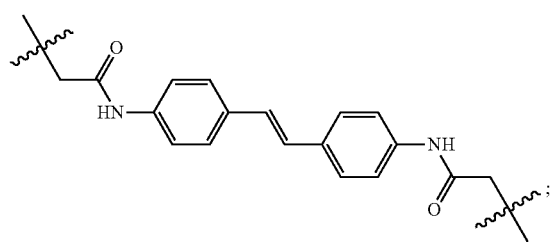 [SMILES: *CC(=O)Nc1ccc(/C=C/c2ccc(NC(=O)C*)cc2)cc1]

in some embodiments, it is substituted

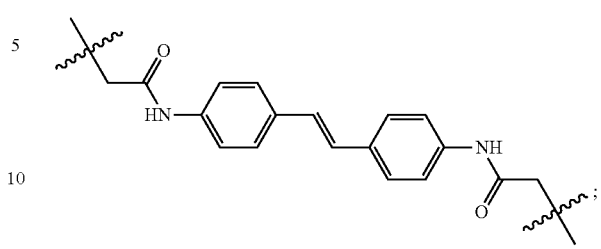

in some embodiments, it comprises an optionally substituted 5-20 (e.g., 5, 6, 7, 8, 9, 10, 11, 12, 13, 14, 15, 16, 17, 18, 19, or 20) membered bicyclic or polycyclic ring having 0-10 (e.g., 0, 1, 2, 3, 4, 5, 6, 7, 8, 9, or 10) heteroatoms (e.g., in some embodiments, selected from nitrogen, oxygen and sulfur), wherein each of the monocyclic rings is independently a 3-10 (e.g., 3, 4, 5, 6, 7, 8, 9, or 10) membered saturated or partially unsaturated ring having 0-10 (e.g., 0, 1, 2, 3, 4, 5, 6, 7, 8, 9, or 10) heteroatoms (e.g., in some embodiments, selected from nitrogen, oxygen and sulfur) or a 5-10 (e.g., 3, 4, 5, 6, 7, 8, 9, or 10) membered aromatic ring having 0-10 (e.g., 0, 1, 2, 3, 4, 5, 6, 7, 8, 9, or 10) heteroatoms (e.g., in some embodiments, selected from nitrogen, oxygen and sulfur); in some embodiments, it is

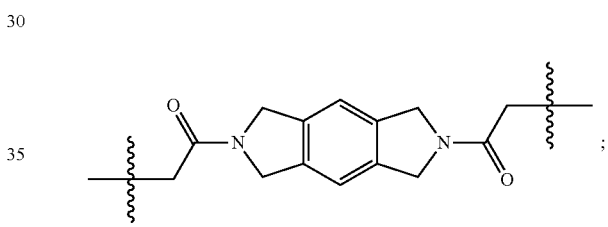

in some embodiments, it is substituted

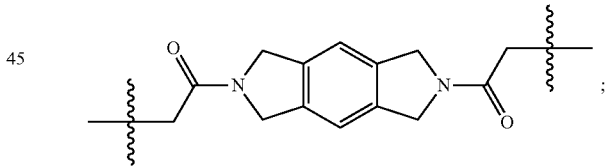

in some embodiments, it is

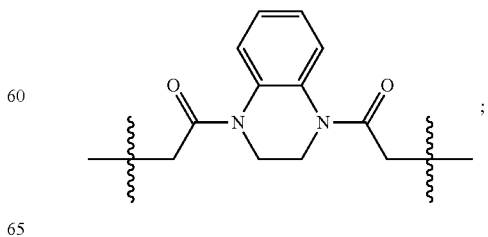

in some embodiments, it is substituted
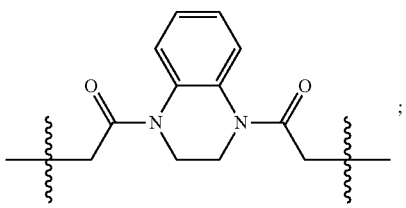 [SMILES: *CC(=O)N1CCN(C(=O)C*)c2ccccc21]
in some embodiments, it is
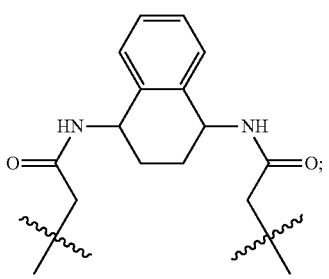 [SMILES: *CC(=O)NC1CCC(NC(=O)C*)c2ccccc21]
in some embodiments, it is substituted
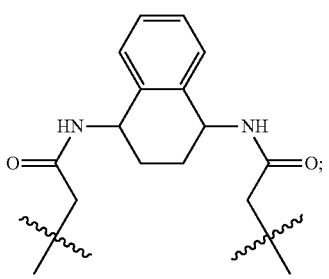 [SMILES: *CC(=O)NC1CCC(NC(=O)C*)c2ccccc21]
in some embodiments, it is
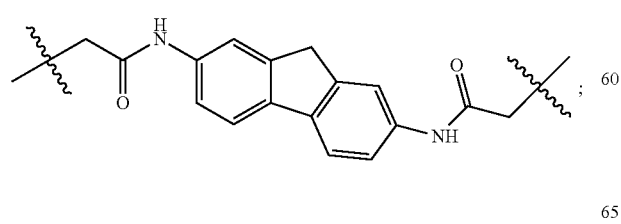
in some embodiments, it is substituted
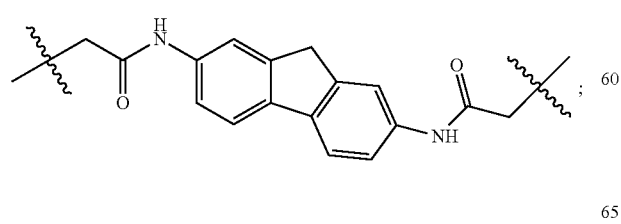
in some embodiments, it is
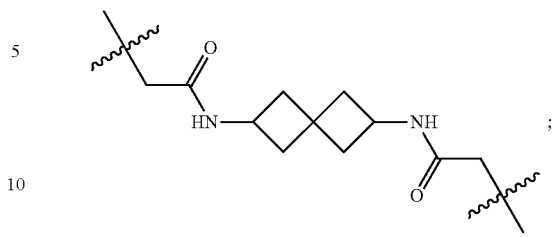
in some embodiments, it is substituted
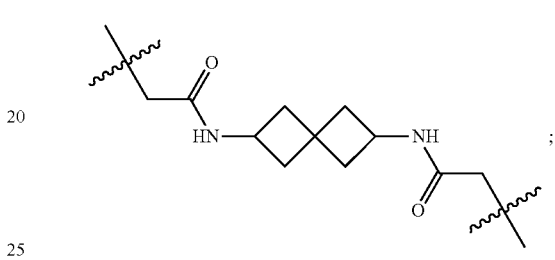
in some embodiments, it is
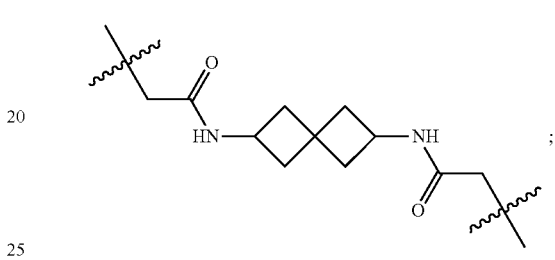
in some embodiments, it is substituted
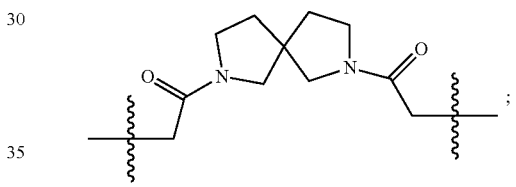
in some embodiments, it is
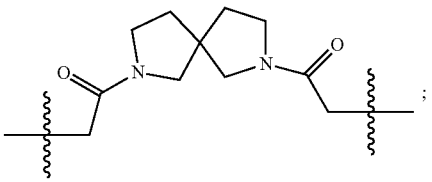 [SMILES: *CC(=O)N1CCC2(CCN(C(=O)C*)C2)C1]
in some embodiments, it is substituted
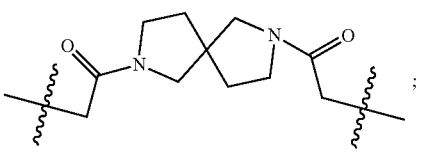 [SMILES: *CC(=O)N1CCC2(CCN(C(=O)C*)C2)C1]

in some embodiments, it is

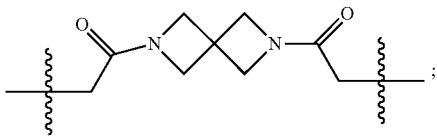 [SMILES: *CC(=O)N1CC2(C1)CN(C(=O)C*)C2]

in some embodiments, it is substituted

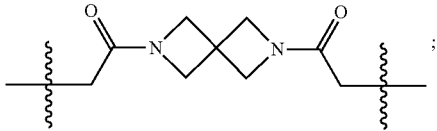 [SMILES: *CC(=O)N1CC2(C1)CN(C(=O)C*)C2]

in some embodiments, it is

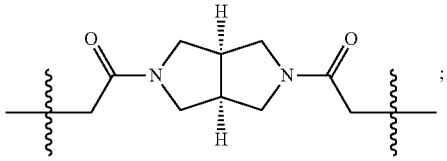 [SMILES: *CC(=O)N1C[C@H]2CN(C(=O)C*)C[C@H]2C1]

in some embodiments, it is substituted H

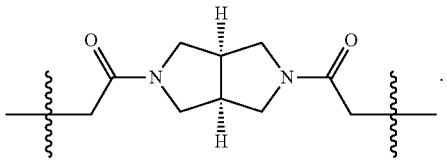 [SMILES: *CC(=O)N1C[C@H]2CN(C(=O)C*)C[C@H]2C1]

In some embodiments, $L^s$ or $L^{s2}$ is

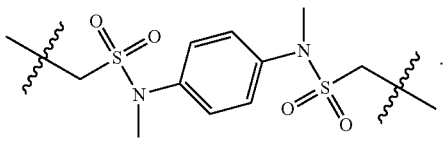

In some embodiments, $L^s$ or $L^{s2}$ is substituted

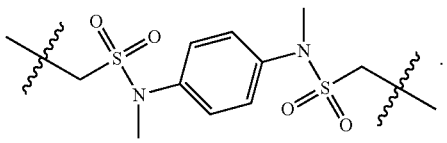 [SMILES: *CS(=O)(=O)N(C)c1ccc(N(C)S(=O)(=O)C*)cc1]

In some embodiments, $L^s$ or $L^{s2}$ is

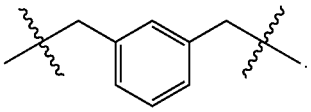 [SMILES: *Cc1cccc(C*)c1]

In some embodiments, $L^s$ or $L^{s2}$ is substituted

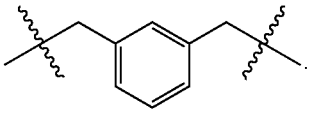 [SMILES: *Cc1cccc(C*)c1]

As described herein, rings can be of various sizes. In some embodiments, non-aromatic rings are 3-20 membered. In some embodiments, aromatic rings are 5-20 membered. In some embodiments, a ring is 3-10 membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is 9-membered. In some embodiments, a ring is 10-membered. In some embodiments, a ring is 11-membered. In some embodiments, a ring is 12-membered. In some embodiments, a ring is 13-membered. In some embodiments, a ring is 14-membered. In some embodiments, a ring is 15-membered. Rings may also have various numbers and types of heteroatoms. In some embodiments, a ring has 0-10 heteroatoms. In some embodiments, a ring has 0 heteroatom. In some embodiments, a ring has 1 heteroatom. In some embodiments, a ring has 2 heteroatom. In some embodiments, a ring has 3 heteroatom. In some embodiments, a ring has 4 heteroatom. In some embodiments, a ring has 5 heteroatom. In some embodiments, a ring has 6 heteroatom. In some embodiments, a ring has 7 heteroatom. In some embodiments, a ring has 8 heteroatom. In some embodiments, a ring has 9 heteroatom. In some embodiments, a ring has 10 heteroatom. In some embodiments, a heteroatom is selected from nitrogen, oxygen and sulfur. In some embodiments, at least one heteroatom is nitrogen. In some embodiments, at least one heteroatom is oxygen. In some embodiments, at least one heteroatom is sulfur. In some embodiments, a ring is saturated. In some embodiments, a ring is partially unsaturated. In some embodiments, a ring is aromatic. In some embodiments, a ring is a cycloaliphatic ring. In some embodiments, a ring is a cycloalkyl ring. In some embodiments, a ring is a heteroaliphatic ring. In some embodiments, a ring is a heterocyclyl ring. In some embodiments, a ring is a heterocycloalkyl ring. In some embodiments, a ring is an aryl ring. In some embodiments, a ring is a heteroaryl ring. As appreciated by those skilled in the art, rings are independently and optionally substituted—either substituted or unsubstituted.

Many additional technologies are useful for preparing stapled peptides in accordance with the present disclosure. For example, in some embodiments, amino acid residues having side chains comprising double or triple bonds and optionally various heteroatoms may be utilized to construct various types of staples, e.g., hydrocarbon staples, amino- or carbamate-containing staples, etc.

As those skilled in the art will appreciate, after stapling using reagents described herein, portions of reagents' structures are incorporated into staples in the products. Thus, various embodiments of $L^s$, $L^{s2}$, $-L^{x1}-C(O)Q-L'-QC(O)-L^{x1}-$, $-CH_2C(O)Q-L'-QC(O)CH_2-$, $L^{x1}$, $Q$, $L'$, etc. described for reagents can be utilized in staples and vice versa.

Stapled Peptides

Stapled peptides as described herein are peptides in which two or more amino acids of a peptide chain are linked through bonding of two peptide backbone atoms of the amino acid residues and, as is understood by those skilled in the art, the resulting bond is not through the peptide backbone between the linked amino acid residues. In some embodiments, a stapled peptide comprises a staple. A staple as described herein is a linker that can link one amino acid residue to another amino acid residue through bonding two peptide backbone atoms of the amino acid residues and, as is understood by those skilled in the art, the resulting bond is not through the peptide backbone between the linked amino acid residues. In some embodiments, a staple bonds to the peptide backbone by replacing one or more hydrogen and/or substituents (e.g., side chains, O, S, etc.) on peptide backbone atoms (e.g., C, N, etc.).

As will be appreciated by those of ordinary skill in the art, a variety of peptide stapling technologies are available, including both hydrocarbon-stapling and non-hydrocarbon-stapling technologies.

In some embodiments, a staple as described herein is a hydrocarbon staple. In some embodiments, a staple as described herein is a non-hydrocarbon staple. In some embodiments, a non-hydrocarbon staple comprises one or more chain heteroatoms wherein a chain of a staple is the shortest covalent connection within the staple from one end of the staple to the other end of the staple. In some embodiments, a non-hydrocarbon staple is a comprises at least one sulfur atom derived from an amino acid residue of a polypeptide. In some embodiments, a non-hydrocarbon staple comprises two sulfur atom derived from two different amino acid residues of a polypeptide. In some embodiments, a non-hydrocarbon staple comprises two sulfur atoms derived from two different cysteine residues of a polypeptide. In some embodiments, a staple is a cysteine staple. In some embodiments, a staple is a non-cysteine staple.

In some embodiments, the present disclosure provides a stapled peptide having a structure:
$[X^1]_{p1}[X^2]_{p2}[X^3]_{p3}[X^4]_{p4}[X^5]_{p5}[X^6]_{p6}[X^7]_{p7}[X^8]_{p8}[X^9]_{p9}$
$[X^{10}]_{p10}[X^{11}]_{p11}[X^{12}]_{p12}[X^{13}]_{p13}$-
$X^{14}X^{15}X^{16}X^{17}X^{18}X^{19}-[X^{20}]_{p20}[X^{20}]_{p21}$ $[X^{22}]_{p22}$
$[X^{23}]_{p23}$ $[X^{24}]_{p24}$ $[X^{25}]_{p25}$ $[X^{26}]_{p26}$ $[X^{27}]_{p27}$ $[X^{28}]_{p28}$
$[X^{29}]_{p29}$ $[X^{30}]_{p30}[X^{31}]_{p31}[X^{32}]_{p32}$, wherein:
each of p1, p2, p3, p4, p5, p6, p7, p8, p9, p10, p11, p12, p13, p20, p21, p22, p23, p24, p25, p26, p27, p28, p29, p30, p31, p32 is independently 0 or 1;
each of $X^1$ to $X^{32}$ is independently an amino acid residue;
at least two of $X^1$ to $X^{32}$ comprise side chains that are optionally linked together to form a staple.

In some embodiments, a provided peptide is a stapled peptide, and at least two of $X^1$ to $X^{32}$ comprise side chains that are linked together to form a staple. In some embodiments, a provided peptide is an unstapled peptide, wherein at least two of $X^1$ to $X^{32}$ comprise side chains that can be linked together to form a staple. In some embodiments, a stapled peptide, or an unstapled peptide once stapled, interacts with a target of interest at one or more sites on the target of interest.

In some embodiments, each of $X^1$ to $X^{32}$ is independently an amino acid residue of an amino acid having the structure of formula A-I.

In some embodiments, $X^i$ and $X^{i+m}$, each independently comprises a side chain comprising a thiol, and the two side chains can be linked together to form a staple. In some embodiments, $X^i$ and $X^{i+m}$, each independently comprises a cysteine side chain, and the two side chains can be linked together to form a cysteine staple.

In some embodiments, $X^i$ and $X^{i+m}$, each independently comprises a side chain that comprises an olefin. In some embodiments, both of the olefins are terminal olefins. In some embodiments, at least one of $X^i$ and $X^{i+m}$ comprises a side chain comprising an olefin and a nitrogen atom. In some embodiments, at least one of $X^i$ and $X^{i+m}$ comprises $-C(R^{2a})(R^{3a})$ being $-C(-L^a-R')(R^{3a})$, wherein at least one methylene unit of $L^a$ is replaced with $-N(R')-$ and R' comprises an olefin. In some embodiments, at least one of X and $X_1+^m$ comprises $-C(R^{2a})(R^{3a})$ being $-C(-L^a-CH=CH_2)(R^{3a})$, wherein at least one methylene unit of $L^a$ is replaced with $-N(R')-$.

In some embodiments, i is an integer of 1 to 31 inclusive, and is m an integer of 1 to 12 inclusive.

In some embodiments, i is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31. In some embodiments, i is 1. In some embodiments, i is 2. In some embodiments, i is 3. In some embodiments, i is 4. In some embodiments, i is 5. In some embodiments, i is 6. In some embodiments, i is 7. In some embodiments, i is 8. In some embodiments, i is 9. In some embodiments, i is 10. In some embodiments, i is 11. In some embodiments, i is 12. In some embodiments, i is 13. In some embodiments, i is 14. In some embodiments, i is 15. In some embodiments, i is 16. In some embodiments, i is 17. In some embodiments, i is 18. In some embodiments, i is 17. In some embodiments, i is 18. In some embodiments, i is 19. In some embodiments, i is 20. In some embodiments, i is 21. In some embodiments, i is 22. In some embodiments, i is 23. In some embodiments, i is 24. In some embodiments, i is 25. In some embodiments, i is 26. In some embodiments, i is 27. In some embodiments, i is 28. In some embodiments, i is 29. In some embodiments, i is 30. In some embodiments, i is 31. In some embodiments, i is 32.

In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12.

In some embodiments, a stapled peptide comprise one or more staples. In some embodiments, a stapled peptide comprises one and no more than one staple. In some embodiments, a stapled peptide comprises one and no more than one staples from cysteine stapling. In some embodiments, a stapled peptide comprises one and no more than one staples having the structure of

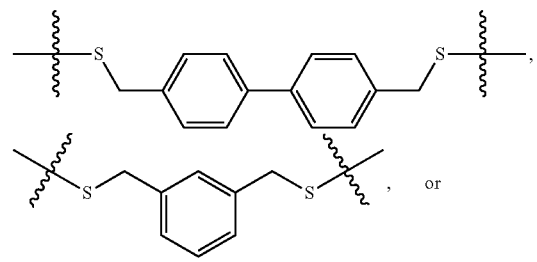

-continued

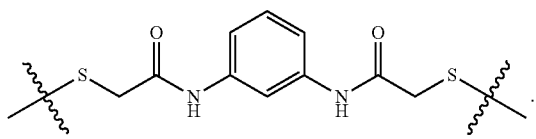

In some embodiments, a stapled peptide comprises one and no more than one staples having the structure of

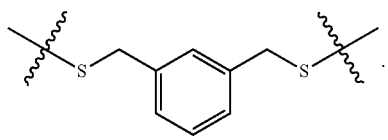 [SMILES: *SCc1cccc(CS*)c1]

In some embodiments, a stapled peptide comprises one and no more than one staples having the structure of

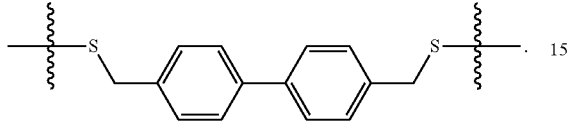

In some embodiments, a stapled peptide comprises one and no more than one staples having the structure of

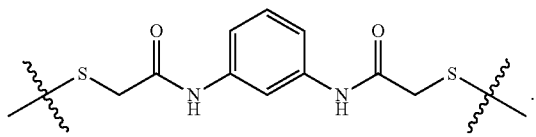 [SMILES: *SCC(=O)Nc1cccc(NC(=O)CS*)c1]

In some embodiments, a stapled peptide comprises no staples having the structure of

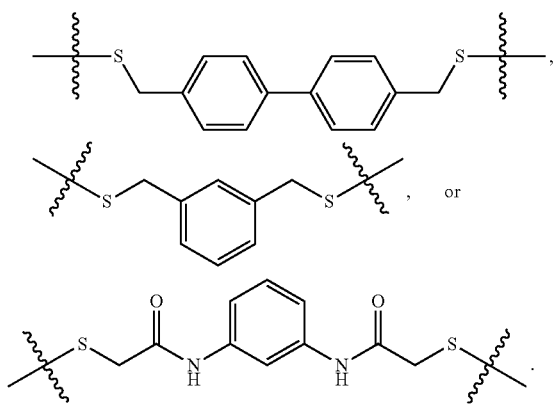

In some embodiments, a stapled peptide comprises no staples having the structure of

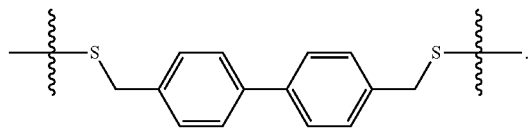

In some embodiments, a stapled peptide comprises no staples having the structure of

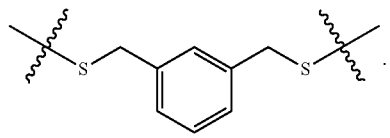 [SMILES: *SCc1cccc(CS*)c1]

In some embodiments, a stapled peptide comprises no staples having the structure of

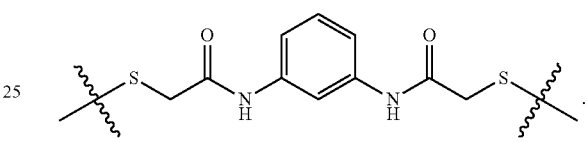

In some embodiments, peptides, e.g., staple peptides, of the present disclosure is or comprises a helix structure. As those skilled in the art will appreciate, helixes can have various lengths. In some embodiments, lengths of helixes range from 5 to 30 amino acid residues. In some embodiments, a length of a helix is 5, 6, 7, 8, 9, 10, 11, 12, 13, 14, 15, 16, 17, 18, 19, or 20, or more, amino acid residues. In some embodiments, a length of a helix is 6 amino acid residues. In some embodiments, a length of a helix is 8 amino acid residues. In some embodiments, a length of a helix is 10 amino acid residues. In some embodiments, a length of a helix is 12 amino acid residues. In some embodiments, a length of a helix is 14 amino acid residues. In some embodiments, a length of a helix is 16 amino acid residues. In some embodiments, a length of a helix is 17 amino acid residues. In some embodiments, a length of a helix is 18 amino acid residues. In some embodiments, a length of a helix is 19 amino acid residues. In some embodiments, a length of a helix is 20 amino acid residues.

Cysteine Stapling

In some embodiments, the present disclosure provides useful technologies relating to cysteine stapling. Among other things, the present disclosure appreciates that peptides amenable to cysteine stapling and/or comprising one or more cysteine staples, can be produced and/or assessed in a biological system. The present disclosure further appreciates that certain such systems permit development, production, and/or assessment of cysteine stapled peptides having a range of different structures (e.g., different amino acid sequences), and in fact can provide a user with complete control over selection and implementation of amino acid sequences to be incorporated into stapled peptides.

Cysteine stapling, as described herein, involves linking one cysteine residue to another cysteine residue, where the resulting bond is not through the peptide backbone between the linked cysteine residues.

In some embodiments, a stapled peptide as described herein comprises a staple which staple is $L^s$, wherein:

$L^s$ is $-L^{s1}\text{-S-}L^{s2}\text{-S-}L^{s3}\text{-}$;

$L^{s1}$ and $L^{s3}$ are each independently L;

$L^{s2}$ is L and comprises at least one —C(O)—; and each L is independently a covalent bond, or an optionally substituted, bivalent $C_1$-$C_{25}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —CO$_2$R, or —SO$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond; or two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, L is independently a bivalent $C_1$-$C_{25}$ aliphatic group. In some embodiments, L is independently a bivalent $C_1$-$C_{20}$ aliphatic group. In some embodiments, L is independently a bivalent $C_1$-$C_{10}$ aliphatic group. In some embodiments, L is independently a bivalent $C_1$-$C_5$ aliphatic group. In some embodiments, L is independently a bivalent $C_1$ aliphatic group. In some embodiments, L is —CH$_2$—.

In some embodiments, $L^{s1}$ is —CH$_2$—. In some embodiments, $L^{s3}$ is —CH$_2$—. In some embodiments, $L^{s1}$ and $L^{s3}$ are both —CH$_2$—. In some embodiments, $L^s$ is —CH$_2$—S—$L^{s2}$—S—CH$_2$—.

In some embodiments, $L^{s2}$ comprises —C(R')$_2$-L'-C(R')$_2$—, wherein L' is described in the present disclosure. In some embodiments, $L^{s2}$ is -$L^{x1}$-C(O)Q-L'-QC(O)-$L^{x1}$-, wherein each variable is independently as described in the present disclosure. In some embodiments, $L^{s2}$ is —CH$_2$C(O)Q-L'-QC(O)CH$_2$—, wherein each —CH$_2$— is independently and optionally substituted. In some embodiments, $L^{s2}$ is —CH$_2$C(O)Q-L'-QC(O)CH$_2$—.

In some embodiments, $L^{s2}$ is L and comprises at least one —C(O)—. In some embodiments, $L^{s2}$ is L and comprises at least two —C(O)—. In some embodiments, $L^{s2}$ is L and comprises at least one —C(O)Q-, wherein Q is selected from the group consisting of: a covalent bond, —N(R')—, —O—, and —S—. In some embodiments, $L^{s2}$ is L and comprises at least one —C(O)Q-, wherein Q is selected between —N(R')— and —O—. In some embodiments, $L^{s2}$ is L and comprises at least two —C(O)Q-, wherein Q is selected from the group consisting of: —N(R')—, —O—, and —S—. In some embodiments, $L^{s2}$ is L and comprises at least two —C(O)Q-, wherein Q is selected between —N(R')— and —O—. In some embodiments, $L^{s2}$ is L and comprises at least one —C(O)N(R')—. In some embodiments, $L^{s2}$ is L and comprises at least two —C(O)N(R')—. In some embodiments, $L^{s2}$ is L and comprises at least one —C(O)O—. In some embodiments, $L^{s2}$ is L and comprises at least two —C(O)O—.

In some embodiments, $L^{s2}$ comprises -Q-L'-Q-, wherein Q is independently selected from the group consisting of: —N(R')—, —O—, and —S, wherein L' is described in the present disclosure.

In some embodiments, $L^{s2}$ comprises -Q-L'-Q-, wherein Q is independently selected between —N(R')— and —O—, wherein L' is described in the present disclosure. In some embodiments, $L^{s2}$ comprises —C(O)Q-L'-QC(O)—, wherein Q is independently selected from the group consisting of: —N(R')—, —O—, and —S, wherein L' is described in the present disclosure. In some embodiments, $L^{s2}$ comprises —C(O)Q-L'-QC(O)—, wherein Q is independently selected between —N(R')— and —O, wherein L' is described in the present disclosure. In some embodiments, $L^{s2}$ comprises —C(R')$_2$C(O)Q-L'-QC(O)C(R')$_2$—, wherein Q is independently selected from the group consisting of: —N(R')—, —O—, and —S, wherein L' is described in the present disclosure. In some embodiments, $L^{s2}$ comprises —C(R')$_2$C(O)Q-L'-QC(O)C(R')$_2$—, wherein Q is independently selected between —N(R')— and —O, wherein L' is described in the present disclosure.

In some embodiments, $L^{s2}$ comprises —N(R')-L'-N(R')—, wherein L' is described in the present disclosure. In some embodiments, $L^{s2}$ comprises —C(O)N(R')-L'-N(R')C(O)—, wherein L' is described in the present disclosure. In some embodiments, $L^{s2}$ is —C(R')$_2$C(O)N(R')-L'-N(R')C(O)C(R')$_2$—, wherein L' is described in the present disclosure.

In some embodiments, $L^{s2}$ comprises —O(R')-L'-O(R')—, wherein L' is described in the present disclosure. In some embodiments, $L^{s2}$ comprises —C(O)O-L'-OC(O)—, wherein L' is described in the present disclosure. In some embodiments, $L^{s2}$ is —C(R')$_2$C(O)O-L'-OC(O)C(R')$_2$—, wherein L' is described in the present disclosure.

In some embodiments, R' is an optionally substituted $C_{1-30}$ aliphatic. In some embodiments, R' is an optionally substituted $C_{1-15}$ aliphatic. In some embodiments, R' is an optionally substituted $C_{1-10}$ aliphatic. In some embodiments, R' is an optionally substituted $C_{1-5}$ aliphatic. In some embodiments, R' is hydrogen.

In some embodiments, L' is optionally substituted bivalent $C_1$-$C_{19}$ aliphatic. In some embodiments, L' is optionally substituted bivalent $C_1$-$C_{15}$ aliphatic. In some embodiments, L' is optionally substituted bivalent $C_1$-$C_{10}$ aliphatic. In some embodiments, L' is optionally substituted bivalent $C_1$-$C_9$ aliphatic. In some embodiments, L' is optionally substituted bivalent $C_1$-$C_8$ aliphatic. In some embodiments, L' is optionally substituted bivalent $C_1$-$C_7$ aliphatic. In some embodiments, L' is optionally substituted bivalent $C_1$-$C_6$ aliphatic. In some embodiments, L' is optionally substituted bivalent $C_1$-$C_5$ aliphatic. In some embodiments, L' is optionally substituted bivalent $C_1$-$C_3$ aliphatic. In some embodiments, L' is optionally substituted bivalent $C_1$-$C_2$ aliphatic. In some embodiments, L' is optionally substituted bivalent $C_1$ aliphatic. In some embodiments, L' is —$CH_2$—. In some embodiments, L' is —$(CH_2)_2$—. In some embodiments, L' is —$(CH_2)_3$—. In some embodiments, L' is —$(CH_2)_4$—. In some embodiments, L' is —$(CH_2)_5$—. In some embodiments, L' is —$(CH_2)_6$—. In some embodiments, L' is —$(CH_2)_7$—. In some embodiments, L' is —$(CH_2)_5$—.

In some embodiments, L' is optionally substituted bivalent $C_{6-20}$ aryl ring. In some embodiments, L' is optionally substituted bivalent $C_{6-14}$ aryl ring. In some embodiments, L' is optionally substituted bivalent $C_{6-10}$ aryl ring. In some embodiments, L' is optionally substituted bivalent $C_6$ aryl ring. In some embodiments, L' is bivalent $C_6$ aryl substituted with at least one halogen. In some embodiments, L' is bivalent $C_6$ aryl substituted with at least two halogen. In some embodiments, L' is bivalent $C_6$ aryl substituted with at least three halogen. In some embodiments, L' is bivalent $C_6$ aryl substituted with four halogen. In some embodiments, L' is bivalent $C_6$ aryl substituted with at least one fluorine. In some embodiments, L' is bivalent $C_6$ aryl substituted with at least two fluorine. In some embodiments, L' is bivalent $C_6$ aryl substituted with at least three fluorine. In some embodiments, L' is bivalent $C_6$ aryl substituted with four fluorine. In some embodiments, L' is bivalent $C_6$ aryl substituted with at least one chlorine. In some embodiments, L' is bivalent $C_6$ aryl substituted with at least two chlorine. In some embodiments, L' is bivalent $C_6$ aryl substituted with at least three chlorine. In some embodiments, L' is bivalent $C_6$ aryl substituted with four chlorine. In some embodiments, L' is bivalent $C_6$ aryl substituted at with least one —$O(CH_2)_{0-4}CH_3$. In some embodiments, L' is bivalent $C_6$ aryl substituted with at least two —$O(CH_2)_{0-4}CH_3$. In some embodiments, L' is bivalent $C_6$ aryl substituted with at least three —$O(CH_2)_{0-4}CH_3$. In some embodiments, L' is bivalent $C_6$ aryl substituted with four —$O(CH_2)_{0-4}CH_3$.

In some embodiments, L' is bivalent 5-20 membered heteroaryl ring having 1-10 heteroatoms independently selected from oxygen, nitrogen, sulfur, phosphorus and silicon. In some embodiments, L' is bivalent 5-6 membered heteroaryl ring having 1-4 heteroatoms independently selected from oxygen, nitrogen, sulfur, phosphorus and silicon. In some embodiments, L' is bivalent 5-6 membered heteroaryl ring having 1-4 heteroatoms independently selected from oxygen, nitrogen, and sulfur. In some embodiments, L' is bivalent 6 membered heteroaryl ring having 1-2 heteroatoms independently selected from oxygen, nitrogen, and sulfur. In some embodiments, L' is bivalent 6 membered heteroaryl ring having 2 nitrogen.

In some embodiments, L' is optionally substituted bivalent $C_{3-20}$ cycloaliphatic ring. In some embodiments, L' is optionally substituted bivalent $C_{3-15}$ cycloaliphatic ring. In some embodiments, L' is optionally substituted bivalent $C_{3-10}$ cycloaliphatic ring. In some embodiments, L' is optionally substituted bivalent $C_{3-9}$ cycloaliphatic ring. In some embodiments, L' is optionally substituted bivalent $C_{3-8}$ cycloaliphatic ring. In some embodiments, L' is optionally substituted bivalent $C_{3-7}$ cycloaliphatic ring. In some embodiments, L' is optionally substituted bivalent $C_{3-6}$ cycloaliphatic ring. In some embodiments, L' is optionally substituted bivalent $C_{3-5}$ cycloaliphatic ring. In some embodiments, L' is optionally substituted bivalent $C_{3-4}$ cycloaliphatic ring. In some embodiments, L' is optionally substituted bivalent $C_3$ cycloaliphatic ring. In some embodiments, L' is optionally substituted bivalent $C_4$ cycloaliphatic ring. In some embodiments, L' is optionally substituted bivalent $C_5$ cycloaliphatic ring. In some embodiments, L' is optionally substituted bivalent $C_5$ cycloalkyl ring. In some embodiments, L' is optionally substituted bivalent $C_5$ cycloalkenyl ring. In some embodiments, L' is optionally substituted bivalent $C_6$ cycloaliphatic ring. In some embodiments, L' is optionally substituted bivalent $C_6$ cycloalkyl ring.

In some embodiments, $L^{s2}$ comprises —N(R')-L'-N(R')— and L' is a covalent bond. In some embodiments $L^{s2}$ comprises —N(R)—N(R)—, wherein:

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments $L^{s2}$ comprises —N(R)—N(R)—, wherein:

each R is independently optionally substituted $C_{1-30}$ aliphatic; or two or more R groups on two or more atoms are optionally and independently taken together with their intervening atoms to form an optionally substituted, 3-30 membered monocyclic ring.

In some embodiments, $L^{s2}$ is a staple selected from the group consisting of:

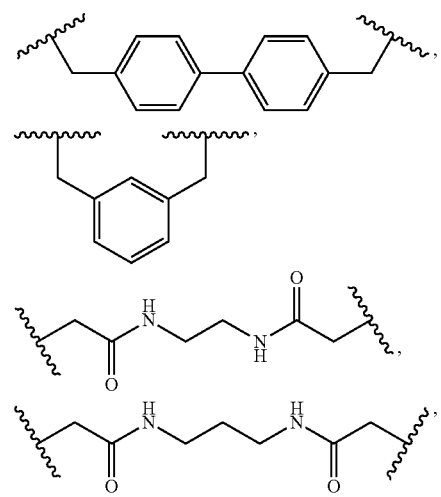

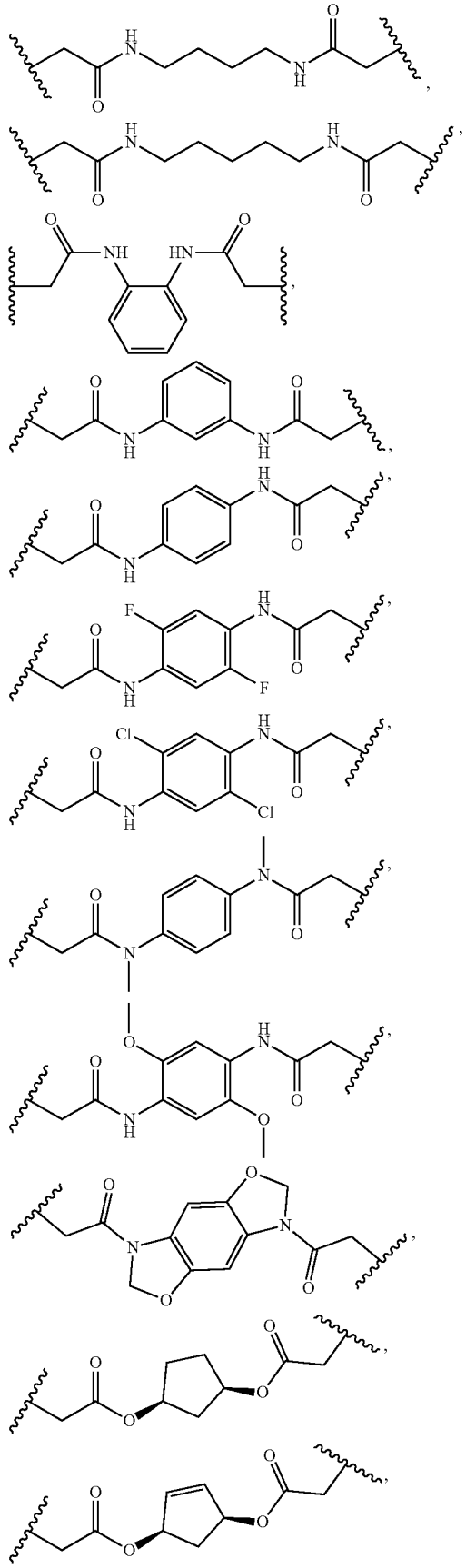

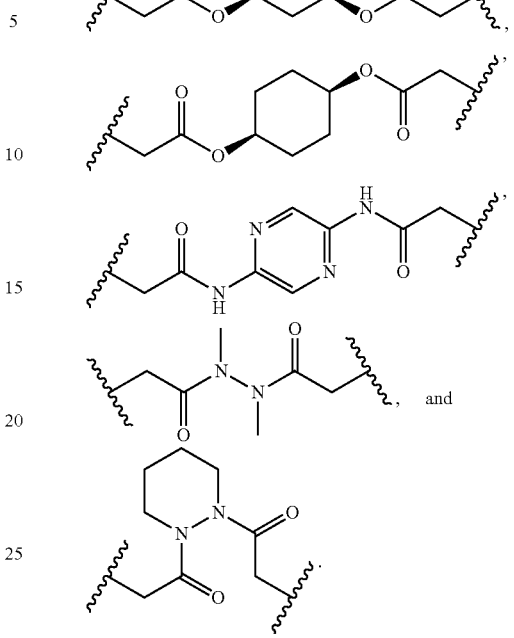

As those skilled in the art will appreciate, provided technologies can be utilized to prepare collection of peptides using non-cysteine residues and suitable chemistry therefor. For example, in some embodiments, cysteine stapling is replaced with lysine stapling, wherein the cysteine residues for cysteine stapling are replaced with lysine residues for lysine stapling (e.g., using agents that can crosslink two lysine residues, for example, through reactions with side chain amino groups). In some embodiments, for lysine stapling, $R^E$ in various formulae is or comprises an activated carboxylic acid group (e.g., NHS ester group), an imidoester group, etc. Suitable reagents are widely known in the art including many commercially available ones. In some embodiments, cysteine stapling is replaced with methionine stapling. In some embodiments, cysteine residues for cysteine stapling are replaced with methionine residues for methionine stapling. In some embodiments, cysteine stapling is replaced with tryptophan stapling. In some embodiments, cysteine residues for cysteine stapling are replaced with tryptophan residues for tryptophan stapling. As those skilled in the art will appreciate, various technologies (e.g., reagents, reactions, etc.) are described in the art and can be utilized in accordance with the present disclosure for, e.g., methionine stapling, tryptophan stapling, etc. In some embodiments, such stapling can be performed using reagents having various formulae described herein, wherein $R^E$ is or comprises a group that are suitable for methionine and/or tryptophan stapling. In some embodiments, stapling may be performed using one residue at a first position, and a different residue at a second position. Useful reagents for such stapling may comprise a first reactive group for stapling at a first position (e.g., through a first $R^E$), and a second reactive group for stapling at a second position (e.g., through a second $R^E$).

In some embodiments, for various types of stapling (e.g., cysteine stapling, or non-cysteine stapling), stapling is between residues (e.g., cysteine residues for cysteine stapling) separated by two residues (i+3 stapling). In some embodiments, stapling is between residues separated by three residues (i+4 stapling). In some embodiments, stapling is between residues separated by six residues (i+7 stapling).

As appreciated by those skilled in the art, in some embodiments, more than two residues can be stapled at the same time. For example, in some embodiments, three or more cysteines are stapled using crosslinking reagents containing three or more reactive groups (e.g., $R^E$ groups).

Non-Cysteine Stapling

In some embodiments, the present disclosure provides useful technologies relating to non-cysteine stapling. Among other things, the present disclosure appreciates that peptides amenable to cysteine stapling and/or comprising one or more non-cysteine staples, can have its cysteine residues and cysteine staple replaced with other amino acids and staples (e.g. hydrocarbon and other non-hydrocarbon amino acid and staples). In some embodiments, the resulting non-cysteine stapled peptide maintains the same or similar interaction with a target of interest when compared to a reference cysteine stapled peptide. Described herein are non-cysteine amino acids and non-cysteine staples involving such non-cysteine amino acid residues.

In some embodiments, an amino acid of formula A-I is a compound having the structure of formula A-II:

$$NH(R^{a1})\text{-}L^{a1}\text{-}C(\text{-}L^{a}\text{-}CH\!=\!CH_2)(R^{a3})\text{-}L^{a2}\text{-}COOH, \qquad \text{A-II}$$

or a salt thereof, wherein each variable is independently as described in the present disclosure.

In some embodiments, an amino acid of formula A-I is a compound having the structure of formula A-III:

$$NH(R^{a1})\text{—}C(\text{-}L^{a}\text{-}CH\!=\!CH_2)(R^{a3})\text{—}COOH, \qquad \text{A-III}$$

or a salt thereof, wherein each variable is independently as described in the present disclosure.

In some embodiments, $L^a$ comprises at least one —N(R')— wherein R' is independently as described in the present disclosure.

In some embodiments, an amino acid of formula A-I is a standard amino acid. In

TABLE A-I

Exemplary amino acids (Fmoc-Protected).

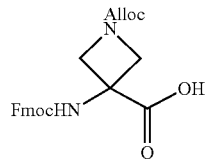 Monomer A ($M_A$)

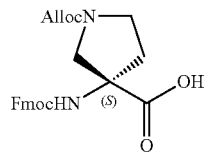 Monomer B ($M_B$)

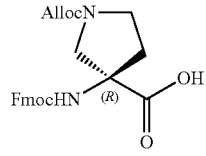 Monomer C ($M_C$)

TABLE A-II

Exemplary amino acids (Fmoc-Protected).

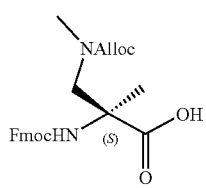 Monomer D ($M_D$)

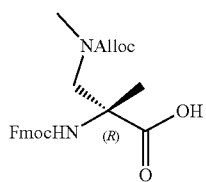 Monomer E ($M_E$)

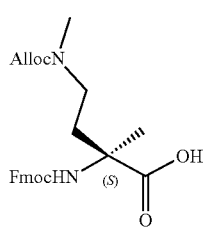 Monomer F ($M_F$)

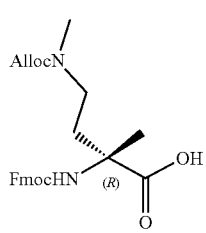 Monomer G ($M_G$)

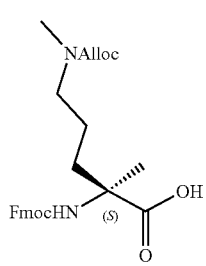 Monomer H ($M_H$)

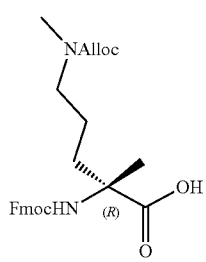 Monomer I ($M_I$)

TABLE A-III
Exemplary amino acids (Fmoc-Protected).
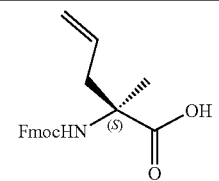 S₃
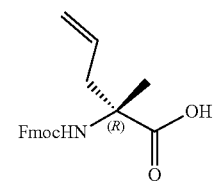 R₃
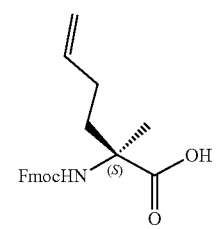 S₄
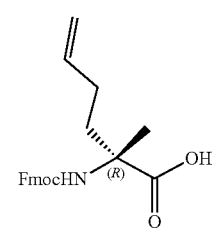 R₄
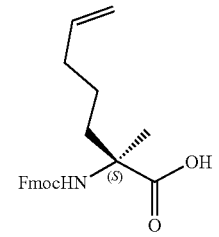 S₅
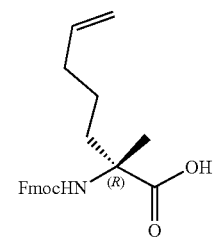 R₅
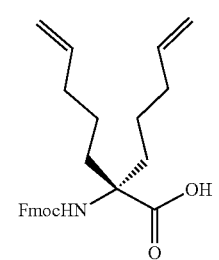 B₅
TABLE A-III-continued
Exemplary amino acids (Fmoc-Protected).
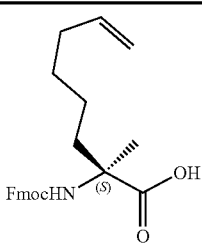 S₆
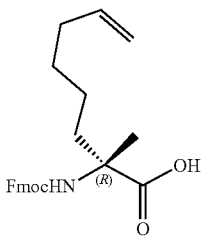 R₆
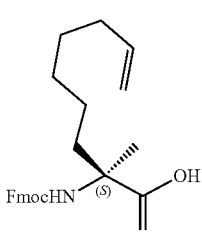 S₇
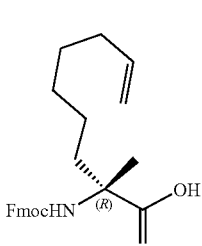 R₇
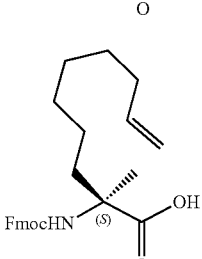 S₈
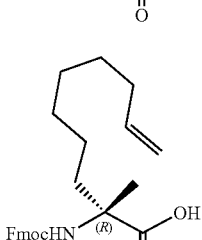 R₈
In some embodiments, an amino acid is an alpha-amino acid. In some embodiments, an amino acid is an L-amino acid. In some embodiments, an amino acid is a D-amino acid. In some embodiments, the alpha-carbon of an amino acid is achiral. In some embodiments, an amino acid is a beta-amino acid. In some embodiments, an amino acid is a gamma-amino acid.

In some embodiments, a provided amino acid sequence contains two or more amino acid residues whose side chains are linked together to form one or more staples. In some embodiments, a provided amino acid sequence contains two or more amino acid residues, each of which independently has a side chain comprising an olefin. In some embodiments, a provided amino acid sequence contains two or more amino acid residues, each of which independently has a side chain comprising a terminal olefin. In some embodiments, a provided amino acid sequence contains two and no more than two amino acid residues, each of which independently has a side chain comprising an olefin. In some embodiments, a provided amino acid sequence contains two and no more than two amino acid residues, each of which independently has a side chain comprising a terminal olefin. In some embodiments, a provided amino acid sequence comprises at least one residue of an amino acid that comprises an olefin and a nitrogen atom other than the nitrogen atom of its amino group. In some embodiments, a provided amino acid sequence comprises at least one residue of an amino acid that comprises a terminal olefin and a nitrogen atom other than the nitrogen atom of its amino group. In some embodiments, a provided amino acid sequence comprises at least one residue of an amino acid that has a side chain than comprises a terminal olefin and a nitrogen atom. In some embodiments, a provided amino acid sequence comprises at least one residue of an amino acid of formula A-I, wherein $R^{a2}$ comprising an olefin and a —N(R')— moiety, wherein R' is as described in the present disclosure (including, in some embodiments, optionally taken together with $R^{a3}$ and their intervening atoms to form an optionally substituted ring as described in the present disclosure). In some embodiments, $R^{a2}$ comprising a terminal olefin and a —N(R')— moiety wherein R' is as described in the present disclosure. In some embodiments, a provided amino acid sequence comprises at least one residue of an amino acid selected from Table A-I. In some embodiments, a provided amino acid sequence comprises at least one residue of an amino acid selected from Table A-II. In some embodiments, a provided amino acid sequence comprises at least one residue of an amino acid selected from Table A-III. In some embodiments, two olefins from two side chains are linked together through olefin metathesis to form a staple. In some embodiments, a staple is preferably formed by side chains of amino acid residues that are not at the corresponding positions of a target of interest. In some embodiments, a formed staple does not disrupt interaction between the peptide and a target of interest.

In some embodiments, a provided staple is a hydrocarbon staple. In some embodiments, a hydrocarbon staple comprises no chain heteroatoms wherein a chain of a staple is the shortest covalent connection within the staple from one end of the staple to the other end of the staple.

In some embodiments, a provided staple is a non-hydrocarbon staple. In some embodiments, a non-hydrocarbon staple comprises one or more chain heteroatoms wherein a chain of a staple is the shortest covalent connection within the staple from one end of the staple to the other end of the staple. In some embodiments, a non-hydrocarbon staple is a carbamate staple in that it comprises a —N(R')—C(O)—O— moiety in its chain. In some embodiments, a non-hydrocarbon staple is an amino staple in that it comprises a —N(R')— moiety in its chain, wherein the —N(R')— moiety is not part of —N(R')—C(O)—O—. In some embodiments, a non-hydrocarbon staple is an amino staple in that it comprises a —N(R')— moiety in its chain, wherein the —N(R')— moiety is not bonded to a carbon atom that additionally forms a double bond with a heteroatom (e.g., —C(=O), —C(=S), —C(=N—R'), etc.).

In some embodiments, a provided stapled peptide comprises a staple which staple is $L^s$, wherein $L^s$ is $-L^{s1}-L^{s2}-L^{s3}-$, each of $L^{s1}$, $L^{s2}$, and $L^{s3}$ is independently L, wherein each L is independently as described in the present disclosure. In some embodiments, a provided staple is $L^s$.

In some embodiments, $L^{s1}$ comprises at least one —N(R')—, wherein R' is as described in the present disclosure. In some embodiments, the —N(R')— is bonded to two carbon atoms, wherein neither of the two carbon atoms forms a double bond with a heteroatom. In some embodiments, the —N(R')— is not bonded to —C(O)—. In some embodiments, the —N(R')— is not bonded to —C(S)—. In some embodiments, the —N(R')— is not bonded to —C(=NR')—. In some embodiments, $L^{s1}$ is -L'-N(R')—, wherein L' is optionally substituted bivalent $C_1$-$C_{19}$ aliphatic. In some embodiments, $L^{s1}$ is -L'-N(CH$_3$)—, wherein L' is optionally substituted bivalent $C_1$-$C_{19}$ aliphatic.

In some embodiments, R' is optionally substituted $C_{1-6}$ alkyl. In some embodiments, R' is $C_{1-6}$ alkyl. In some embodiments, R' is methyl. In some embodiments, the peptide backbone atom to which $L^{s1}$ is bonded is also bonded to $R^1$, and R' and $R^1$ are both R and are taken together with their intervene atoms to form an optionally substituted ring as described in the present disclosure. In some embodiments, a formed ring has no additional ring heteroatoms in addition to the nitrogen atom to which R' is bonded. In some embodiments, a formed ring is 3-membered. In some embodiments, a formed ring is 4-membered. In some embodiments, a formed ring is 5-membered. In some embodiments, a formed ring is 6-membered.

In some embodiments, L' is optionally substituted bivalent $C_1$-$C_{20}$ aliphatic. In some embodiments, L' is optionally substituted bivalent $C_1$-$C_{19}$ aliphatic. In some embodiments, L' is optionally substituted bivalent $C_1$-$C_{15}$ aliphatic. In some embodiments, L' is optionally substituted bivalent $C_1$-$C_{10}$ aliphatic. In some embodiments, L' is optionally substituted bivalent $C_1$-$C_9$ aliphatic. In some embodiments, L' is optionally substituted bivalent $C_1$-$C_8$ aliphatic. In some embodiments, L' is optionally substituted bivalent $C_1$-$C_7$ aliphatic. In some embodiments, L' is optionally substituted bivalent $C_1$-$C_6$ aliphatic. In some embodiments, L' is optionally substituted bivalent $C_1$-$C_5$ aliphatic. In some embodiments, L' is optionally substituted bivalent $C_1$-$C_4$ aliphatic. In some embodiments, L' is optionally substituted alkylene. In some embodiments, L' is optionally substituted alkenylene. In some embodiments, L' is unsubstituted alkylene. In some embodiments, L' is —CH$_2$—. In some embodiments, L' is —(CH$_2$)$_2$—. In some embodiments, L' is —(CH$_2$)$_3$—. In some embodiments, L' is —(CH$_2$)$_4$—. In some embodiments, L' is —(CH$_2$)$_5$—. In some embodiments, L' is —(CH$_2$)$_6$—. In some embodiments, L' is —(CH$_2$)$_7$—. In some embodiments, L' is —(CH$_2$)$_5$—. In some embodiments, L' is bonded to a peptide backbone atom. In some embodiments, L' is optionally substituted alkenylene. In some embodiments, L' is unsubstituted alkenylene. In some embodiments, L' is —CH$_2$—CH=CH—CH$_2$—.

In some embodiments, $L^{s1}$ comprises at least one —N(R')C(O)—, wherein R' is as described in the present disclosure. In some embodiments, $L^{s1}$ is -L'-N(R')C(O)—, wherein each of L' and R' is independently as described in the present disclosure. In some embodiments, $L^{s1}$ is -L'-N(CH$_3$)C(O)—, wherein L' is independently as described in the present disclosure.

In some embodiments, $L^{s1}$ is a covalent bond.

In some embodiments, $L^{s1}$ is L', wherein L' is as described in the present disclosure.

In some embodiments, $L^{s2}$ is L, wherein L is as described in the present disclosure. In some embodiments, $L^{s2}$ is L', wherein L' is as described in the present disclosure. In some embodiments, $L^{s2}$ comprises —CH$_2$—CH=CH—CH$_2$—. In some embodiments, $L^{s2}$ is —CH$_2$—CH=CH—CH$_2$—. In some embodiments, $L^{s2}$ comprises —(CH$_2$)$_4$—. In some embodiments, $L^{s2}$ is —(CH$_2$)$_4$—.

In some embodiments, $L^{s3}$ comprises at least one —N(R')—, wherein R' is as described in the present disclosure. In some embodiments, the —N(R')— is bonded to two carbon atoms, wherein neither of the two carbon atoms forms a double bond with a heteroatom. In some embodiments, the —N(R')— is not bonded to —C(O)—. In some embodiments, the —N(R')— is not bonded to —C(S)—. In some embodiments, the —N(R')— is not bonded to —C(=NR')—. In some embodiments, $L^{s3}$ is -L'-N(R')—, wherein L' is optionally substituted bivalent C$_1$-C$_{19}$ aliphatic. In some embodiments, $L^{s3}$ is -L'-N(CH$_3$)—, wherein L' is optionally substituted bivalent C$_1$-C$_{19}$ aliphatic.

In some embodiments, $L^{s3}$ comprises at least one —N(R')C(O)—, wherein R' is as described in the present disclosure. In some embodiments, $L^{s3}$ is -L'-N(R')C(O)—, wherein each of L' and R' is independently as described in the present disclosure. In some embodiments, $L^{s3}$ is -L'-N(CH$_3$)C(O)—, wherein L' is independently as described in the present disclosure.

In some embodiments, $L^{s3}$ is L', wherein L' is as described in the present disclosure. In some embodiments, $L^{s3}$ is optionally substituted alkylene. In some embodiments, $L^{s3}$ is unsubstituted alkylene.

In some embodiments, $L^s$ comprises at least one —N(R')—, wherein R' is as described in the present disclosure. In some embodiments, the —N(R')— is bonded to two carbon atoms, wherein neither of the two carbon atoms forms a double bond with a heteroatom. In some embodiments, the —N(R')— is not bonded to —C(O)—. In some embodiments, the —N(R')— is not bonded to —C(S)—. In some embodiments, the —N(R')— is not bonded to —C(=NR')—. In some embodiments, $L^s$ comprises at least one —N(R')C(O)—, wherein R' is as described in the present disclosure.

In some embodiments, L comprises at least one —N(R')—, wherein R' is as described in the present disclosure. In some embodiments, the —N(R')— is bonded to two carbon atoms, wherein neither of the two carbon atoms forms a double bond with a heteroatom. In some embodiments, the —N(R')— is not bonded to —C(O)—. In some embodiments, the —N(R')— is not bonded to —C(S)—. In some embodiments, the —N(R')— is not bonded to —C(=NR')—. In some embodiments, L is -L'-N(R')—, wherein L' is optionally substituted bivalent C$_1$-C$_{19}$ aliphatic. In some embodiments, L is -L'-N(CH$_3$)—, wherein L' is optionally substituted bivalent C$_1$-C$_{19}$ aliphatic.

In some embodiments, L comprises at least one —N(R')C(O)—, wherein R' is as described in the present disclosure. In some embodiments, L is -L'-N(R')C(O)—, wherein each of L' and R' is independently as described in the present disclosure. In some embodiments, L is -L'-N(CH$_3$)C(O)—, wherein L' is independently as described in the present disclosure.

In some embodiments, L is L', wherein L' is as described in the present disclosure. In some embodiments, L is optionally substituted alkylene. In some embodiments, L is unsubstituted alkylene.

In some embodiments, L is optionally substituted bivalent C$_1$-C$_{25}$ aliphatic. In some embodiments, L is optionally substituted bivalent C$_1$-C$_{20}$ aliphatic. In some embodiments, L is optionally substituted bivalent C$_1$-C$_{15}$ aliphatic. In some embodiments, L is optionally substituted bivalent C$_1$-C$_{10}$ aliphatic. In some embodiments, L is optionally substituted bivalent C$_1$-C$_9$ aliphatic. In some embodiments, L is optionally substituted bivalent C$_1$-C$_8$ aliphatic. In some embodiments, L is optionally substituted bivalent C$_1$-C$_7$ aliphatic. In some embodiments, L is optionally substituted bivalent C$_1$-C$_6$ aliphatic. In some embodiments, L is optionally substituted bivalent C$_1$-C$_8$ aliphatic. In some embodiments, L is optionally substituted bivalent C$_1$-C$_4$ aliphatic. In some embodiments, L is optionally substituted alkylene. In some embodiments, L is optionally substituted alkenylene. In some embodiments, L is unsubstituted alkylene. In some embodiments, L is —CH$_2$—. In some embodiments, L is —(CH$_2$)$_2$—. In some embodiments, L is —(CH$_2$)$_3$—. In some embodiments, L is —(CH$_2$)$_4$—. In some embodiments, L is —(CH$_2$)$_5$—. In some embodiments, L is —(CH$_2$)$_6$—. In some embodiments, L is —(CH$_2$)$_7$—. In some embodiments, L is —(CH$_2$)$_5$—. In some embodiments, L is bonded to a peptide backbone atom. In some embodiments, L is optionally substituted alkenylene. In some embodiments, L is unsubstituted alkenylene. In some embodiments, L is —CH$_2$—CH=CH—CH$_2$—.

In some embodiments, one end of a staple is connected to an atom $A^{n1}$ of the peptide backbone, wherein $A^{n1}$ is optionally substituted with $R^1$ and is an atom of an amino acid residue at amino acid position $n^1$ of the peptide from the N-terminus, and the other end is connected to an atom $A^{n2}$ of the peptide backbone, wherein $A^{n2}$ is optionally substituted with $R^2$ (in some embodiments, $R^1$ and/or $R^2$ is R which can be hydrogen) and is an atom of an amino acid residue at amino acid position $n^2$ of the peptide from the N-terminus, wherein each of $n^1$ and $n^2$ is independently an integer, and $n^2=n^1+m$, wherein m is 3-12.

In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, a staple is referred to a (i, i+m) staple.

In some embodiments, $A^{n1}$ is a carbon atom. In some embodiments, $A^{n1}$ is achiral. In some embodiments, $A^{n1}$ is chiral. In some embodiments, $A^{n1}$ is R. In some embodiments, $A^{n1}$ is S.

In some embodiments, $A^{n2}$ is a carbon atom. In some embodiments, $A^{n2}$ is achiral. In some embodiments, $A^{n2}$ is chiral. In some embodiments, $A^{n2}$ is R. In some embodiments, $A^{n2}$ is S.

In some embodiments, $A^{n1}$ is achiral and $A^{n2}$ is achiral. In some embodiments, $A^{n1}$ is achiral and $A^{n2}$ is R. In some embodiments, $A^{n1}$ is achiral and $A^{n2}$ is S. In some embodiments, $A^{n1}$ is R and $A^{n2}$ is achiral. In some embodiments, $A^{n1}$ is R and $A^{n2}$ is R. In some embodiments, $A^{n1}$ is R and $A^{n2}$ is S. In some embodiments, $A^{n1}$ is S and $A^{n2}$ is achiral. In some embodiments, $A^{n1}$ is S and $A^{n2}$ is R. In some embodiments, $A^{n1}$ is S and $A^{n2}$ is S.

In some embodiments, provided stereochemistry at staple-backbone connection points and/or combinations thereof, optionally together with one or more structural elements of provided peptide, e.g., staple chemistry (hydrocarbon, non-hydrocarbon), staple length, etc. can provide various benefits, such as improved preparation yield, purity, and/or selectivity, improved properties (e.g., improved solubility, improved stability, lowered toxicity, improved selectivities, etc.), improved activities, etc. In some embodiments, provided stereochemistry and/or stereochemistry combinations are different from those typically used, e.g., those of U.S. Pat. No. 9,617,309, US 2015-0225471, US 2016-0024153, US 2016-0215036, US 2016-0244494, WO 2017/062518, and provided one or more of benefits described in the present disclosure.

In some embodiments, a staple can be of various lengths, in some embodiments, as represent by the number of chain atoms of a staple. In some embodiments, a chain of a staple is the shortest covalent connection in the staple from a first end (connection point with a peptide backbone) of a staple to a second end of the staple, wherein the first end and the second end are connected to two different peptide backbone atoms. In some embodiments, a staple comprises 5-30 chain atoms, e.g., 5, 6, 7, 8, 9, or 10 to 11, 12, 13, 14, 15, 16, 17, 18, 19, 20, 21, 22, 23, 24, or 25 chain atoms. In some embodiments, a staple comprises 5 chain atoms. In some embodiments, a staple comprises 6 chain atoms. In some embodiments, a staple comprises 7 chain atoms. In some embodiments, a staple comprises 8 chain atoms. In some embodiments, a staple comprises 9 chain atoms. In some embodiments, a staple comprises 10 chain atoms. In some embodiments, a staple comprises 11 chain atoms. In some embodiments, a staple comprises 12 chain atoms. In some embodiments, a staple comprises 13 chain atoms. In some embodiments, a staple comprises 14 chain atoms. In some embodiments, a staple comprises 15 chain atoms. In some embodiments, a staple comprises 16 chain atoms. In some embodiments, a staple comprises 17 chain atoms. In some embodiments, a staple comprises 18 chain atoms. In some embodiments, a staple comprises 19 chain atoms. In some embodiments, a staple comprises 20 chain atoms. In some embodiments, a staple has a length of 5 chain atoms. In some embodiments, a staple has a length of 6 chain atoms. In some embodiments, a staple has a length of 7 chain atoms. In some embodiments, a staple has a length of 8 chain atoms. In some embodiments, a staple has a length of 9 chain atoms. In some embodiments, a staple has a length of 10 chain atoms. In some embodiments, a staple has a length of 11 chain atoms. In some embodiments, a staple has a length of 12 chain atoms. In some embodiments, a staple has a length of 13 chain atoms. In some embodiments, a staple has a length of 14 chain atoms. In some embodiments, a staple has a length of 15 chain atoms. In some embodiments, a staple has a length of 16 chain atoms. In some embodiments, a staple has a length of 17 chain atoms. In some embodiments, a staple has a length of 18 chain atoms. In some embodiments, a staple has a length of 19 chain atoms. In some embodiments, a staple has a length of 20 chain atoms. In some embodiments, a staple has a length of 8-15 chain atoms. In some embodiments, a staple has 8-12 chain atoms. In some embodiments, a staple has 9-12 chain atoms. In some embodiments, a staple has 9-10 chain atoms. In some embodiments, a staple has 8-10 chain atoms. In some embodiments, length of a staple can be adjusted according to the distance of the amino acid residues it connects, for example, a longer staple may be needed for a (i, i+7) staple than a (i, i+4) staple. Staple lengths may be otherwise described. For example, in some embodiments, staple lengths may be described as the total number of chain atoms and non-chain ring atoms, where a non-chain ring atom is an atom of the staple which forms a ring with one or more chain atoms but is not a chain atom in that it is not within the shortest covalent connection from a first end of the staple to a second end of the staple. In some embodiments, staples formed using Monomer A (which comprises a azetidine moiety), Monomer B (which comprises a pyrrolidine moiety), and/or Monomer C (which comprises a pyrrolidine moiety) may comprise one or two non-chain ring atoms as illustrated in the exemplary stapled peptides.

In some embodiments, a staple has no heteroatoms in its chain. In some embodiments, a staple comprises at least one heteroatom in its chain. In some embodiments, a staple comprises at least one nitrogen atom in its chain.

In some embodiments, a staple is $L^s$, wherein $L^s$ is an optionally substituted, bivalent $C_{8-14}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, a staple is $L^s$, wherein $L^s$ is an optionally substituted, bivalent $C_{9-13}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, a staple is $L^s$, wherein $L^s$ is an optionally substituted, bivalent $C_{10-15}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, a staple is $L^s$, wherein $L^s$ is an optionally substituted, bivalent $C_{11-14}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, a staple is a (i, i+4) staple in that not including the two amino acid residues that are directly connected to the staple, there are three amino acid residues between the two amino acid residues that are directly connected to the staple. In some embodiments, a staple is a (i, i+7) staple in that not including the two amino acid residues that are directly connected to the staple, there are six amino acid residues between the two amino acid residues that are directly connected to the staple.

In some embodiments, for each of $L^s$, $L^{s1}$, $L^{s2}$, and $L^{s3}$, any replacement of methylene units, if any, is replaced with —N(R')— or —N(R')—C(O)—.

In some embodiments, an olefin in a staple is a Z-olefin. In some embodiments, an olefin in a staple in an E-olefin. In some embodiments, a provided composition comprises stapled peptides comprising a staple that contains a Z-olefin and stapled peptides comprising a staple that contains an E-olefin. In some embodiments, a provided composition comprises stapled peptides comprising a staple that contains a Z-olefin. In some embodiments, a provided composition comprises stapled peptides comprising a staple that contains an E-olefin. In some embodiments, otherwise identical stapled peptides that differ only in the E Z configuration of staple olefin demonstrate different properties and/or activities as demonstrated herein. In some embodiments, stapled peptides with E-olefin in a staple may provide certain desirable properties and/or activities given the context. In some embodiments, stapled peptides with Z-olefin in a staple may provide certain desirable properties and/or activities given the context.

In some embodiments, two staples may be bonded to the same atom of the peptide backbone, forming a "stitch" structure.

In some embodiments, a staple is Pro-lock in that one end of the staple is bonded to the alpha-carbon of a proline residue.

In some embodiments, an exemplary staple is a staple as illustrated below in Tables S-1, S-2, S-3, and S-4 (with exemplary peptide backbone illustrated for clarity (can be applied to other peptide backbone), X being amino acid residues). In some embodiments, the olefin is Z. In some embodiments, the olefin is E. In some embodiments, an (i, i+4) staple is selected from Table S-1. In some embodiments, an (i, i+4) staple is selected from Table S-2. In some embodiments, an (i, i+7) staple is selected from Table S-3. In some embodiments, an (i, i+7) staple is selected from Table S-4.

TABLE S-1

Exemplary staples.

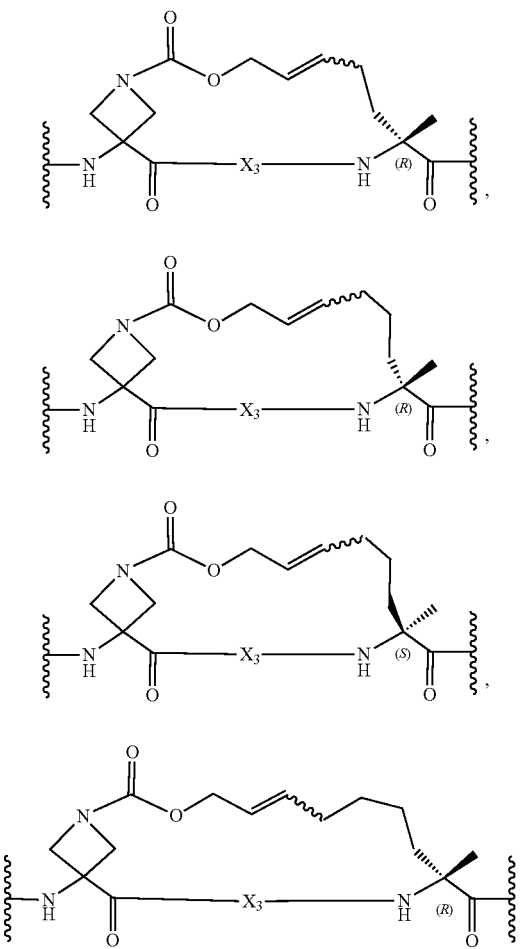

TABLE S-1-continued

Exemplary staples.

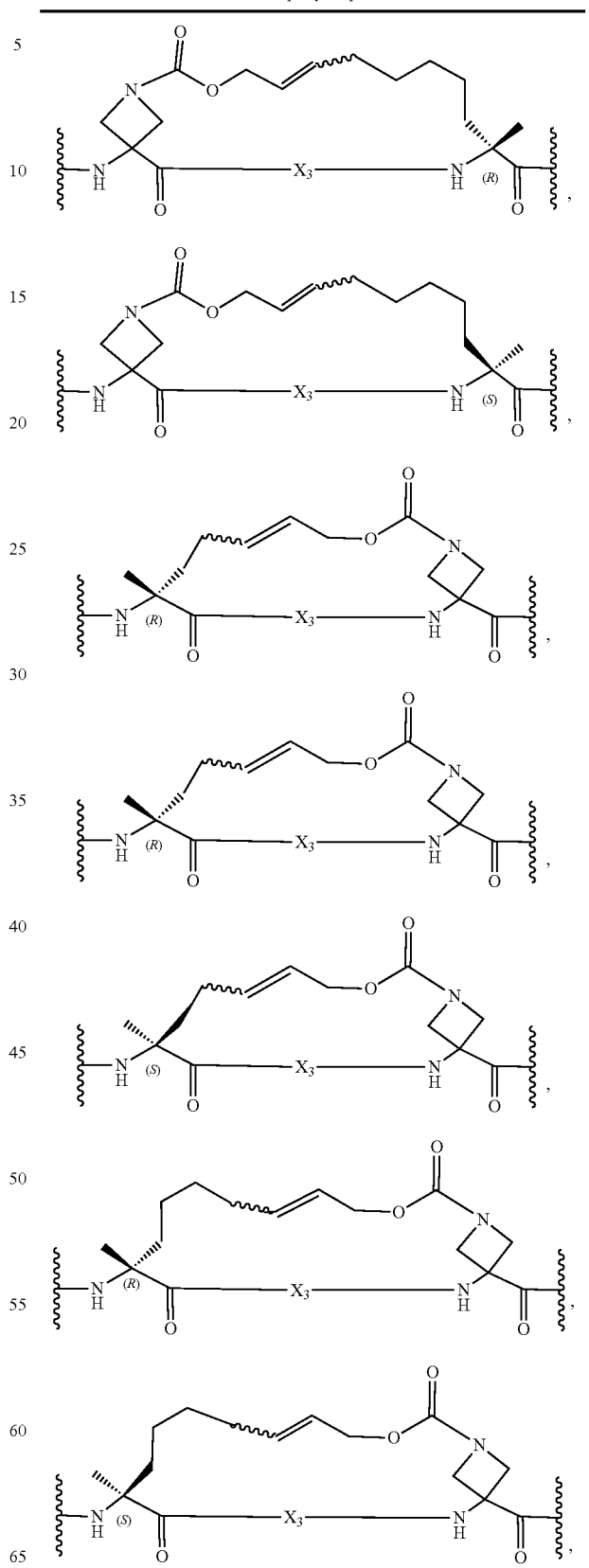

TABLE S-1-continued
Exemplary staples.
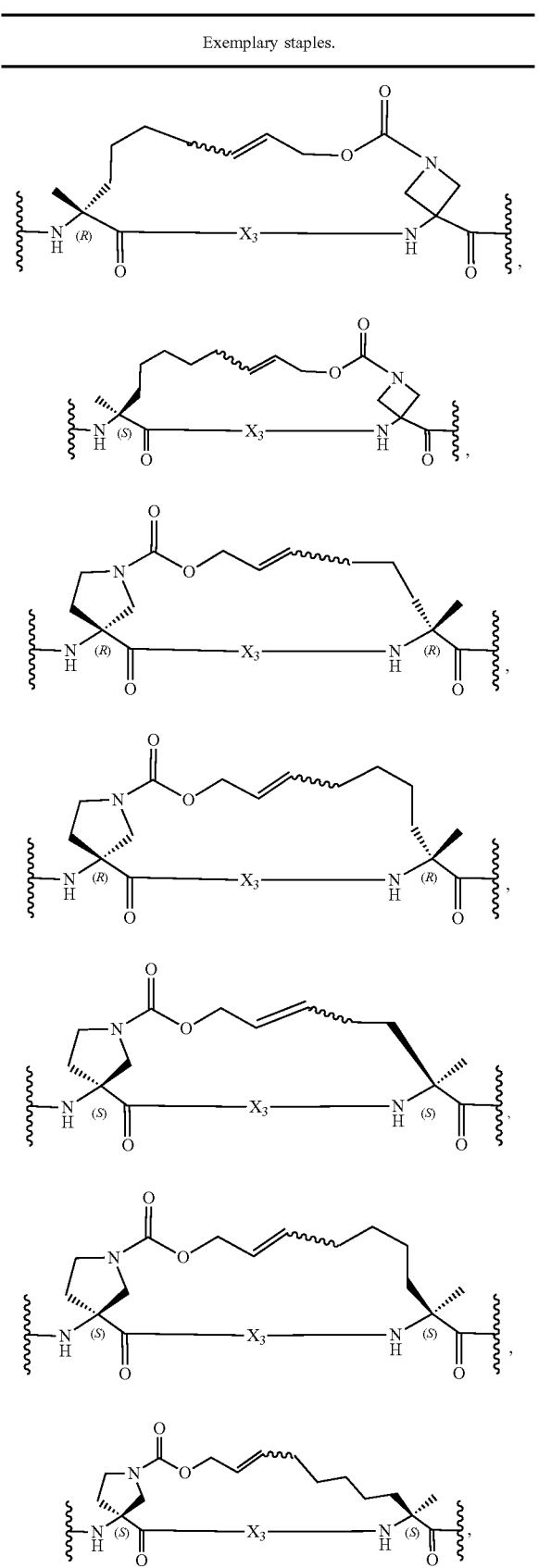
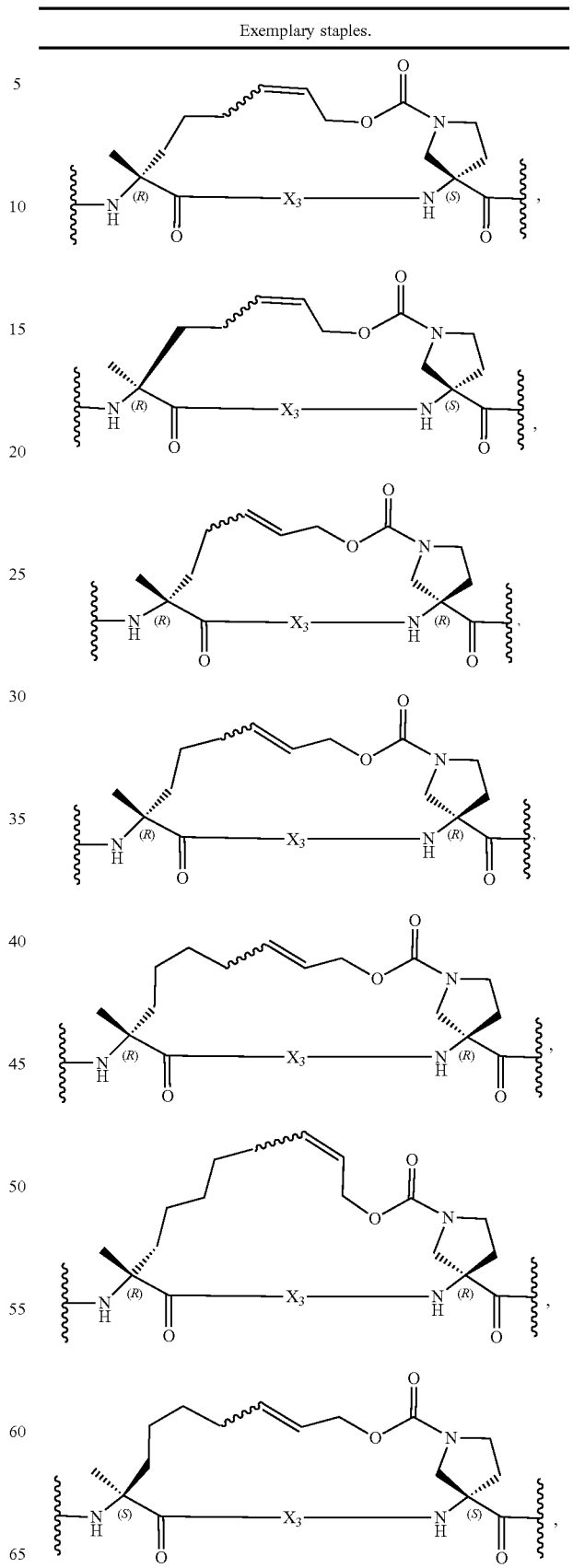

TABLE S-1-continued
Exemplary staples.
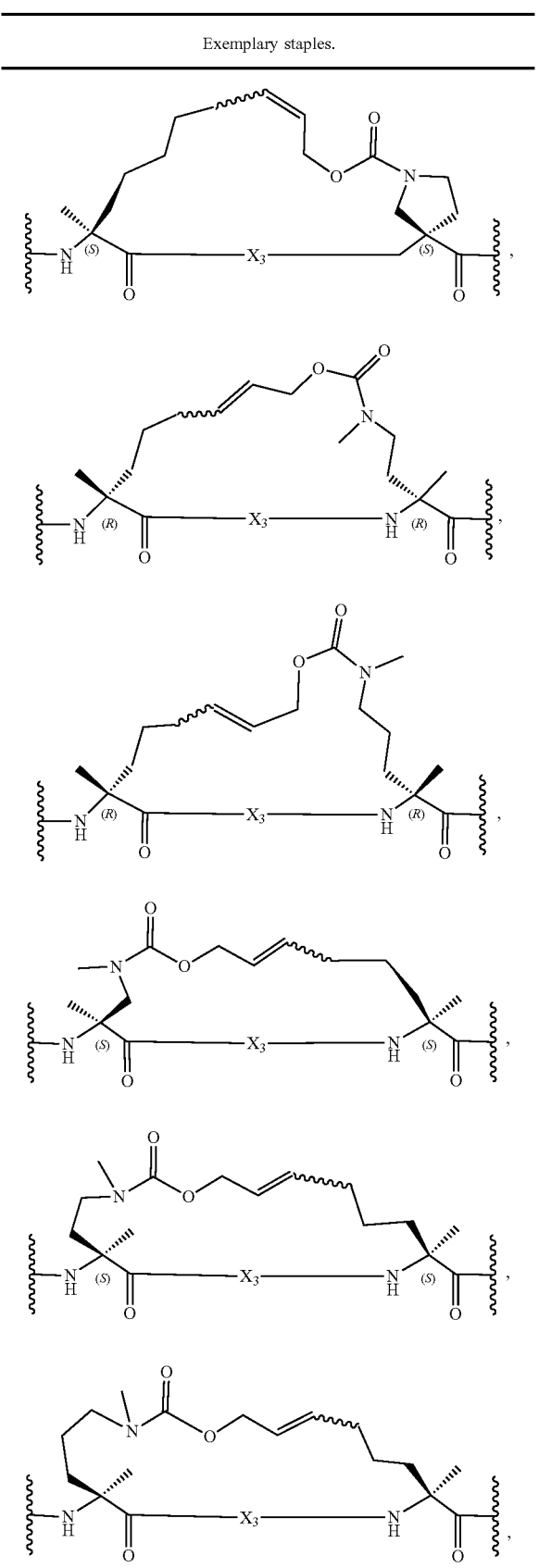
TABLE S-1-continued
Exemplary staples.
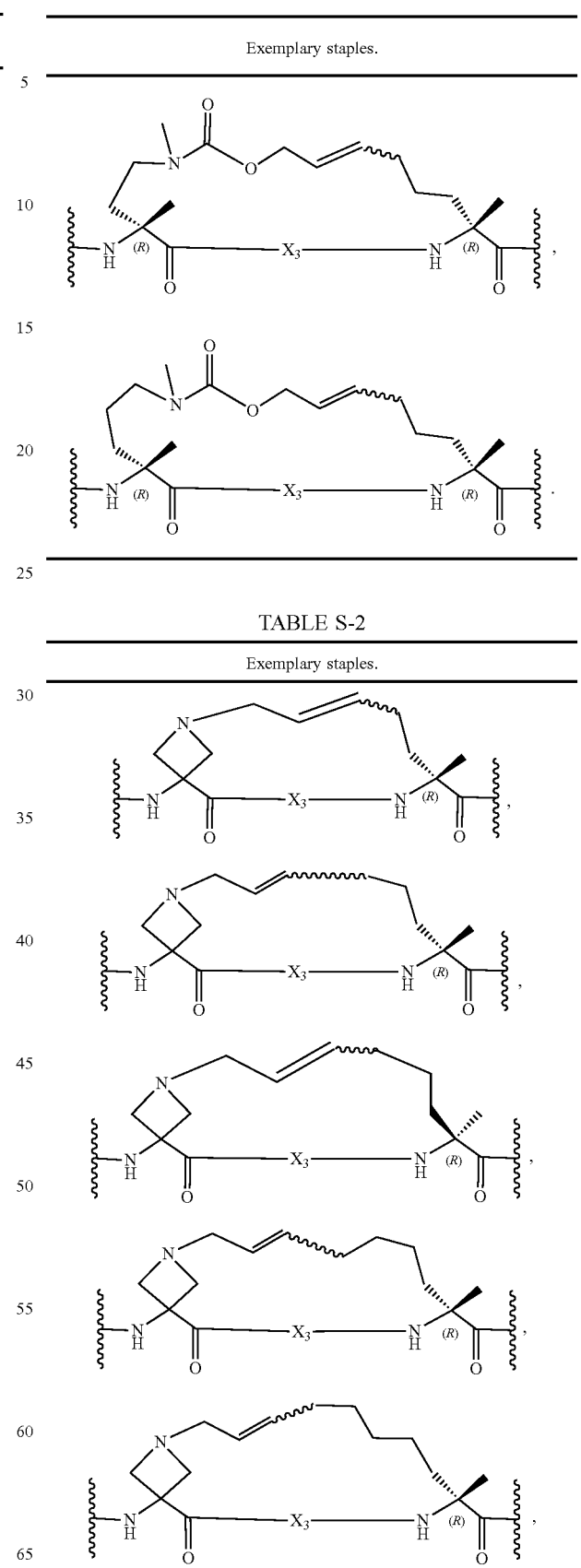
TABLE S-2
Exemplary staples.

TABLE S-2-continued
Exemplary staples.
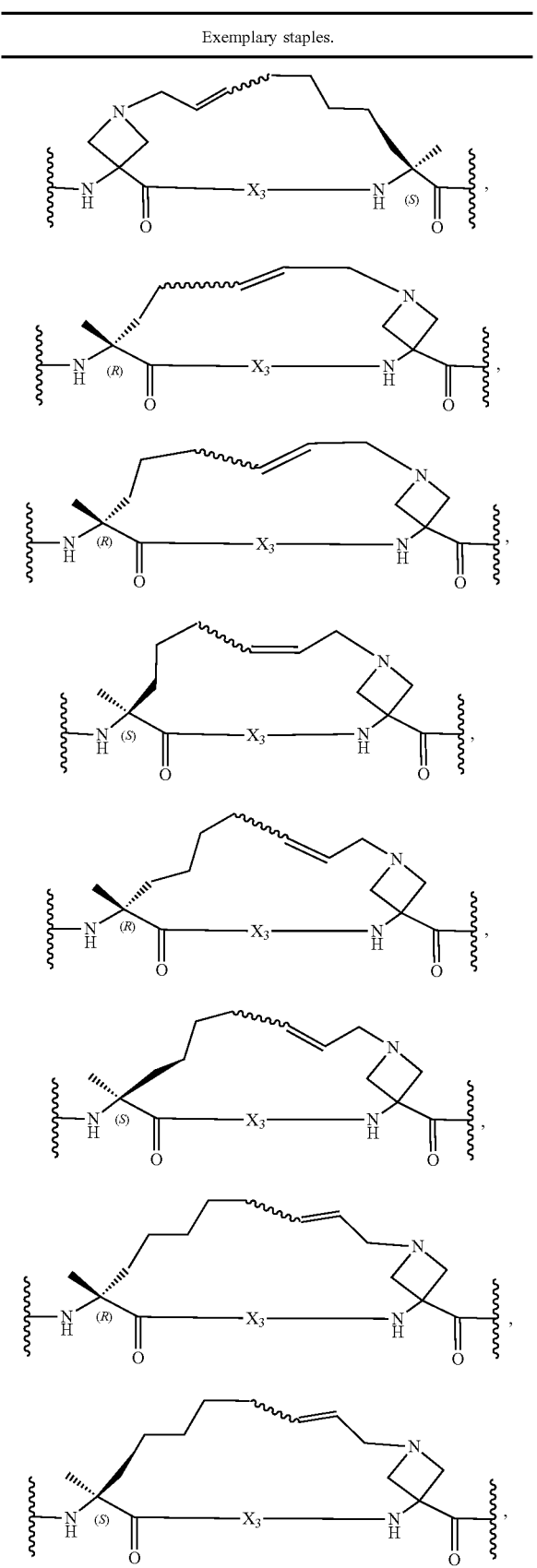
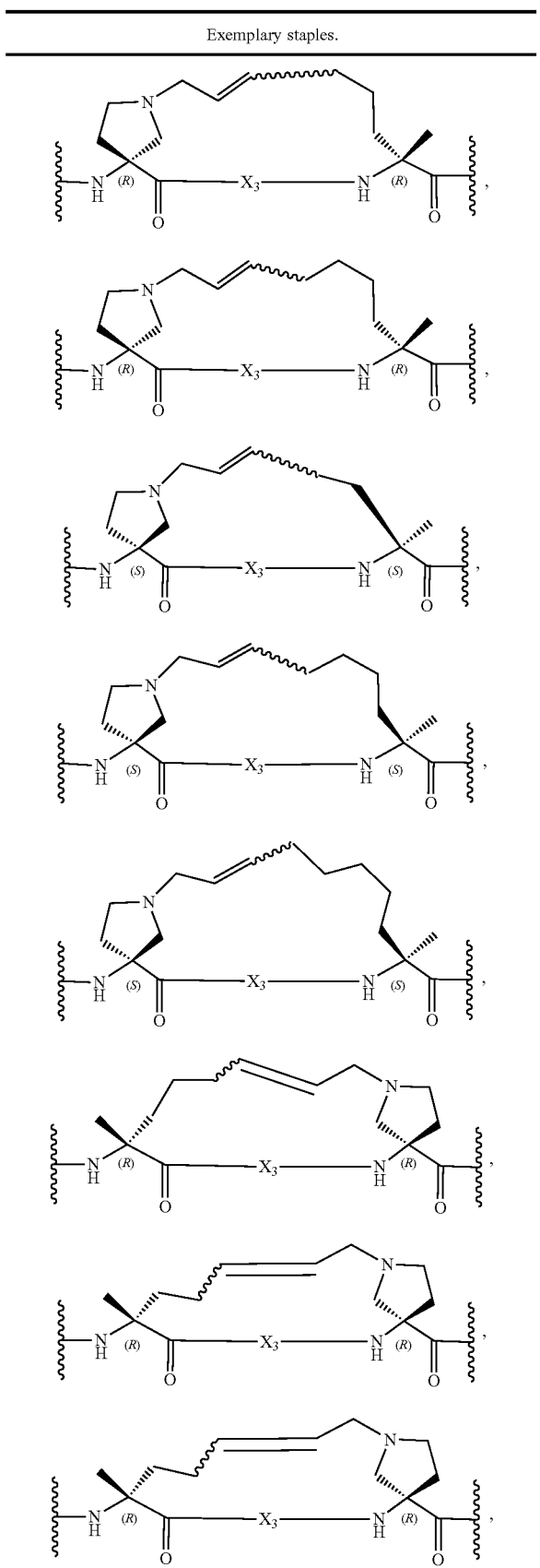

TABLE S-2-continued
Exemplary staples.
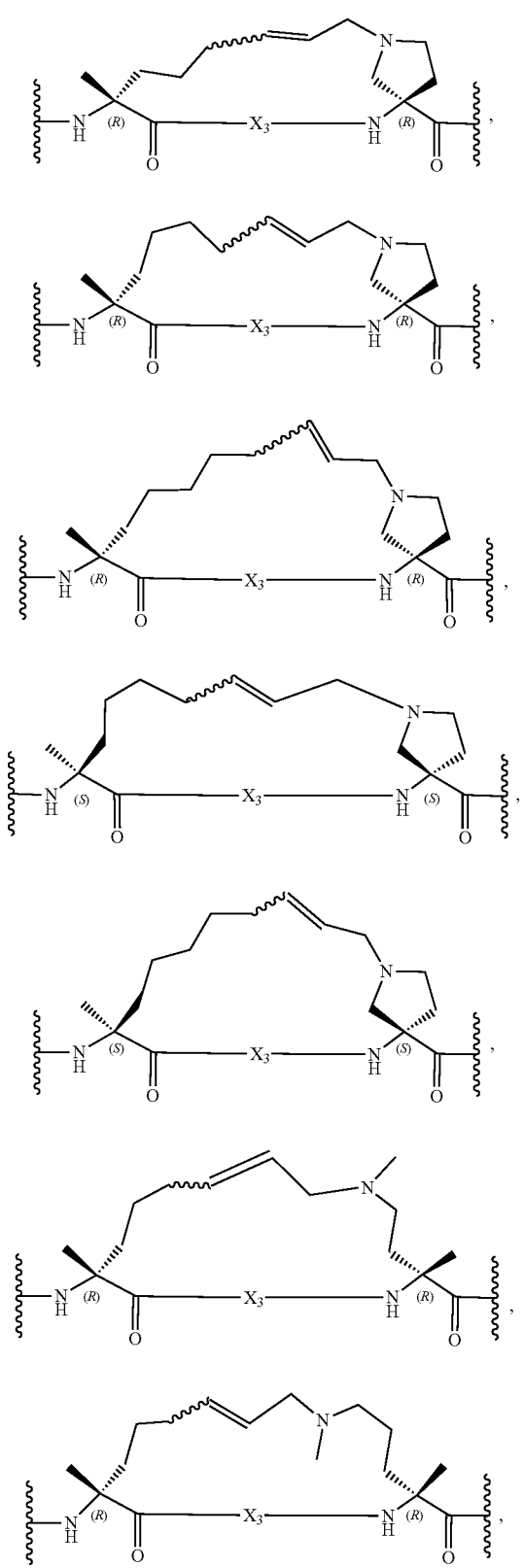
TABLE S-2-continued
Exemplary staples.
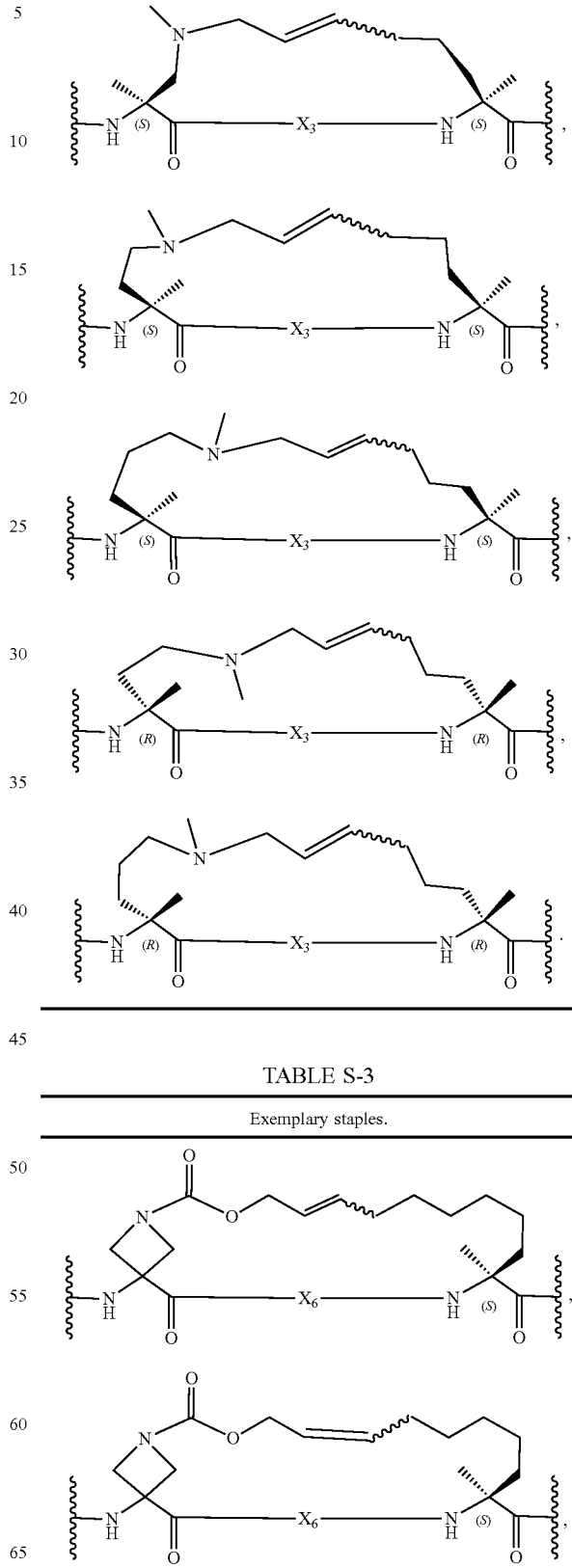
TABLE S-3
Exemplary staples.

TABLE S-3-continued
Exemplary staples.
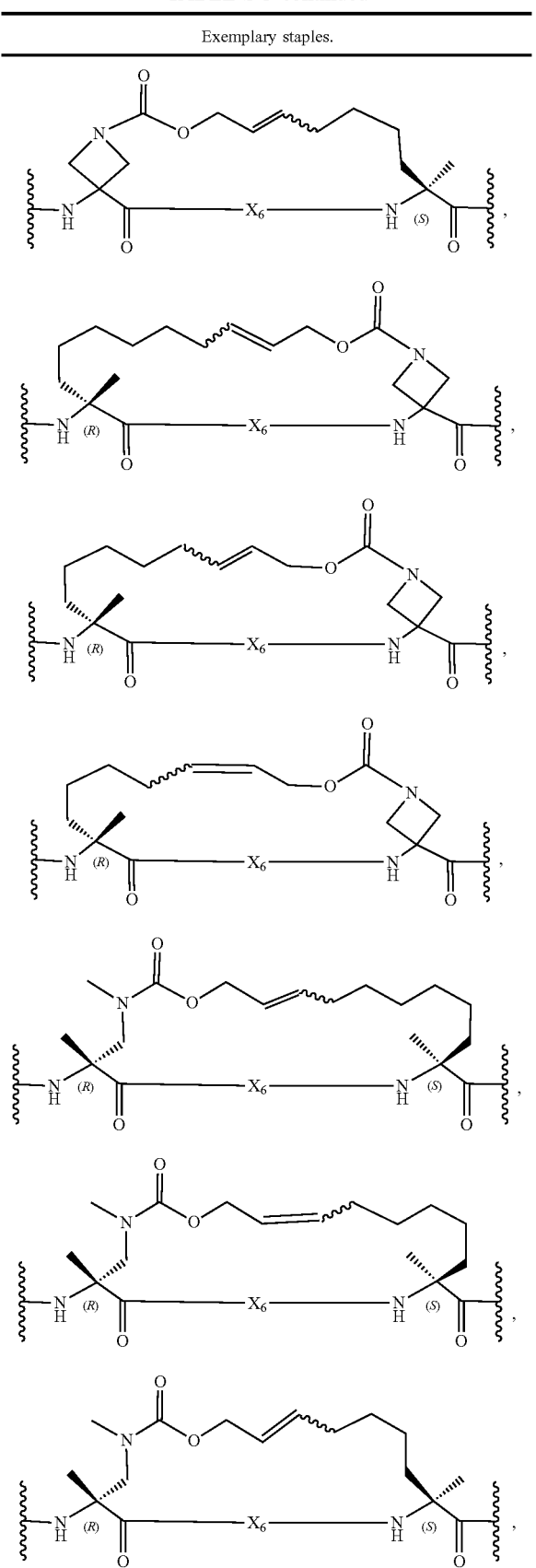
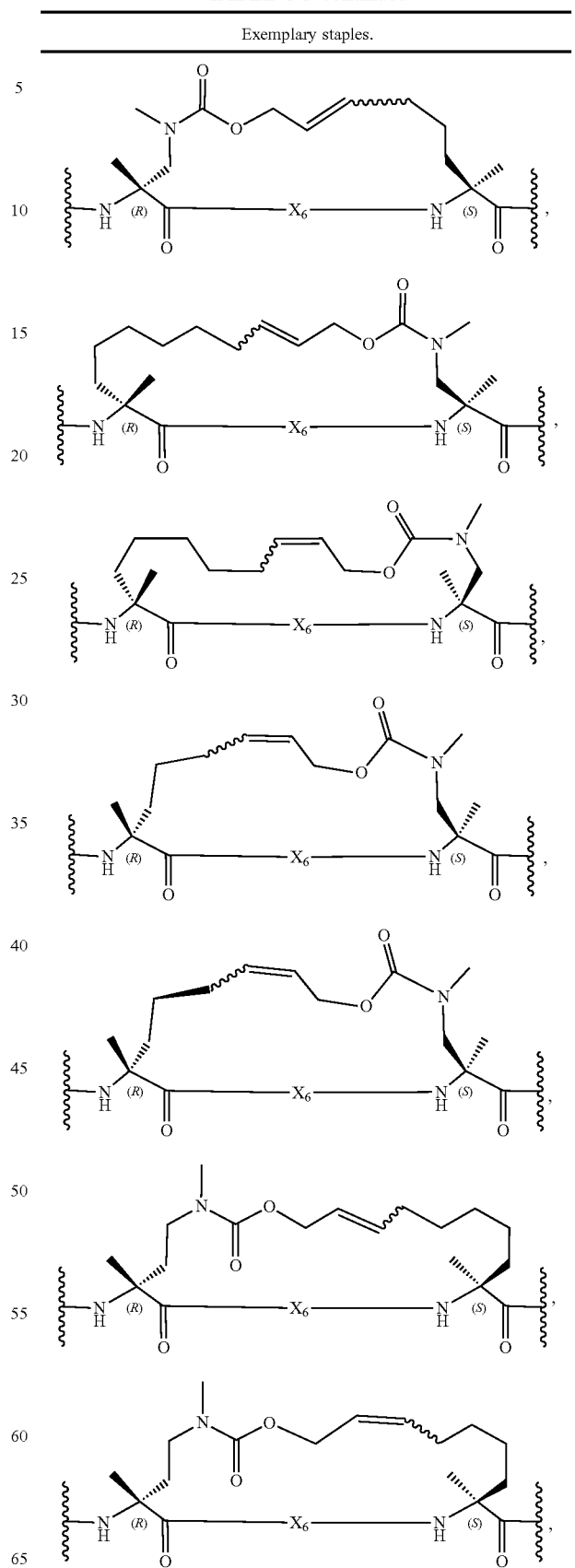

109
TABLE S-3-continued
Exemplary staples.
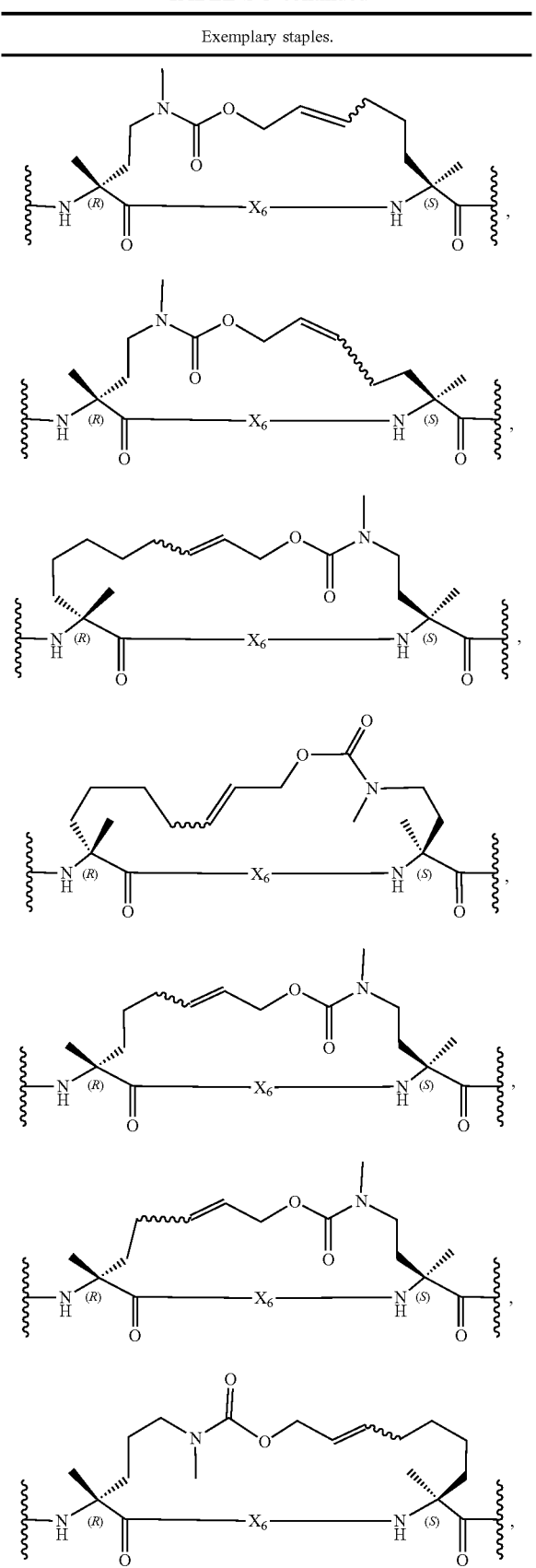
110
TABLE S-3-continued
Exemplary staples.
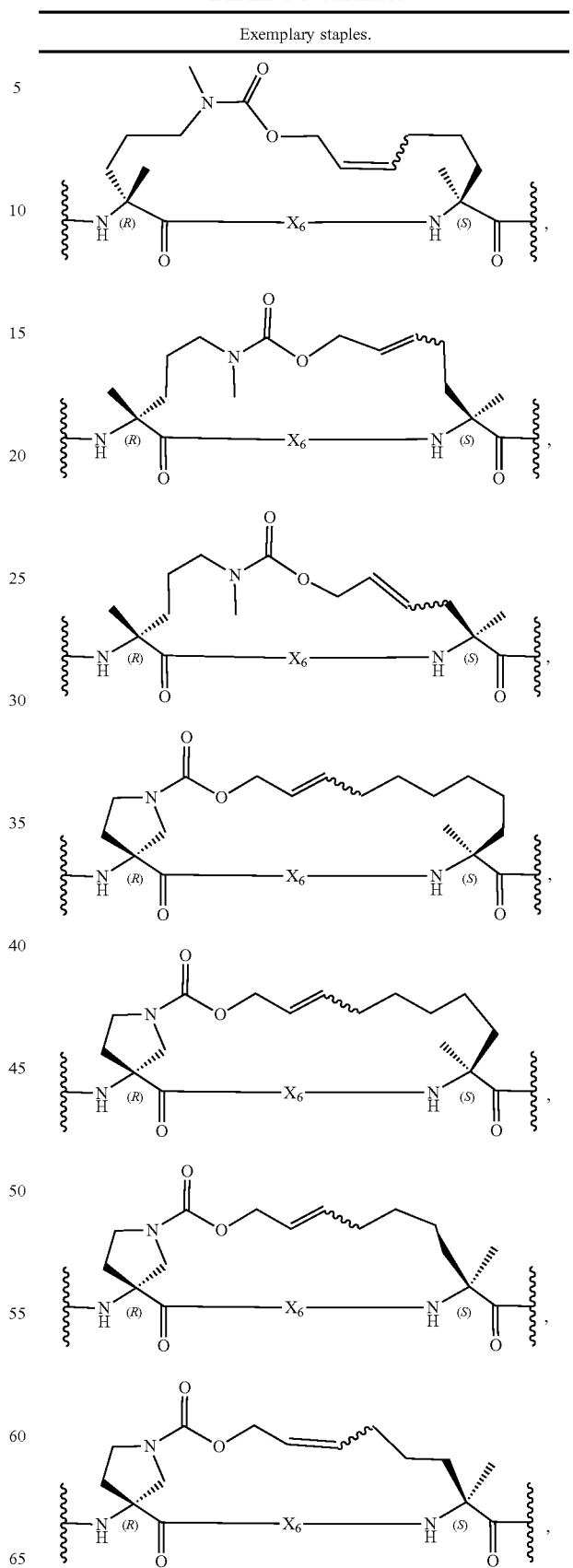

TABLE S-3-continued
Exemplary staples.
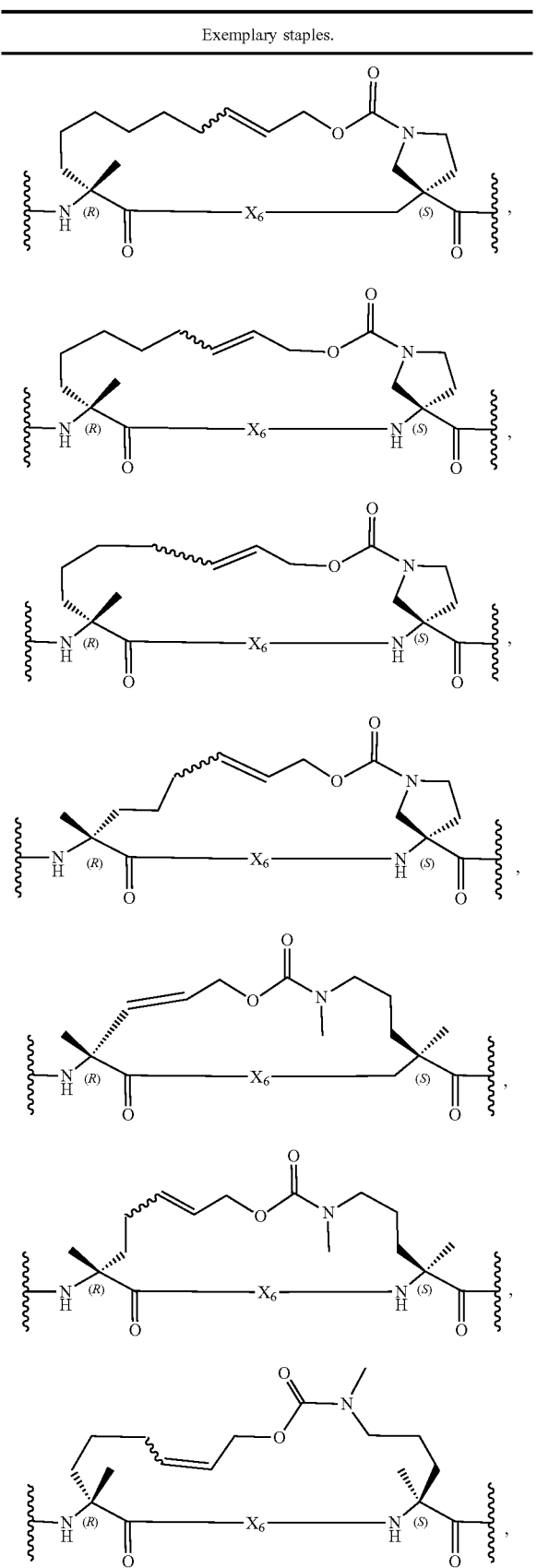
TABLE S-3-continued
Exemplary staples.
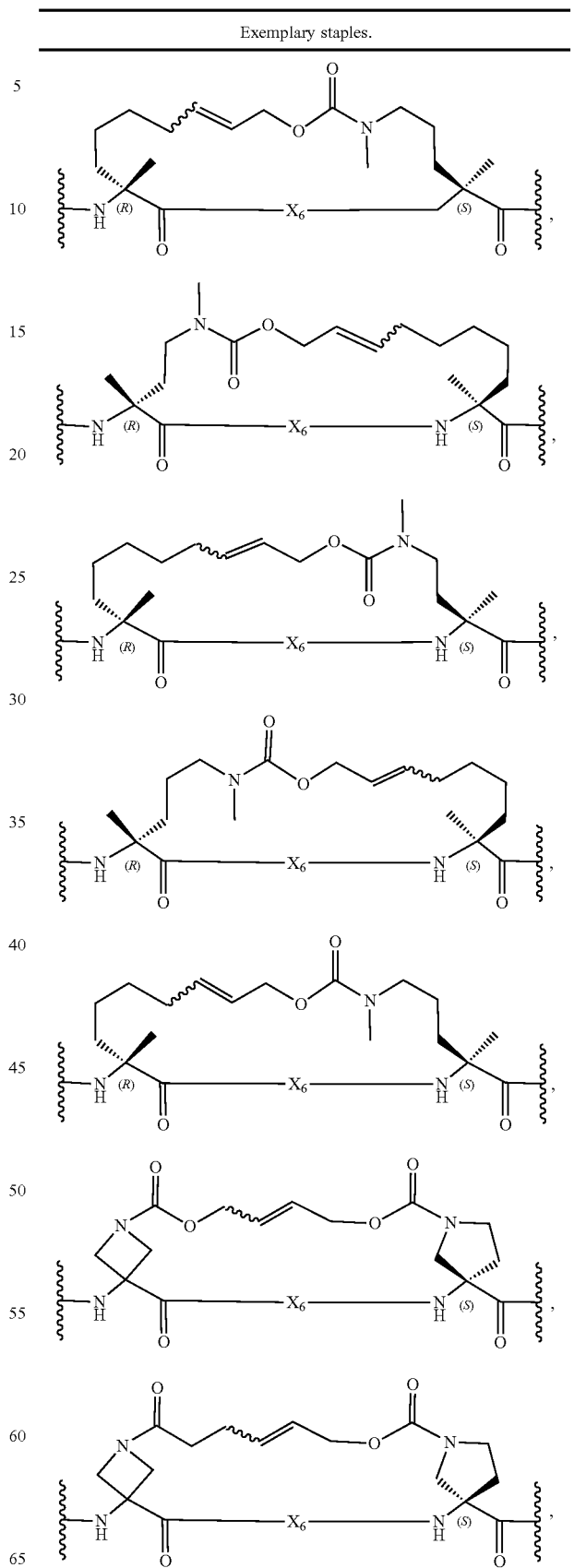

TABLE S-3-continued
Exemplary staples.
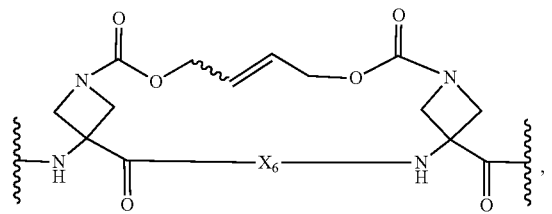
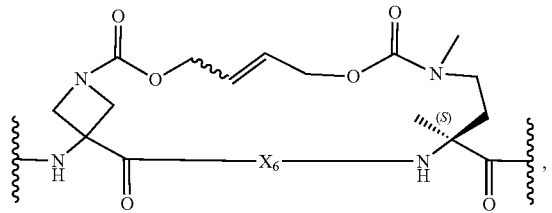
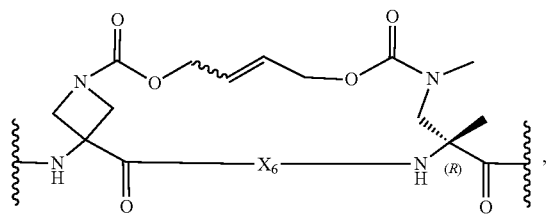
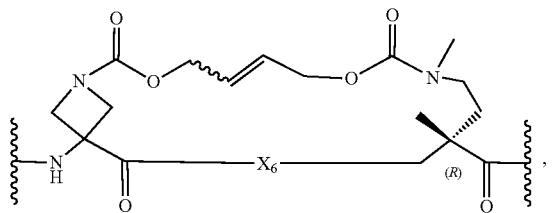
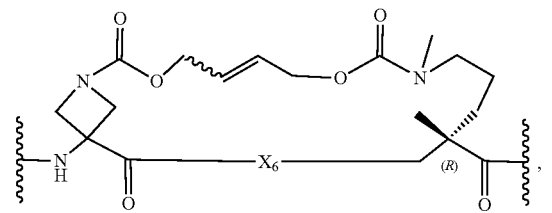
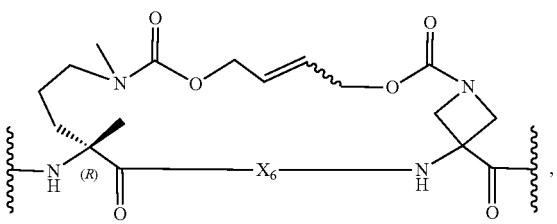
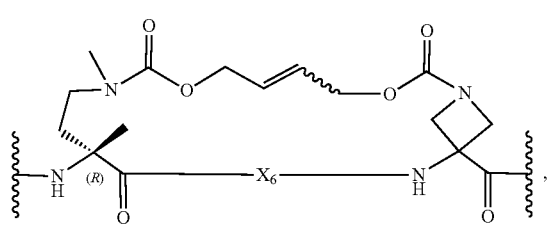
TABLE S-3-continued
Exemplary staples.
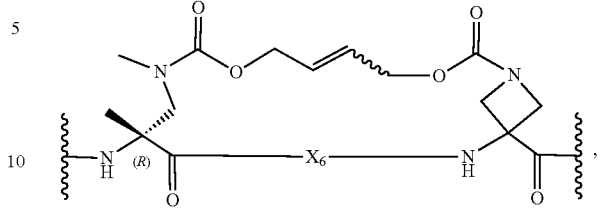
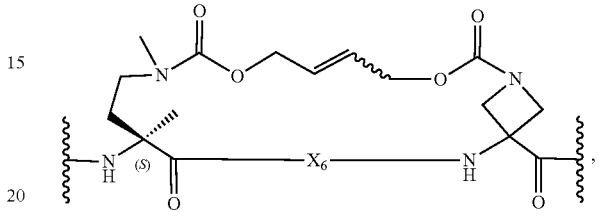
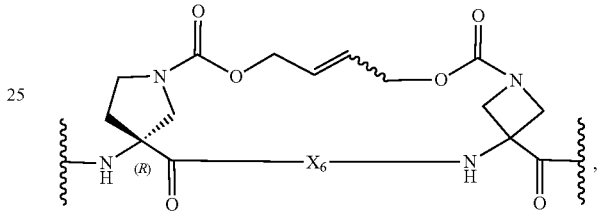
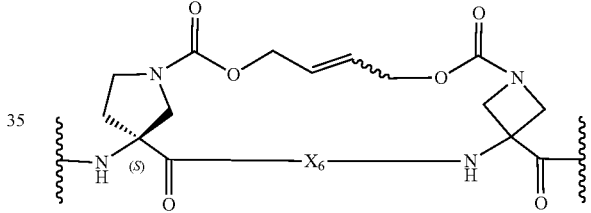
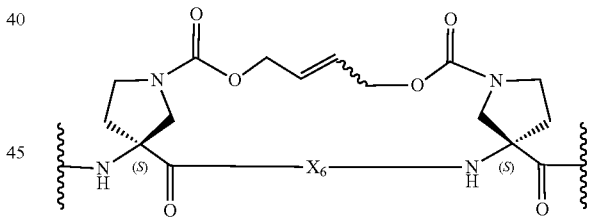
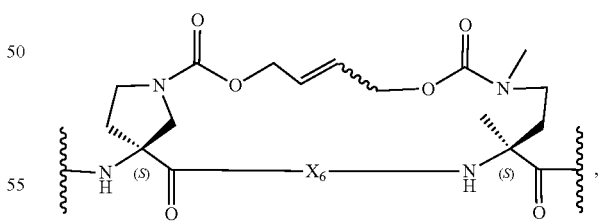
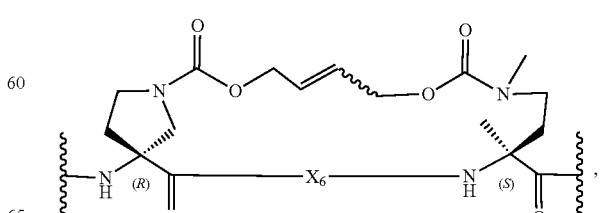

TABLE S-3-continued
Exemplary staples.
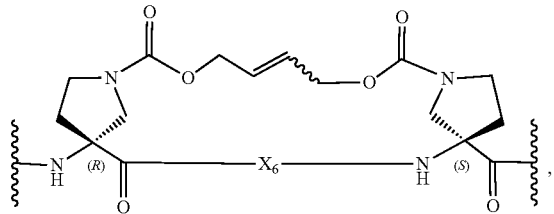
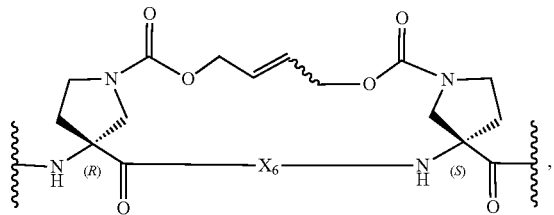
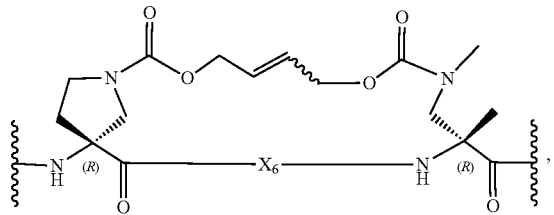
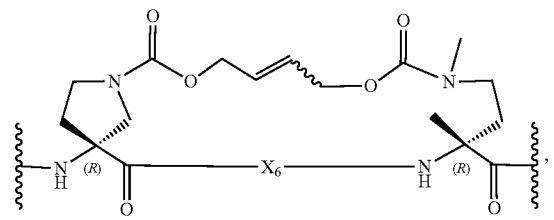
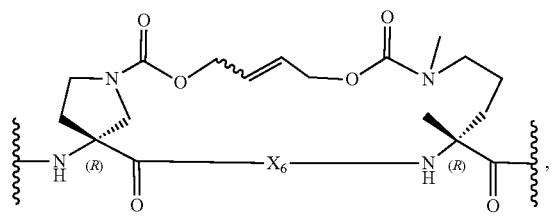
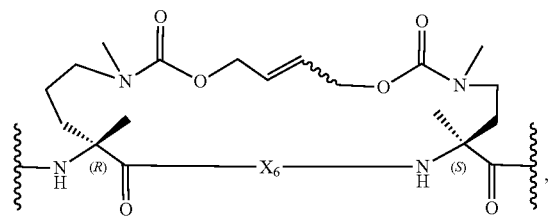
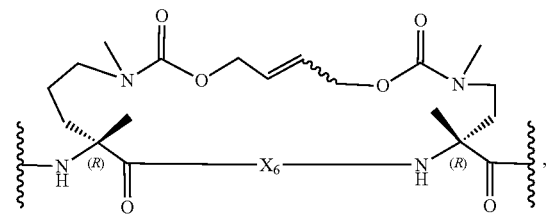
TABLE S-3-continued
Exemplary staples.
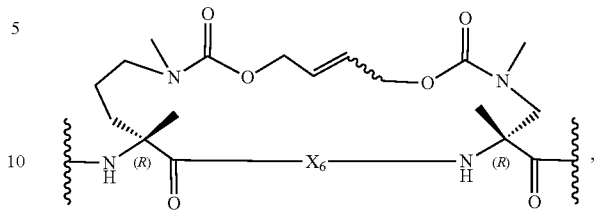
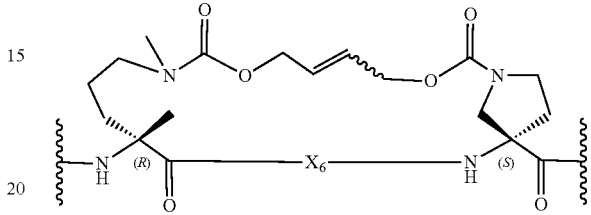
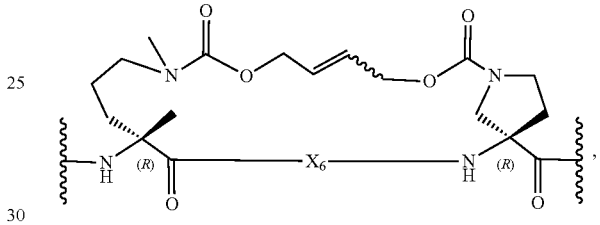
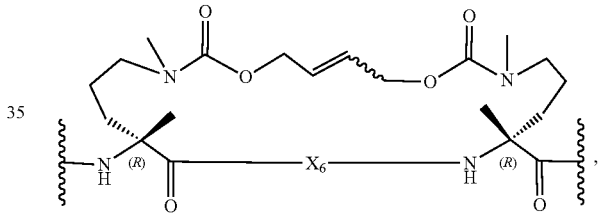
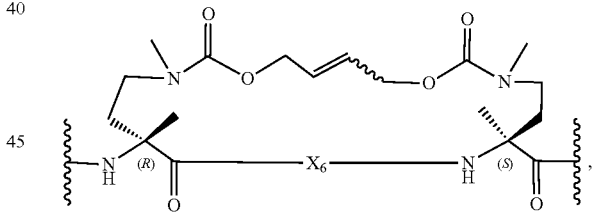
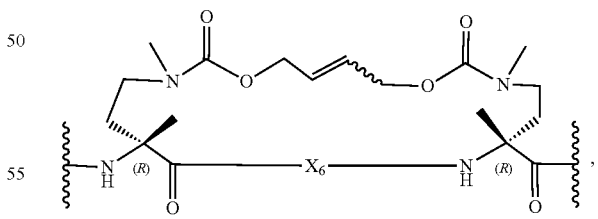
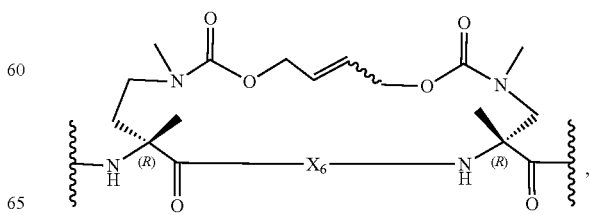

TABLE S-3-continued
Exemplary staples.
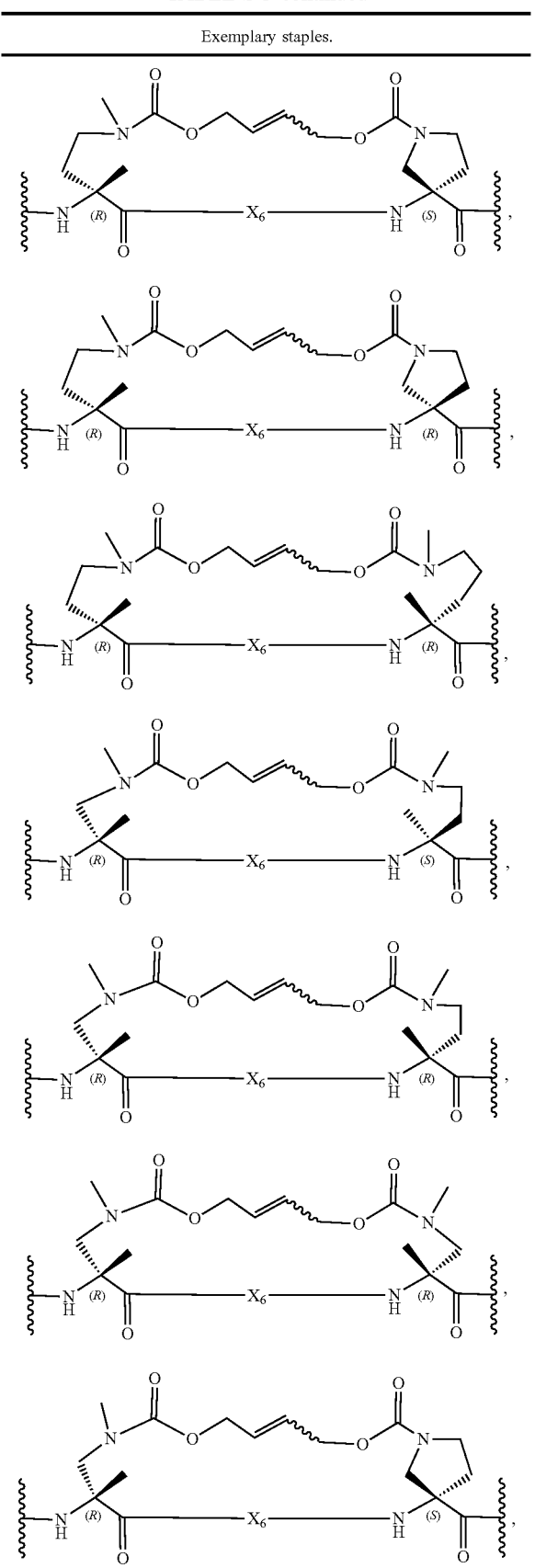
TABLE S-3-continued
Exemplary staples.
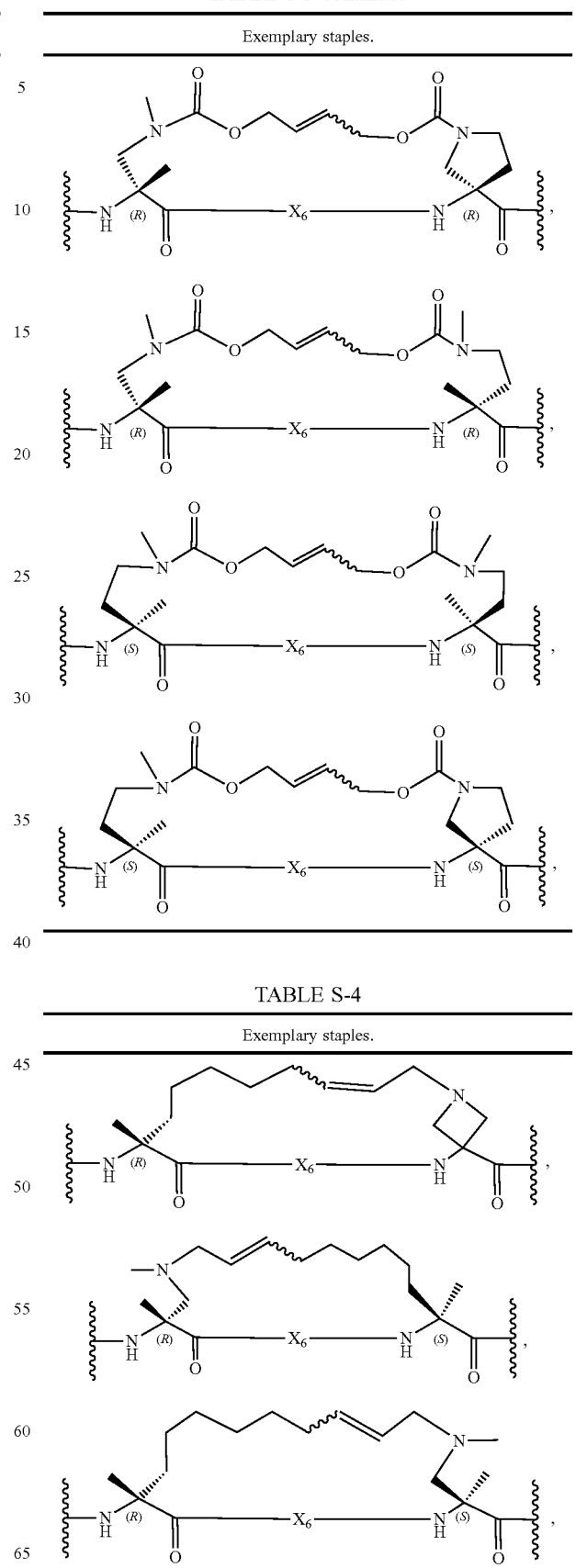
TABLE S-4
Exemplary staples.
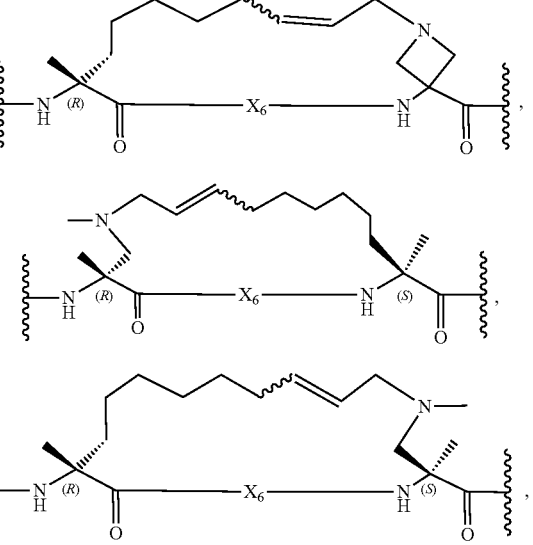

TABLE S-4-continued

Exemplary staples.

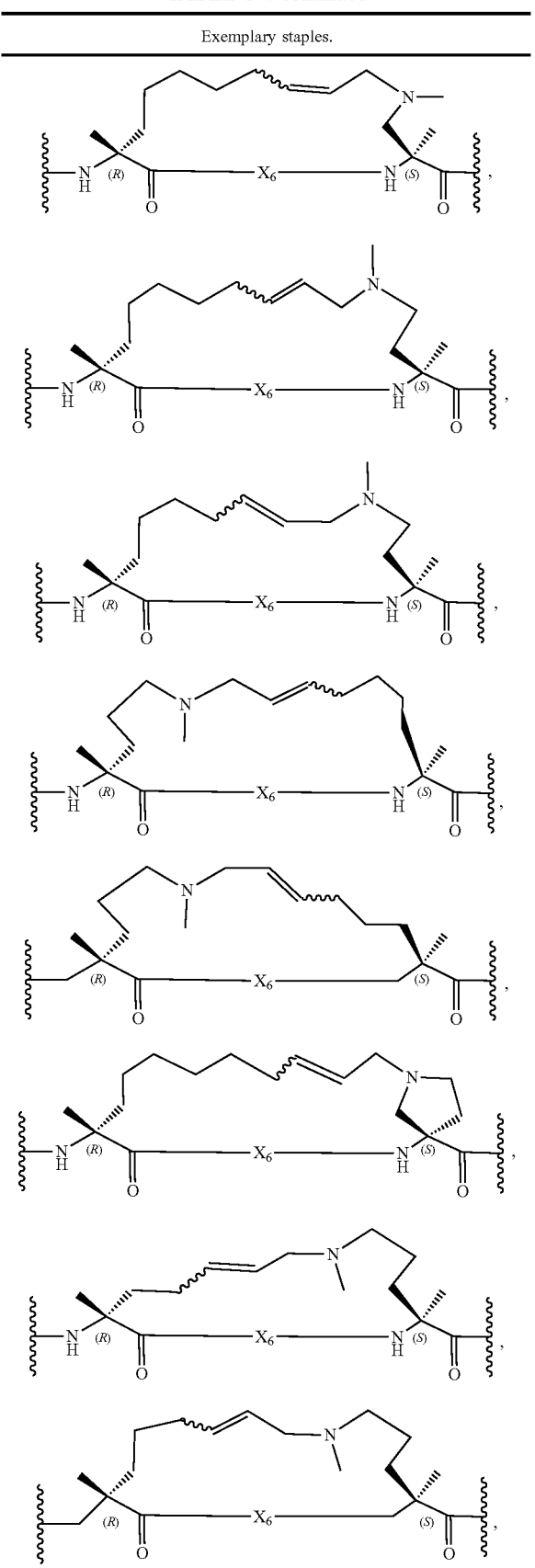

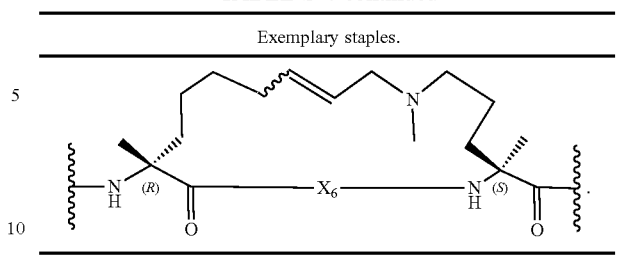

Peptide Characterization

In some embodiments, peptides as described herein (e.g., stapled peptides, e.g., cysteine stapled peptides, non-cysteine stapled peptides that are variants of cysteine stapled peptides, as described herein, and/or collections thereof) are characterized with respect to, for example, one or more characteristics selected from the group consisting of: binding characteristics—e.g., with respect to a particular target of interest; stability characteristics, for example in solution or in dried form; cell permeability characteristics, etc., and combinations thereof.

In some embodiments, a binding characteristic may be or comprise specificity, affinity, on-rate, off-rate, etc, optionally under (or over a range of) specified conditions such as, for example, concentration, temperature, pH, cell type, presence or level of a particular competitor, etc.

As will be appreciated by those skilled in the art, assessments of characteristics as described herein may involve comparison with an appropriate reference (e.g., a positive or negative control) which may, in some embodiments, be a contemporaneous reference or, in some embodiments, a historical reference.

In some embodiments, desirable peptide characteristics may be, for example: binding to a desired target (e.g., binding affinity of at least less than 1 μM, and preferably less than 50 nM); cell penetration (e.g., as measured by fluorescence-based assays or mass spectrometry of cellular fractions, etc.); activity (e.g., modulating one or more functions of a target, which may be assessed in a cellular reporter assay (e.g., with an IC50 of less than a concentration, e.g., 1 μM, 500 nM, etc.), an animal model and/or a subject; stability, which may be assessed using a number of assays (e.g., in a rat pharmacokinetic study (e.g., administered via oral, iv, ip, etc.) with a terminal half-life of greater than a suitable time, e.g., 1 hour); low toxicity, which might be assessed by a number of assays (e.g., a standard ADME/toxicity assays); and/or low levels of cytotoxicity (e.g., low levels of lactate dehydrogenase (LDH) released from cells when treated at a suitable concentration, e.g., about 10 μM of a peptide).

Peptide Production

Various technologies are known in the art for producing stapled peptides of may be utilized in accordance with the present disclosure. Those skilled in the art, reading the present disclosure, will well appreciate which such technologies are applicable in which aspects of the present disclosure.

In some embodiments, as described herein, certain stapled peptides, and in particular cysteine stapled peptides, may be provided in and/or produced by a biological system and reacting with a provided reagent, e.g., one having the structure of $R^x$-$L^{s2}$-$R^x$ formula R-I, or a salt thereof.

In some embodiments, peptides are prepared on solid phase on a synthesizer using, typically, Fmoc chemistry.

In some embodiments, staples are formed by olefin metathesis. In some embodiments, a product double bond of metathesis is reduced/hydrogenated. In some embodiments, $CO_2$ are extruded from a carbamate moiety of a staple. In some embodiments, provided stapled peptides are further modified, and/or conjugated to other entities. Conditions and/or reagents of these reactions are widely known in the art and can be performed in accordance with the present disclosure to provide stapled peptides.

Properties and/or activities of provided stapled peptides can be readily assessed in accordance with the present disclosure, for example, through use of one or more methods described in the examples.

In some embodiments, technologies for preparing and/or assessing provided stapled peptides include those described in U.S. Pat. No. 9,617,309, US 2015-0225471, US 2016-0024153, US 2016-0215036, US2016-0244494, WO 2017/062518, etc.

In some embodiments, a provided agent, e.g., a provided peptide, has a purity of 60%-100%. In some embodiments, a provided agent has a purity of at least 60%, 65%, 70%, 75%, 80%, 85%, 90%, 91%, 92%, 93%, 94%, 95%, 96%, 97%, 98%, or 99%. In some embodiments, a purity is at least 60%. In some embodiments, a purity is at least 70%. In some embodiments, a purity is at least 80%. In some embodiments, a purity is at least 85%. In some embodiments, a purity is at least 90%. In some embodiments, a purity is at least 91%. In some embodiments, a purity is at least 92%. In some embodiments, a purity is at least 93%. In some embodiments, a purity is at least 94%. In some embodiments, a purity is at least 95%. In some embodiments, a purity is at least 96%. In some embodiments, a purity is at least 97%. In some embodiments, a purity is at least 98%. In some embodiments, a purity is at least 99%. In some embodiments, a purity is at least 99.5%.

In some embodiments, provided methods provide high yields. In some embodiments, a yield is 50%-100%. In some embodiments, a yield is at least 60%, 65%, 70%, 75%, 80%, 85%, 90%, 91%, 92%, 93%, 94%, 95%, 96%, 97%, 98% or 99%. In some embodiments, a yield is at least 60%. In some embodiments, a yield is at least 65%. In some embodiments, a yield is at least 70%. In some embodiments, a yield is at least 75%. In some embodiments, a yield is at least 80%. In some embodiments, a yield is at least 85%. In some embodiments, a yield is at least 90%. In some embodiments, a yield is at least 91%. In some embodiments, a yield is at least 92%. In some embodiments, a yield is at least 93%. In some embodiments, a yield is at least 94%. In some embodiments, a yield is at least 95%. In some embodiments, a yield is at least 96%. In some embodiments, a yield is at least 97%. In some embodiments, a yield is at least 98%. In some embodiments, a yield is at least 99%.

In some embodiments, a provided method delivers high E/Z selectivity for olefin. In some embodiments, provided selectivity favors the E isomer. In some embodiments, provided selectivity favors the Z isomer. In some embodiments, a E:Z ratio is at least 1:1, 1.5:1, 2:1, 3:1, 4:1, 5:1, 6:1, 7:1, 8:1, 9:1, 10:1, 20:1, 30:1, 40:1, 50:1, or 100:1. In some embodiments, a Z:E ratio is at least 1:1, 1.5:1, 2:1, 3:1, 4:1, 5:1, 6:1, 7:1, 8:1, 9:1, 10:1, 20:1, 30:1, 40:1, 50:1, 80:1, 90:1, 95:1, 99:1, or 100:1. In some embodiments, a ratio is at least 1:1. In some embodiments, a ratio is at least 1.5:1. In some embodiments, a ratio is at least 2:1. In some embodiments, a ratio is at least 3:1. In some embodiments, a ratio is at least 4:1. In some embodiments, a ratio is at least 5:1. In some embodiments, a ratio is at least 6:1. In some embodiments, a ratio is at least 7:1. In some embodiments, a ratio is at least 8:1. In some embodiments, a ratio is at least 9:1. In some embodiments, a ratio is at least 10:1. In some embodiments, a ratio is at least 20:1. In some embodiments, a ratio is at least 30:1. In some embodiments, a ratio is at least 40:1. In some embodiments, a ratio is at least 50:1. In some embodiments, a ratio is at least 80:1. In some embodiments, a ratio is at least 90:1. In some embodiments, a ratio is at least 95:1. In some embodiments, a ratio is at least 99:1. In some embodiments, a ratio is at least 100:1.

In some embodiments, a provide method comprises a period of time at a temperature higher than room temperature. In some embodiments, a temperature is about 25-200° C. In some embodiments, a temperature is about 25° C. In some embodiments, a temperature is about 30° C. In some embodiments, a temperature is about 35° C. In some embodiments, a temperature is about 40° C. In some embodiments, a temperature is about 45° C. In some embodiments, a temperature is about 50° C. In some embodiments, a temperature is about 55° C. In some embodiments, a temperature is about 60° C. In some embodiments, a temperature is about 65° C. In some embodiments, a temperature is about 70° C. In some embodiments, a temperature is about 75° C. In some embodiments, a temperature is about 80° C. In some embodiments, a temperature is about 85° C. In some embodiments, a temperature is about 90° C. In some embodiments, a temperature is about 95° C. In some embodiments, a temperature is about 100° C. In some embodiments, a temperature is about 150° C. In some embodiments, a temperature is higher than about 150° C.

Peptide Compositions

Among other things, the present disclosure provides compositions that comprise or otherwise relate to peptides, e.g., stapled peptides, as described herein.

For example, in some embodiments, provided compositions are or comprise elements of a phage display system that encodes and/or expresses stapled peptides (e.g., cysteine stapled peptides), or a collection thereof, as described herein.

In some embodiments, provided compositions are or comprise an assay system for characterizing (and optionally including) a stapled peptide as described herein.

In some embodiments, provided compositions are pharmaceutical compositions e.g., that comprise or deliver one or more stapled peptides (e.g., in particular one or more non-cysteine stapled peptides that may, in some embodiments, correspond to and/or be a variant of a parent cysteine stapled peptide as described herein).

In some embodiments, a pharmaceutical composition comprises a peptide agent in combination with a pharmaceutically acceptable excipient (e.g., carrier).

In some embodiments, a peptide composition may include or deliver a particular form (e.g., a particular optical isomer, diastereomer, salt form, covalent conjugate form [e.g., covalently attached to a carrier moiety], etc., or combination thereof) of a peptide agent as described herein). In some embodiments, a peptide agent included or delivered by a pharmaceutical composition is described herein is not covalently linked to a carrier moiety.

In some embodiments, a provided therapeutic composition may comprise one or more additional therapeutic agents and/or one or more stabilizing agents and/or one or more agents that alters (e.g., extends or limits to a particular tissue, location or site) rate or extent of delivery over time.

Uses and Applications

In some embodiments, the present disclosure provides certain stapled peptides and/or other technologies (e.g., collections of stapled peptides, and/or a biological system adapted to express or display and/or expressing or displaying such stapled peptide(s), etc.) for the development and/or use of stapled peptides (e.g., that bind a target of interest).

In some embodiments, the present disclosure provides certain stapled peptides, or collections thereof (e.g., including collections in which individual peptides may be fused with a phage coat protein), and/or a biological system adapted to express or display and/or expressing or displaying such cysteine stapled peptide(s). In some embodiments, certain provided stapled peptides and/or other technologies can be utilized to identify and/or characterize one or more desirable structural features (e.g., amino acid sequence, staple location and/or structure [e.g., length, composition, degree of constraint, etc.]) of a stapled peptide that interacts with (e.g., binds to) a target of interest. In some embodiments, certain provided stapled peptides and/or other technologies are useful for the development of stapled peptides (e.g., non-cysteine stapled peptides) that correspond to (e.g., share significant structural identity with, and optionally structural identity with, a reference cysteine stapled peptide, except for substitution of the cysteine(s) for other non-cysteine staple-forming residue(s)).

In some embodiments, a provided peptide or collection thereof, whose amino acid sequence, includes at least two appropriately spaced cysteine residues, is used to prepare a cysteine stapled peptide, or collection thereof (e.g., by reaction with a compound of formula R-I. certain provided stapled peptides and/or other technologies In some embodiments, certain provided stapled peptides can be identified and synthesized by technologies and examples described in the present disclosure. In some embodiments, a certain provided stapled peptide is a cysteine stapled peptide. In some embodiments, a cysteine stapled peptide that binds a target of interest may have a cysteine staple and corresponding cysteine residues replaced by a non-cysteine staple and amino acids necessary to facilitate such a non-cysteine staple.

In some embodiments, a provided collection of peptides (or nucleic acids that encode them) is characterized in that peptides of the collection all include cysteine residues (e.g. a pair of cysteine residues), spaced relative to one another to permit cysteine stapling as described herein, but otherwise have independent amino acid sequences and, optionally, in that peptides of the collection all have the same length. In some embodiments, degeneracy and/or bias is introduced in one or more positions through genetic engineering and/or expression of selected nucleic acid sequences in a biological system. In some embodiments, degree of degeneracy or bias at one or more positions in peptides of a peptide collection or library as described here is informed and/or selected by prior assessment one or more binding characteristics of a related library or collection (e.g., with comparable cysteine residues). In some embodiments, such prior assessment is by high-throughput analysis (e.g., screening) of a collection or collections of stapled peptides against a target of interest and the use of high-throughput sequencing to decode the genotypes of a subset of the collection of stapled peptides can inform the production of a biased library.

In some embodiments, a collection of stapled peptides comprises cysteine stapled peptides fused to another molecule for use in a biological system (e.g. phage display) or non-biological system. In some embodiments, after screening a collection of stapled peptides in the context of a biological system or non-biological system, high throughput sequencing will identify particular cysteine stapled peptides that interact with a target of interest. In some embodiments, a particular cysteine stapled peptide, when not fused to another molecule for use in a biological system, will exhibit the same or similar interaction with a target of interest as the particular cysteine stapled peptide when fused to said molecule. In some embodiments, a particular cysteine stapled peptide, when not fused to another molecule for use in a biological system, can have its cysteine residues and cysteine staple replaced with other amino acids and staples. In some embodiments, the resulting peptide maintains the same or similar interaction with a target of interest.

In some embodiments, certain provided stapled peptides and/or other technologies as described herein may be useful to modulate one or more biological events or statuses, e.g., by binding with a relevant target of interest.

In some embodiments, certain provided stapled peptides and/or other technologies agents as described herein may be useful in the treatment of one or more diseases, disorders or conditions. In some embodiments, a therapeutic composition as described herein, that comprises and/or delivers a stapled peptide (e.g., a non-cysteine stapled peptide, for example corresponding to a parent cysteine stapled peptide identified and/or characterized as described herein) is administered to a subject in need thereof. In some embodiments, a subject may have received and/or be receiving other therapy so that, in some embodiments, therapy with a provided peptide agent may be administered in combination with other therapy; in some such embodiments, a peptide agent as described herein may be administered via a composition that contains and/or delivers another therapeutic agent; in some embodiments, separate compositions are employed.

Various strategies for administering stapled peptides are available in the art and can be utilized in accordance with the present disclosure. In some embodiments, provided peptides have enhanced cell penetration properties compared otherwise identical but non-stapled peptides.

In some particular embodiments, certain provided stapled peptides and/or other technologies are useful to bind to and/or modulate one or more activities or effects of, beta-catenin.

In some embodiments, certain provided stapled peptides and/or other technologies are useful in treatment of a condition, disorder, or disease associated with one or more components involved in Wnt/beta-catenin signaling and/or specifically with one or more beta-catenin functions.

In some embodiments, certain provided stapled peptides and/or other technologies are useful in modulating, e.g., reducing the interaction between beta-catenin and another protein, for example, Axin, APC, BCL9, TCF4/TCF7L2, TCF3/TCF7L1, and TCF7.

In some embodiments, certain provided stapled peptides and/or other technologies are useful in treatment of a condition, disorder, or disease associated with interactions between beta-catenin and one or more beta-catenin sites that interact with one or more proteins in Wnt/beta-catenin signaling. In some embodiments, certain provided stapled peptides compete with and/or otherwise interfere with or reduce binding between beta-catenin and BCL9. In some embodiments, a condition disorder or disease is associated with interactions between beta-catenin and one or more beta-catenin sites that interact with BCL9. In some embodiments, a condition, disorder, or disease is associated with interactions with and one or more proteins that compete with BCL9 for interaction with beta-catenin. In some embodiments, certain provided stapled peptide antagonizes beta-catenin interaction with another protein whose one or more binding sites are identical or overlap with, or are in close proximity to, one or more beta-catenin sites that interact with BCL9 or a provided stapled peptide. In some embodiments, a condition, disorder, or disease is associated with interactions between beta-catenin and BCL9. In some embodiments, provided stapled peptides interacts with beta-catenin at one or more beta-catenin sites that interacts with BCL9. In some embodiments, provided stapled peptides inhibit one or more BCL9 activities. In some embodiments, provided stapled peptides inhibit one or more Wnt/beta-catenin pathway activities.

In some embodiments, certain provided stapled peptides and/or other technologies are useful in treatment of a condition, disorder, or disease is selected from cancer, cardiac disease, dilated cardiomyopathy, fetal alcohol syndrome, depression, and diabetes.

In some embodiments, a condition, disorder, or disease is a heart condition, disorder, or disease.

In some embodiments, a condition, disorder, or disease is cancer. In some embodiments a cancer is selected from: colon cancer, colorectal cancer, rectal cancer, prostate cancer familial adenomatous polyposis (FAP), Wilms Tumor, melanoma, hepatocellular carcinoma, ovarian cancer, endometrial cancer, medulloblastoma pilomatricomas, primary hetpatocellular carcinoma, ovarial carcinoma, breast cancer, lung cancer, glioblastoma, pliomatrixoma, medulloblastoma, thyroid tumors, ovarian neoplasms. In some embodiments, a cancer is colorectal cancer. In some embodiments, a cancer is hepatocellular cancer. In some embodiments, a cancer is prostate cancer. In some embodiments, a cancer is melanoma. In some embodiments, a cancer is associated with Wnt/beta-catenin signaling. In some embodiments, a cancer is associated with beta-catenin. As appreciated by those skilled in the art, provided technologies are applicable to various targets, including many protein targets associated with cancer.

EXAMPLES

Example 1—Preparation of Compounds Useful for Peptide Stapling

Among other things, the present disclosure provides compounds that are useful for construct staples, e.g., $R^x$-$L^s$-$R^x$ or a salt thereof or formula R—I or a salt thereof. Various technologies can be utilized to prepare provided compounds of the present disclosure. In some embodiments, the present disclosure provides compounds listed in Table E-1.

TABLE E-I

Several exemplary cysteine staples synthesized:

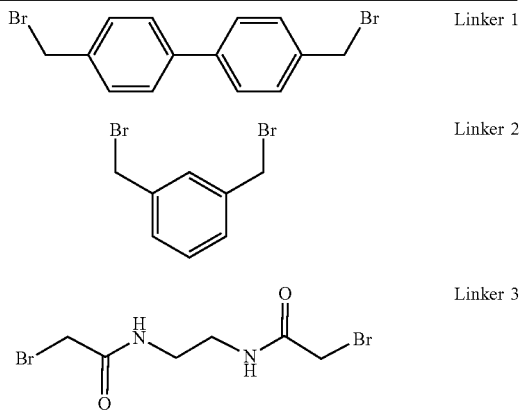

Linker 1

Linker 2

Linker 3

TABLE E-I-continued

Several exemplary cysteine staples synthesized:

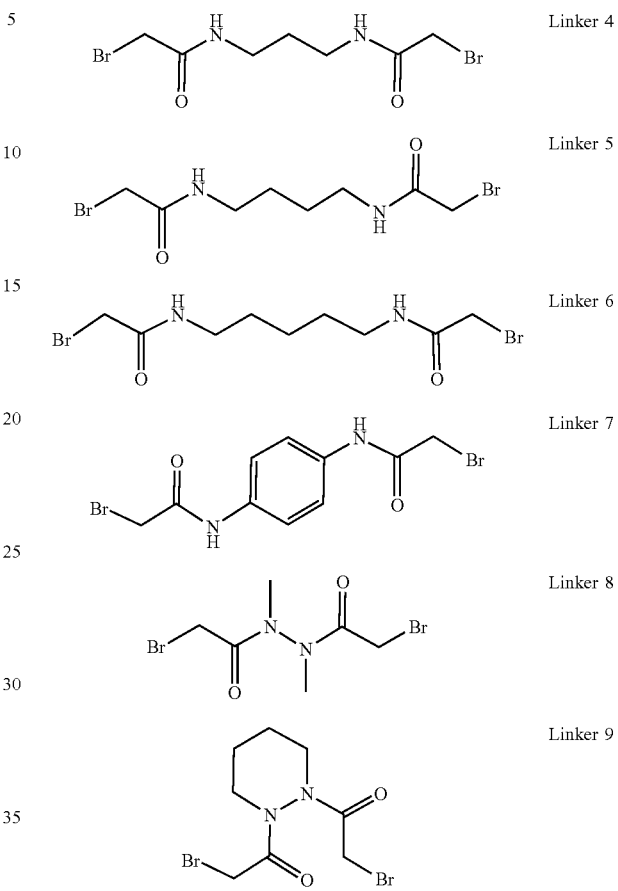

Linker 4

Linker 5

Linker 6

Linker 7

Linker 8

Linker 9

In a procedure for preparing compounds in Table E-1, 50 mmol of the respective diaminoalkanes (ethylenediamine for 3, propylenediamine for 4, butylenediamine for 5, pentylenediamine for 6, and benzene-1,4-diamine for 7) were dissolved in 100 mL of chloroform and then 100 mL of a 1.5 M aqueous $K_2CO_3$ solution was added. Using an ice bath, the solution was cooled for 20 min. Under constant stirring, 100 mL of a 1.5 M bromoacetyl bromide solution was added dropwise to the mixture for 30 min. The mixture was then stirred at room temperature for 12 h. Insoluble solid was subsequently filtered through a glass funnel. The filtered solid was washed repeatedly with water and dried using a centrifugal evaporator at 60° C. The organic layer remaining from the filtering was separated using a separation funnel. The aqueous layer was washed twice with chloroform. All organic collections were then combined, washed with $H_2O$ thrice and dried over anhydrous $Na_2SO_4$. The organic solvent was then evaporated in an rotary evaporator. The combined products were analyzed using mass spectrometry (MS) and nuclear magnetic resonance spectrometry (NMR).

Linkers 8 and 9 were synthesized according to a similar protocol. Instead of using two phases during the reaction, only an aqueous phase was used. The reagents were the dihydrochloride salts of 1,2-dimethylhydrazine and hexahydropyridazine. All other reaction conditions remained the same. The reaction was terminated after 2 h of stirring at room temperature after the bromoacetyl bromide was added.

Various technologies can be utilized for purification. For example, linkers 3-6 and 8-9 were purified using normal phase flash chromatography. In one preparation, silica gel of 40-60 m pore size was used. Standard protocol was followed. All linkers showed good separation in thin layer chromatography, with a mobile phase of 80% (v/v) ethyl acetate and 20% (v/v) hexane. TLC plates were then stained using a potassium permanganate stain (6 g $KMnO_4$, 40 g $K_2CO_3$, 10 mL 5% (w/v) aqueous NaOH, 600 mL $H_2O$). The retention factor, $R_f$, values of the linkers for this mobile phase lay between 0.2 and 0.4, depending on the polarity of the linker. The samples were dissolved in chloroform and subsequently loaded onto the column. The collected fractions were then checked using thin layer chromatography. The fractions, that contained the linker were combined and evaporated in a rotary evaporator. The purified and dried linkers were ran on a LC/MS, as well as the Q Exactive Plus, in order to confirm the correct mass of the peptides. The samples were sent out for $^1$H NMR analysis. $^1$H NMR samples were prepared, using $CDCl_3$ as a solvent, and 128 scans at 400 MHz were taken (FIGS. 1-7).

Example 2—Preparation of Compounds Useful for Peptide Stapling

Preparation of additional exemplary compounds that are useful e.g., for construct staples, e.g., $R^x$-$L^s$-$R^x$ or a salt thereof or formula R—I or a salt thereof, were described Examples 2-11.

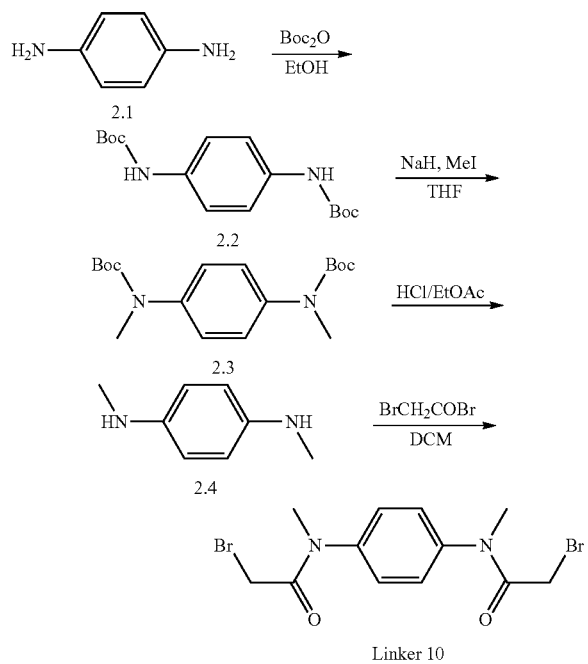

Scheme E-1

Linker 10

To a solution of compound 2.1 (2.50 g, 23.12 mmol, 1.00 equiv) in EtOH (50 mL) was added $Boc_2O$ (12.1 g, 55.48 mmol, 12.7 mL, 2.40 equiv) and guanidine hydrochloride (331 mg, 3.47 mmol, 278 µL, 0.15 equiv) in portions. After the addition was complete, the reaction mixture was stirred for 8 hr at 40° C. LC-MS showed compound 2.1 was entirely consumed. The solvent was removed under reduced pressure. Then ethyl acetate (100 mL) was added and the mixture was stirred for 30 min at 20° C. The mixture was filtered and the wet cake was washed with ethyl acetate (50.0 mL×5). The organic phase was dried under vacuum to give Compound 2.2 (5.00 g, crude) as an off-white solid.

To a solution of compound 2.2 (1.70 g, 5.51 mmol, 1.00 equiv) in THF (30.0 mL) was added NaH (330 mg, 8.27 mmol, 60% purity, 1.50 equiv) in portions at 0° C. The mixture was stirred for 10 min after the addition was complete. Then MeI (2.60 g, 18.32 mmol, 1.14 mL, 3.32 equiv) was added in portions at 0° C. Then the mixture was stirred for 2 hr at 20° C. $NH_4Cl$ (10.0 mL, saturated) was added into the mixture at 0° C. Then the water layer was extracted with ethyl acetate (10.0 mL×3). The organic extractions were dried over $Na_2SO_4$ and concentrated to give 1.70 g of a yellow oil. $^1$H NMR showed compound 2.3 (1.70 g, crude) was obtained as yellow oil. $^1$H NMR (400 MHz, DMSO-$d_6$): δ 7.23 (s, 4H), 3.17 (s, 6H), 1.40 (s, 18H).

A solution of compound 2.3 (1.60 g, 4.76 mmol, 1.00 equiv) in HCl/ethyl acetate (4 M, 48.0 mL, 40.3) was stirred for 2 hr at 20° C. TLC (petroleum ether/ethyl acetate=1/1, $R_f$=0.06) showed the reaction was complete. The reaction mixture was concentrated under vacuum to give an off-white solid (880 mg, crude, 2-HCl salt). $^1$H NMR (400 MHz, DMSO-$d_6$): δ 9.67 (br s, 4H), 7.27 (br s, 4H), 2.78 (s, 6H).

Compound 2.4 (835 mg, 3.99 mmol, 1 equiv, 2HCl) was dissolved in water (10.0 mL) and $K_2CO_3$ (1.21 g, 8.78 mmol, 2.20 equiv) was added to the mixture in portions in order to adjust the pH of the mixture to 8. Then dichloromethane (10.0 mL×5) was added to extract the product. The organic layer were combined, dried over $Na_2SO_4$, and concentrated to give a yellow oil (0.50 g, crude, free base). $^1$H NMR (400 MHz, DMSO-$d_6$): δ 6.41 (br s, 4H), 4.74 (br s, 2H), 2.58 (br s, 6H).

To a solution of compound 2.4 (500 mg, 3.67 mmol, 1.00 equiv) in dichloromethane (150 mL) was added pyridine (697 mg, 8.81 mmol, 711.17 µL, 2.40 equiv) and DMAP (13.5 mg, 110.14 mol, 0.03 equiv) in one portion at 0° C. After that, 2-bromoacetyl bromide (1.63 g, 8.08 mmol, 702.71 µL, 2.20 equiv) was added dropwise to the mixture at approximately 0-5° C. After the addition was complete, the reaction mixture was stirred for 2 hr at 20° C. LC-MS showed compound 2.4 was consumed entirely and a main compound with desired mass. The reaction mixture was washed with HCl (0.5 N, 50.0 mL×2), then brine (50.0 mL×2). The organic layer was dried over $Na_2SO_4$ and then concentrated under vacuum to give Linker 10 (1.50 g, crude) as a light yellow solid.

Crude Linker 10 (500 mg) was purified by slurry in a solution of dichloromethane/petroleum ether (1 mL, 1/1) for 30 min. The mixture was filtered and the residue was dried under vacuum to give 120 mg of a light yellow solid (120 mg, 317.41 mol, 24.0% yield). HPLC showed purity of 99.48%. $^1$H NMR: (400 MHz, chloroform-d): δ 7.41 (s, 4H), 3.70 (s, 4H), 3.35 (br s, 6H).

Example 3—Preparation of Compounds Useful for Peptide Stapling

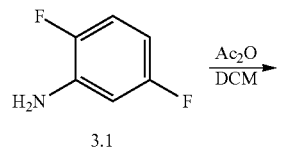

Scheme E-2

3.1

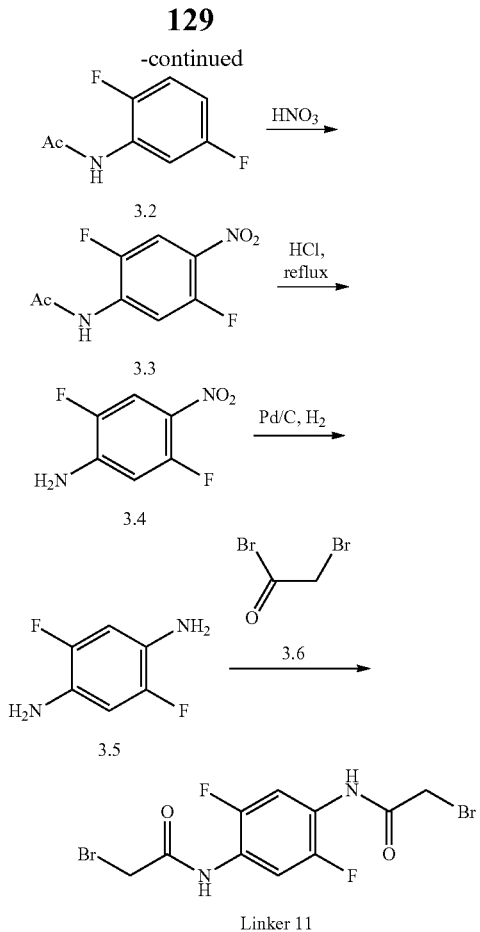

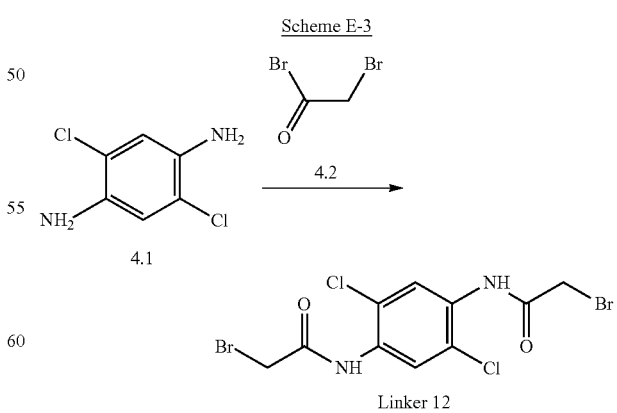

To a solution of compound 3.1 (10.0 g, 77.46 mmol, 1 equiv) in dichloromethane (35 mL) was added Ac$_2$O (9.47 g, 92.75 mmol, 8.69 mL, 1.20 equiv) in portions at 20° C. After addition was complete, the reaction mixture was stirred at 20° C. for 16 hr. LC-MS showed compound 1 consumed, and the main product was compound 3.2 (r.t.=0.626 min, [M+H]$^+$=171.8). The reaction mixture was concentrated under reduced pressure. Then water (80 mL) was added to the residue and an off-white solid was collected by filtration and dried under vacuum to give compound 3.2 (12.3 g, 71.87 mmol, 92.8% yield). $^1$H NMR (400 MHz, CDCl$_3$) δ 8.23-8.12 (m, 1H), 7.46 (br s, 1H), 7.03 (dt, J=4.8, 9.8 Hz, 1H), 6.72 (br t, J=8.2 Hz, 1H), 2.24 (s, 3H).

To a stirred HNO$_3$ solution (21.9 g, 333.27 mmol, 15.63 mL, 96% purity, 11.41 equiv) was added dropwise compound 3.2 (5.00 g, 29.22 mmol, 1 equiv) at 0° C. After addition was complete, the reaction mixture was stirred at 0° C. for 2 hr. LC-MS and TLC (petroleum ether/ethyl acetate=1/1, R$_f$=0.61) showed compound 3.2 was consumed, and the main product was compound 3.3 (r.t.=0.746 min, [M+H]=216.7). The reaction mixture was poured into ice water (50 mL), stirred for 10 min and then filtered. The resulting cake was washed with water (50 mL×3) and dried under reduced pressure to give compound 3.3 (5.72 g, 26.46 mmol, 90.6% yield) as a yellow solid. $^1$H NMR (400 MHz DMSO-d$_6$): δ 10.47 (br s, 1H), 8.36 (dd, J=6.5, 14.1 Hz, 1H), 8.21 (dd, J=7.0, 10.8 Hz, 1H), 2.20 (s, 3H).

To a solution of compound 3.3 (5.60 g, 25.91 mmol, 1 equiv) in EtOH (25 mL) was added HCl (12 M, 58.28 mL, 26.99 equiv). After addition was complete, the reaction mixture was stirred and refluxed at 80° C. for 2 h. TLC (petroleum ether/ethyl acetate=1/1, R$_f$=0.08) and LC-MS showed compound 3.3 was all consumed, and the main product was compound 3.4 (r.t.=0.719 min, [M+H]$^+$=174.8). The reaction mixture was concentrated under reduced pressure. Water (60 mL) was added and stirred for 30 min, and then filtered. The resulting cake was washed with water (50 mL×3). The resulting brown solid was dried under reduced pressure to give compound 3.4 (3.10 g, 17.81 mmol, 68.8% yield) as a brown solid. $^1$H NMR (400 MHz DMSO-d$_6$): δ 7.89 (dd, J=7.2, 11.4 Hz, 1H), 7.08 (br s, 2H), 6.62 (dd, J=7.3, 13.8 Hz, 1H).

To a solution of compound 3.4 (2.50 g, 14.36 mmol, 1 equiv) in MeOH (30 mL) was added Pd/C (600 mg, 10% purity) under N$_2$. The suspension was degassed under vacuum and purged with H$_2$ several times. The mixture was stirred under H$_2$ (15 psi) at 20° C. for 5 hr. LC-MS showed compound 3.4 was consumed, and the main product was compound 3.5 (r.t.=0.114 min, [M+H]=144.7). The reaction mixture was filtered through a celite pad, and the filtrate was concentrated under reduced pressure to give compound 3.5 (1.82 g, 12.63 mmol. 88.0% yield) as a black-brown solid. $^1$H NMR (400 MHz, DMSO-d$_6$): δ 6.48 (t, J=10.4 Hz, 2H), 4.45 (br s, 4H).

To a solution of compound 3.5 (1.00 g, 6.94 mmol, 1 equiv) in dichloromethane (150 mL) was added pyridine (1.32 g, 16.65 mmol, 1.34 mL, 2.4 equiv) and DMAP (25.4 mg, 208.16 mol, 0.03 equiv) in one portion at 0° C. After that, a solution of compound 3.6 (3.08 g, 15.26 mmol, 1.33 mL, 2.2 equiv) in dichloromethane (50 mL) was added dropwise to the mixture at approximately 0-5° C. After addition was complete, the reaction mixture was stirred at 20° C. for 2 hr. TLC (dichloromethane/MeOH=15/1) and LC-MS showed compound 3.5 (R$_f$=0.23) was consumed. A new spot was observed (R$_f$=0.62). The mixture was filtered and the residue was washed with dichloromethane (10 mL×3). The residue was dried under vacuum to give 2.30 g brown solid. The crude material (200 mg) was triturated in a solution of DMSO/MeOH (6 mL, 1/5 ratio) for 30 min to give Linker 11 (120 mg, 299.82 mol, 57.9% yield, 96.44% purity) as a gray solid. $^1$H NMR (400 MHz DMSO-d$_6$): δ 10.37 (s, 2H), 7.95 (t, J=9.8 Hz, 2H), 4.16 (s, 4H).

Example 4—Preparation of Compounds Useful for Peptide Stapling

Scheme E-3

To a solution of compound 4.1 (1.00 g, 5.65 mmol, 1 equiv) in dichloromethane (150 mL) was added pyridine (1.07 g, 13.56 mmol, 1.09 mL, 2.4 equiv) and DMAP (20.7 mg, 169.46 mol, 0.03 equiv) in one portion at 0° C. After that, a solution of compound 4.2 (2.51 g, 12.43 mmol, 1.08 mL, 2.2 equiv) in dichloromethane (50 mL) was added dropwise to the mixture at approximately 0-5° C. After the addition was complete, the reaction mixture was stirred at 20° C. for 2 hr. TLC (dichloromethane/MeOH=15/1) showed compound 4.1 ($R_f$=0.23) was consumed. A new spot could be observed ($R_f$=0.62). The mixture was filtered and the residue was washed with dichloromethane (10 mL×3). The residue was dried under vacuum to give a white solid (2.30 g). The crude material (500 mg) was triturated in a solution of dichloromethane/MeOH (6 mL, 1/1 ratio) for 30 min to give Linker 12 (120 mg, 285.06 mol, 23.9% yield, 99.51% purity) as a white solid. $^1$H NMR (400 MHz, DMSO-$d_6$): δ 10.10 (s, 2H), 7.94 (s, 2H), 5.77 (s, 1H), 4.19 (s, 4H).

Example 5—Preparation of Compounds Useful for Peptide Stapling

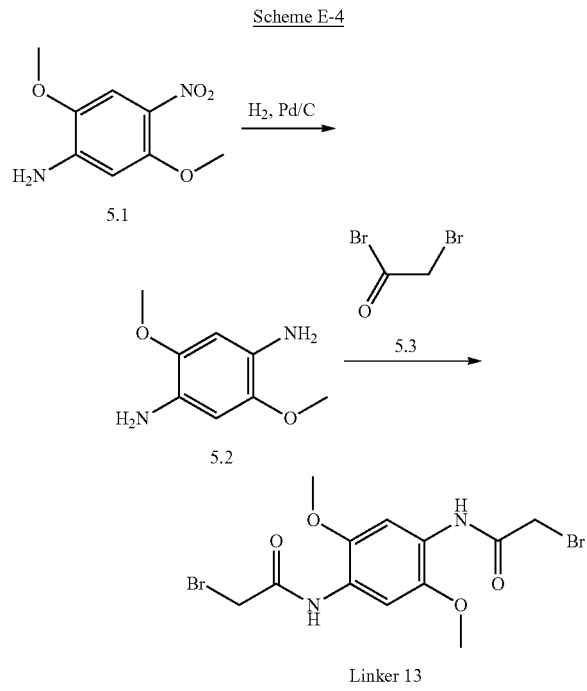

To a solution of compound 5.1 (1.00 g, 5.05 mmol, 1 equiv) in EtOH (150 mL) was added Pd/C (0.30 g, 10.0% purity) in one portion, then the reaction mixture was stirred at 20° C. for 16 hr under a $H_2$ atmosphere (15 psi). TLC (dichloromethane/MeOH=15/1) showed compound 5.1 ($R_f$=0.70) was consumed. A new spot could be observed ($R_f$=0.41). The reaction mixture was filtered through a celite pad, and the filtrate was concentrated to give compound 5.2 (800 mg, crude) as a black-brown solid.

To a solution of compound 5.2 (800 mg, 4.76 mmol, 1 equiv) in dichloromethane (100 mL) was added pyridine (903 mg, 11.42 mmol, 921.39 μL, 2.4 equiv) and DMAP (17.4 mg, 142.69 mol, 0.03 equiv) in one portion at 0° C. After that, a solution of compound 5.3 (2.11 g, 10.46 mmol, 910.43 μL, 2.2 equiv) in dichloromethane (50 mL) was added dropwise to the mixture at approximately 0-5° C. After the addition was complete, the reaction mixture was stirred at 20° C. for 2 hr. LC-MS showed compound 5.2 was consumed, the product was Linker 13 (r.t.=0.796 min, [M+H]=410.9). The reaction mixture was diluted with water (50 mL) and extracted with EtOAc (30 mL×3). The combined organic layers were dried over $Na_2SO_4$, filtered and concentrated under reduced pressure to give a residue. The residue was purified by column chromatography ($SiO_2$, petroleum ether/ethyl acetate=10/1 to about 1/1) to give 300 mg crude product. Next, the residue was purified by prep-HPLC to give Linker 13 (103 mg, 241.46 mol, 5.08% yield, 96.13% purity) as a yellow solid. $^1$H NMR (400 MHz, DMSO-$d_6$): δ 9.65 (s, 2H), 7.83 (s, 2H), 4.19 (s, 4H), 3.77 (s, 7H).

Example 6—Preparation of Compounds Useful for Peptide Stapling

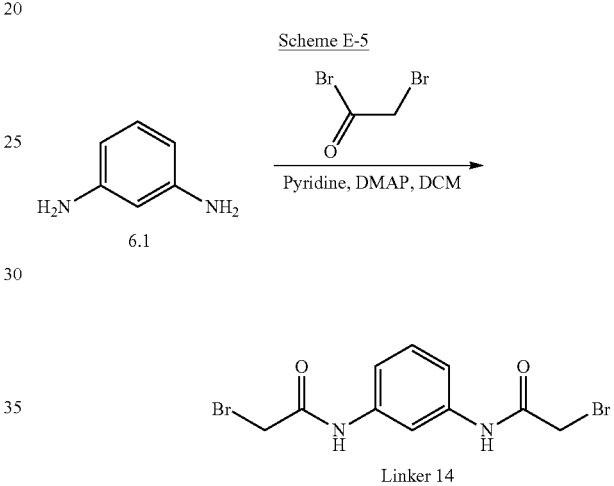

To a solution of compound 6.1 (1.00 g, 9.25 mmol, 1.00 equiv) in dichloromethane (150 mL) was added pyridine (1.76 g, 22.2 mmol, 1.79 mL, 2.40 equiv) and DMAP (33.9 mg, 277 mol, 0.03 equiv) in one portion at 0° C. After that, a solution of 2-bromoacetyl bromide (4.11 g, 20.3 mmol, 1.77 mL, 2.20 equiv) in DCM (50.0 mL) was added dropwise to the mixture at approximately 0-5° C. After the addition was complete, the reaction mixture was stirred for 2 hr at 20° C. During the stirring, white precipitate could be observed. LC-MS showed compound 6.1 was consumed and the product possessed the desired mass. The mixture was filtered and the residue was wash with DCM (10.0 mL×3). The residue was dried under vacuum to give Linker 14 as an off-white solid (2.50 g).

Crude Linker 14 (200 mg) was triturated in a solution of dichloromethane/ethyl acetate (2.00 mL, 1/1 ratio) for 30 min. The mixture was filtered to give a residue. The residue was dried under vacuum to give Linker 14 as a white solid (110 mg, 314.28 mol, about 100% purity). $^1$H NMR (400 MHz, DMSO-$d_6$): δ 10.43 (br s, 2H), 7.94 (br s, 1H), 7.38-7.20 (m, 3H), 4.02 (s, 4H).

Example 7—Preparation of Compounds Useful for Peptide Stapling

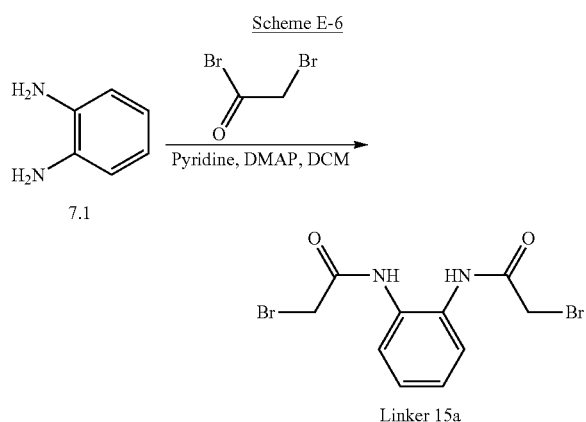

To a solution of compound 7.1 (500 mg, 4.62 mmol, 1.00 equiv) in dichloromethane (150 mL) was added pyridine (878 mg, 11.10 mmol, 895 µL, 2.4 equiv) and DMAP (17 mg, 138.71 mol, 0.03 equiv) in one portion at 0° C. After that, a solution of 2-bromoacetyl bromide (2.05 g, 10.17 mmol, 885 µL, 2.20 equiv) in dichloromethane (50 mL) was added dropwise to the mixture at approximately 0-5° C. After the addition was complete, the reaction mixture was stirred for 2 hr at 20° C. During the stirring, white precipitate could be observed. TLC (dichloromethane/methanol=15/1) showed compound 7.1 ($R_f$=0.43) was consumed. A new spot could be observed ($R_f$=0.73). The mixture was filtered and the residue was washed with dichloromethane (10.0 mL×3). The residue was dried in vacuum to give Linker 15a (1.07 g) as an off-white solid.

Crude Linker 15a (500 mg) was purified by silica gel chromatography (dichloromethane/methanol=100/1 to 100/1, 1.00 L) to give an off-white solid (110 mg, 312.27 mol, 21.8% yield, 99.36% purity). $^1$H NMR (400 MHz, DMSO-$d_6$): δ 9.72 (s, 2H), 7.52 (dd, J=3.8, 5.8 Hz, 2H), 7.21 (dd, J=3.5, 6.0 Hz, 2H), 4.11 (s, 4H).

Example 8—Preparation of Compounds Useful for Peptide Stapling

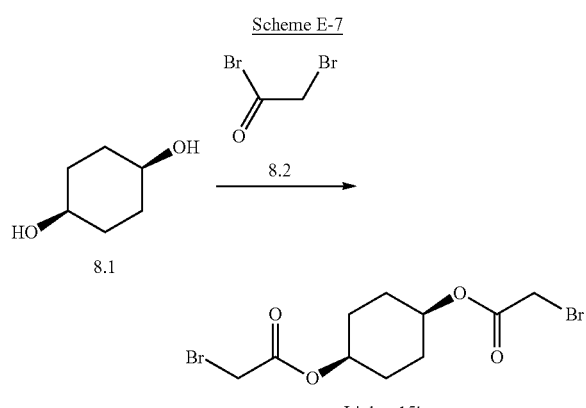

To a solution of compound 8.1 (500 mg, 4.30 mmol, 1 equiv) in dichloromethane (50 mL) was added pyridine (818 mg, 10.33 mmol, 833.84 µL, 2.4 equiv) in one portion at 0° C. After that, a solution of compound 8.2 (1.91 g, 9.47 mmol, 823.92 µL, 2.2 equiv) in dichloromethane (50 mL) was added dropwise to the mixture at 0° C. After the addition was complete, the reaction mixture was stirred at 20° C. for 2 hr. TLC (petroleum ether/ethyl acetate=0/1) showed compound 8.1 was all consumed ($R_f$=0.35); no new spot was detected. The reaction mixture was diluted with water (50 mL) and extracted with EtOAc (30 mL×3). The combined organic phases were dried over $Na_2SO_4$, filtered, and concentrated under reduced pressure to give a residue. The residue was purified by column chromatography ($SiO_2$, petroleum ether/ethyl acetate=30/1 to about 20/1) to give Linker 15b (120 mg, 326.00 mol, 7.57% yield, 97.2633% GC purity) as a colorless oil. $^1$H NMR (400 MHz $CDCl_3$): δ 4.94 (br s, 2H), 3.84 (s, 4H), 1.96-1.83 (m, 4H), 1.82-1.70 (m, 4H).

Example 9—Preparation of Compounds Useful for Peptide Stapling

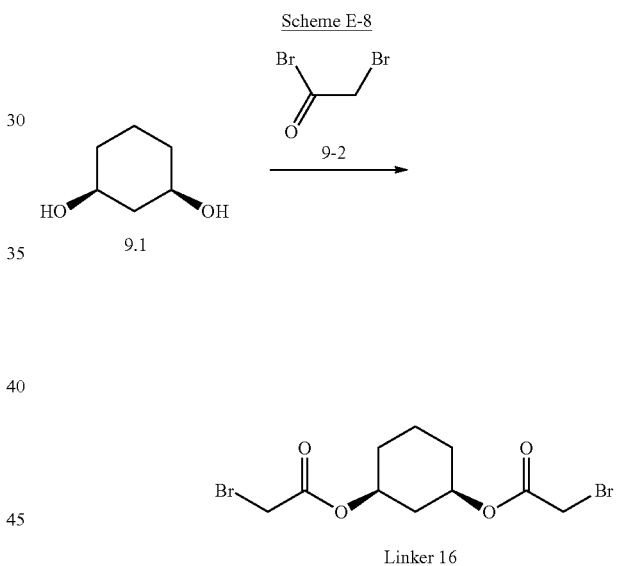

To a solution of compound 9.1 (500 mg, 4.30 mmol, 1 equiv) in dichloromethane (50 mL) was added pyridine (818 mg, 10.33 mmol, 833.84 µL, 2.4 equiv) in one portion at 0° C. After that, a solution of compound 9.2 (1.91 g, 9.47 mmol, 823.92 µL, 2.2 equiv) in dichloromethane (50 mL) was added dropwise to the mixture at 0° C. After the addition was complete, the reaction mixture was stirred at 20° C. for 2 hr. TLC (petroleum ether/ethyl acetate=0/1) showed compound 9.1 was consumed ($R_f$=0.31); no new spot was detected. The reaction mixture was diluted with water (50 mL) and extracted with EtOAc (30 mL×3). The combined organic phases were dried over $Na_2SO_4$, filtered, and concentrated under reduced pressure to give a residue. The residue was purified by column chromatography ($SiO_2$, petroleum ether/ethyl acetate=30/1 to about 20/1) to give Linker 16 (120 mg, 322.01 mol, 7.48% yield, 96.0736% GC purity) as a colorless oil. $^1$H NMR (400 MHz, $CDCl_3$): δ 4.91-4.77 (m, 2H), 3.81 (s, 4H), 2.32-2.25 (m, 1H), 2.02-1.86 (m, 3H), 1.67-1.57 (m, 1H), 1.46-1.33 (m, 3H).

Example 10—Preparation of Compounds Useful for Peptide Stapling

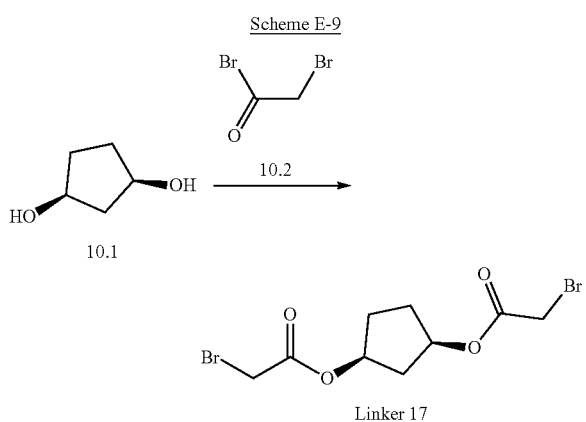

Linker 17

To a solution of compound 10.1 (500 mg, 4.90 mmol, 1 equiv) in dichloromethane (100 mL) was added pyridine (930 mg, 11.75 mmol, 948.36 μL, 2.4 equiv) in one portion at 0° C. After that, a solution of compound 10.2 (2.17 g, 10.77 mmol, 937.08 μL, 2.2 equiv) in dichloromethane (20 mL) was added dropwise to the mixture at 0° C. After the addition was completed, the reaction mixture was stirred at 0° C. for 1 hr. TLC (petroleum ether/ethyl acetate=0/1) and LC-MS showed compound 10.1 was consumed ($R_f$=0.35), no new spot was detected. The reaction mixture was diluted with water (50 mL) and extracted with EtOAc (30 mL×3). The combined organic phases were dried over $Na_2SO_4$, filtered, and concentrated under reduced pressure to give 1.5 of a residue. The residue (500 mg) was purified by column chromatography ($SiO_2$, petroleum ether/ethyl acetate=100/0 to about 5/1) to give Linker 17 (120 mg, 334.18 μmol, 22.9% yield, 95.7976% GC purity) as a light yellow oil. $^1$H NMR (400 MHz, $CDCl_3$): δ 5.22 (br s, 2H), 3.82 (s, 4H), 2.36-2.24 (m, 1H), 2.09-1.93 (m, 5H)

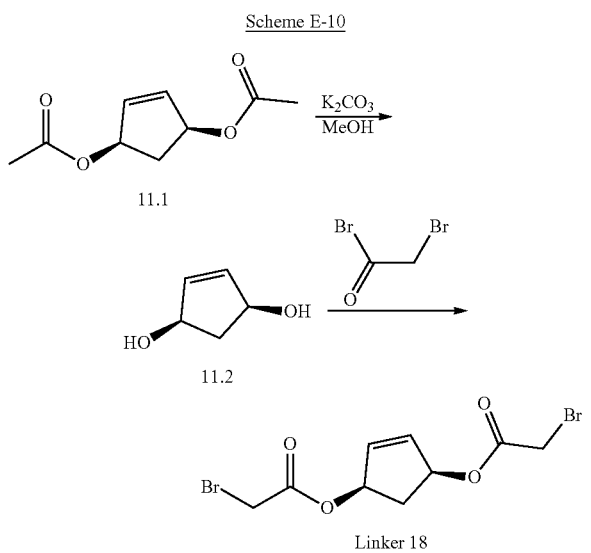

Linker 18

To a solution of compound 11.1 (1.00 g, 5.43 mmol, 1.00 equiv) in MeOH (10.0 mL) was added $K_2CO_3$ (2.00 g, 14.47 mmol, 2.67 equiv) in one portion at 0° C. After the addition was complete, the reaction mixture was stirred for 4 hr at 0° C. TLC (petroleum ether/ethyl acetate=5/1) showed compound 11.1 was consumed ($R_f$=0.08) and a new spot could be observed ($R_f$=0.63). The mixture was filtered and the filtrate was concentrated under vacuum to give a compound 11.2 (800 mg, crude) as a yellow oil. $^1$H NMR (400 MHz, DMSO-$d_6$): δ 5.65 (s, 2H), 4.25 (dd, J=2.6, 6.9 Hz, 2H), 2.16 (td, J=6.9, 13.5 Hz, 1H), 1.34 (br d, J=13.6 Hz, 1H).

To a solution of compound 11.2 (600 mg, 5.99 mmol, 1.00 equiv) in dichloromethane (80 mL) was added pyridine (1.14 g, 14.38 mmol, 1.16 mL, 2.40 equiv) and DMAP (22.0 mg, 179.79 mol, 0.03 equiv) in one portion at 0° C. After that, a solution of 2-bromoacetyl bromide (2.66 g, 13.18 mmol, 1.15 mL, 2.20 equiv) in dichloromethane (12.0 mL) was added dropwise to the mixture at approximately 0-5° C. After the addition was complete, the reaction mixture was stirred for 2 hr at 20° C. TLC (petroleum ether/ethyl acetate=5/1) showed compound 11.2 was consumed ($R_f$=0.08) and a new spot could be observed ($R_f$=0.63). HCl (1N, 40.0 mL) was added into the reaction in portions at 0° C. The mixture was separated and the organic layer was washed with $NaHCO_3$ (20.0 mL×3, saturated). The mixture was dried over $Na_2SO_4$ and filtered. The filtrate was concentrated to give crude Linker 18 (1.50 g) as a light yellow oil.

Crude Linker 18 (200 mg) was purified by silica gel chromatography (petroleum ether/ethyl acetate=100/0 to about 10/1) to give Linker 18 as a light yellow oil (120 mg, 344.01 mol, 23.4% yield, 97.4727% purity). $^1$H NMR (400 MHz, chloroform-d): δ 6.23-6.15 (m, 2H), 5.67-5.58 (m, 2H), 3.85 (s, 4H), 2.93 (td, J=7.5, 15.2 Hz, 1H), 1.85 (td, J=3.6, 15.1 Hz, 1H).

Example 12—Peptide Stapling Using Certain Compounds

As described herein, provided agents, e.g., compounds of $R^x$-$L^{s2}$-$R^x$ or a salt thereof or formula R—I or a salt thereof, can be utilized to prepare stapled peptides, particularly via cysteine stapling. In one set of preparation, (i, i+4) and (i, i+7) peptide binders and non-binders to beta-catenin were synthesized using solid-phase peptide synthesis and purification techniques well known to a person skilled in the art. These peptides include derivatives of xStAx41, a peptide described in, e.g., Grossman et al. Proc Natl Acad Sci U.S.A., 2012, 109(44), 174942-17947. The binding affinity of these peptides stapled by Ruthenium metathesis was determined. The unnatural amino acids of these peptides were replaced with cysteine residue and stapled with Linkers 1-9.

After the (i, i+4) and (i, i+7) peptide binders and non-binders to beta-catenin were stapled with Linkers 1-9, stapling efficiency was assessed via LC-MS. The stapling efficiency of peptides was determined by comparing the ratios of integrals of the $A_{280}$ peaks between the stapled and the unstapled peptides. This calculation is summarized by the equation:

$$\% \text{ Efficiency} = \frac{Area_{stapled}}{Area_{stapled} + Area_{unstapled}}.$$

Figure 8:
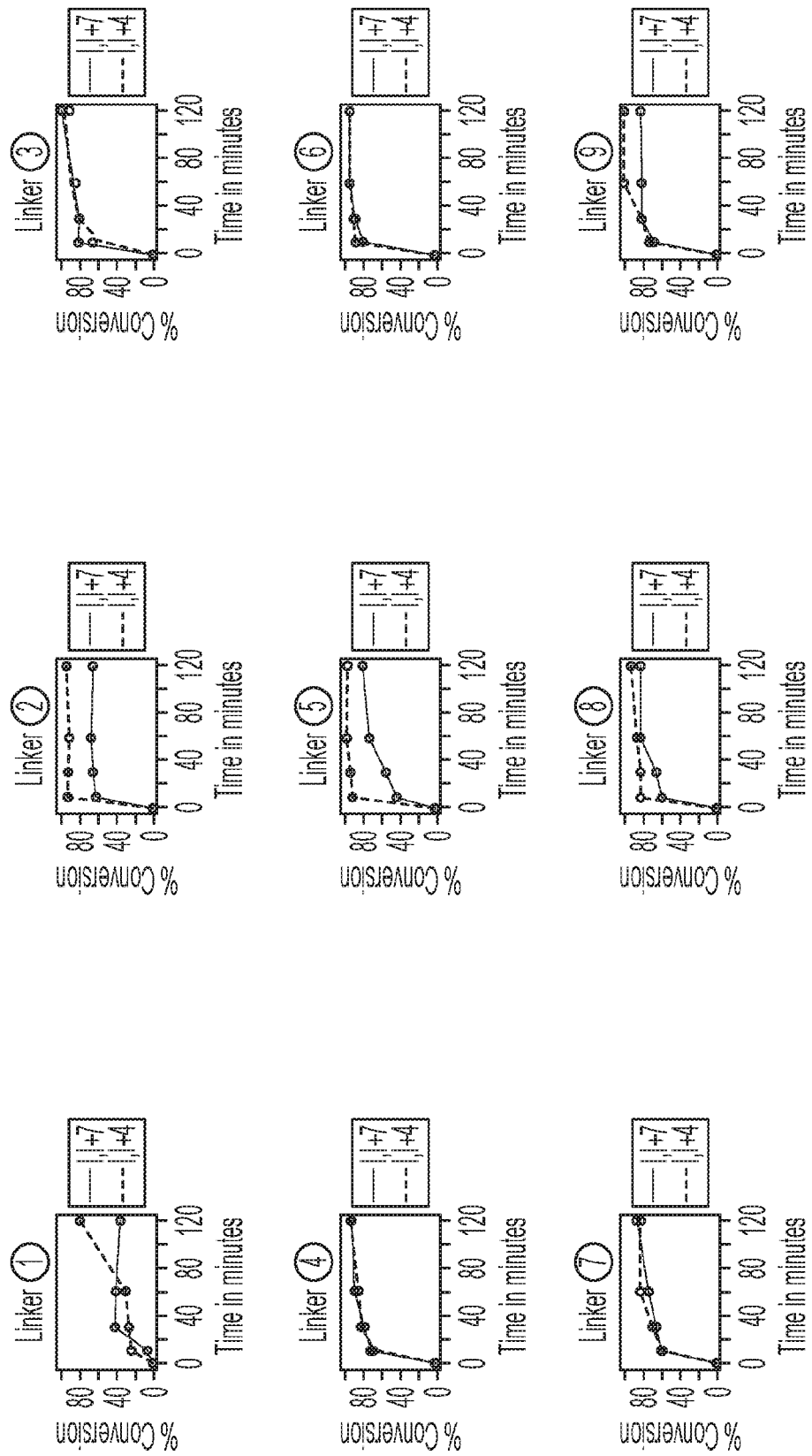
FIG. 8. Stapling conversion efficiencies versus time, as characterized by LC-MS, for Linkers 1-9 with peptide derivatives of xStAx41 comprising cysteines at positions (i, i+4) or (i, i+7); xStAx41 is a peptide disclosed in Grossman et al. Proc Natl Acad Sci U.S.A., 2012, 109(44), 174942-17947.

Four time points are chosen for the determination of the stapling efficiency: 10 min, 30 min, 1 h and 2 h. Two peptides were chosen, one (i, i+4) and one (i, i+7). The reaction for the set time points was quenched by adding TFA to the samples in order to give a final concentration of 1% (v/v) TFA. The readings were then taken using by LC-MS. The Agilent software allows for peak integration. The areas of the specific $A_{280}$ peaks were then inserted into an R-script, which gives plots that allow comparisons of the stapling efficiencies at the set time points of all linkers in two separate peptides (FIG. 8).

As demonstrated, provided compounds can be utilized for stapling at different positions, e.g., (i, i+4), (i, i+7), etc. In some embodiments, provided compounds provide fast stapling. In some embodiments, provided compounds provide high percentage of stapling. In some embodiments, provided compounds provide similar stapling efficiency for staples at different positions, e.g., (i, i+4), (i, i+7), etc. In some embodiments, a higher ratio of linker to peptide can be utilized and did not yield side products of two linkers connected to one peptide. In some embodiments, the only substantial side products that were detected resulted from nucleophilic substitution with other side chains of a peptide. In some embodiments, such side reactions could be circumvented by the addition of DTT as a quenching substance. In some embodiments, stapling reactions nearly went to completion and no post-stapling purification was performed.

Example 13-Cysteine Stapled Peptides Interact with Targets

As demonstrated herein, provided cysteine-stapled peptides interact with their targets. In one procedure, (i, i+4) and (i, i+7) peptide binders and non-binders to beta-catenin stapled with Linkers 1-9 were evaluated for binding to beta-catenin using a fluorescence polarization (FP) assay. The fluorescence polarization buffer was comprised of 50 mM Tris, pH 8.0, 250 mM NaCl, 2% (v/v) glycerol, 0.5 mM TCEP, 0.5 mM EDTA, 0.02% (w/v) sodium azide. Frozen peptide solutions were serially diluted on a 500 µL LoBind Eppendorf plate.

To each well of the plate, a probe mixture comprising a peptide with a known binding constant was added. The target/probe mixture was prepared by adding the buffer, then the target, and then then the probe. The fluorescence readings of each well are taken on a SpectramaxM5. An R-script was composed to read the data and calculate the relevant FP data. This R-script used the raw fluorescence readings of each well and normalizes them, in order to allow comparison between all samples. The readings are then plotted an d interpreted using the following equation:

$$f_b = \frac{c^n}{K_D + c^n}.$$

Figure 9:
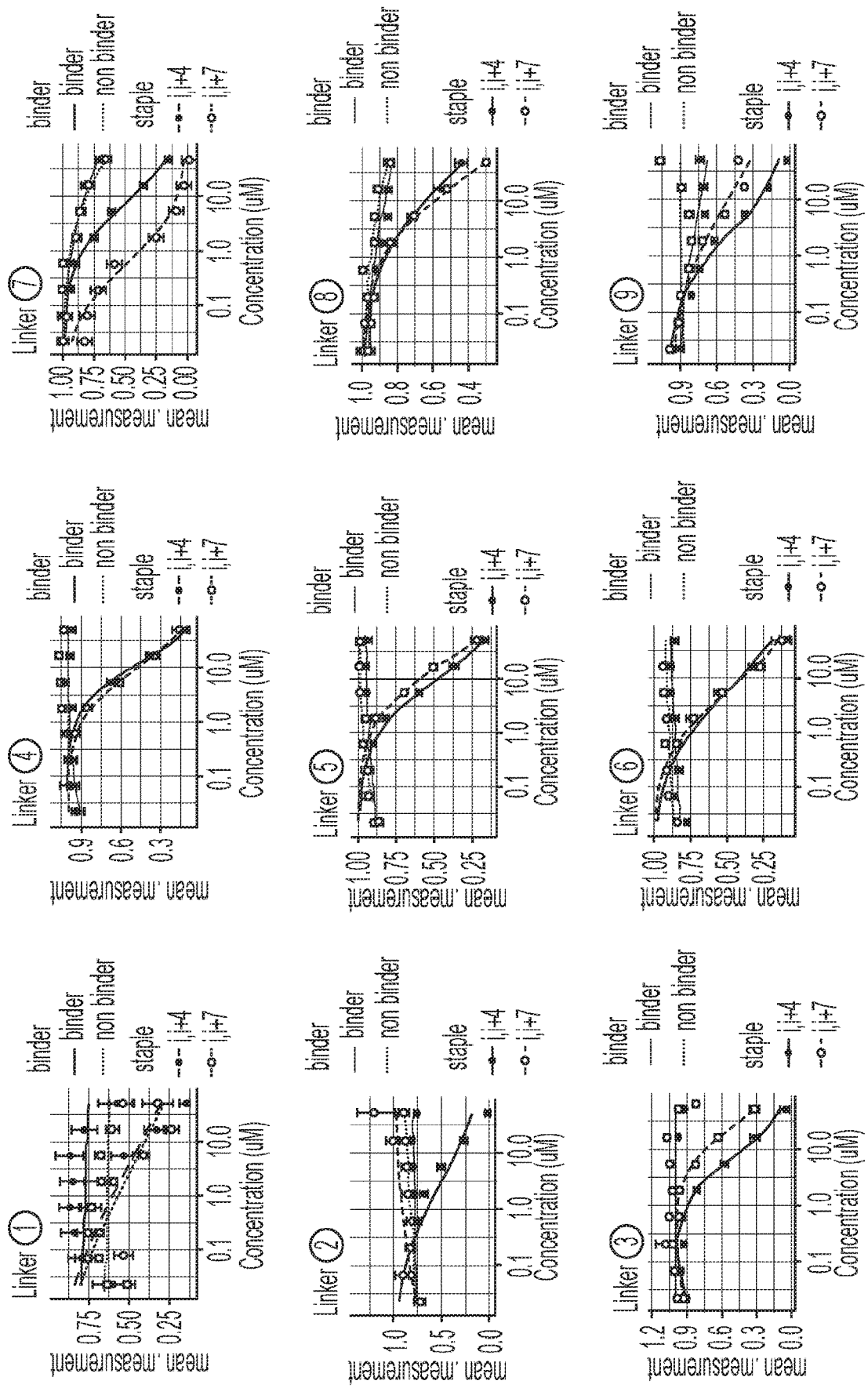
FIG. 9. Mean, normalized fluorescence polarization versus concentration of peptide as characterized by a fluorescence plater reader. Each data point represents the average of three fluorescence polarization runs. Peptides used were binding and non-binding derivatives of xStAx41 stapled at positions (i, i+4) or (i, i+7) with Linkers 1-9.

(FIG. 9 and FIG. 10). This equation depicts the Hill equation used to interpret binding affinities of tested peptides. $f_b$ is the fraction of peptide bound to the target, c is the concentration of peptide, n is the Hill coefficient and $K_D$ is the apparent dissociation constant. The value of $K_D$ is then used to compare the binding affinities of separate peptides. It is given in units of concentration and stands for the required substrate concentration to yield a fraction of bound target of 0.5.

Example 14—Peptides Expression and Stapling

Among other things, the present disclosure provides technologies for identifying and designing useful amino acid sequences and stapled peptides. In one example, phage displayed peptides or peptide libraries were prepared (for technologies useful for constructing such libraries, see e.g., Sidhu et al., Methods Enzymol. 2000; 328: 333-363; or Chen and Heinis, Methods Mol Biol., 2015; 1248: 119-137). Oligonucleotides encoding either single clones or degenerate libraries were assembled into a phage or phagemid vector such as fADL, pADL, or M13KE using standard molecular biology techniques, and transformed into a suitable host, such as *E. coli* strain ER2738 or TG1, using electroporation. Phage particles were amplified by expanding the *E. coli* culture for 5 h in LB media with shaking at 37° C., pelleting *E. coli* cells at 5000×g, precipitating phage particles from the supernatant by addition of ⅕ volume of 20% (w/v) polyethylene glycol 8000, 2.5 M NaCl followed by overnight incubation at 4° C., pelleting at 5000×g, and resuspending in Tris-buffered saline (TBS). Phage particles can be further purified by repeating the precipitation, pelleting, and resuspension steps. Phage displayed peptides or peptide libraries were covalently crosslinked ("stapled") by diluting the phage particle solution in TBS to an OD600 of 1.0 and adding dithiothreitol to a concentration of 1 mM, followed by dialysis against 100 volumes of 20 mM $NH_4CO_3$, 2 mM EDTA, pH ~8 for 30-60 min, followed by addition of the dialyzed phage to a solution of crosslinker prepared in of 20 mM $NH_4CO_3$, 2 mM EDTA, pH ~8 (final crosslinker concentration is 200 PM) and incubation for 2 h at 32° C. Excess crosslinker was removed first by pelleting at 5000×g, followed by addition of dithiothreitol to a concentration of 0.25 mM with incubation for 10 min, and then addition of iodoacetamide to a concentration of 0.75 mM with incubation for a further 10 min. Phage particles were further purified by repeating the precipitation, pelleting, and resuspension steps described above for purification from *E. coli* culture.

Figure 11:
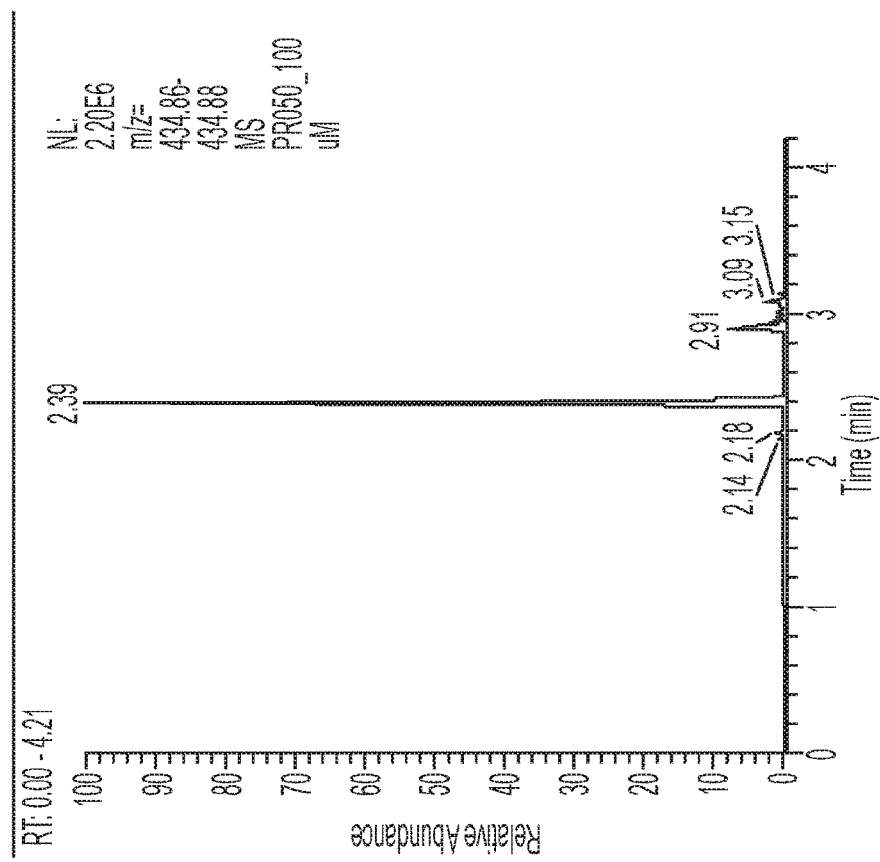
FIG. 11. Liquid chromatography-mass spectrometry traces for i) Panel A: trypsinized ACILDCHIQR (SEQ ID NO: 1) fused to the phage coat protein pIII that was stapled with Linker 9; and Panel B: trypsinized ACILDAHICR (SEQ ID NO: 2) fused to the phage coat protein pIII that was stapled with Linker 7.
Figure 11:
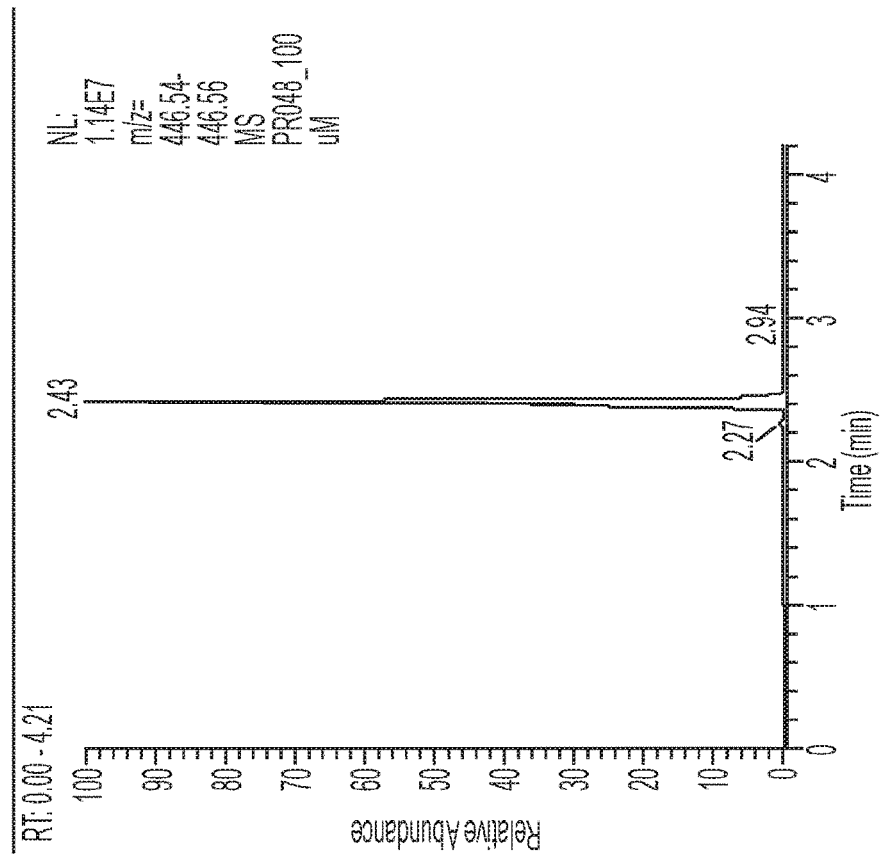
Figure 11:
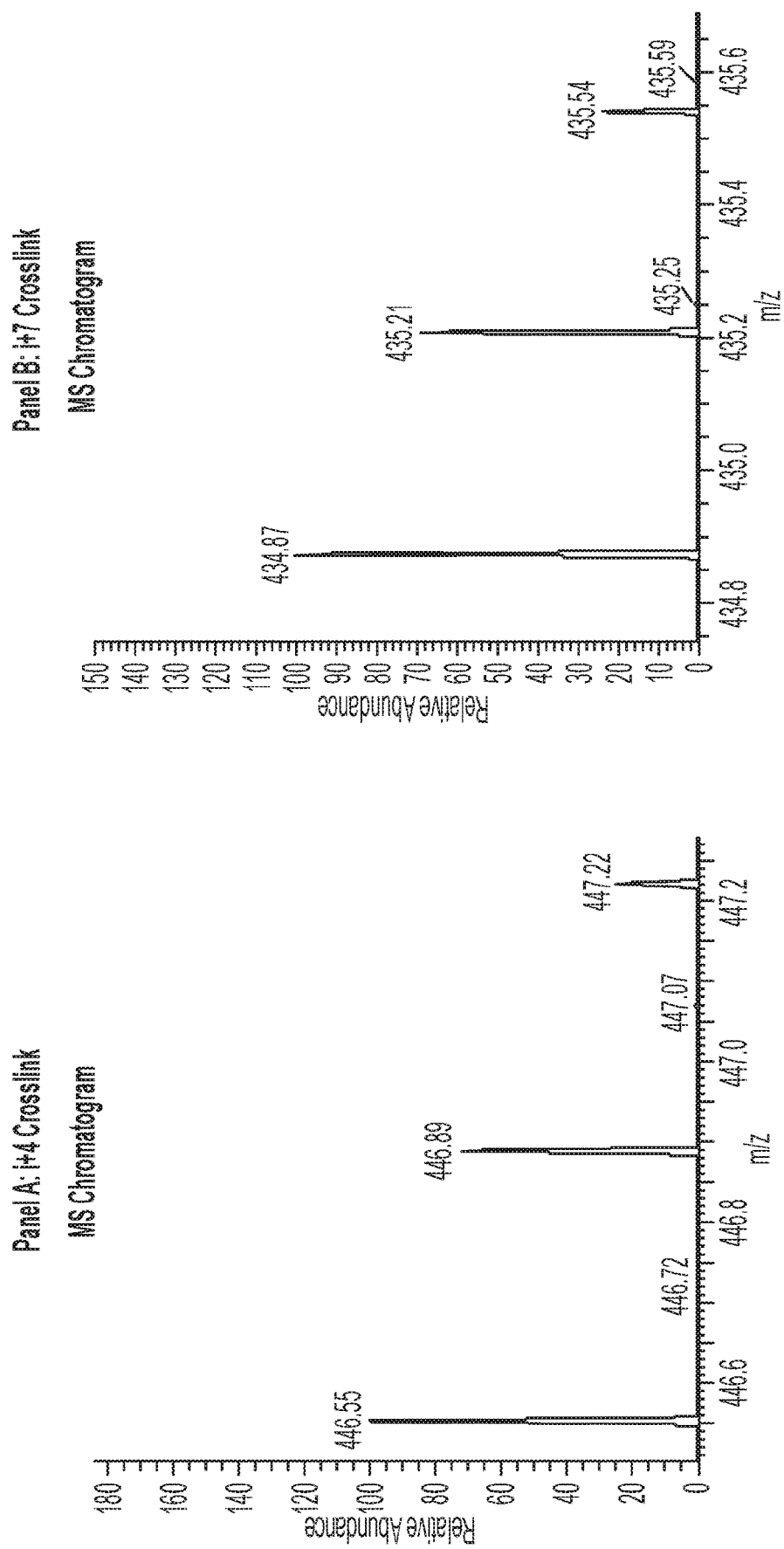

FIG. 11 depicts mass spectrometry data for the crosslinking of two representative peptide clones on phage. In Panel A, Linker 9 was used to crosslink a peptide with the sequence of ACILDCHIQR (SEQ ID NO: 1) fused to the phage coat protein pIII. In Panel B, Linker 7 was used to crosslink a peptide with the sequence of ACILDAHICR (SEQ ID NO: 2) fused to the coat protein pIII. Following the above on-phage crosslinking protocol, the phage particles were mixed with 2 g of trypsin (from porcine pancreas), incubated for 1 h at 37° C., and then analyzed on a Thermo Q-Exactive Plus equipped with an UltiMate 3000 LC system and Phenomenex Aeris C18 column, using a 4 min gradient of 5-100% acetonitrile in water containing 0.1% formic acid. The extracted ion trace shows the expected crosslinked and trypsinized products of MW=1336.643 (Panel A, observed mass is (M+3H)/3 ion of 446.555) and MW=1301.601 (Panel B, observed mass is (M+3H)/3 ion of 434.874).

Example 15—Preparation Stapled Peptide Library and Identification of Useful Sequences and Stapled Peptides Many technologies may be utilized to prepare peptide libraries in accordance with the present disclosure. In one procedure, phage displayed peptides or peptide libraries were prepared using standard methods, e.g., as described above. In some preferred embodiments, the library contains two cysteine residues spaced with 3 or 6 amino acids between the two cysteine residues (i, i+4 or i, i+7 spacing). In some embodiments, a library contains two cysteine residues spaced with 2, 5, 8, 10, 11, or 12 residues apart between the two cysteine residues. In some embodiments, the library contains multiple pairs of cysteines, each pair being spaced with 3 or 6 amino acids between a pair of two cysteine residues apart. Certain exemplary library designs are listed below:
 a) XXXXXCXXXXXXCXXXXX
 b) XXXXXCXXAAXXCXXXXX (SEQ ID NO: 19)
 C) XXXXXCXXXCXXXXX
 d) ADPAXXXCXXXXXXCXXX (SEQ ID NO: 20)
 e) ADPAXXXCXXAAXXCXXX (SEQ ID NO: 3)
 f) ADPAXXXCXXXCXXX (SEQ ID NO: 21)
 g) PXXXCXXXXXXCXXX
 h) PXXXCXXAAXXCXXX (SEQ ID NO: 22)
 i) PXXXCXXXCXXX.

In some embodiments, 'X' is a position where multiple amino acids are possible in the library design, e.g., it is a randomized position. As appreciated by those skilled in the art, incorporation of randomized positions can be done by encoding a degenerate codon in an oligonucleotide primer used to generate a library, for example, NNN or NNK where N=A, T, C, G and K=T, G. Alternatively, randomized positions can be incorporated by the use of trimer phosphoroamidite mixtures, e.g., those available from Glen research, wherein a defined mixture of trimer codons that encode a corresponding defined mixture of amino acids are incorporated in the oligonucleotide primer used to generate the library. For example, a library could be constructed using a mixture of all 20 naturally occurring amino acids, or alternatively by using a subset of all 20 naturally occurring amino acids (e.g., A, D, E, F, H, I, L, M, N, Q, R, S, T, V, W, Y, etc.). In some embodiments, non-natural amino acids may also be incorporated using various available technologies.

Libraries may contain fixed or a subset of preferred amino acids within the sequence for a desired property and/or activity, e.g., in some embodiments, to favor an alpha-helical conformation. For example, incorporation of alanine residues at defined positions in the middle of the peptide (e.g. library designs b), e), and h) above), a proline at the N-terminus (e.g. library designs g), h), i) above), or an aspartic acid followed by a proline at the N-terminus (e.g. library designs d), e), f) in the list above). Oligonucleotides encoding these libraries can be assembled into a phage or phagemid vector and amplified and purified using a number of technologies. Phage library sizes may range from $10^5$ unique members to $10^{10}$ or even more unique members. Typically, a size is $10^8$ unique members. Library diversity can be determined e.g., by titering the phage transformations using standard methods. Libraries can be modified using crosslinkers to form peptide staples.

The following tables showed certain representative clones obtained from two of the library designs listed above. These clones were sequenced by plating a subset of the library following transformation, amplifying and isolating phage as described above, and sequencing directly from the phage using the primer 5'-CCCTCATAGTTAGCGTAACG-3' (SEQ ID NO: 23). The diversity of library design f) was $6.2 \times 10^8$ unique transformations and the diversity of library design e) was $6.5 \times 10^8$ unique transformations.

| Library (f) | Sequence |
| --- | --- |
| Clone 1 | ADPASVYCEMVCWTF (SEQ ID NO: 24) |
| Clone 2 | ADPALHSCHWMCAWQ (SEQ ID NO: 25) |
| Clone 3 | ADPAFMQCHNTCYTT (SEQ ID NO: 26) |
| Clone 4 | ADPAWEICEVNCFQS (SEQ ID NO: 27) |
| Clone 5 | ADPARMACQFVCEVF (SEQ ID NO: 28) |
| Clone 6 | ADPATWSCESMCWYE (SEQ ID NO: 29) |

| Library (e) | Sequence |
| --- | --- |
| Clone 1 | ADPAQIFCDMAAARCMEI (SEQ ID NO: 30) |
| Clone 2 | ADPAMQTCTNAALLCQQQ (SEQ ID NO: 31) |
| Clone 3 | ADPAEFVCMDAADTCDME (SEQ ID NO: 32) |
| Clone 4 | ADPANLICWDAAVACYWI (SEQ ID NO: 33) |
| Clone 5 | ADPARHFCQLAAHLCQWY (SEQ ID NO: 34) |
| Clone 6 | ADPASYACVRAAFSCDYI (SEQ ID NO: 35) |

Example 16—Additional Peptide Libraries and Uses Thereof

Other exemplary library designs include, but are not limited to libraries based on a "PYY" based scaffold:

j)
(SEQ ID NO: 36)
AGPAKPEAPGEDASPXELXXYYXXLXXYLXXVA, wherein 'X' is a position where multiple amino acids are possible in the library design, e.g., it is a randomized position, as described above. The following tables show representative clones obtained from the library listed above. These clones were sequenced as described in Example 15. The diversity of library j) was $2.6 \times 10^8$ unique transformations.

| Library (j) | Sequence |
| --- | --- |
| Template | AGPAKPEAPGEDASPXELXXYYXXLXXYLXXVAGGS (SEQ ID NO: 37) |
| Clone 1 | AGPAKPEAPGEDASPTELRNYYHNLTMYLHMVAGGS (SEQ ID NO: 38) |
| Clone 2 | AGPAKPEAPGEDASPWELQNYYLSLQNYLYIVAGGS (SEQ ID NO: 39) |
| Clone 3 | AGPAKPEAPGEDASPMELTRYYSQLMEYLATVAGGS (SEQ ID NO: 40) |
| Clone 4 | AGPAKPEAPGEDASPFELHMYYQNLYFYLPAVAGGS (SEQ ID NO: 41) |
| Clone 5 | AGPAKPEAPGEDASPFELQFYYNYLIDYLADVAGGS (SEQ ID NO: 42) |

Example 17—Exemplary Technologies for Library Screening

Various technologies can be utilized to screen provided libraries. In one example, screening of phage libraries against biomolecule targets is performed using known methods (e.g., Sidhu et al., Methods Enzymol. 2000; 328: 333-363; Chen and Heinis, Methods Mol Biol., 2015; 1248: 119-137; etc.) in accordance with the present disclosure. An exemplary protocol is as follows. A phage library comprising a 100-fold over-representation is added to a buffer containing 1X TBS, 1 mM $MgCl_2$, 1% (w/v) BSA, 0.1% (v/v) Tween-20, 0.02% (w/v) sodium azide, 5% (w/v) nonfat milk, then mixed with magnetic beads that do not bear a target protein (e.g., Thermo Fisher Dynabeads His-Tag Isolation and Pulldown or Dynabeads MyOne Streptavidin T1). After 1 h of incubation, the beads are separated from the phage to remove phage library members that nonspecifically bind to the beads. The target biomolecule of interest is then attached to the same type of magnetic beads using standard affinity capture methods (e.g. hexahistidine (SEQ ID NO: 43) tagged protein with nickel or cobalt affinity (IMAC) beads, biotin-tagged protein with streptavidin beads, or FLAG-tagged protein with anti-FLAG antibody beads). The resulting beads are then mixed with the phage library and incubated for 1 hour at room temperature, followed by repeated washing to remove unbound phage. The resulting beads, which contain target biomolecule and bound phage, are heated to 95° C. in a buffer containing 25 mM Tris pH 8, 50 mM NaCl, 0.5% (v/v) Tween-20 to dissociate phage DNA. The resulting DNA is then sequenced (see subsequent Examples for details).

Multiple screens may be performed in parallel to assess specificity, potency, or mechanism of binding, for example by performing screens with other biomolecule targets immobilized onto beads, by screening beads bearing no target, or by screening beads immobilized with a given target in the presence and absence of a known binder to that protein. Differences in binding strength, as assessed using a "spike-in" method described below, are used to determine the specificity of peptide/peptide cluster binding or to predict the peptide binding site on the target protein.

Example 18—Additional Screening Technologies

Screening of provided libraries, e.g., phage peptide libraries, against cell or tissue targets may be performed using various methods (e.g., those described in, e.g., Pasqualini and Ruoslahti, Nature (1996); Ivanenkov et al, Biochimica et Biophysica Acta 1448 (1999); Rangel et al, nature protocols Vol. 8 No. 10 (2013); etc.). In some embodiments, control screens may be performed in parallel to assess specificity or potency of binding, for example by isolating other tissue types in addition to the tissue of interest, or screening alternate cell lines or empty tissue culture wells.

Example 19—High-Throughput Sequencing in Screening and Data Processing

In some embodiments, as described herein, a peptide is associated with an identifier which can be utilized to identify the peptide during screening. In some embodiments, an identifier is a nucleic acid, e.g., one comprising a sequence encoding the peptide or a sufficient portion thereof for identifying the peptide. For example, in some embodiments, a library is a phage displayed peptide library, and a peptide can be identified through a nucleic acid sequence that can encode the peptide. In some embodiments, phage DNA that results from screens were sequenced using next-generation sequencing methods and translated into peptide sequences to determine the relative abundance of phage library members that bound to a typically immobilized target of interest (e.g. biomolecule, cell, tissue, etc.). Sequences that were selective for a target of interest were identified by comparing sequence counts in screens for the target to sequence counts in screens for controls, such as blank beads, beads containing other targets, or alternate cell or tissue types. Sequences that were identified using this method are further analyzed to identify groups of related sequences ("families" or "clusters").

Prior to identification of candidate sequences, all sequence counts are optionally normalized based on one or more internal standards (for example, by the addition of a known quantity of a specific "spike-in" sequence to each screening or sequencing sample after the dissociation of phage DNA as described above but before PCR and sequencing). Normalization involves linearly scaling the counts for each sequence in a screening sample such that the counts for internal standard sequence matches the number of internal standard phage particles spiked into the sample. Among other things, this can adjust the counts for a sequence to be the absolute count of eluted phage with that sequence, rather than number of reads for that sequence.

Sequences may be rank ordered based on their fold enrichment in screens with the target of interest compared to fold enrichment profile across multiple control screening conditions (e.g. buffer conditions, different target biomolecules, cells, and tissues, different reagent concentrations, etc.) or total counts. If a range of target concentrations were screened, an effective IC50 can be computed for each sequence and used for ranking. Top-ranked sequences may be considered as candidate drugs.

Figure 12:
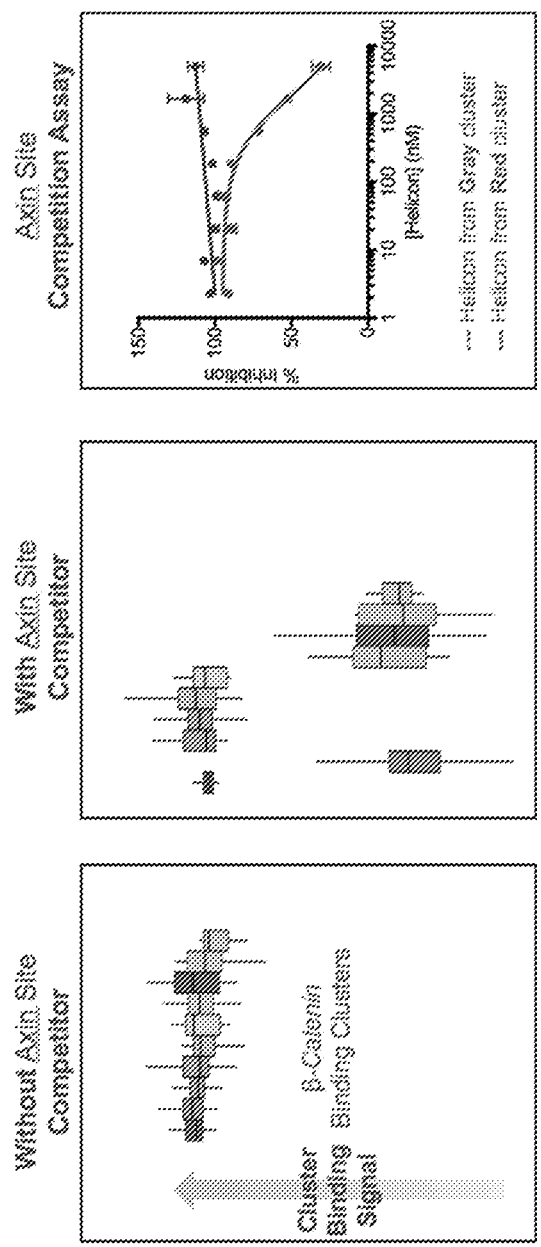
FIG. 12. Analysis for clusters of sequences identified in a screen against beta-catenin, using a combination of the "spike-in" method and the addition of a known competitor to the Axin/TCF binding site of beta-catenin to determine the effect of competitor addition on cluster binding signal. The left panel shows a box plot representation of the binding strength of ten clusters that were identified in a screen against β-catenin. The middle panel shows the same but when the known competitor to the Axin/TCF binding site is added. Five clusters decrease significantly in binding signal, indicating that they likely compete with the same binding site on beta-catenin. The right panel shows the in vitro binding behavior of a representative peptide from the leftmost cluster and the third cluster from the right in an assay that measures the competition with binders to the Axin/TCF binding site, demonstrating that the predicted binding behavior matches the measured in vitro binding behavior.

As an example, FIG. 12 shows an analysis for clusters of sequences identified in a screen against beta-catenin, using a combination of the "spike-in" method and the addition of a known competitor to the "Axin/TCF binding site" of beta-catenin to determine the effect of competitor addition on cluster binding signal.

Top-ranked sequences can additionally be clustered to identify sequence families. Pairwise distances between each candidate sequence can be computed using any one of a variety of sequence distance measures, including $$\text{distance} = \left(1 - \frac{score_{ij}}{score_{ii}}\right)\left(1 - \frac{score_{ij}}{score_{jj}}\right),$$

where $score_{ij}$ is the alignment score between sequences i and j. Alignment scores can be computed using standard sequence similarity scoring matrices (e.g. BLOSUM and PAM matrices, etc.). Given a matrix of pairwise sequence distances, the sequences can be clustered using hierarchical clustering, k-means clustering, or any other clustering method. Sequence families representing an underlying sequence motif can then be identified by the resulting clusters. Sequences that do not fall into clusters of similar sequences may represent false positives from the screen, whereas sequences that fall into clusters with many similar sequences are supported by the shared sequence motif that underlies that cluster and thus are more likely to validate as binders of the target of interest in further testing.

Individual sequences or groups of sequences in a cluster or family can also be investigated for their specificity to the target of interest. These sequences can be examined in screens against other targets using the same library, either within the same sequencing run or from a screen run and sequenced separately. Sequences or sequence families that show an increase in counts between control screens and screens against other targets may exhibit nonspecific binding, and could potentially be deprioritized in favor of sequences that show no significant difference. Sequences and sequence families can be examined for their specificity at any stage in the hit prioritization process, including before clustering such that sequences that do not meet a given specificity condition may be excluded from further analysis. Furthermore, if a given specificity profile is desired across a set of homologous proteins, then this specificity profile can be used to prioritize sequences and families before or after clustering.

In one embodiment, sequence counts are normalized based on the known amount of a "spike-in" phage, and sequences are ranked by their fold increase in counts in the presence of the target biomolecule compared to control sample. In some embodiments, pairwise distances between the top 3000 ranked sequences are computed using the distance measure above and the PAM70 sequence alignment scoring matrix. Hierarchical clustering is used to cluster the sequences, and 50 distance thresholds are selected uniformly from the set of all internal node heights in the dendrogram. Clusters are defined using each distance threshold. At the same time, 3000 sequences are selected at random and subjected to the same hierarchical clustering. This is repeated 1000 times to generate a set of null hypothesis dendrograms. The number and size of clusters at each threshold for the top-ranked sequences are compared to the distribution of number and size of clusters at the same threshold in all 1000 null hypothesis dendrograms in order to compute an empirical p-value for both the threshold (number of clusters) and each cluster at that threshold (cluster size). Only clusters with p-values less than or equal to 0.05 are considered. Sequence logos can be constructed for each cluster to visualize the underlying sequence motif and facilitate selection of candidate peptides. Additionally, target specificity of each cluster is manually examined by looking at for significant difference between control screening sample and screening samples for other targets, and families that show a lack of specificity are omitted from further consideration. The process is then repeated for the next 3000 ranked sequences, and so on, until no clusters meet the significance criteria.

Example 20—Follow-Up Libraries

In some embodiments, screening results, e.g., sequencing information obtained from the aforementioned screens, can be used to prepare "focused libraries" or "optimization libraries." This can be done using the same library construction methodology described above, except that in positions that are "randomized," the amino acids allowed at each position are restricted based on the sequences in the same sequence family or cluster.

For example for each family of sequences identified in Example 6, the allowed amino acids at each position are defined as those whose frequency is above a threshold, e.g., 10%. If no amino acids meet this criterion, then all amino acids (or a predefined subset of all amino acids) may be assumed to be allowed. In some embodiments, for each position, the most restrictive degenerate codon that covers all allowed amino acids is selected. Together, the set of degenerate codons at each position define an optimization library. The library size is then computed based on the size of the sequence space encoded by the selected codons at each position. The threshold can then be varied to produce a library whose size meets some pre-determined criteria, for example the largest library under $10^6$ members. These libraries can be made and screened such that nearly all sequence within the library's sequence space are present in sufficient numbers to enable its detection in a screen.

The focused libraries can be screened, sequenced and analyzed as described above. In some embodiments, the present disclosure provides near-complete sampling of the sequence space around each family of candidate sequences, and focused libraries can provide detailed information about amino acid preference at each position, including tolerated and non-tolerated amino acids, and quantitative effects of different amino acids on selectivity over control samples can be provided.

Example 21—Identified Peptides Bind to Targets

Figure 13:
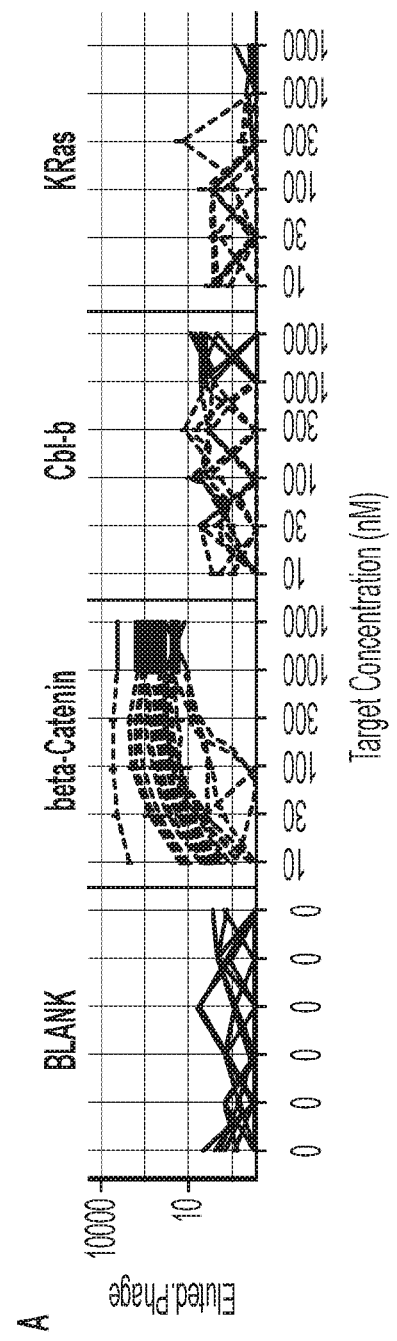
FIG. 13. A library (ADPAXXXCXXAAXXCXXX (SEQ ID NO: 3)) was stapled with Linker 7 and screened against beta-catenin. Panel A: Dose-response profile for top 15 binding sequences across three different target proteins and blank beads, demonstrating binding specificity for beta-Catenin. Grey lines are used to connect the counts for each sequence within the same experimental target concertation conditions. Panels B-D: Sequence logos (B), dose response profile (C), and boxplot of dose response profile (D) are shown for top 5, top 10, top 15, and all sequences within a cluster (top to bottom) based on effective IC50. The gray boxplots in the bottom of D show the count distribution for sequences not included in the clustering that match the sequence motif shown in panel A. Panel E: Sequence (SEQ ID NOs 75-104, respectively, in order of columns), effective IC50, sequence split by amino acid, and counts for each beta-catenin concentration.
Figure 13:
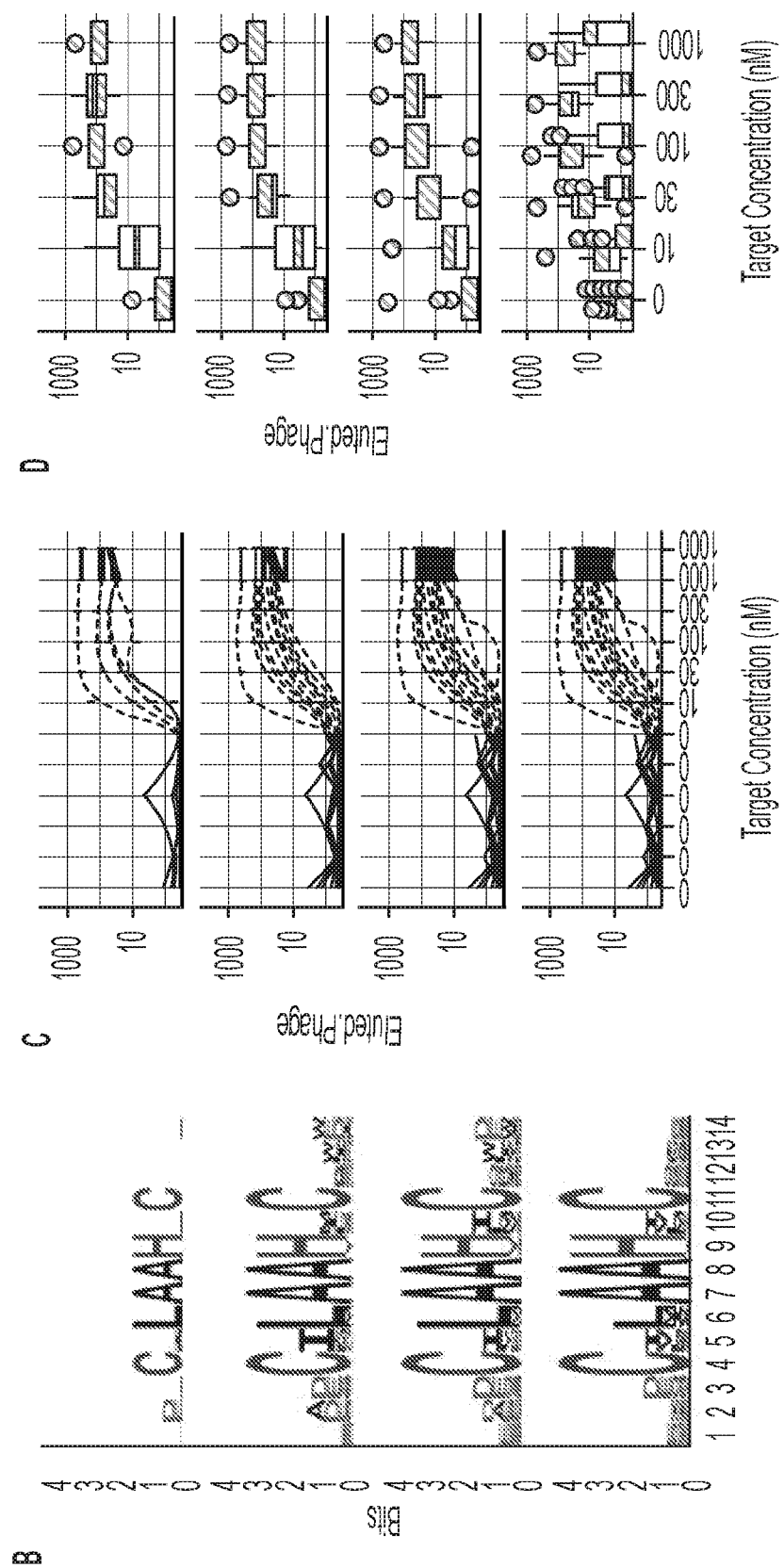
Figure 14:
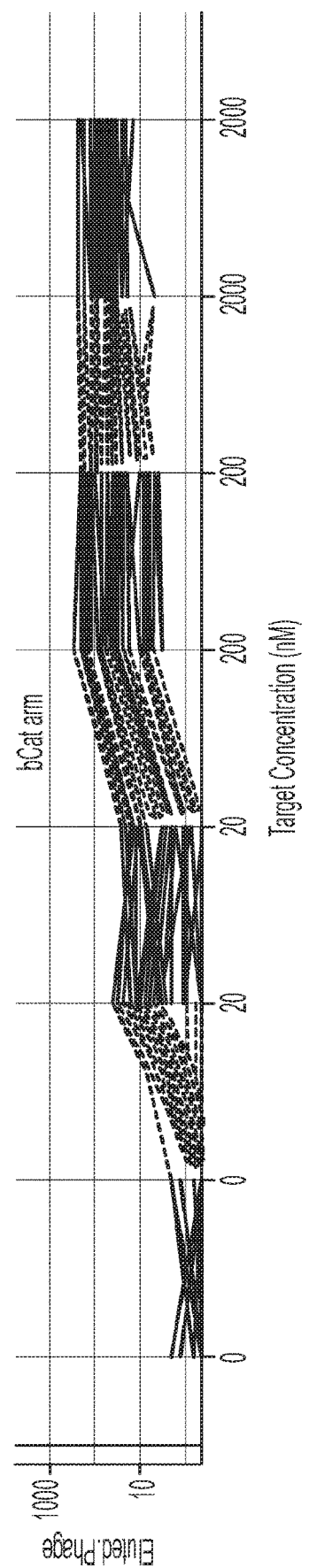
FIG. 14. A library (ADPAXXXCXXAAXXCXXX (SEQ ID NO: 3)) was stapled with Linker 7 and screened against beta-catenin. Panel A: Eluted phage counts for sequences from a sequence cluster. Black lines connect the counts for each sequence across different target concentrations. Grey lines are used to connect the counts for each sequence within the same experimental target concertation conditions. Panels B-D: Sequence logos (B), dose response profile (C), and boxplot of dose response profile (D) are shown for top 5, top 10, top 15, and all sequences within a cluster (top to bottom) based on effective IC50. The gray boxplots in the bottom of D show the count distribution for sequences not included in the clustering that match the sequence motif shown in panel A. Panel E: Sequence (SEQ ID NOs 105-134, respectively, in order of columns), effective IC50, sequence split by amino acid, and counts for each beta-catenin concentration. Compound 1 was identified as a possible beta-catenin binder.
Figure 14:
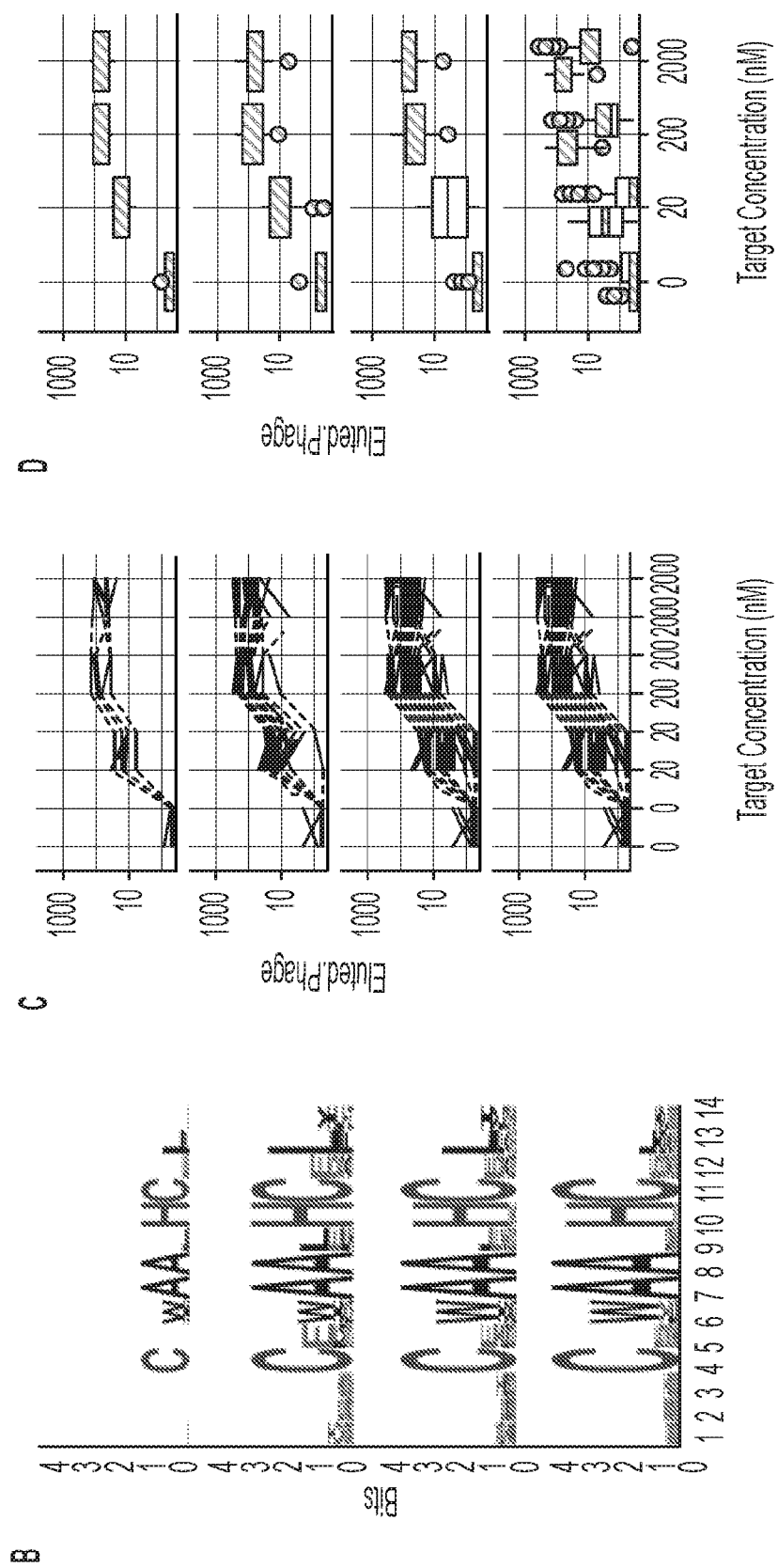
Figure 15:
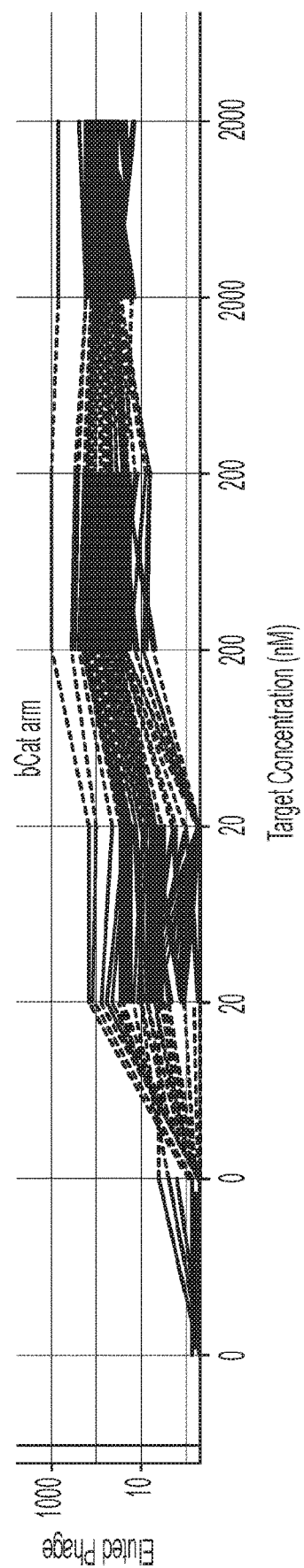
FIG. 15. A library (ADPAXXXCXXAAXXCXXX (SEQ ID NO: 3)) was stapled with Linker 7 and screened against beta-catenin. Panel A: Eluted phage counts for sequences from a sequence cluster. Black lines connect the counts for each sequence across different target concentrations. Grey lines are used to connect the counts for each sequence within the same experimental target concertation conditions. Panels B-D: Sequence logos (B), dose response profile (C), and boxplot of dose response profile (D) are shown for top 5, top 10, top 15, and all sequences within a cluster (top to bottom) based on effective IC50. The gray boxplots in the bottom of D show the count distribution for sequences not included in the clustering that match the sequence motif shown in panel A. Panel E: Sequence (SEQ ID NOs 135-164, respectively, in order of columns), effective IC50, sequence split by amino acid, and counts for each beta-catenin concentration. Compound 2 was identified as a possible beta-catenin binder.
Figure 15:
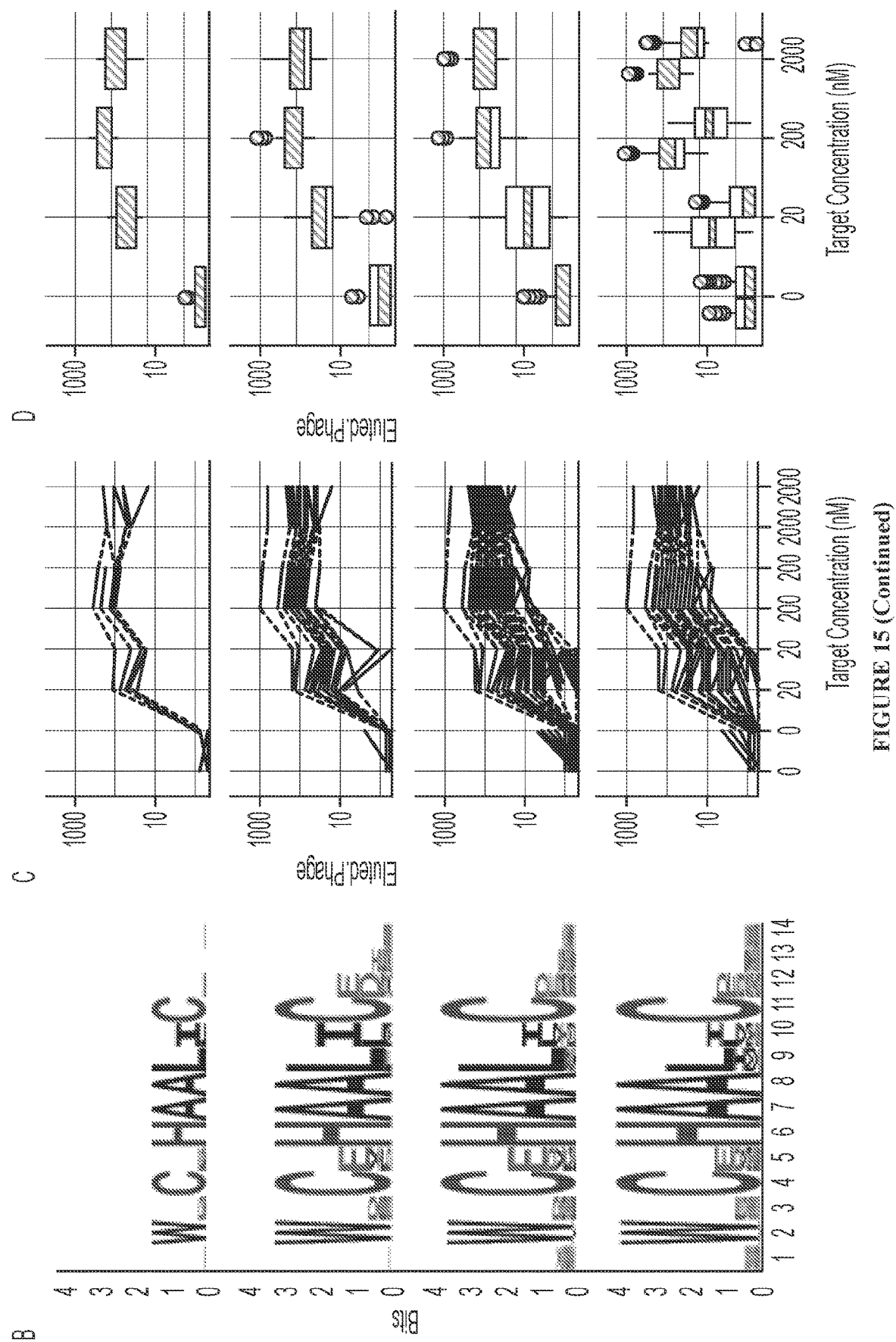
Figure 16:
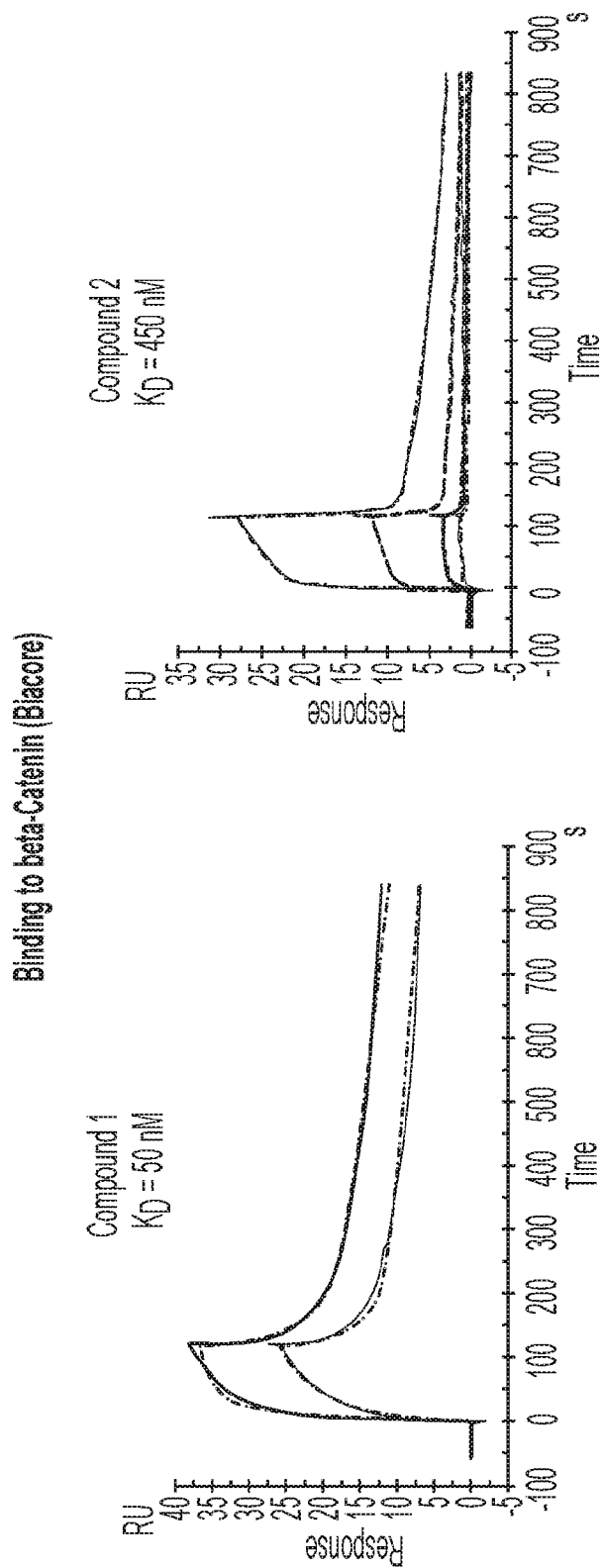
FIG. 16. Binding affinity examples for purified Compounds 1 and 2, chemically synthesized by solid-phage peptide synthesis and crosslinked with Linker 7 (i.e. not displayed on phage), using a Biacore System.

In some embodiments, provided technologies provide peptides whose amino acid sequences are very different from known natural amino sequences that bind to a target. In some embodiments, provided technologies can provide peptides for targets no known binders exist. In one example, a cysteine stapled collection of peptides was screened against beta-catenin. A library with 10 random sites (AD-PAXXXCXXAAXXCXXX (SEQ ID NO: 3)) was stapled with Linker 7 and enrichment of certain sequences was achieved (FIGS. 12, 13, and 14). From these sequences, Compounds 1 and 2 were each evaluated for their binding to beta-catenin using a Biacore system (FIG. 15). Approximately 6 nmol dried peptide diluted in buffer (50 mM Tris pH 8.0, 300 mM NaCl, 2% (v/v) glycerol, 0.5 mM TCEP, 0.5 mM EDTA, 0.005% (v/v) Tween-20, 1 mg/mL CM Dextran, 0.02% (w/v) sodium azide) and quantified by absorbance at 280 nm. Each peptide was assayed on a Biacore X100 using the Biacore Biotin CAPture Kit (GE Healthcare) and biotinylated beta-Catenin; results were analyzed using the Biacore X100 Evaluation Software (FIG. 15).

Example 22—Various Stapled Peptides Bind to Target Protein

A number of peptides were prepared and assessed using technologies described herein. Certain useful technologies are described below as an example.

Peptide synthesis and purification: Peptides were synthesized by solid phase assembly on ProTide resin (0.65 mmol/g) using the Fmoc strategy. All couplings were performed with fourfold excess of amino acids and coupling reagents, such as HATU and DIPEA. Peptides were released from resin by treating with a cleavage cocktail composed of water (2.5% (v/v)), triisopropylsilane (2.5% (v/v)) and trifluoroacetic acid (95% (v/v)) for 1.5 h. The peptides were precipitated by addition of ice-cold ether.

Cross-linking (stapling): Lyophilized crude peptide solution (-3-5 mg/mL) was dissolved in 50% acetonitrile/water. The solution was treated with diisopropylethylamine (-3 eq) and shaken for 5 min. The alkylating agent (e.g. Linker 7) in DMF (1.1 equiv) was added to the solution and stirred at 37° C. for 30 min. The reaction was quenched by adding 2 eq of 1M DTT to quench remaining linker. The crude mixture was purified by reverse-phase HPLC using a C18 column and a gradient of solvent A: $H_2O$, $HCO_2H$ (0.1% (v/v)); solvent B: $CH_3CN$, $HCO_2H$ (0.1% (v/v)). Various technologies are available for peptide characterization. In some embodiments, peptides were characterized by analytical HPLC and mass spectrometry.

Peptide assessment: In one assay for assessing binding to beta-catenin, peptide solutions were prepared in buffer (50 mM Tris pH 8.0, 250 mM NaCl, 2% glycerol, 0.5 mM EDTA, 0.02% w/v sodium azide) using a 3-fold serial dilution from 5 μM. Probe solution (15 nM full-length β-Catenin, 20 nM FITC labeled Axin peptide in buffer ([FAM-PEG1-RRWPR(S5)ILD(S5)HVRRVWR (SEQ ID NO: 44)] where the two S5 residues are stapled, as reported in: Proc Natl Acad Sci USA. 2012 Oct. 30; 109(44):17942-7)) was prepared and incubated for 5 minutes, then 40 μL per well plated in a black polystyrene 384-well plate (Corning). Equal volume of the titrated peptide was added to the plate and incubated protected from light for 15 minutes prior to read. Reads were performed on a Spectramax M5 (Molecular Devices) in duplicate.

Measurement of LogD: LogD values were measured on a Agilent 1260 HPLC with UV detector (254, 220 nm), using a Gemini NX C-18 50×3 mm column (Phenomenex) with a 6-minute 0-100% mobile phase gradient of A) 50 mM ammonium acetate pH 7.4 and B) Acetonitrile at 25° C. with a flow rate of 1 mL/min and injection volume of 3-5 uL. Calibration mixture C-18 was purchased from Bio-mimetic Chromatography Ltd and used to run calibration, calculate CHI value, then calculate CHI logD using equation: CHI log D=0.0525*CHI−1.467.

Measurement of LogK: LogK values were measured on a Agilent 1260 HPLC with UV detector (254,280 nm) using a IAM.PC.DD2 100×4.6 mm column (Regis Technologies 1-774011-300) with a 6.5 min gradient of 0-90% B with mobile phase A of 50 mM ammonium acetate pH 7.4, and mobile phase B of Acetonitrile. The temperature was 30° C., the flow rate 1.5 mL/min, and the injection volume 3-5 uL. Calibration mixture IAM was purchased from Bio-mimetic Chromatography Ltd and used to run calibration, calculate CHI IAM value, then calculate logk IAM using equation: log k IAM=0.046*CHI IAM+0.42.

Figure 17:
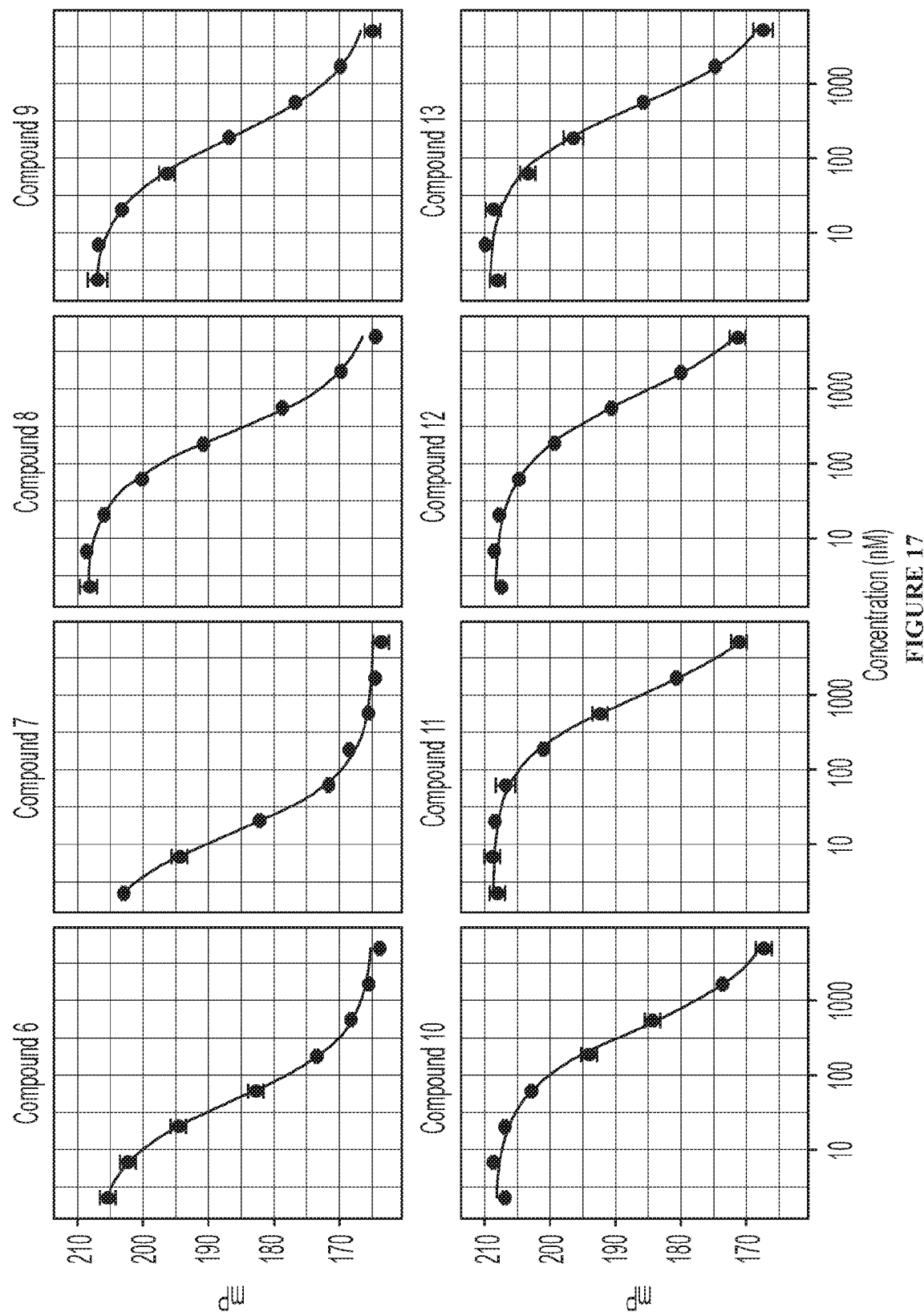
FIG. 17. Competition fluorescence polarization curves for eight selected peptides. mP (milli-polarization) units are on the Y-axis, and concentration of peptide is on the X-axis. As increasing amount of peptide is added, mP values decline as the FITC-labeled probe peptide is displaced from the beta-Catenin protein.

Data from certain measurements are presented below and in FIG. 17. As demonstrated herein, certain peptides, e.g., those comprising cysteine staples from various linkers, can effectively bind to beta-catenin (e.g., with EC50 no more than 50, 100, 150, 200, 500, 1000, 2000, 3000, 5000 or 10000 nM).

| ID* | Staple Type** | Sequence | SEQ ID NO: | LogD | LogK | bCat EC50 (nM) |
| --- | --- | --- | --- | --- | --- | --- |
| 1 | Linker 7 | ADPATHRCEWAALHCELV | 45 | 0.57 | 1.3 | 5197 |
| 2 | Linker 7 | ADPALWACEHAALICETQ | 46 | 0.62 | 1.16 | 2802 |
| 3 | Linker 7 | ADPAYEECILAAHICQTW | 47 | 0.74 | 1.54 | ND |
| 4 | Linker 7 | ADPALADCILAAHMCQLW | 48 | 1.24 | 1.78 | 5519 |
| 5 | Linker 7 | ADPAHAECVLDYHICQIW | 49 | 1.09 | 2.1 | 117 |
| 6 | Linker 7 | ADPAQDHCILDTHICRIW | 50 | 1 | 1.53 | 47 |
| 7 | Linker 7 | ADPAEDECILNNHICRIW | 51 | 0.82 | 2.39 | 14 |
| 8 | Linker 7 | ADPAEDECILAAHMCRWW | 52 | 0.92 | 1.85 | 255 |
| 9 | Linker 7 | ADPADEDC1LAAHICQWD | 53 | 0.29 | 1.67 | 188 |
| 10 | Linker 7 | ADPAQWHCEHAALICELD | 54 | 0.39 | 1.98 | 417 |
| 11 | Linker 7 | ADPAPWQCEHAALLCELE | 55 | 0.47 | 1.74 | 922 |
| 12 | Linker 7 | ADPADWECEHAALICDAM | 56 | 0.39 | 1.66 | 815 |
| 13 | Linker 7 | ADPAYWLCEHAALICEVE | 57 | 0.8 | 1.75 | 456 |
| 14 | Linker 7 | ADPAQWPCEHAALLCEIE | 58 | 0.47 | 1.59 | 404 |
| 15 | | GPAKPEAPGEDASPDELHHYYQNLETYLYRVA | 59 | 0.82 | 1.67 | >10000 |
| 16 | | GPAKPEAPGEDASPDELIHYYNSLDEYLYEVA | 60 | 0.53 | 1.67 | >10000 |
| 17 | | GPAKPEAPGEDASPDELYHYYTHLEEYLYDVA | 61 | 0.64 | | >10000 |
| 18 | | GPAKPEAPGEDASPDELMHYYTSLEDYLDHVP | 62 | 0.52 | | >10000 |
| 19 | | GPAKPEAPGEDASPDELTYYYDELRDYLYSVA | 63 | 0.82 | | >10000 |
| 20 | | GPAKPEAPGEDASPDELIFYYDHLSRYLTDVA | 64 | 0.91 | | >10000 |
| 21 | | GPAKPEAPGEDASPDELRMYYHELDNYLDQVA | 65 | 0.44 | | >10000 |
| 22 | | GPAKPEAPGEDASPDELHTYYDTLYHYLTSVA | 66 | 1.09 | 1.87 | >10000 |
| 23 | | GPAKPEAPGEDASPDELYYYYDDLRQYLSTVA | 67 | 0.81 | | >10000 |
| 24 | | GPAKPEAPGEDASPTELYYYYDHLTDYLDVVP | 68 | 0.66 | | >10000 |
| 25 | | GPAKPEAPGEDASPNELYYYYDELHYYLHDVA | 69 | 0.59 | 1.68 | >10000 |

-continued

| ID* | Staple Type** | Sequence | SEQ ID NO: | LogD | LogK | bCat EC50 (nM) |
|---|---|---|---|---|---|---|
| 26 | | GPAKPEAPGEDASPQELHDYYEILDNYLDWVA | 70 | 0.87 | 1.81 | >10000 |
| 27 | | GPAKPEAPGEDASPNELHYYYWELDSYLENVA | 71 | 0.64 | 1.69 | >10000 |
| 28 | | GPAKPEAPGEDASPEELYHYYWDLDDYLDRVA | 72 | 0.62 | 1.68 | >10000 |
| 29 | | GPAKPEAPGEDASPIELWEYYESLETYLDNVA | 73 | 0.73 | 1.86 | >10000 |
| 30 | | GPAKPEAPGEDASPLELNLYYLDLHDYLQQVA | 74 | 0.98 | 1.69 | >10000 |
| 31 | Linker 10 | ADPATHRCEWAALHCELV | 45 | 0.68 | 1.19 | >10000 |
| 32 | Linker 11 | ADPATHRCEWAALHCELV | 45 | 0.61 | 1.34 | 5165 |
| 33 | Linker 12 | ADPATHRCEWAALHCELV | 45 | 0.68 | 1.4 | 5352 |
| 34 | Linker 13 | ADPATHRCEWAALHCELV | 45 | 0.63 | 1.32 | 4318 |
| 35 | Linker 15a | ADPATHRCEWAALHCELV | 45 | 0.77 | 1.16 | >10000 |
| 36 | Linker 15b | ADPATHRCEWAALHCELV | 45 | 0.77 | 1.35 | >10000 |
| 37 | Linker 16 | ADPATHRCEWAALHCELV | 45 | 0.84 | 1.34 | >10000 |
| 38 | Linker 17 | ADPATHRCEWAALHCELV | 45 | 0.8 | 1.25 | >10000 |
| 39 | Linker 18 | ADPATHRCEWAALHCELV | 45 | 0.75 | 1.27 | >10000 |
| 40 | Linker 10 | ADPALWACEHAALICETQ | 46 | 0.73 | 1.12 | 9546 |
| 41 | Linker 11 | ADPALWACEHAALICETQ | 46 | 0.73 | 1.21 | 3024 |
| 42 | Linker 12 | ADPALWACEHAALICETQ | 46 | 0.84 | 1.3 | 4516 |
| 43 | Linker 13 | ADPALWACEHAALICETQ | 46 | 0.75 | 1.19 | 4593 |
| 44 | Linker 15a | ADPALWACEHAALICETQ | 46 | 0.7 | 1.08 | 7334 |
| 45 | Linker 15b | ADPALWACEHAALICETQ | 46 | 1.03 | 1.31 | 5569 |
| 46 | Linker 16 | ADPALWACEHAALICETQ | 46 | 0.94 | 1.24 | 5821 |
| 47 | Linker 17 | ADPALWACEHAALICETQ | 46 | 0.91 | 1.21 | >10000 |
| 48 | Linker 18 | ADPALWACEHAALICETQ | 46 | 0.93 | 1.22 | >10000 |

*Parent sequences for 15-30 (not stapled) are PYY.
**Linker agents link two cysteine residues (-S- replacing leaving groups such as -Br).

The invention claimed is:

1. A collection of stapled peptides, each of which independently comprises ADPAXXXCXXAAXXCXXX (SEQ ID NO: 3), wherein:
   each X is independently an amino acid residue;
   the two cysteine residues are covalently linked with one another via a linker having the structure of —S-$L^{s2}$-S—, where each S is independently a sulfur atom of one of the two cysteine residues; and
   $L^{s2}$ is

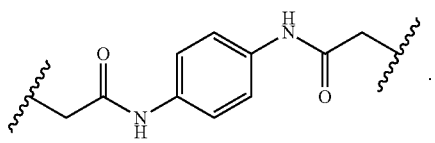 [SMILES: *CC(=O)Nc1ccc(NC(=O)C*)cc1]

2. The collection of claim 1, wherein each individual stapled peptide in the collection is covalently bound to a phage particle.

3. The collection of claim 1, wherein each stapled peptide of the collection is discretely associated with an identifier so that the amino acid sequence of the stapled peptide can be independently identified.

4. The collection of claim 3, wherein the identifier comprises a nucleic acid sequence that encodes the amino acid sequence of the stapled peptide or a portion thereof.

5. The collection of claim 4, wherein the amino acid sequence of the stapled peptide is expressed by a system that comprises the identifier.

6. The collection of claim 2, wherein each stapled peptide of the collection is discretely associated with an identifier so that the amino acid sequence of the stapled peptide can be independently identified.

7. The collection of claim 6, wherein the identifier comprises a nucleic acid sequence that encodes the amino acid sequence of the stapled peptide or a portion thereof.

8. The collection of claim 7, wherein the amino acid sequence is expressed by a phage system that comprises the identifier.

9. The collection of claim 1, wherein the stapled peptides of the collection are each fused to a phage protein.

10. The collection of claim 8, wherein the stapled peptides of the collection are each fused to a phage protein.

11. The collection of claim 5, wherein the stapled peptides of the collection are each fused to a phage protein.

* * * * *